(12) United States Patent
Nichols et al.

(10) Patent No.: US 11,596,633 B2
(45) Date of Patent: Mar. 7, 2023

(54) SHP2 INHIBITOR COMPOSITIONS AND METHODS FOR TREATING CANCER

(71) Applicant: Revolution Medicines, Inc., Redwood City, CA (US)

(72) Inventors: Robert J. Nichols, Redwood City, CA (US); Mark A. Goldsmith, Redwood City, CA (US); Christopher Schulze, Redwood City, CA (US); Jacqueline Smith, Redwood City, CA (US); David E. Wildes, Redwood City, CA (US); Stephen Kelsey, Redwood City, CA (US); Mallika Singh, Redwood City, CA (US)

(73) Assignee: Revolution Medicines, Inc., Redwood City, CA (US)

( * ) Notice: Subject to any disclaimer, the term of this patent is extended or adjusted under 35 U.S.C. 154(b) by 0 days.

(21) Appl. No.: 16/810,525

(22) Filed: Mar. 5, 2020

(65) Prior Publication Data

US 2020/0368238 A1    Nov. 26, 2020

Related U.S. Application Data

(63) Continuation of application No. PCT/US2018/049744, filed on Sep. 6, 2018.

(60) Provisional application No. 62/681,001, filed on Jun. 5, 2018, provisional application No. 62/653,831, filed on Apr. 6, 2018, provisional application No. 62/558,255, filed on Sep. 13, 2017, provisional application No. 62/555,400, filed on Sep. 7, 2017.

(51) Int. Cl.
*A61K 31/519* (2006.01)
*A61P 35/00* (2006.01)
*A61K 45/06* (2006.01)

(52) U.S. Cl.
CPC ............ *A61K 31/519* (2013.01); *A61P 35/00* (2018.01); *A61K 45/06* (2013.01)

(58) Field of Classification Search
CPC .... A61K 31/497; A61K 31/4985; A61P 35/00
See application file for complete search history.

(56) References Cited

U.S. PATENT DOCUMENTS

| | | | |
|---|---|---|---|
| 2,636,882 A | 4/1953 | Dunlop et al. | |
| 3,701,779 A | 10/1972 | Donninger et al. | |
| 5,262,564 A | 11/1993 | Kun et al. | |
| 8,703,770 B2 | 4/2014 | Coleman et al. | |
| 9,169,261 B2 | 10/2015 | Fan et al. | |
| 9,394,368 B2 | 7/2016 | Brogdon et al. | |
| 10,590,090 B2 * | 3/2020 | Koltun ............... | C07D 401/04 |
| 11,220,501 B2 | 1/2022 | Li et al. | |
| 2004/0213795 A1 | 10/2004 | Collins et al. | |
| 2006/0189664 A1 | 8/2006 | Barth et al. | |
| 2008/0176309 A1 * | 7/2008 | Wu ....................... | C07D 209/40 |
| | | | 435/184 |
| 2009/0325973 A1 | 12/2009 | Watterson et al. | |
| 2010/0190980 A1 | 7/2010 | Umemiya et al. | |
| 2011/0257184 A1 | 10/2011 | Qu et al. | |
| 2012/0034186 A1 | 2/2012 | Wu et al. | |
| 2012/0266264 A1 | 10/2012 | Lee | |
| 2013/0005949 A1 | 1/2013 | Fertig et al. | |
| 2014/0154179 A1 | 6/2014 | Fan et al. | |
| 2016/0031976 A1 | 2/2016 | Seubert et al. | |
| 2017/0042881 A1 | 2/2017 | Fagin et al. | |
| 2017/0204187 A1 | 7/2017 | Neve et al. | |
| 2018/0200381 A1 * | 7/2018 | Kannan ............... | A61K 47/6807 |
| 2019/0210977 A1 | 7/2019 | Jogalekar et al. | |
| 2020/0017511 A1 | 1/2020 | Blank et al. | |
| 2020/0017517 A1 | 1/2020 | Gill et al. | |
| 2020/0108071 A1 | 4/2020 | Chin et al. | |
| 2020/0339552 A1 | 10/2020 | Li et al. | |
| 2020/0368238 A1 | 11/2020 | Nichols et al. | |
| 2020/0407372 A1 | 12/2020 | Koltun et al. | |
| 2021/0101870 A1 | 4/2021 | Koltun et al. | |
| 2021/0154190 A1 | 5/2021 | Wildes | |

FOREIGN PATENT DOCUMENTS

| | | |
|---|---|---|
| CN | 103181918 A | 7/2013 |
| EA | 201691442 A1 | 12/2016 |
| EP | 0 088 593 A2 | 9/1983 |
| EP | 0 579 835 A1 | 1/1994 |
| GB | 1459571 A | 12/1976 |
| JP | H02-049775 A | 2/1990 |
| JP | H04-112877 A | 4/1992 |
| WO | WO 93/09664 | 5/1993 |

(Continued)

OTHER PUBLICATIONS

Chen (Nature, vol. 535 pp. 148-165 published 2016) (Year: 2016).*
3-Amino-6-phenyl-4-trifluoromethylpyridine, C12H9F3N2, PubChem CID 129781129, retrieved from https://pubchem.ncbi.nlm.nih.gov/compound/129781129 on Oct. 20, 2021. (8 pages).
Anonymous: "RMC-4630," Jul. 20, 2018 (Jul. 20, 2018), pp. 1-1, Retrieved from the Internet: URL: https://integrity.clarivate.com/integrity/xmlxsl/pk.
Araki et al., "Tyrosyl phosphorylation of Shp2 is required for normal ERK activation in response to some, but not all, growth factors," J. Biol. Chem. vol. 278, No. 45, pp. 41677-41684, Oct. 24, 2003.
Aronheim et al., "Membrane targeting of the nucleotide exchange factor Sos is sufficient for activating the Ras signaling pathway," Cell 78, 949-961 (1994).

(Continued)

*Primary Examiner* — Theodore R. Howell
*Assistant Examiner* — George W Kosturko
(74) *Attorney, Agent, or Firm* — McNeill Baur PLLC

(57) ABSTRACT

The present invention is directed to compositions and methods of treating or preventing diseases or disorders with inhibitors of SHP2, alone, and in combination with other therapeutic agents such as RAS pathway inhibitors (e.g., MEK inhibitors); methods of establishing appropriate treatment plans for subjects based upon the expression of one or more biomarker indicative of SHP2 inhibitor sensitivity; and methods of determining sensitivity to a SHP2 inhibitor based on a phosphorylation status of SHP2.

21 Claims, 26 Drawing Sheets

Specification includes a Sequence Listing.

(56) References Cited

FOREIGN PATENT DOCUMENTS

| WO | WO 97/29109 A1 | 8/1997 | | |
|---|---|---|---|---|
| WO | WO 98/56376 | 12/1998 | | |
| WO | WO 01/16097 A1 | 3/2001 | | |
| WO | WO 03/029422 A2 | 4/2003 | | |
| WO | WO 03/082191 A2 | 10/2003 | | |
| WO | WO 2004/024719 A1 | 3/2004 | | |
| WO | WO 2004/111034 | 12/2004 | | |
| WO | WO 2005/016894 A1 | 2/2005 | | |
| WO | WO 2005/040151 | 5/2005 | | |
| WO | WO 2005/000817 A2 | 6/2005 | | |
| WO | WO 2005/106286 | 11/2005 | | |
| WO | WO 2006/113704 | 10/2006 | | |
| WO | WO 2007/048067 A2 | 4/2007 | | |
| WO | WO 2008/122615 | 10/2008 | | |
| WO | WO 2009/020642 A1 | 2/2009 | | |
| WO | WO 2010/011666 A2 | 1/2010 | | |
| WO | WO 2011/022440 A2 | 2/2011 | | |
| WO | WO 2012/055942 | 5/2012 | | |
| WO | WO 2013/105063 | 7/2013 | | |
| WO | 2014113584 A1 | 7/2014 | | |
| WO | WO 2014/121885 | 8/2014 | | |
| WO | WO 2015/107493 A1 | 7/2015 | | |
| WO | WO 2015/107494 A1 | 7/2015 | | |
| WO | WO 2015/107495 A1 | 7/2015 | | |
| WO | WO 2016/112295 A1 | 7/2016 | | |
| WO | 2016125169 A1 | 8/2016 | | |
| WO | WO 2016/161282 A1 | 10/2016 | | |
| WO | WO 2016/203404 A1 | 12/2016 | | |
| WO | WO 2016/203405 A1 | 12/2016 | | |
| WO | WO 2016/203406 A1 | 12/2016 | | |
| WO | WO 2017/059207 A1 | 4/2017 | | |
| WO | WO 2017/079723 A1 | 5/2017 | | |
| WO | WO 2017/156397 A1 | 9/2017 | | |
| WO | WO 2017/211303 A1 | 12/2017 | | |
| WO | WO 2017/216706 A1 | 12/2017 | | |
| WO | WO 2018/013597 A1 | 1/2018 | | |
| WO | WO-2018013597 A1 * | 1/2018 | ........... | C07D 487/04 |
| WO | WO 2018/057884 A1 | 3/2018 | | |
| WO | WO 2018/081091 A1 | 5/2018 | | |
| WO | WO 2018/130928 A1 | 7/2018 | | |
| WO | WO 2018/136264 A1 | 7/2018 | | |
| WO | WO 2018/136265 A1 | 7/2018 | | |
| WO | WO 2018/172984 A1 | 9/2018 | | |
| WO | WO 2018/187401 A1 | 10/2018 | | |
| WO | WO 2018/187423 A1 | 10/2018 | | |
| WO | WO 2018/218133 A1 | 11/2018 | | |
| WO | WO 2019/051084 A1 | 3/2019 | | |
| WO | WO 2019/075265 A1 | 4/2019 | | |
| WO | WO 2019/118909 A1 | 6/2019 | | |
| WO | WO 2019/199792 A1 | 10/2019 | | |
| WO | 2020094104 A1 | 5/2020 | | |
| WO | WO 2020/106647 A2 | 5/2020 | | |
| WO | 2020108590 A1 | 6/2020 | | |

OTHER PUBLICATIONS

Belanger, David B. et al., "Discovery of imidazo [1, 2-a] pyrazine-based Aurora kinase inhibitors," Bioorganic & medicinal chemistry letters 20.17 (2010): 5170-5174.

Bennett et al., "Protein-tyrosine-phosphatase SHPTP2 couples platelet-derived growth factor receptor beta to Ras," Proc Natl Acad Sci USA, vol. 91, pp. 7335-7339, Jul. 1994.

Bhatia et al., "A Review on Bioisosterism: A Rational Approach for Drug Design and Molecular Modification," *Pharmacologyonline* 1:272-299, 2011.

Cancer Genome Atlas Research Network "Comprehensive molecular profiling of lung adenocarcinoma," Nature 511, 533-550 (2014).

Chen et al., "Discovery of a novel shp2 protein tyrosine phosphatase inhibitor," Mol Pharmacol. Aug. 2006; 70(2):562-70.

Corbalan-Garcia et al., "Identification of the mitogen-activated protein kinase phosphorylation sites on human Sos1 that regulate interaction with Grb2," Molecular and Cellular Biology, Oct. 1996, vol. 16, No. 10, pp. 5674-5682.

Database Registry, Compound with CAS Registry No. 1119718-06-7-1,4-Dioxa-8-azaspiro [4.5] decane, 8-[5-(6,7-dimethoxy-4-cinnolinyl)-3-methyl-2-pyridinyl], Mar. 12, 2009.

Database Registry, Compound with CAS Registry No. 1384576-77-5, 1,4-Dioxa-8-azaspiro [4.5] decane, 8-[6-(3-fluorophenyl)-4-methyl-3-pyridazinyl], Jul. 27, 2012.

Domagala et al., "KRAS mutation testing in colorectal cancer as an example of the pathologist's role in personalized targeted therapy: a practical approach," Pol J Pathol 3: 145-164 (2012).

Fedele et al., "SHP2 Inhibition Prevents Adaptive Resistance to MEK inhibitors in Multiple Cancer Models," Cancer Discov. Oct. 2018; 8(10): 1237-1249.

Gao Y., et al., "Allele-Specific Mechanisms of Activation of MEK1 Mutants Determine Their Properties," Cancer Discov. May 2018; 8(5):648-661.

Gilmartin et al., "GSK1120212 (JTP-74057) is an inhibitor of MEK activity and activation with favorable pharmacokinetic properties for sustained in vivo pathway inhibition," Clin Cancer Res. Mar. 1, 2011;17(5):989-1000.

Hydrates, products of the addition of water (hydration) to molecules, atoms, or ions. M. b. gaseous, liquid, and solid; the last called. crystal hydrates. XUMUK, Wayback internet archive machine, Oct. 27, 2007. (machine translated from Russian) [retrieved Sep. 3, 2021] Retrieved from the Internet: <URL: https://xumuk.ru/encyklopedia/1022.html>.

International Preliminary Report on Patentability dated Oct. 13, 2020, for International Application No. PCT/US2019/026543, 15 pages.

International Search Report dated Sep. 2, 2019, for International Application No. PCT/US2019/026543, 9 pages.

Jordan, "Tamoxifen: A Most Unlikely Pioneering Medicine," Nature Reviews: Drug Discovery, vol. 2, Mar. 2003, 205-213.

Kamioka et al., "Multiple Decisive Phosphorylation Sites for the Negative Feedback Regulation of SOS1 via ERK," Journal of Biological Chemistry, vol. 285, No. 43, pp. 33540-33548, Oct. 22, 2010.

Kath, John C., "Patent focus: inhibitors of tumour cell growth," Exp. Opin. Ther. Patents (2000) 10(6):803-818.

Krauthammer, M. et al., "Exome sequencing identifies recurrent mutations in NF1 and RASopathy genes in sun-exposed melanomas," Nat Genet. Sep. 2015; 47(9): 996-1002.

Larochelle et al. "Structural reorganization of SHP2 by oncogenic mutations and implications for oncoprotein resistance to allosteric inhibition", Nature Communications, vol. 9, No. 1, Oct. 30, 2018, 10 pages.

Larochelle et al., "Structural and Functional Consequences of Three Cancer-Associated Mutations of the Oncogenic Phosphatase SHP2," Biochemistry, vol. 55, No. 15, Apr. 11, 2016, pp. 2269-2277.

Lofts, F. J. et al., "Growth factor receptors as targets", New Molecular Targets for Cancer Chemotherapy, ed. Workman, Paul and Kerr, David, CRC press 1994, London, 22 pages.

Lu et al., "Site-specific incorporation of a phosphotyrosine mimetic reveals a role for tyrosine phosphorylation of SHP-2 in cell signaling," Molecular Cell, vol. 8, 759-769, Oct. 2001.

Masuda H. et al., "Synthesis of Alkoxy-, (Alkylthio)-, Phenoxy-, and (Phenylthio)pyrazines and their Olfactive Properties," J. Agric. Food Chem., 1986, 34(2), pp. 377-381.

McDonald et al., "Bivalent Binding Drives the Formation of Grb2-Gab1 Signaling Complex in a Non-Cooperative Manner," FEBS J. Jun. 2012, 279(12): 2156-2173.

McDonald et al., "Project DRIVE: A Compendium of Cancer Dependencies and Synthetic Lethal Relationships Uncovered by Large-Scale, Deep RNAi Screening," Cell 170, 577-586, Jul. 27, 2017.

Modem Pharmaceutics, Third Edition, Revised and Expanded by, Banker et al., Marcel Dekker, Inc. pp. 451 and 596, 1976. (3 pages).

Monson et al., "The Reactions of Some Ketones With Hexamethylphosphoric Triamide a Novel Synthesis of 3,5-dialkyl-2,6-diphenylpyridines," *Tetrahedron* 31:1145-1147, 1975.

Nichols et al., "Efficacy of SHP2 phosphatase inhibition in cancers with nucleotide-cycling oncogenic RAS, RAS-GTP dependent oncogenic BRAF and NF1 loss," bioRxiv preprint first posted online Sep. 14, 2017, 16 pages.

(56) References Cited

OTHER PUBLICATIONS

Nieto, P. et al., "A Braf kinase-inactive mutant induces lung adenocarcinoma," Nature. Aug. 10, 2017; 548(7666):239-243.
Nissan, M. H. et al., "Loss of NF1 in cutaneous melanoma is associated with RAS activation and MEK dependence," Cancer Res. Apr. 15, 2014; 74(8): 2340-2350.
Patani et al., "Bioisosterism: A Rational Approach in Drug Design," Chemical Reviews, 1996, 96, 3147-3176.
Patricelli et al., "Selective Inhibition of Oncogenic KRAS Output with Small Molecules Targeting the Inactive State," Cancer Discov. Mar. 2016;6(3):316-29.
Philpott et al., "The NF1 somatic mutational landscape in sporadic human cancers," Human Genomics (2017) 11:13.
Poulikakos et al., "RAF inhibitor resistance is mediated by dimerization of aberrantly spliced BRAF(V600E)," Nature, Nov. 23, 2011;480(7377):387-90.
Prahallad, A. et al., "PTPN11 Is a Central Node in Intrinsic and Acquired Resistance to Targeted Cancer Drugs," CellReports, vol. 12, Sep. 29, 2015, pp. 1978-1985.
Preusser et al., "Prospects of immune checkpoint modulators in the treatment of glioblastoma," Nat Rev Neurol. Sep. 2015; 11(9):504-514.
Redig, A. J. et al., "Clinical and Molecular Characteristics of NF1-Mutant Lung Cancer," Clin Cancer Res. Jul. 1, 2016; 22(13): 3148-3156.
Regad, "Targeting RTK Signaling Pathways in Cancer," Cancers 2015, 7, 1758-1784.
Sayer, James Richard, "The Synthesis of Imidazo [1, 2-a] pyrazines as Inhibitors of the VirB11 ATPase and their Incorporation into Bivalent Compounds," Diss. UCL (University College London), 2013, 396 pages.
Schlessinger, "Cell signaling by receptor tyrosine kinases," Cell, vol. 103, pp. 211-225, Oct. 13, 2000.
Shawver et al., "Receptor tyrosine kinases as targets for inhibition of angiogenesis," DDT vol. 2, No. 2 Feb. 1997.
Sun et al., "Selective inhibition of leukemia-associated SHP2E69K mutant by the allosteric SHP2 inhibitor SHP099," Leukemia, Nature Publishing Group UK, London, vol. 32, No. 5, Jan. 30, 2018, 4 pages.
Sun, J. et al., "Antagonism between binding site affinity and conformational dynamics tunes alternative cisinteractions within Shp2," Nat Commun 4, 2037 (2013).
Vernier et al., "Thioether benzenesulfonamide inhibitors of carbonic anhydrases II and IV: structure-based drug design, synthesis, and biological evaluation," Bioorganic & Medicinal Chemistry, vol. 18, Issue 9, May 1, 2010, pp. 3307-3319.
Vippagunta et al., "Crystalline solids," Advanced Drug Delivery Reviews 48, 2001, 3-26.
Wada, Makoto, et al. "The dual RAF/MEK inhibitor CH5126766/RO5126766 may be a potential therapy for RAS-mutated tumor cells." PLoS One 9.11 (2014): e113217.
Wolff, "Burger's Medicinal Chemistry and Drug Discovery," Fifth Edition, vol. 1: Principles and Practice, New York: John Wiley & Sons, 1995, 975-977.
Xiao et al., "Myeloid-restricted ablation of Shp2 restrains melanoma growth by amplifying the reciprocal promotion of CXCL9 and IFN-γ production in tumor microenvironment," Oncogene, May 7, 2018, 13 pages.
Yamanishi Y. et al., "Syntheses of trimethylpyrazines and their antibacterial properties," Yakugaku Zasshi, 1967, 87(1), pp. 105-107.
Yao, Z. et al., "BRAF Mutants Evade ERK-Dependent Feedback by Different Mechanisms that Determine Their Sensitivity to Pharmacologic Inhibition," Cancer Cell. Sep. 14, 2015; 28(3): 370-383.
Yao, Z. et al., "Tumours with class 3 BRAF mutants are sensitive to the inhibition of activated RAS," Nature, Aug. 10, 2017; 548(7666):234-238.
Zhao et al., "SHP2 inhibition triggers anti-tumor immunity and synergizes with PD-1 blockade," Acta Pharmaceutica Sinica B 2019;9(2):304-315.
Zhou, Xin, et al. "MAP kinase kinase kinase (MAPKKK)-dependent and-independent activation of Sty 1 stress MAPK in fission yeast," Journal of Biological Chemistry 285.43 (2010): 32818-32823.
International Search Report and Written Opinion dated Dec. 20, 2017, for PCT/US2017/041577, 18 pages.
International Search Report and Written Opinion dated Sep. 21, 2018, for PCT/US2018/013018, 10 pages.
International Search Report and Written Opinion dated Apr. 5, 2018, for PCT/US2018/013023, 13 pages.
International Search Report and Written Opinion dated Jan. 24, 2019, for PCT/US2018/055502, 16 pages.
International Search Report and Written Opinion dated Dec. 12, 2018, for PCT/US2018/049744, 13 pages.
International Search Report and Written Opinion dated Feb. 20, 2019, for PCT/US2018/065817, 11 pages.
Chen et al., "Allosteric inhibition of SHP2 phosphatase inhibits cancers driven by receptor tyrosine kinases," Nature 2016, 535, 148-152.
Chen et al., "Identification of demethylincisterol A3 as a selective inhibitor of protein tyrosine phosphatase Shp2," Eur J Pharmacol. Jan. 15, 2017;795:124-133.
Ellsworth et al., "Discovery of pyrazine carboxamide CB1 antagonists: The introduction of a hydroxyl group improves the pharmaceutical properties and in vivo efficacy of the series," Bioorganic & Medicinal Chemistry Letters, vol. 17, No. 14, Jul. 1, 2007, pp. 3978-3982.
Fortanet et al., "Allosteric Inhibition of SHP2: Identification of a Potent, Selective, and Orally Efficacious Phosphatase Inhibitor," J. Med. Chem. 2016, 59, 7773-7782.
Giori et al., "Synthesis of 6,7-Disubstituted Pteridine-2,4-Diones," Heterocycles, vol. 32, No. 1, 1991, 6 pages.
Larochelle et al., "Identification of an allosteric benzothiazolopyrimidone inhibitor of the oncogenic protein tyrosine phosphatase SHP2," Bioorg. Med. Chem. 2017, 17, 31394-31399.
Meurer et al., "Synthesis and SAR of 5,6-diarylpyridines as human CB1 inverse agonists," Bioorg Med Chem Lett. Feb. 1, 2005 ;15(3):645-51.
Mohi et al., "The role of Shp2 (PTPN11) in cancer," Curr Opin Genet Dev. Feb. 2007;17(1):23-30.
Nichols et al., "RAS nucleotide cycling underlies the SHP2 phosphatase dependence of mutant BRAF-, NF1- and RAS-driven cancers," Nat Cell Biol. Sep. 2018;20(9):1064-1073.
Ruess et al., "Mutant KRAS-driven cancers depend on PTPN11/SHP2 phosphatase," Nat Med. Jul. 2018;24(7):954-960.
Wustrow D.J. et al., "Aminopyrazine CB1 receptor inverse agonists," Bioorganic & Medicinal Chemistry Letters, vol. 18, No. 11, 2008, p. 3376-3381.
Xie et al., "Allosteric Inhibitors of SHP2 with Therapeutic Potential for Cancer Treatment," J. Med. Chem. 2017, 60, 10205-10219.
Database Registry [Online] Chemical Abstracts Service, Columbus, Ohio, US; Apr. 27, 2011 (Apr. 27, 2011), XP002787392, retrieved from STN Database accession No. 1286273-60-6 compound with CAS registry No. 1286273-60-6.
Database Registry [Online] Chemical Abstracts Service, Columbus, Ohio, US; Nov. 9, 2007 (Nov. 9, 2007), XP002787393, retrieved from stn Database accession No. 952723-55-6 compound with CAS registry No. 952723-55-6.
Database Registry [Online] Chemical Abstracts Service, Columbus, Ohio, US; Jan. 22, 2015 (Jan. 22, 2015), XP002787394, retrieved from stn Database accession No. 1643677-14-8 compound with CAS registry No. 1643677-14-8.
Database Registry [Online] Chemical Abstracts Service, Columbus, Ohio, US; Nov. 16, 1984 (Nov. 6, 1984), XP002787395, retrieved from stn Database accession No. 86663-20-9 compound with CAS registry No. 86663-20-9.
Database Registry [Online] Chemical Abstracts Service, Columbus, Ohio, US; Dec. 18, 1984 (Dec. 18, 1984), XP002787396, retrieved from stn Database accession No. 93034-72-1 compound with CAS registry No. 93034-72-1.

(56) References Cited

OTHER PUBLICATIONS

Database Registry [Online] Chemical Abstracts Service, Columbus, Ohio, US; Nov. 16, 1984 (Nov. 16, 1984), XP002787397, retrieved from stn Database accession No. 68559-45-5 compound with CAS registry No. 68559-45-5.
Database Registry [Online] Chemical Abstracts Service, Columbus, Ohio, US; Nov. 23, 2004 (Nov. 23, 2004), XP002787398, retrieved from stn Database accession No. 786652-86-6 compound with CAS registry No. 786652-86-6.
Database Registry [Online] Chemical Abstracts Service, Columbus, Ohio, US; Nov. 23, 2004 (Nov. 23, 2004), XP002787399, retrieved from stn Database accession No. 786652-83-3 compound with CAS registry No. 786652-83-3.
Database Registry [Online] Chemical Abstracts Service, Columbus, Ohio, US; Apr. 6, 1990 (Apr. 6, 1990), XP002787400, Database accession No. 126317-60-0 compound with CAS registry No. 126317-60-0.
Database Registry [Online] Chemical Abstracts Service, Columbus, Ohio, US; May 31, 2006 (May 31, 2006), XP002787401, retrieved from stn Database accession No. 886208-65-7 compound with CAS registry No. 886208-65-7.
Database Registry [Online] Chemical Abstracts Service, Columbus, Ohio, US; Aug. 27, 2010 (Aug. 27, 2010), XP002787406, retrieved from stn Database accession No. 1239320-06-9 compound with CAS registry No. 1239320-06-9.
Database Registry, Compound with CAS Registry No. 78246-19-2. 3-Methyl-5-(2-methylpropyl)-2-(phenylthio)pyrazine. Nov. 16, 1984 Citation is not enclosed due to copyright restrictions.
Database Registry, Compound with CAS Registry No. 15033-82-6. 4-[(3,5,6-Trimethyl-2-pyrazinyl)sulfonyl]benzenamine. Nov. 16, 1984 Citation is not enclosed due to copyright restrictions.
Co-pending U.S. Appl. No. 16/518,796, filed Jul. 22, 2019; previously cited as US 2020/0017517.
Co-pending U.S. Appl. No. 16/518,798, filed Jul. 22, 2019; previously cited as US 2020/0017511.
Co-pending U.S. Appl. No. 16/845,539, filed Apr. 10, 2020; also cited herein as US 2020/0339552.
Co-pending U.S. Appl. No. 16/899,446, filed Jun. 11, 2020; also cited herein as US 2020/0407372.
Co-pending U.S. Appl. No. 16/905,884, filed Jun. 18, 2020; previously cited as US 2021/0101870.
Co-pending U.S. Appl. No. 17/064,317, filed Oct. 6, 2020; previously cited as US 2021/0154190.
Co-pending U.S. Appl. No. 17/537,113, filed Nov. 29, 2021.
Hao et al., "Tumor Instrinsic Efficacy by SHP2 and RTK Inhibitors in KRAS-Mutant Cancers," Molecular Cancer Therapeutics, vol. 18, No. 12, pp. 2368-2380 (2019).
Hobbs et al., "RAS isoforms and mutations in cancer at a glance," Journal of Cell Science, vol. 129, pp. 1287-1292 (2016).
Hunter et al., "Biochemical and Structural Analysis of Common Cancer-Associated KRAS Mutations," Molecular Cancer Research, vol. 13, No. 9, pp. 1325-1335 (2015).
Mainardi et al., "SHP2 is required for growth of KRAS-mutant non-small-cell lung cancer in vivo," Nature Medicine, vol. 24, pp. 961-967 (2018).
Rauen, "The RASopathies," Annual Review of Genomics and Human Genetics, vol. 14, pp. 355-369 (2013).
Yap et al., "The NF1 gene revisited—from bench to bedside," Oncotarget, vol. 5, No. 15, pp. 5873-5892 (2014).
Ran, Hao et al., "Sticking It to Cancer with Molecular Glue for SHP2", Cancer Cell. Aug. 8, 2016; 30(2) 194-196.
Amato, C. et al., "Modulation of a proteolytic enzyme activity by means of a photochromic inhibitor", Journal of Photochemistry and Photobiology, 1995, 28(1), p. 71-75.
Pisaneschi, Federica et al., "The 3S Enantiomer Drives Enolase Inhibitory Activity in SF2312 and Its Analogues", Molecules, 2019, 24(13) 2510, p. 1-18.
Tol, Jolien et al., "Chemotherapy, Bevacizumab, and Cetuximab in Metastatic Colorectal Cancer", N Engl J Med 2009, 360: 563-72.
Yu, Helena A. et al., "A Phase 1/2 Trial of Ruxolitinib and Erlotinib in Patients with EGFR-Mutant Lung Adenocarcinomas with Acquired Resistance to Erlotinib", Journal of Thoracic Oncology, 2017, v. 12(1), p. 102-109.
Gagné-Sansfaçon et al., "SHP-2 phosphatase contributes to KRAS-driven intestinal oncogenesis but prevents colitis-associated cancer development", Oncotarget, 7(40), pp. 65676-65695 (2016).
Manchado, Eusebio et al., "A combinatorial strategy for treating KRAS mutant lung cancer", Nature. Jun. 30, 2016; 534(7609): 647-651.
Nguyen, Lien Ai et al., "Chiral Drugs: An Overview", International Journal of Biomedical Science, Jun. 2006; 2(2) 85-100.

* cited by examiner

FIGURE 1
FIG. 1A
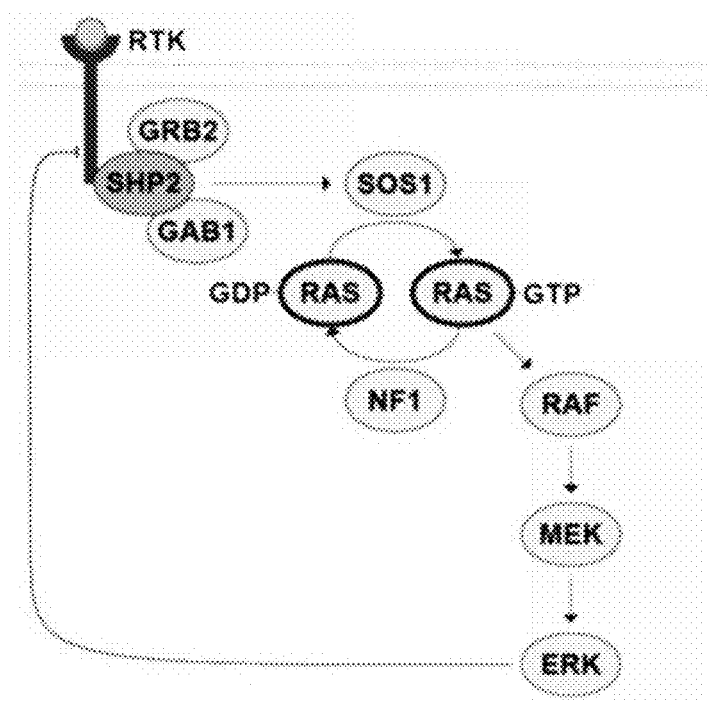
FIG. 1B
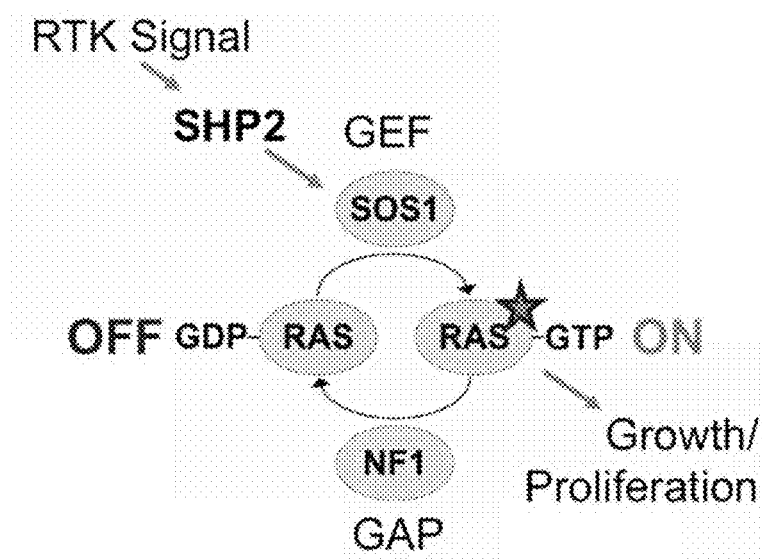

FIGURE 3
FIG. 3A
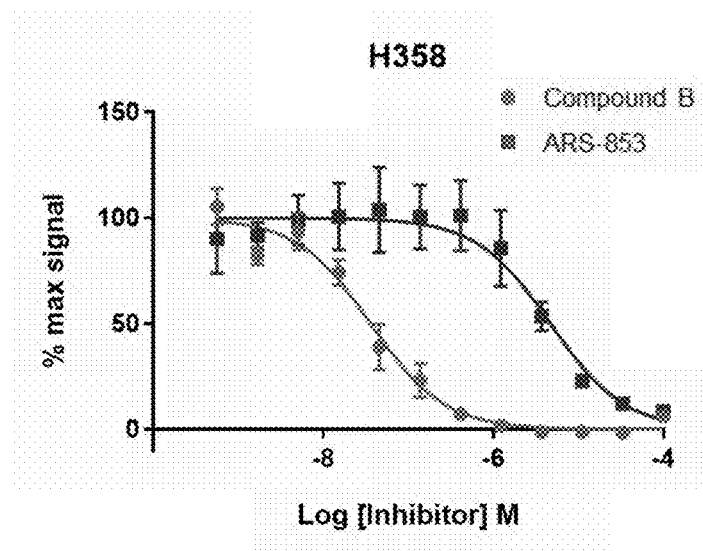
FIG. 3B
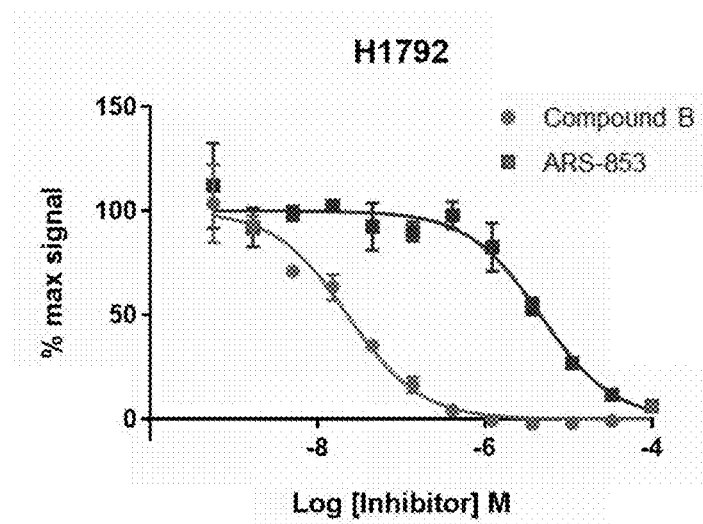

FIGURE 4
FIG. 4A
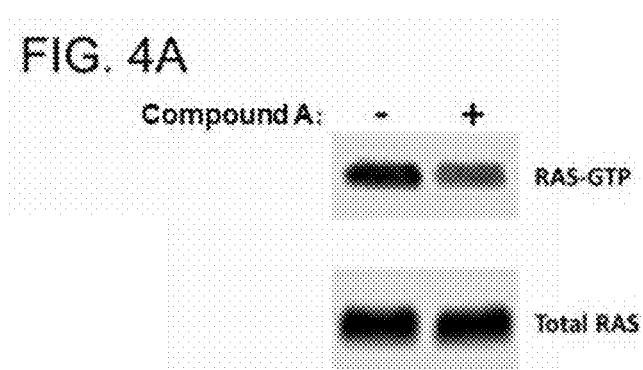
FIG. 4B
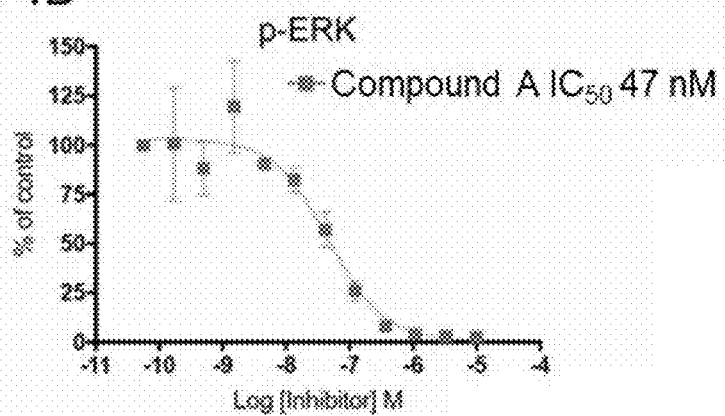
FIG. 4C
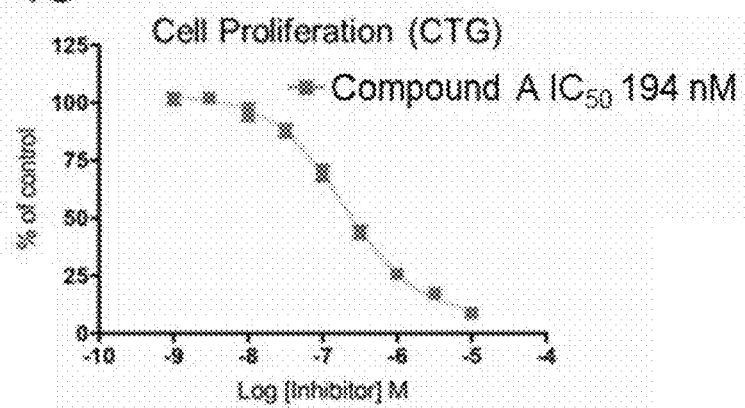

FIGURE 11
FIG. 11A
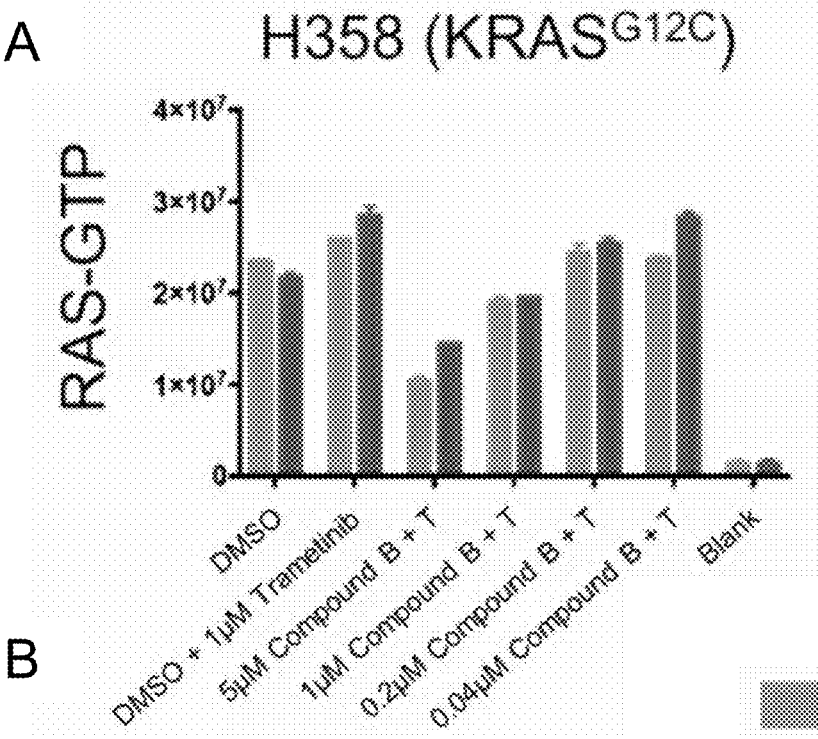
FIG. 11B
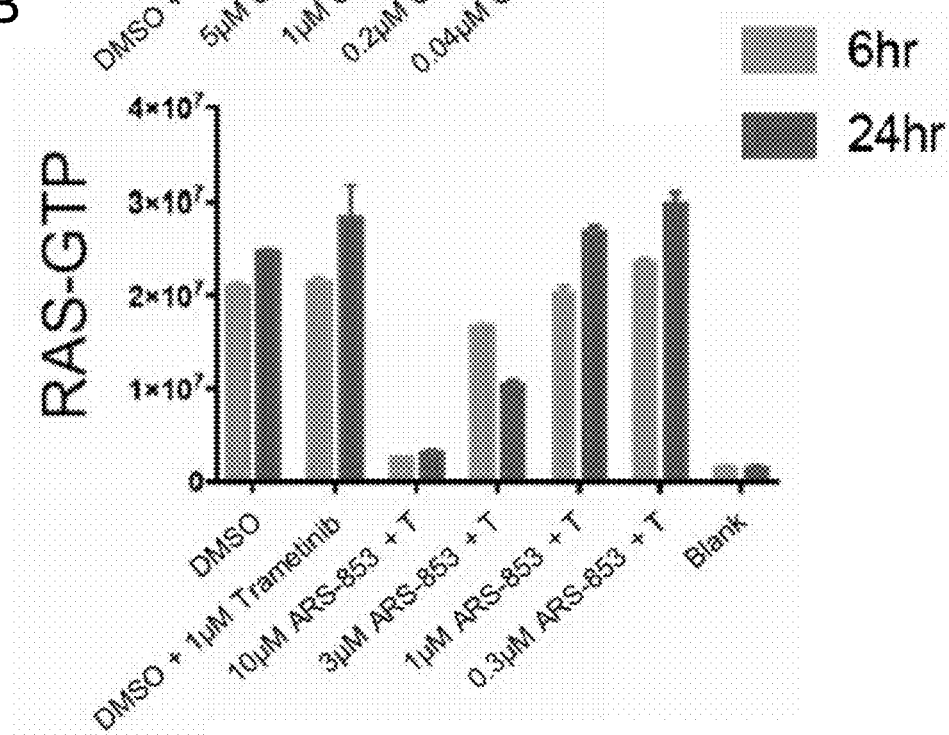

FIGURE 11 (continued)
FIG. 11C
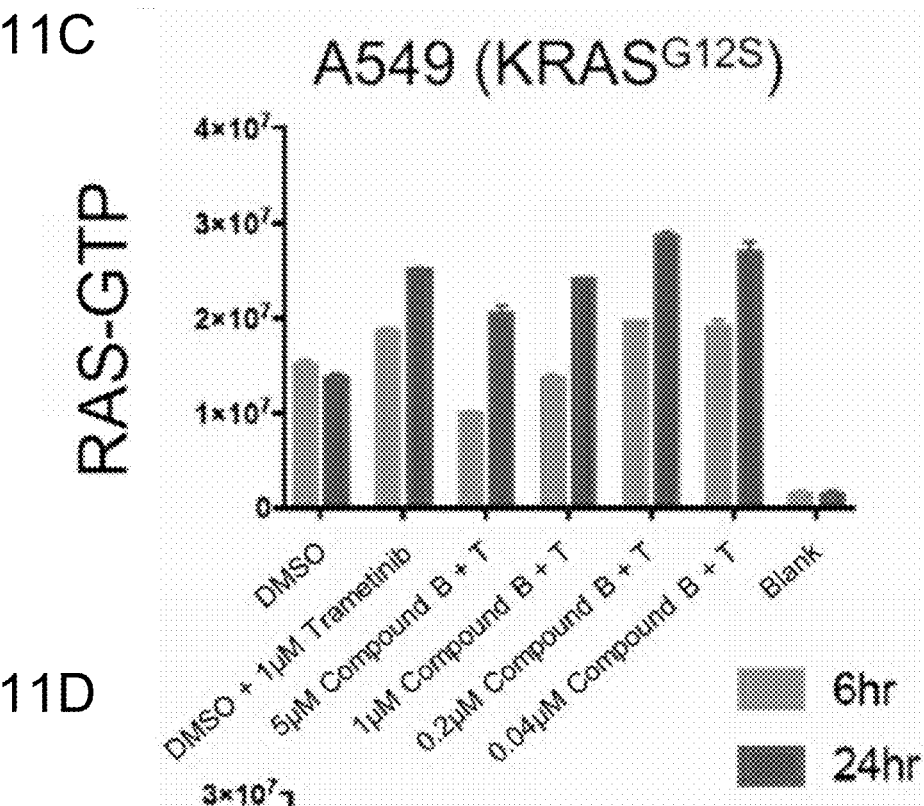
FIG. 11D
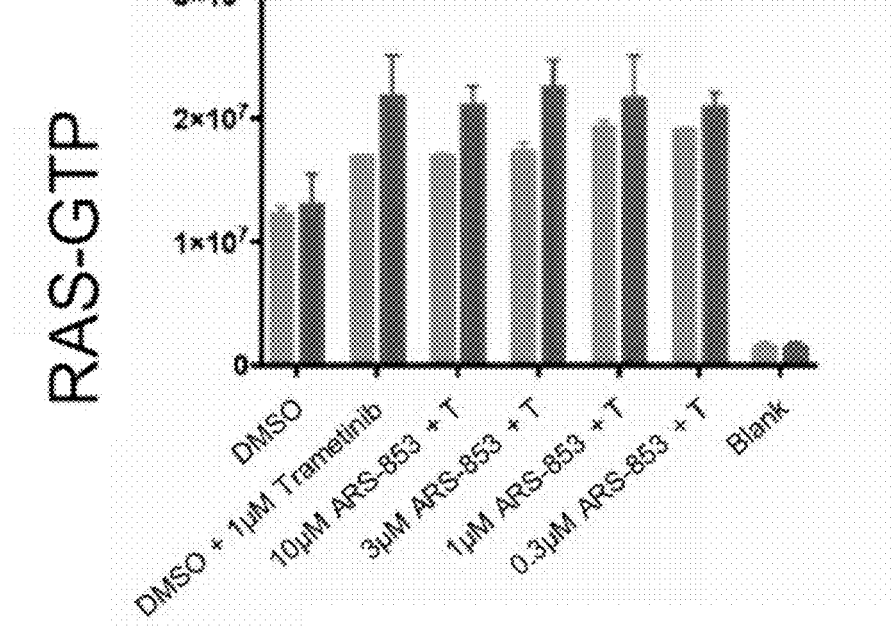

FIGURE 14 (continued)
FIG. 14C
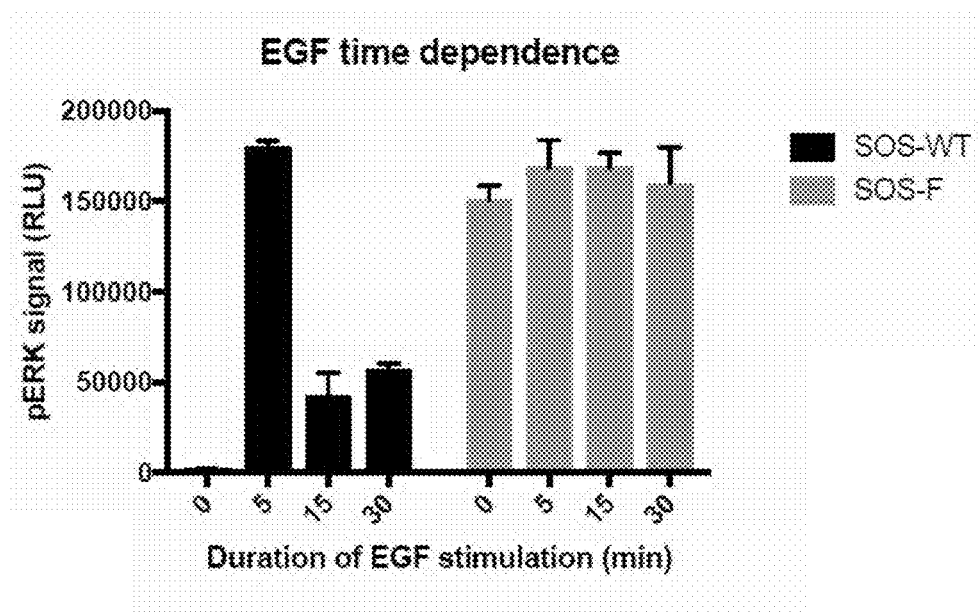
FIGURE 15
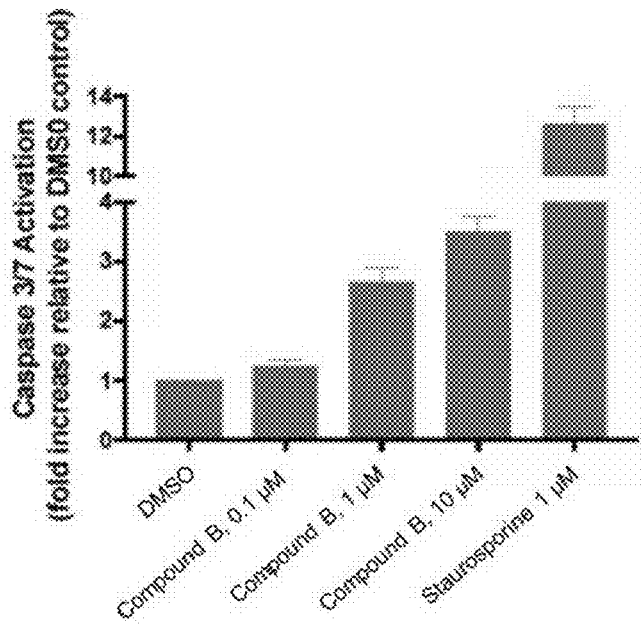

FIGURE 16
FIG. 16A
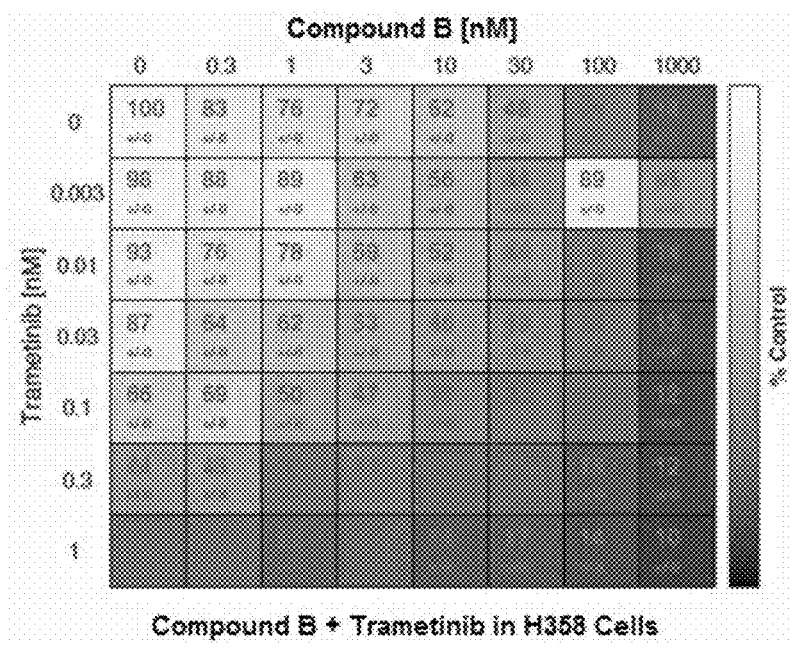
FIG. 16B
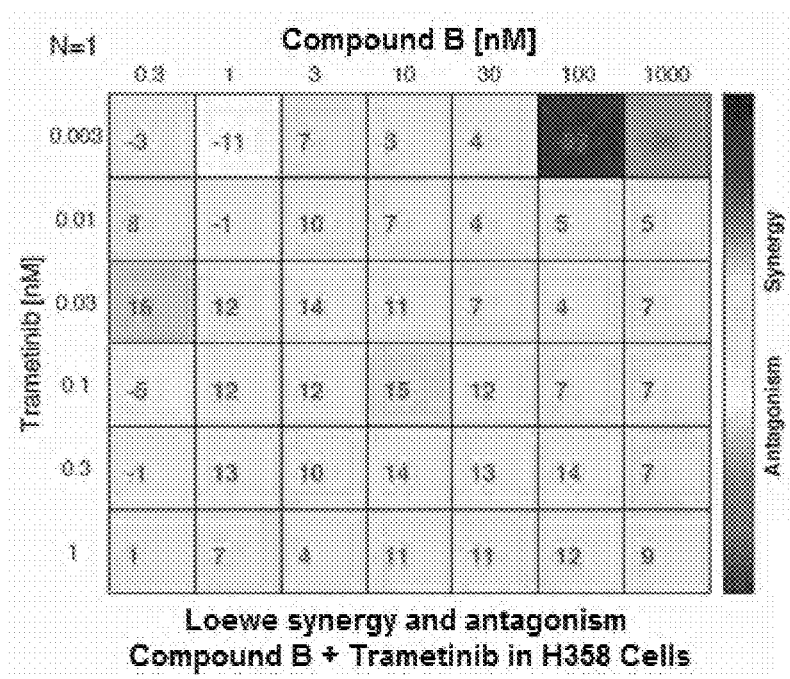

FIGURE 16 (continued)
FIG. 16C
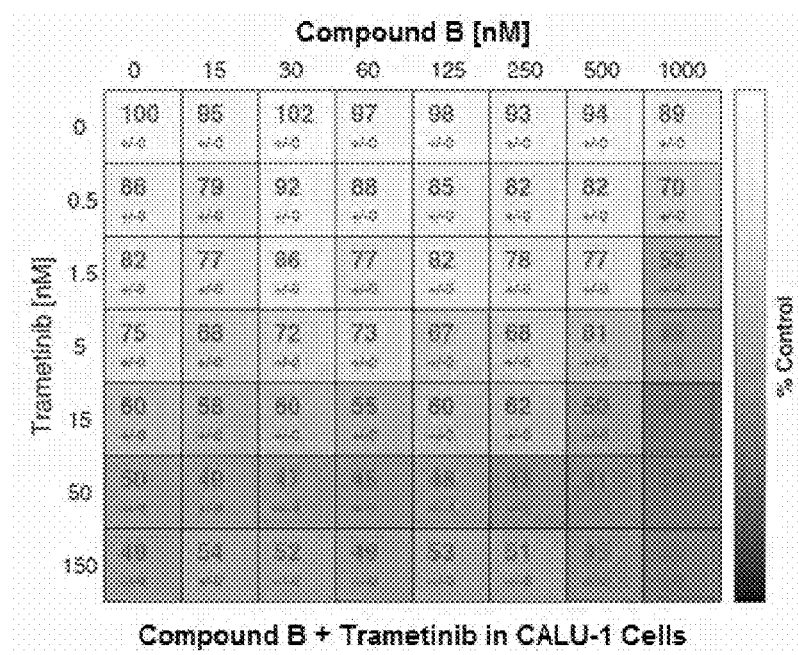
FIG. 16D
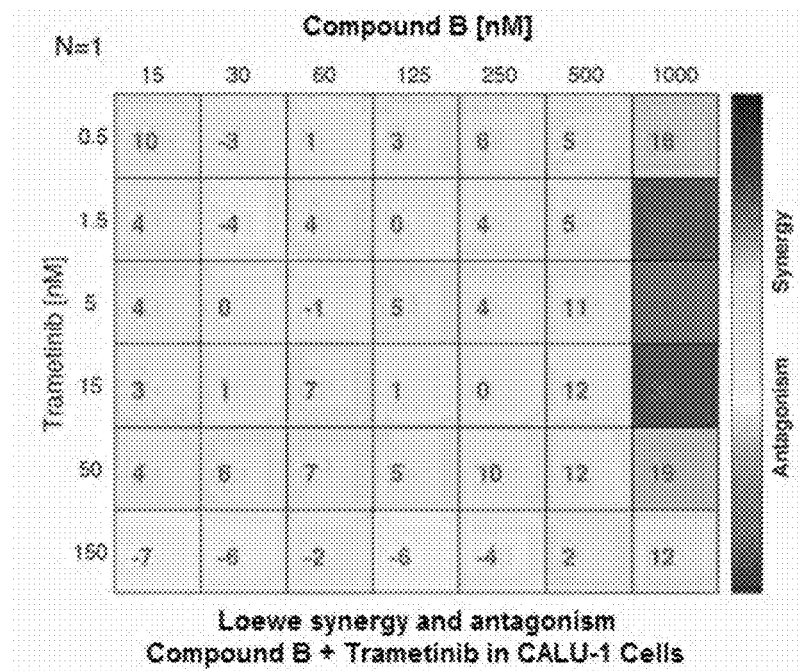

FIG. 20A LUN023 BRAF$^{D594N}$

FIG. 20B LUN037 BRAF$^{N581D}$

FIG. 20C LUN092 KRAS$^{G12C}$

FIG. 20D LUN156 KRAS$^{G12C}$

FIGURE 21
FIG. 21A
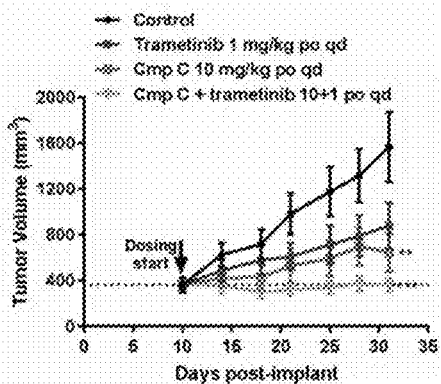
FIG. 21B
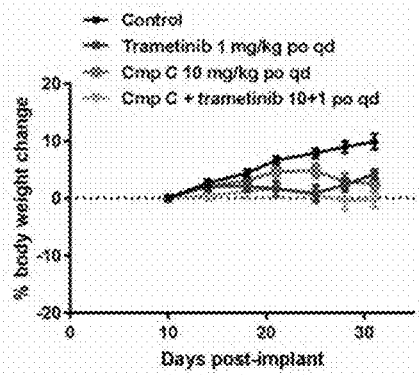
FIG. 21C
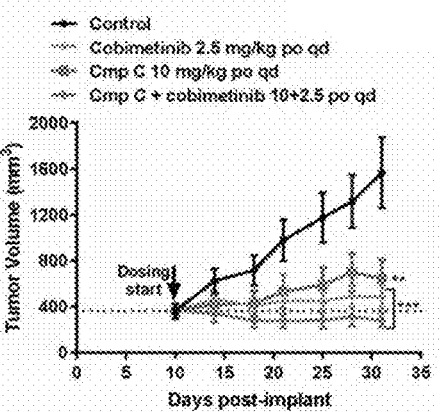
FIG. 21D
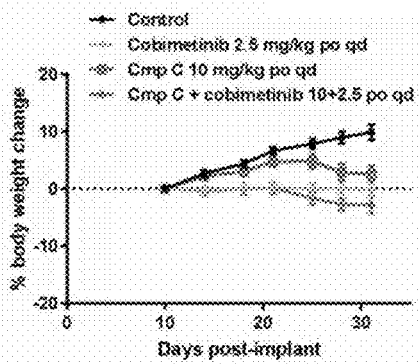
FIG. 21E
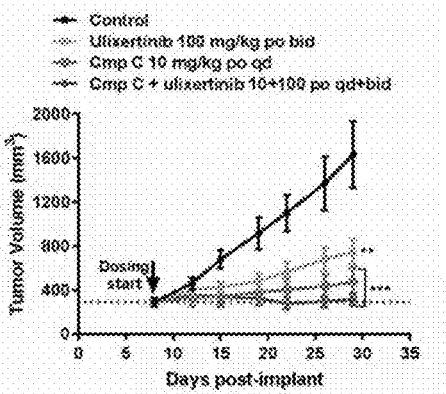
FIG. 21F
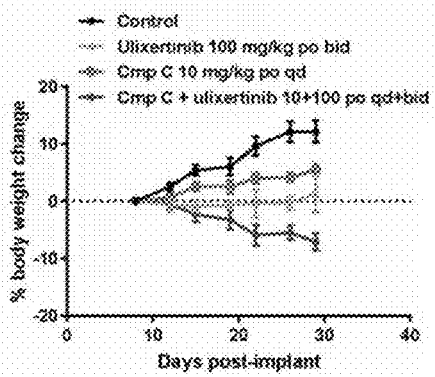

SEQUENCE LISTING

<160> NUMBER OF SEQ ID NOS: 5

<210> SEQ ID NO 1
<211> LENGTH: 39
<212> TYPE: DNA
<213> ORGANISM: Artificial Sequence
<220> FEATURE:
<223> OTHER INFORMATION: Primer sequence

<400> SEQUENCE: 1
acaggtaagc ttatgtaccc atacgatgtt ccagattac                    39

```
<210> SEQ ID NO 2
<211> LENGTH: 38
<212> TYPE: DNA
<213> ORGANISM: Artificial Sequence
<220> FEATURE:
<223> OTHER INFORMATION: Primer sequence

<400> SEQUENCE: 2
agactagcgg ccgctcagga agaatgggca ttctccaa              38

<210> SEQ ID NO 3
<211> LENGTH: 36
<212> TYPE: DNA
<213> ORGANISM: Artificial Sequence
<220> FEATURE:
<223> OTHER INFORMATION: Primer sequence

<400> SEQUENCE: 3
gatcgagcgg ccgctcagga gagcacacac ttgcag                36

<210> SEQ ID NO 4
<211> LENGTH: 18
<212> TYPE: PRT
<213> ORGANISM: Artificial Sequence
<220> FEATURE:
<223> OTHER INFORMATION: Made in Lab - activating peptide

<400> SEQUENCE: 4

Leu Asn Ile Asp Leu Asp Leu Val Leu Ser Thr Ala Ser Ile Asn Phe
1               5                   10                  15

Gln Lys

<210> SEQ ID NO 5
<211> LENGTH: 17
<212> TYPE: PRT
<213> ORGANISM: Artificial Sequence
<220> FEATURE:
<223> OTHER INFORMATION: Made in Lab - activating peptide

<400> SEQUENCE: 5

Leu Asn Ala Gln Leu Trp His Ala Leu Thr Ile Ala Thr Ile Arg Arg
1               5                   10                  15

Phe
```

SHP2 INHIBITOR COMPOSITIONS AND METHODS FOR TREATING CANCER

CROSS REFERENCE TO RELATED APPLICATIONS

This application is a continuation of International Patent Application No. PCT/US2018/049744, filed Sep. 6, 2018, which claims the benefit of U.S. Provisional Application No. 62/555,400, filed Sep. 7, 2017; U.S. Provisional Application No. 62/558,255, filed Sep. 13, 2017; U.S. Provisional Application No. 62/653,831, filed Apr. 6, 2018; and U.S. Provisional Application No. 62/681,001, filed Jun. 5, 2018, the contents of which are incorporated herein by reference in their entireties.

INCORPORATION OF SEQUENCE LISTING

This application is being filed electronically via EFS-Web and includes an electronically submitted sequence listing in .txt format. The .txt file contains a sequence listing entitled REME-006_04US_SeqList.txt created on Aug. 14, 2020, and having a size of 2,000 bytes. The sequence listing contained in this .txt file is part of the specification and is incorporated herein by reference in its entirety.

FIELD OF THE INVENTION

The present disclosure relates to compositions and methods for the treatment of diseases or disorders (e.g., cancer) with inhibitors of the protein tyrosine phosphatase SHP2, alone and in combination with other therapeutic agents such as a RAS pathway inhibitor (e.g., a MEK inhibitor). Specifically, this invention is concerned with methods of treating diseases or disorders (such as cancer) in certain subsets of patients that are determined to be candidates for treatment with a SHP2 inhibitor.

BACKGROUND OF THE INVENTION

Cancer remains one of the most deadly threats to human health. In the U.S., cancer affects nearly 1.3 million new patients each year, and is the second leading cause of death after heart disease, accounting for approximately 1 in 4 deaths (US20170204187). Many cancers are caused by constitutive or aberrant activation of receptor tyrosine kinases (RTKs) and/or RAS pathway modulators.

RTKs are transmembrane proteins having an extracellular ligand binding domain, a transmembrane domain, and a tyrosine kinase domain. Receptor tyrosine kinases are an important class of receptor that are involved in many fundamental cellular processes including cell proliferation, survival, metabolism, and migration, e.g. Schlessinger, Cell, 103: 211-225 (2000). Prominent families of this class include, for example, epidermal growth factor receptor (EGFR), platelet derived growth factor receptor (PDGFR), erbB2, erbB4, vascular endothelial growth factor receptor (VEGFR), tyrosine kinase with immunoglobulin-like and epidermal growth factor homology domains (TIE-2), insulin growth factor-I (IGFI) receptor, macrophage colony stimulating factor (MCSF), BTK, ckit, cmet, fibroblast growth factor (FGF) receptors, Trk receptors (TrkA, TrkB, and TrkC), ephrin (eph) receptors, hepatocyte growth factor receptors (HGFR) and the RET protooncogene.

The class of receptor tyrosine kinases is so named because when activated by dimerization, the intracellular domain of RTKs acquire tyrosine kinase activity that can, in turn, activate a variety signal transduction pathways.

FIG. 1. shows a cartoon schematic of a RTK pathway. The RTK is dimerized upon ligand binding, which triggers auto-phosphorylation of the receptor and initiation of downstream signal transduction. Specifically, RTK phosphorylation recruits binding of the GRB2 adapter via its SH2 domain, and GRB2 then recruits (via its SH3 domain) downstream signaling molecules such as the adapter protein GAB1 and the GEF protein SOS1 (McDonald et al., FEBS J. 2012 June 279(2): 2156-2173).

RAS oscillates between GDP-bound "off" and GTP-bound "on" state, facilitated by interplay between a GEF protein (e.g., SOS1), which loads RAS with GTP, and a GAP protein (e.g., NF1), which hydrolyzes GTP, thereby inactivating RAS. Additionally, the SH2 domain-containing protein tyrosine phosphatase-2 (SHP2) associates with the receptor signaling apparatus and becomes active upon RTK activation, and then promotes RAS activation (id).

Activation of RAS results in induction of the serine/threonine kinase RAF. RAF phosphorylates MEK/2 which in turn phosphorylates and activates ERK1/2 leading to downstream signaling, e.g., via transcription, as well as feedback inhibition of the RTK, thereby turning off transduction of the signal. RAF also activates MAP3 kinases that activate MKK4/7, MKKK3/6 and MEK5, which activates JNK1/2, p38 and ERK5, consecutively. MAP3Ks are also activated by inflammatory cytokines, oxidative stress and UV radiation. PI3K is activated by RTK autophosphorylation and results in the activation of Akt, which also induces mTOR within the mTORC1 complex. Akt is also regulated by mTORC2 complex. PLCγ activation leads to $Ca^{+2}$ mobilization and to the activation of PKC. These events play an essential role in proliferation, differentiation, survival and cell migration.

Over-expression or mutation of RTKs and/or RAS pathway signaling molecules have been shown to result in uncontrolled cell growth. The aberrant activity of such kinases has been linked to malignant tissue proliferation, survival, invasion and metastasis. For instance, mutations affecting RTKs and/or RAS pathway components Ras (KRAS, NRAS, HRAS), B-Raf, NF1, PI3K and AKT are common in promoting the malignancy of several types of cancers and from different tissue origins.

Accordingly, RTKs and downstream RAS pathway signal transducers represent attractive therapeutic targets.

However, therapeutic inhibition of the RAS pathway, although often initially efficacious, can ultimately prove ineffective as it may lead to over-activation of RAS pathway signaling via a number of mechanisms including, e.g., reactivation of the pathway via relief of the negative feedback machineries that naturally operate in these pathways. For example, in various cancers, MEK inhibition results in increased ErbB signaling due to its relief of MEK/ERK-mediated feedback inhibition of RTK activation. As a result, cells that were initially sensitive to such inhibitors may become resistant. Thus, a need exists for methods of effectively inhibiting RAS pathway signaling without inducing activation of resistance mechanisms.

SHP2 is a non-receptor protein tyrosine phosphatase encoded by the PTPN11 gene that contributes to multiple cellular functions including proliferation, differentiation, cell cycle maintenance and migration. SHP2 is involved in signaling through the RAS-mitogen-activated protein kinase (MAPK), the JAK-STAT and/or the phosphoinositol 3-kinase-AKT pathways.

SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N-SH2 and PTP domains. Stimulation by, for example, cytokines or growth factors acting through RTKs leads to exposure of the catalytic site resulting in enzymatic activation of SHP2.

Mutations in the PTPN11 gene and subsequently in SHP2 have been identified in several human developmental diseases, such as Noonan Syndrome and Leopard Syndrome, as well as human cancers, such as juvenile myelomonocytic leukemias, neuroblastoma, melanoma, acute myeloid leukemia and cancers of the breast, lung and colon. Some of these mutations destabilize the auto-inhibited conformation of SHP2 and promote autoactivation or enhanced growth factor-driven activation of SHP2.

SHP2, therefore, represents a highly attractive target for the development of novel therapies for the treatment of various diseases including cancer. It has been disclosed previously that either the knockdown of SHP2 expression using RNAi technology or inhibition of SHP2 by an allosteric small molecule inhibitor interferes with signaling from various RTKs involved in driving cancer cell growth. However, this work also concluded that such approaches would be ineffective at blocking growth signaling in cells in which growth is driven by mutations in proteins that act downstream of RTKs, such as those containing activating mutations in Ras or Raf proteins (Chen, Ying-Nan P. 148 Nature Vol 535 7 Jul. 2016 at pg. 151).

SUMMARY OF THE INVENTION

The present disclosure relates to treating or preventing a disease or disorder (e.g., cancer) with a SHP2 inhibitor alone or in combination with another suitable therapeutic agent. Specifically, in some embodiments, the present disclosure relates to the unexpected discovery that contrary to the teachings of the prior art, certain subsets of cancer cells carrying oncogenic RAS pathway mutations are sensitive to SHP2 inhibition and may be effectively treated with SHP2 inhibitors. In some embodiments, the present disclosure relates to the discovery that certain subsets of cancer cells carrying RAS mutations (e.g., $KRAS^{G12C}$ and/or certain other KRAS mutations) are sensitive to SHP2 inhibition. In some embodiments, the present disclosure relates to the discovery that certain subsets of cancer cells carrying $NF1^{LOF}$ mutations are sensitive to SHP2 inhibition.

Accordingly, in various embodiments, the present disclosure provides a method for treating cells (e.g., cancer cells) containing RAS pathway mutations, which render the mutated protein dependent on upstream signaling through SHP2, with an inhibitor of SHP2.

In some embodiments, the present disclosure relates to the unexpected discovery that even though SHP2 activation naturally promotes MAPK signaling, which in turn may promote feedback inhibition of RTK and RAS pathway signaling, inhibition of SHP2 does not result in subsequent over-activation of RTK or RAS pathway signaling via relief of that feedback inhibition. This is particularly surprising given the fact that SHP2 is downstream from the RTKs in the RAS pathway, and SHP2 inhibition blocks transmission of signals from RTKs; thus, the expected outcome of SHP2 inhibition was hyperactivation of RTKs due to feedback disinhibition. Thus, the present disclosure demonstrates that unlike MAPK inhibitors, which may induce resistance by relief of feedback inhibition, SHP2 inhibitors do not, and they are able to attenuate hyperactivation of RAS in response to MEK inhibitor treatment that may contribute to MEK inhibitor drug resistance.

In some embodiments, the present disclosure relates to the discovery that SHP2 inhibition is an effective means for preventing and delaying the emergence of tumor resistance to various cancer therapies and for re-sensitizing a tumor that is resistant to a MAPK inhibitor to that inhibitor.

In some embodiments, the discoveries disclosed herein provide a method for treating cells (e.g., cancer cells) with a SHP2 inhibitor, wherein the cells have been rendered dependent on SHP2 by means of a therapeutic intervention (e.g., administration of a MAPK inhibitor). In some embodiments, such a therapeutic intervention rendering the cells dependent on SHP2 signaling results in overactivation of the RAS pathway via relief of a natural RAS pathway negative feedback mechanism.

In some embodiments, the present disclosure relates to the surprising discovery that contrary to the teachings of the prior art, SHP2 phosphorylation at Y580 occurs after, and is dependent on prior phosphorylation at Y542, and allosteric inhibition of SHP2 activity occurs by stabilizing the closed state of the enzyme, thereby preventing the phosphorylation of Y580, but not Y542.

In some embodiments, the present invention provides a method of determining whether a SHP2 inhibitor has engaged its target (i.e., SHP2), the method comprising determining whether Y542, but not Y580 on SHP2 is phosphorylated in response to growth factor stimulation.

Accordingly, the present invention relates to compositions and methods for treating or preventing diseases or disorders (e.g., cancer) with inhibitors of the protein tyrosine phosphatase SHP2. The present invention also relates to methods of establishing appropriate treatment plans for subjects based upon the expression of one or more biomarker in a tissue sample from the subject, wherein the biomarker is indicative of SHP2 inhibitor sensitivity. The present invention also relates to methods determining sensitivity to a SHP2 inhibitor based upon a phosphorylation status of SHP2.

In some embodiments, the present disclosure provides a method of treating a subject having a disease or disorder comprising a cell containing a mutation encoding the $KRAS^{G12C}$ variant, comprising providing to the subject an inhibitor of SHP2. In some embodiments, the disease or condition is a tumor. In some embodiments, the tumor is selected from an NSCLC, a colon cancer, an oesophageal cancer, a rectal cancer, JMML, breast cancer, melanoma, Scwannoma, and a pancreatic cancer. In some embodiments, the method further comprises providing to the subject an inhibitor of the RAS pathway. In some embodiments, the inhibitor of the RAS pathway is a MAPK inhibitor. In some embodiments, the inhibitor of the RAS pathway is a MEK inhibitor or ERK inhibitor. In some embodiments, the inhibitor of the Ras pathway is selected from one or more of Trametinib, Binimetinib, Selumetinib, Cobimetinib, LErafAON (NeoPharm), ISIS 5132; Vemurafenib, Pimasertib, TAK733, RO4987655 (CH4987655); CI-1040; PD-0325901; CH5126766; MAP855; AZD6244; Refametinib (RDEA 119/BAY 86-9766); GDC-0973/XL581; AZD8330 (ARRY-424704/ARRY-704); RO5126766; ARS-853 and GSK1120212. In some embodiments, the RAS pathway inhibitor is Abemaciclib or Ulixertinib or Ulixertinib. In some embodiments, the SHP2 inhibitor is selected from (i) Compound A; (ii) Compound B; (iii) SHP099; (iv)

NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof.

In some embodiments, the present disclosure provides a method of treating a subject having a disease or disorder comprising a cell with a mutation encoding an NF loss of function ($NF1^{LOF}$) variant, comprising providing to the subject an inhibitor of SHP2. In some embodiments, the disease or condition is a tumor. In some embodiments, the tumor is selected from an NSCLC, a colon cancer, an oesophageal cancer, a rectal cancer, JMML, breast cancer, melanoma, Scwannoma, and a pancreatic cancer. In some embodiments, the method further comprises providing to the subject an inhibitor of the RAS pathway. In some embodiments, the inhibitor of the RAS pathway is a MAPK inhibitor. In some embodiments, the inhibitor of the RAS pathway is a MEK inhibitor or ERK inhibitor. In some embodiments, the inhibitor of the Ras pathway is selected from one or more of Trametinib, Binimetinib, Selumetinib, Cobimetinib, LErafAON (NeoPharm), ISIS 5132; Vemurafenib, Pimasertib, TAK733, RO4987655 (CH4987655); CI-1040; PD-0325901; CH5126766; MAP855; AZD6244; Refametinib (RDEA 119/BAY 86-9766); GDC-0973/XL581; AZD8330 (ARRY-424704/ARRY-704); RO5126766; ARS-853 and GSK1120212. In some embodiments, the RAS pathway inhibitor is Abemaciclib or Ulixertinib or Ulixertinib. In some embodiments, the SHP2 inhibitor is selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof.

In some embodiments, the present disclosure provides a method of treating a subject having a disease or disorder associated with a RAS pathway mutation in a cell of the subject that renders the cell at least partially dependent on signaling flux through SHP2, comprising providing to the subject an inhibitor of SHP2. In some embodiments, the RAS pathway mutation is a mutation in a RAS, RAF, NF1, MEK, ERK, or SOS, including any specific isoforms or alleotypes thereof. In some embodiments, the RAS pathway mutation is a mutation in a RAS, RAF, NF1, or SOS, including any specific isoforms or alleotypes thereof. In some embodiments, the RAS pathway mutation is a RAS mutation selected from a KRAS mutation, an NRAS mutation, an HRAS mutation, and a Class III BRAF mutation. In some embodiments, the KRAS mutation is selected from a $KRAS^{G12A}$ mutation, a $KRAS^{G12C}$ mutation, a $KRAS^{G12D}$ mutation, a $KRAS^{G12F}$ mutation, a $KRAS^{G12I}$ mutation, a $KRAS^{G12L}$ mutation, a $KRAS^{G12R}$ mutation, a $KRAS^{G12S}$ mutation, a $KRAS^{G12V}$ mutation, and a $KRAS^{G12Y}$ mutation. In some particular embodiments the KRAS mutation is $KRAS^{G12C}$. In some particular embodiments the KRAS mutation is $KRAS^{G12A}$. In some embodiments, the Class III BRAF mutation is selected from one or more of the following amino acid substitutions in human BRAF: D287H; P367R; V459L; G466V; G466E; G466A; S467L; G469E; N581S; N581I; D594N; D594G; D594A; D594H; F595L; G596D; G596R and A762E. In some embodiments, the MEK mutation is a MEK1 or MEK2 mutation. In some embodiments, the MEK1 mutation is a RAF dependent MEK1 mutation (i.e., a "Class I" MEK1 mutation). In some embodiments, the MEK1 mutation is a RAF regulated MEK1 mutation (i.e., a "Class II" MEK1 mutation). In some embodiments, the Class I MEK1 mutation is selected from D67N; P124L; P124S; and L177V. In some embodiments, the Class II MEK mutation is selected from ΔE51-Q58; ΔF53-Q58; E203K; L177M; C121S; F53L; K57E; Q56P; and K57N. In some embodiments, the RAF mutation is a ARAF or CRAF mutation. In some embodiments, the NF1 mutation is an NF1 loss of function mutation. In some embodiments, the SOS mutation leads to altered function of SOS. In some embodiments, the disease or condition is a tumor. In some embodiments, the tumor is selected from an NSCLC, a colon cancer, an oesophageal cancer, a rectal cancer, JMML, breast cancer, melanoma, Scwannoma, and a pancreatic cancer. In some embodiments, the method further comprises providing to the subject an inhibitor of the RAS pathway. In some embodiments, the inhibitor of the RAS pathway is a MAPK inhibitor. In some embodiments, the inhibitor of the RAS pathway is a MEK inhibitor or ERK inhibitor. In some embodiments, the inhibitor of the Ras pathway is selected from one or more of Trametinib, Binimetinib, Selumetinib, Cobimetinib, LErafAON (NeoPharm), ISIS 5132; Vemurafenib, Pimasertib, TAK733, RO4987655 (CH4987655); CI-1040; PD-0325901; CH5126766; MAP855; AZD6244; Refametinib (RDEA 119/BAY 86-9766); GDC-0973/XL581; AZD8330 (ARRY-424704/ARRY-704); RO5126766; ARS-853 and GSK1120212. In some embodiments, the RAS pathway inhibitor is Abemaciclib or Ulixertinib. In some embodiments, the SHP2 inhibitor is selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof.

In some embodiments, the present disclosure provides a method of treating a subject having a disease associated with an NF1 loss of function mutation, comprising providing to the subject an inhibitor of SHP2. In some embodiments, the disease or condition is a tumor. In some embodiments, the tumor is selected from an NSCLC, a colon cancer, an oesophageal cancer, a rectal cancer, JMML, breast cancer, melanoma, Scwannoma, and a pancreatic cancer. In some embodiments, the disease is a tumor comprising cells with an NF1 loss of function mutation. In some embodiments, the tumor is an NSCLC or melanoma tumor. In some embodiments, the disease is selected from neurofibromatosis type I, neurofibromatosis type II, schwannomatosis, and Watson syndrome. In some embodiments, the method further comprising providing to the subject an inhibitor of the RAS pathway. In some embodiments, the method further comprises providing to the subject an inhibitor of the RAS pathway. In some embodiments, the inhibitor of the RAS pathway is a MAPK inhibitor. In some embodiments, the inhibitor of the RAS pathway is a MEK inhibitor or ERK inhibitor. In some embodiments, the inhibitor of the Ras pathway is selected from one or more of Trametinib, Binimetinib, Selumetinib, Cobimetinib, LErafAON (NeoPharm), ISIS 5132; Vemurafenib, Pimasertib, TAK733, RO4987655 (CH4987655); CI-1040; PD-0325901; CH5126766; MAP855; AZD6244; Refametinib (RDEA 119/BAY 86-9766); GDC-0973/XL581; AZD8330 (ARRY-424704/ARRY-704); RO5126766; ARS-853 and GSK1120212. In some embodiments, the RAS pathway inhibitor is Abemaciclib or Ulixertinib or Ulixertinib. In some embodiments, the SHP2 inhibitor is selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof.

In some embodiments, the present disclosure provides a method for treating a subject having a tumor comprising: (a) determining whether a biological sample obtained from the subject is classified as a KRAS mutant; and (b) administering to the subject an inhibitor of SHP2 if the biological sample is classified as a $KRAS^{G12C}$ mutant, a $KRAS^{G12D}$ mutant, a $KRAS^{G12S}$ mutant, or a $KRAS^{G12V}$ mutant. In some embodiments, the SHP2 inhibitor is selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof. In some embodiments, the tumor is selected from an NSCLC, a colon cancer, an oesophageal cancer, a rectal cancer, JMML, breast cancer, melanoma, Scwannoma, and a pancreatic cancer.

In some embodiments, the present disclosure provides a method for treating a subject having a tumor comprising: (a) determining whether a biological sample obtained from the subject is classified as an $NF1^{LOF}$ mutant; and (b) administering to the subject an inhibitor of SHP2 if the biological sample is classified as an $NF1^{LOF}$ mutant. In some embodiments, the SHP2 inhibitor is selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof. In some embodiments, the tumor is selected from an NSCLC, a colon cancer, an oesophageal cancer, a rectal cancer, JMML, breast cancer, melanoma, Scwannoma, and a pancreatic cancer.

In some embodiments, the present disclosure provides a method for treating a subject having a tumor comprising: (a) determining whether a biological sample obtained from the subject is classified as an Class 3 BRAF mutant; and (b) administering to the subject an inhibitor of SHP2 if the biological sample is classified as an Class 3 BRAF mutant. In some embodiments, the SHP2 inhibitor is selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof. In some embodiments, the tumor is selected from an NSCLC, a colon cancer, an oesophageal cancer, a rectal cancer, JMML, breast cancer, melanoma, Scwannoma, and a pancreatic cancer.

In some embodiments, the present disclosure provides a method for treating a subject having a tumor comprising: (a) determining whether a biological sample obtained from the subject is classified as an Class 1 MEK1 mutant; and (b) administering to the subject an inhibitor of SHP2 if the biological sample is classified as an Class 1 MEK1 mutant. In some embodiments, the SHP2 inhibitor is selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof. In some embodiments, the tumor is selected from an NSCLC, a colon cancer, an oesophageal cancer, a rectal cancer, JMML, breast cancer, melanoma, Scwannoma, and a pancreatic cancer. In some embodiments, the Class I MEK1 mutation is selected from D67N; P124L; P124S; and L177V.

In some embodiments, the present disclosure provides a method for treating a subject having a tumor comprising: (a) determining whether a biological sample obtained from the subject is classified as an Class 2 MEK1 mutant; and (b) administering to the subject an inhibitor of SHP2 if the biological sample is classified as an Class 2 MEK1 mutant. In some embodiments, the SHP2 inhibitor is selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof. In some embodiments, the tumor is selected from an NSCLC, a colon cancer, an oesophageal cancer, a rectal cancer, JMML, breast cancer, melanoma, Scwannoma, and a pancreatic cancer. In some embodiments, the Class II MEK mutation is selected from ΔE51-Q58; ΔF53-Q58; E203K; L177M; C121S; F53L; K57E; Q56P; and K57N.

In some embodiments, the present disclosure provides a method for treating or preventing drug resistance in a subject receiving administration of a RAS pathway inhibitor, comprising administering to the subject a SHP2 inhibitor. In some embodiments, the subject comprises a tumor containing cells with an $NF1^{LOF}$ mutation. In some embodiments, the subject comprises a tumor containing a $KRAS^{G12C}$ mutation, a $KRAS^{G12D}$ mutation, a $KRAS^{G12A}$ mutation, a $KRAS^{G12S}$ mutation, or a $KRAS^{G12V}$ mutation. In some embodiments, the RAS pathway inhibitor is a MEK inhibitor. In some embodiments, the MEK inhibitor is selected from one or more of Trametinib (GSK1120212); Selumetinib (AZD6244); Cobimetinib (GDC-0973/XL581); Binimetinib; Vemurafenib; Pimasertib; TAK733; RO4987655 (CH4987655); CI-1040; PD-0325901; CH5126766; MAP855; Refametinib (RDEA 119/BAY 86-9766); RO5126766; AZD8330 (ARRY-424704/ARRY-704); and GSK1120212. In some embodiments, the RAS pathway inhibitor is an ERK inhibitor. In some embodiments, the ERK inhibitor is selected from any ERK inhibitor known in the art. In some embodiments, the ERK inhibitor is selected from LY3214996 and BVD523; In some embodiments, the SHP2 inhibitor is selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof.

In some embodiments, the method further comprises providing to the subject an inhibitor of the RAS pathway. In some embodiments, the present disclosure provides a combination therapy comprising administering to a subject in need thereof a RAS pathway inhibitor and a SHP2 inhibitor. In some embodiments, the RAS pathway inhibitor is a MEK inhibitor. In some embodiments, the MEK inhibitor is selected from one or more of Trametinib (GSK1120212); Selumetinib (AZD6244); Cobimetinib (GDC-0973/XL581); Binimetinib; Vemurafenib; Pimasertib; TAK733; RO4987655 (CH4987655); CI-1040; PD-0325901; CH5126766; MAP855; Refametinib (RDEA 119/BAY 86-9766); RO5126766; AZD8330 (ARRY-424704/ARRY-704); and GSK1120212. In some embodiments, the RAS pathway inhibitor is Abemaciclib or Ulixertinib or Ulixertinib. In some embodiments, the RAS pathway inhibitor is the KRASG12C-specific inhibitor ARS-853. In some embodiments, the SHP2 inhibitor is selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof.

In some embodiments, the present disclosure provides a pharmaceutical composition comprising a RAS pathway inhibitor, a SHP2 inhibitor, and one or more pharmaceutically acceptable carrier, excipient, diluent, and/or surfactant. In some embodiments, the SHP2 inhibitor is selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof. In some embodiments, the RAS pathway inhibitor is selected from one or more of Trametinib (GSK1120212) Selumetinib (AZD6244); Cobimetinib (GDC-0973/XL581), Binimetinib, Vemurafenib, Pimasertib, TAK733, RO4987655 (CH4987655); CI-1040; PD-0325901; CH5126766; MAP855; Refametinib (RDEA 119/BAY 86-9766); RO5126766, AZD8330 (ARRY-424704/ARRY-704); and GSK1120212. In some embodiments, the RAS pathway inhibitor is Abemaciclib or Ulixertinib or Ulixertinib.

In some embodiments, the present disclosure provides a method of inhibiting the growth or proliferation of a cell containing a RAS pathway mutation, wherein the RAS pathway mutation renders the cell at least partially dependent on signaling flux through SHP2, the method comprising contacting the cell with an inhibitor of SHP2. The SHP2 inhibitor may be any SHP2 inhibitor known in the art or disclosed herein. In some embodiments, the SHP2 inhibitor is selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof. In some embodiments, the RAS pathway mutation is selected from a KRAS mutation, an NRAS mutation, an HRAS mutation, a SOS mutation, a Class 3 BRAF mutation, a MEK1 mutation, a MEK2 mutation, an ERK mutation and an NF1 mutation. In some embodiments, the KRAS mutation is selected from a KRAS$^{G12A}$ mutation, a KRAS$^{G12C}$ mutation, a KRAS$^{G12D}$ mutation, a KRAS$^{G12F}$ mutation, a KRAS$^{G12I}$ mutation, a KRAS$^{G12L}$ mutation, a KRAS$^{G12R}$ mutation, a KRAS$^{G12S}$ mutation, a KRAS$^{G12V}$ mutation, and a KRAS$^{G12Y}$ mutation. In particular embodiments, the KRAS mutation is KRAS$^{G12C}$ In particular embodiments, the KRAS mutation is KRAS$^{G12A}$ In some embodiments, the Class 3 BRAF mutation is selected from one or more of the following amino acid substitutions in human BRAF: D287H; P367R; V459L; G466V; G466E; G466A; S467L; G469E; N581S; N581I; D594N; D594G; D594A; D594H; F595L; G596D; G596R and A762E. In some embodiments, the MEK1 mutation is selected from D67N; P124L; P124S; and L177V. In some embodiments, the MEK1 mutation is selected from ΔE51-Q58; ΔF53-Q58; E203K; L177M; C121S; F53L; K57E; Q56P; and K57N.

In some embodiments, the method further comprises contacting the cell with an inhibitor of the RAS pathway. In some embodiments, the inhibitor of the RAS pathway is a MAPK inhibitor. In some embodiments, the RAS pathway inhibitor is a SOS inhibitor. In some embodiments, the SOS inhibitor is administered to a cell comprising higher than normal SOS levels or SOS activity. In some embodiments, the inhibitor of the RAS pathway is a MEK inhibitor or ERK inhibitor. In some embodiments, the inhibitor of the Ras pathway is selected from one or more of Trametinib, Binimetinib, Selumetinib, Cobimetinib, LErafAON (NeoPharm), ISIS 5132; Vemurafenib, Pimasertib, TAK733, RO4987655 (CH4987655); CI-1040; PD-0325901; CH5126766; MAP855; AZD6244; Refametinib (RDEA 119/BAY 86-9766); GDC-0973/XL581; AZD8330 (ARRY-424704/ARRY-704); RO5126766; ARS-853; LY3214996; BVD523; and GSK1120212. In some embodiments, the RAS pathway inhibitor is Abemaciclib or Ulixertinib.

In some embodiments, the present disclosure provides a method of inhibiting RAS-GTP accumulation in a cell containing a RAS pathway mutation, wherein the RAS pathway mutation renders the cell at least partially dependent on signaling flux through SHP2, the method comprising contacting the cell with an inhibitor of SHP2. The SHP2 inhibitor may be any SHP2 inhibitor known in the art or disclosed herein. In some embodiments, the SHP2 inhibitor is selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof. In some embodiments, the RAS pathway mutation is selected from a KRAS mutation, an NRAS mutation, an HRAS mutation, a SOS mutation, a Class 3 BRAF mutation, a MEK mutation, an ERK mutation, and an NF1 mutation. In some embodiments, the RAS pathway mutation is selected from a KRAS mutation, an NRAS mutation, an HRAS mutation, a SOS mutation, a Class 3 BRAF mutation, and an NF1 mutation. In some embodiments, the KRAS mutation is selected from a KRAS$^{G12A}$ mutation, a KRAS$^{G12C}$ mutation, a KRAS$^{G12D}$ mutation, a KRAS$^{G12F}$ mutation, a KRAS$^{G12I}$ mutation, a KRAS$^{G12L}$ mutation, a KRAS$^{G12R}$ mutation, a KRAS$^{G12S}$ mutation, a KRAS$^{G12V}$ mutation, and a KRAS$^{G12Y}$ mutation. In particular embodiments, the KRAS mutation is KRAS$^{G12C}$. In particular embodiments, the KRAS mutation is KRAS$^{G12A}$. In some embodiments, the Class 3 BRAF mutation is selected from one or more of the following amino acid substitutions in human BRAF: D287H; P367R; V459L; G466V; G466E; G466A; S467L; G469E; N581S; N581I; D594N; D594G; D594A; D594H; F595L; G596D; G596R and A762E. In particular embodiments, the MEK mutation is a Class I MEK1 mutation selected from D67N; P124L; P124S; and L177V. In some embodiments, the MEK mutation is a Class II MEK1 mutation selected from ΔE51-Q58; ΔF53-Q58; E203K; L177M; C121S; F53L; K57E; Q56P; and K57N. In some embodiments, the method further comprises contacting the cell with an inhibitor of the RAS pathway. In some embodiments, the inhibitor of the RAS pathway is a MAPK inhibitor. In some embodiments, the RAS pathway inhibitor is a SOS inhibitor. In some embodiments, the SOS inhibitor is administered to a cell comprising higher than normal SOS levels or SOS activity. In some embodiments, the inhibitor of the RAS pathway is a MEK inhibitor or ERK inhibitor. In some embodiments, the inhibitor of the Ras pathway is selected from one or more of Trametinib, Binimetinib, Selumetinib, Cobimetinib, LErafAON (NeoPharm), ISIS 5132; Vemurafenib, Pimasertib, TAK733, RO4987655 (CH4987655); CI-1040; PD-0325901; CH5126766; MAP855; AZD6244; Refametinib (RDEA 119/BAY 86-9766); GDC-0973/XL581; AZD8330 (ARRY-424704/ARRY-704); RO5126766; ARS-853; LY3214996; BVD523; and GSK1120212. In some embodiments, the RAS pathway inhibitor is Abemaciclib or Ulixertinib.

In some embodiments, the present disclosure provides a method of inhibiting the growth of a tumor cell, comprising contacting the tumor cell with a combination therapy comprising a MEK inhibitor and a SHP2 inhibitor. Such contacting may be, for example, in vivo, in a subject (e.g., a mammal, preferably a human). Furthermore, such a method may, e.g., in one non-limiting embodiment, comprise contacting the tumor cell with a combination therapy comprising a SHP2 inhibitor and a MEK inhibitor selected from one or more of Trametinib (GSK1120212); Selumetinib (AZD6244); Cobimetinib (GDC-0973/XL581), Binimetinib, Vemurafenib, Pimasertib, TAK733, RO4987655 (CH4987655); CI-1040; PD-0325901; CH5126766; MAP855; Refametinib (RDEA 119/BAY 86-9766); RO5126766, AZD8330 (ARRY-424704/ARRY-704); and GSK1120212. In some embodiments, the RAS pathway inhibitor is Abemaciclib or Ulixertinib. In some non-limiting embodiments, the tumor cell may be contacted with a combination therapy comprising a MEK inhibitor and a SHP2 inhibitor selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof. In some non-limiting embodiments, the tumor cell may be contacted with a combination therapy comprising Compound B and a MEK inhibitor selected from one or more of Trametinib (GSK1120212); Selumetinib (AZD6244); Cobimetinib (GDC-0973/XL581), Binimetinib, CI-1040; PD-0325901; CH5126766; MAP855; Refametinib (RDEA 119/BAY 86-9766); RO5126766, AZD8330 (ARRY-424704/ARRY-704); and GSK1120212. In some non-limiting embodiments, the tumor cell may be contacted with a combination therapy comprising Compound B and Abemaciclib. In some non-limiting embodiments, the tumor cell may be contacted with a combination therapy comprising Trametinib and a SHP2 inhibitor selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof. In some non-limiting embodiments, the tumor cell may be contacted with a combination therapy comprising Trametinib (GSK1120212) and Compound B. In some non-limiting embodiments, the tumor cell may be contacted with a combination therapy comprising Trametinib (GSK1120212) and Compound A. In some non-limiting embodiments, the tumor cell may be contacted with a combination therapy comprising Trametinib (GSK1120212) and SHP099. In some non-limiting embodiments, the tumor cell may be contacted with a combination therapy comprising Trametinib (GSK1120212) and NSC-87877. In some non-limiting embodiments, the tumor cell may be contacted with a combination therapy comprising Trametinib (GSK1120212) and a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof. In all such embodiments, wherein the present disclosure provides a method of inhibiting the growth of a tumor cell comprising contacting the tumor cell with a combination therapy, the tumor cell may be a cell from a tumor selected from tumors of hemopoietic and lymphoid system; a myeloproliferative syndrome; a myelodysplastic syndromes; leukemia; acute myeloid leukemia; juvenile myelomonocytic leukemia; esophageal cancer; breast cancer; lung cancer; colon cancer; gastric cancer; neuroblastoma; bladder cancer; prostate cancer; glioblastoma; urothelial carcinoma; uterine carcinoma; adenoid and ovarian sereous cystadenocarcinoma; paraganglioma; phaeochromocytoma; pancreatic cancer; adrenocortical carcinoma; stomach adenocarcinoma; sarcoma; rhabdomyosarcoma; lymphoma; head and neck cancer; skin cancer; peritoneum cancer; intestinal cancer (small and large intestine); thyroid cancer; endometrial cancer; cancer of the biliary tract; soft tissue cancer; ovarian cancer; central nervous system cancer (e.g.; primary CNS lymphoma); stomach cancer; pituitary cancer; genital tract cancer; urinary tract cancer; salivary gland cancer; cervical cancer; liver cancer; eye cancer; cancer of the adrenal gland; cancer of autonomic ganglia; cancer of the upper aerodigestive tract; bone cancer; testicular cancer; pleura cancer; kidney cancer; penis cancer; parathyroid cancer; cancer of the meninges; vulvar cancer and melanoma. For example, in some embodiments, the present disclosure provides a method of inhibiting the growth of a tumor cell, comprising contacting the tumor cell with a combination therapy comprising a MEK inhibitor and a SHP2 inhibitor, such as combination therapy comprising Trametinib (GSK1120212) and Compound B, wherein the tumor cell is from a NSCLC tumor; wherein the contacting preferably occurs in vivo in a subject (e.g., a mammal, preferably a human). In some alternative embodiments, the method is as above, but the tumor cell is from a colon cancer tumor rather than an NSCLC tumor. In some alternative embodiments, the method is as above, but the tumor cell is esophageal cancer tumor. In some alternative embodiments, the method is as above, but the tumor cell is a rectal cancer tumor. In some alternative embodiments, the method is as above, but the tumor cell is a JMML tumor. In some alternative embodiments, the method is as above, but the tumor cell is a breast cancer tumor. In some alternative embodiments, the method is as above, but the tumor cell is a melanoma tumor. In some alternative embodiments, the method is as above, but the tumor cell is a Scwannoma tumor. In some alternative embodiments, the method is as above, but the tumor cell is a pancreatic cancer tumor.

In various embodiments, the contacting of the tumor cell with the combination therapy comprising the MEK inhibitor and the SHP2 inhibitor results in an inhibition of tumor growth that is more than merely additive with respect to the amount of tumor growth inhibition achievable by contacting the tumor cell with each of the respective MEK and SHP2 inhibitors separately.

In some embodiments, the present disclosure provides a method of treating a subject having a tumor, comprising providing to the subject an inhibitor of SHP2 and an inhibitor of the RAS pathway. In some embodiments, the disease or condition is a tumor. In some embodiments, the tumor is selected from an NSCLC, a colon cancer, an oesophageal cancer, a rectal cancer, JMML, breast cancer, melanoma, Scwannoma, and a pancreatic cancer. In some embodiments, the disease is a tumor comprising cells with an NF1 loss of function mutation. In some embodiments, the tumor is an NSCLC or melanoma tumor. In some embodiments, the disease is selected from neurofibromatosis type I, neurofibromatosis type II, schwannomatosis, and Watson syndrome. In some embodiments, the method further comprising providing to the subject an inhibitor of the RAS pathway. In some embodiments, the inhibitor of the RAS pathway is a MAPK inhibitor. In some embodiments, the inhibitor of the RAS pathway is a MEK inhibitor or ERK inhibitor. In some embodiments, the inhibitor of the Ras pathway is selected from one or more of Trametinib, Binimetinib, Selumetinib, Cobimetinib, LErafAON (NeoPharm), ISIS 5132; Vemurafenib, Pimasertib, TAK733, RO4987655 (CH4987655); CI-1040; PD-0325901; CH5126766; MAP855; AZD6244; Refametinib (RDEA 119/BAY 86-9766); GDC-0973/XL581; AZD8330 (ARRY-424704/

ARRY-704); RO5126766; ARS-853 and GSK1120212. In some embodiments, the RAS pathway inhibitor is Abemaciclib or Ulixertinib. In some embodiments, the SHP2 inhibitor is selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof.

In some embodiments, the present disclosure provides a method of treating a subject having a tumor, comprising contacting the tumor with a combination therapy comprising a MEK inhibitor and a SHP2 inhibitor. Such contacting may be, for example, in vivo, in a subject (e.g., a mammal, preferably a human). Thus, the person of skill in the art will understand that the contacting may be via administration, e.g., to a subject (such as a mammal, preferably a human). Thus, such a method may, e.g., comprise contacting the tumor cell with a combination therapy comprising a SHP2 inhibitor and a MEK inhibitor selected from one or more of Trametinib (GSK1120212); Selumetinib (AZD6244); Cobimetinib (GDC-0973/XL581), Binimetinib, Vemurafenib, Pimasertib, TAK733, RO4987655 (CH4987655); CI-1040; PD-0325901; CH5126766; MAP855; Refametinib (RDEA 119/BAY 86-9766); RO5126766, AZD8330 (ARRY-424704/ARRY-704); and GSK1120212. Such a method may, e.g., comprise contacting the tumor cell with a combination therapy comprising a SHP2 inhibitor and Abemaciclib. In some non-limiting embodiments of such a method of treating a subject having a tumor, the tumor cell may be contacted with a combination therapy comprising a MEK inhibitor and a SHP2 inhibitor selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof. In some non-limiting embodiments of such a method of treating a subject having a tumor, the tumor cell may be contacted with a combination therapy comprising Compound B and a MEK inhibitor selected from one or more of Trametinib (GSK1120212); Selumetinib (AZD6244); Cobimetinib (GDC-0973/XL581), Binimetinib, Vemurafenib, Pimasertib, TAK733, RO4987655 (CH4987655); CI-1040; PD-0325901; CH5126766; MAP855; Refametinib (RDEA 119/BAY 86-9766); RO5126766, AZD8330 (ARRY-424704/ARRY-704); and GSK1120212. In some non-limiting embodiments of such a method of treating a subject having a tumor, the tumor cell may be contacted with a combination therapy comprising a SHP2 inhibitor (e.g., Compound B) and Abemaciclib. In some non-limiting embodiments of such a method of treating a subject having a tumor, the tumor cell may be contacted with a combination therapy comprising Trametinib and a SHP2 inhibitor selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof. In some non-limiting embodiments of such a method of treating a subject having a tumor, the tumor cell may be contacted with a combination therapy comprising Trametinib (GSK1120212) and Compound B. In some non-limiting embodiments of such a method of treating a subject having a tumor, the tumor cell may be contacted with a combination therapy comprising Trametinib (GSK1120212) and Compound A. In some non-limiting embodiments of such a method of treating a subject having a tumor, the tumor cell may be contacted with a combination therapy comprising Trametinib (GSK1120212) and Compound C. In some non-limiting embodiments of such a method of treating a subject having a tumor, the tumor cell may be contacted with a combination therapy comprising Trametinib (GSK1120212) and SHP099. In some non-limiting embodiments of such a method of treating a subject having a tumor, the tumor cell may be contacted with a combination therapy comprising Trametinib (GSK1120212) and NSC-87877. In some non-limiting embodiments of such a method of treating a subject having a tumor, the tumor cell may be contacted with a combination therapy comprising Trametinib (GSK1120212) and a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X and a combination thereof. In some non-limiting embodiments of such a method of treating a subject having a tumor, the tumor cell may be contacted with a combination therapy comprising Trametinib (GSK1120212) and a SHP2 inhibitor compound of TNO155. In some non-limiting embodiments of such a method of treating a subject having a tumor, the tumor cell may be contacted with a combination therapy comprising Trametinib (GSK1120212) and a SHP2 inhibitor disclosed in international PCT application PCT/US2017/041577 (WO2018013597), incorporated herein by reference in its entirety. In some non-limiting embodiments of such a method of treating a subject having a tumor, the tumor cell may be contacted with a combination therapy comprising Trametinib (GSK1120212) and a SHP2 inhibitor listed on Table 1. In some non-limiting embodiments of such a method of treating a subject having a tumor, the tumor cell may be contacted with a combination therapy comprising Trametinib (GSK1120212) and a SHP2 inhibitor listed on Table 2. In all such embodiments of such a method of treating a subject having a tumor comprising contacting the tumor cell with a combination therapy, the tumor cell may be a cell from a tumor selected from tumors of hemopoietic and lymphoid system; a myeloproliferative syndrome; a myelodysplastic syndromes; leukemia; acute myeloid leukemia; juvenile myelomonocytic leukemia; esophageal cancer; breast cancer; lung cancer; colon cancer; gastric cancer; neuroblastoma; bladder cancer; prostate cancer; glioblastoma; urothelial carcinoma; uterine carcinoma; adenoid and ovarian sereous cystadenocarcinoma; paraganglioma; phaeochromocytoma; pancreatic cancer; adrenocortical carcinoma; stomach adenocarcinoma; sarcoma; rhabdomyosarcoma; lymphoma; head and neck cancer; skin cancer; peritoneum cancer; intestinal cancer (small and large intestine); thyroid cancer; endometrial cancer; cancer of the biliary tract; soft tissue cancer; ovarian cancer; central nervous system cancer (e.g.; primary CNS lymphoma); stomach cancer; pituitary cancer; genital tract cancer; urinary tract cancer; salivary gland cancer; cervical cancer; liver cancer; eye cancer; cancer of the adrenal gland; cancer of autonomic ganglia; cancer of the upper aerodigestive tract; bone cancer; testicular cancer; pleura cancer; kidney cancer; penis cancer; parathyroid cancer; cancer of the meninges; vulvar cancer and melanoma. For example, in some embodiments, the present disclosure provides a method of treating a subject having a tumor, comprising contacting the tumor cell with a combination therapy comprising a MEK inhibitor and a SHP2 inhibitor, such as combination therapy comprising Trametinib (GSK1120212) and Compound B, wherein the tumor cell is from a NSCLC tumor; wherein the contacting preferably occurs in vivo in a subject (e.g., a mammal, preferably a human). In some embodiments, the present disclosure provides a method of treating a subject having a tumor, comprising contacting the tumor cell with a combination therapy comprising a MEK inhibitor and a SHP2 inhibitor, such as a combination therapy comprising Trametinib (GSK1120212) and Compound C or a combination therapy comprising Trametinib and a compound selected from the compounds listed on Table 1 and Table 2, wherein the tumor cell is from a NSCLC tumor; wherein the contacting preferably occurs in vivo in a subject (e.g., a mammal, preferably a human). In some alternative embodiments, the method is as above, but the tumor cell is from a colon cancer tumor rather than an NSCLC tumor. In some alternative embodiments, the method is as above, but the tumor cell is esophageal cancer tumor. In some alternative embodiments, the method is as above, but the tumor cell is a rectal cancer tumor. In some alternative embodiments, the method is as above, but the tumor cell is a JMML tumor. In some alternative embodiments, the method is as above, but the tumor cell is a breast cancer tumor. In some alternative embodiments, the method is as above, but the tumor cell is a melanoma tumor. In some alternative embodiments, the method is as above, but the tumor cell is a Scwannoma tumor. In some alternative embodiments, the method is as above, but the tumor cell is a pancreatic cancer tumor.

In various embodiments, the method of treating a subject having a tumor comprising contacting of the tumor cell with the combination therapy comprising the MEK inhibitor and the SHP2 inhibitor results in synergistic inhibition of tumor growth. "Synergistic inhibition of tumor growth" means inhibition of tumor growth that is more than merely additive with respect to the amount of tumor growth inhibition achievable by contacting the tumor cell with each of the respective inhibitors separately. For example, in some embodiments, treatment of a subject having a tumor with a combination therapy comprising Trametinib (GSK1120212) and Compound B results in synergistic inhibition of tumor growth, i.e., inhibition of tumor growth that is more than merely additive with respect to the amount of tumor growth inhibition achievable by contacting the tumor cell with each of the respective Trametinib (GSK1120212) and Compound B inhibitors separately. In some embodiments, treatment of a subject having a tumor with a combination therapy comprising Trametinib (GSK1120212) and a SHP2 inhibitor selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof, results in synergistic inhibition of tumor growth.

In some embodiments, treatment of a subject having a tumor with a combination therapy comprising a SHP2 inhibitor and a MEK inhibitor selected from one or more of Trametinib (GSK1120212); Selumetinib (AZD6244); Cobimetinib (GDC-0973/XL581), Binimetinib, Vemurafenib, Pimasertib, TAK733, RO4987655 (CH4987655); CI-1040; PD-0325901; CH5126766; MAP855; Refametinib (RDEA 119/BAY 86-9766); RO5126766, AZD8330 (ARRY-424704/ARRY-704); and GSK1120212, results in synergistic inhibition of tumor growth.

In some embodiments, treatment of a subject having a tumor with a combination therapy comprising (a) a MEK inhibitor selected from one or more of Trametinib (GSK1120212); Selumetinib (AZD6244); Cobimetinib (GDC-0973/XL581), Binimetinib, Vemurafenib, Pimasertib, TAK733, RO4987655 (CH4987655); CI-1040; PD-0325901; CH5126766; MAP855; Refametinib (RDEA 119/BAY 86-9766); RO5126766, AZD8330 (ARRY-424704/ARRY-704); and GSK1120212; and (b) a SHP2 inhibitor selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof, results in synergistic inhibition of tumor growth.

BRIEF DESCRIPTION OF THE DRAWINGS

FIG. 1 shows a cartoon schematic depicting the receptor tyrosine kinase (RTK) signaling pathway. FIG. 1A shows signaling from RTK ligand binding to activation of ERK and subsequent feedback inhibition of RTK activity. FIG. 1B shows SHP2 modulates RAS-GTP loading by an unknown mechanism, which we posit involves priming the GEF protein SOS1.

FIG. 3A shows inhibition of pERK1/2 levels in H358 cells. FIG. 3B shows inhibition of pERK1/2 levels in H1792 cells.

FIG. 4 shows that the SHP2 allosteric inhibitor Compound A (Compound A) inhibits RAS activation and produces a concentration-dependent inhibition of cellular p-ERK1/2 levels and cell growth (3D culture) in H358 KRAS$^{G12C}$ cells in vitro. FIG. 4A shows a western blot demonstrating that Compound A (Compound A) reduces RAS-GTP. FIG. 4B shows Compound A (Compound A) inhibits p-ERK1/2 levels. FIG. 4C shows Compound A (Compound A) inhibits H358 KRAS$^{G12C}$ cell growth.

FIG. 5 shows that the SHP2 allosteric inhibitor Compound A (Compound A) inhibits Ras activation and produces a concentration-dependent inhibition of cellular p-ERK1/2 levels and cell growth in H1838 NF1$^{LOF}$ cells in vitro.

FIG. 11 shows that the SHP2 allosteric inhibitor Compound B (Compound B) suppressed RAS-GTP accumulation resulting from MEK inhibition by trametinib in H358 (KRAS$^{G12C}$) and A549 (KRAS$^{G12S}$) cells. FIG. 11A shows the effect on RAS-GTP accumulation of 6 hour and 24 hour MEK inhibition in H358 (KRAS$^{G12C}$) cells with and without SHP2 inhibition by Compound B. FIG. 11B shows the effect on RAS-GTP accumulation of 6 hour and 24 hour MEK inhibition in H358 (KRAS$^{G12C}$) cells with and without the KRAS$^{G12C}$-specific inhibitor ARS-853. FIG. 11C shows the effect on RAS-GTP accumulation of 6 hour and 24 hour MEK inhibition in A549 (KRAS$^{G12S}$) cells with and without SHP2 inhibition by Compound B. FIG. 11D shows the effect on RAS-GTP accumulation of 6 hour and 24 hour MEK inhibition in A549 (KRAS$^{G12S}$) cells with and without the KRAS$^{G12C}$-specific inhibitor ARS-853.

FIG. 13A shows the effect of Compound B (Compound B) on proliferation of Class I (A375, BRAF$^{V600E}$)) and Class II (NCI-H1755 BRAF$^{G469A}$) BRAF mutant cell lines in 3D culture. FIG. 13B shows the effect of Compound B (Compound B) on RAS-GTP levels in Class I A375 and Class II NCI-H1755 cells grown in 2D culture. FIG. 13C shows the effect of Compound B (Compound B) on p-ERK levels in Class I A375 and Class II NCI-H1755 cells grown in 2D culture. FIG. 13D shows the effect of Compound B (Compound B) on proliferation of two Class III BRAF mutant cell lines (Cal-12T, BRAFG466V/+; NCI-H1666, BRAFG466V/+) cells in 3D culture. FIG. 13E shows the effect of Compound B (Compound B) on RAS-GTP levels in Class III Cal-12T cells. FIG. 13F shows the effect of Compound B (Compound B) on p-ERK levels in Class III Cal-12T and NCI-H1666 cells.

FIG. 14C shows expression of SOS-F in HEK293 cells leads to EGF-independent pERK signaling.

FIG. 15 shows caspase 3/7 activity in NCI-H358 cells grown on ULA plates as spheroids. Culture spheroids were treated with Compound B (Compound B) or staurosporine, as a positive control, and assayed for caspase 3/7 activity after 22 h.

FIG. 16 shows synergistic tumor cell growth inhibition via the combined in vitro treatment of human non-small cell lung cancer cell lines CALU-1 and NCI-H358 with varying concentrations of Compound B (Compound B) in combination with trametinib. FIG. 16A shows normalized percent inhibition relative to vehicle control in H358 NSCLC tumor cells grown in spheroids (3D culture), and treated for five days with increasing amounts of Compound B (Compound B) and Trametinib. FIG. 16B shows a fit of the Loewe Model of Additivity to the normalized growth inhibition data in FIG. 16A. FIG. 16C shows normalized percent inhibition relative to vehicle control in CALU-1 NSCLC tumor cells grown in spheroids (3D culture), and treated for five days with increasing amounts of Compound B (Compound B) and Trametinib. FIG. 16D shows a fit of the Loewe Model of Additivity to the normalized growth inhibition data in FIG. 16C. For each of FIGS. 16B and 16D, numbers in the positive range (mapped in blue) are indicative of synergy.

FIG. 19A and FIG. 19B show the effect of Compound B on proliferation of NF loss-of-function cells in 3D culture. One day after seeding cells were treated with Compound B and cell viability measured on Day 7 using CTG. FIG. 19B lists the geometric mean IC50 values for proliferation inhibition by Compound B and NF1 mutational status in the cancer cell lines evaluated. FIG. 19C and FIG. 19D show NCI-H1838 and MeWo NF1 LOF cells were grown in 2D culture and incubated with increasing concentrations of Compound B for one hour. Cellular lysates were prepared and levels of RAS-GTP (b) and pERK (c) determined. RAS-GTP levels in NCI-H1838 and MeWo cells were inhibited in a concentration-dependent manner by Compound B. The geometric mean IC50 value for reduction in pERK was 29 nM in NCI-H1838 cells, and 24 nM in MeWo cells (data representative of ≥3 independent observations, each performed in duplicate; figures show mean+/−S.D. for pERK and mean+/−S.E.M. for RAS-GTP).

FIGS. 20A and 20B show the effect of Compound B (Cmp B) on proliferation of NF1 loss-of-function cells in 3D culture. One day after seeding cells were treated with Compound B and cell viability measured on Day 7 using CTG. FIG. 20B lists the geometric mean IC50 values for proliferation inhibition by Compound B and NF1 mutational status in the cancer cell lines evaluated. FIGS. 20C and 20D show NCI-H1838 and MeWo NF1 LOF cells were grown in 2D culture and incubated with increasing concentrations of Compound B for one hour. Cellular lysates were prepared and levels of RAS-GTP (b) and pERK (c) determined. RAS-GTP levels in NCI-H1838 and MeWo cells were inhibited in a concentration-dependent manner by Compound B. The geometric mean IC50 value for reduction in pERK was 29 nM in NCI-H1838 cells, and 24 nM in MeWo cells (data representative of ≥3 independent observations, each performed in duplicate; figures show mean+/−S.D. for pERK and mean+/−S.E.M. for RAS-GTP).

FIG. 21 shows the efficacy of repeated daily dosing of SHP2 inhibitor Compound C ("Cmp C") at 10 mg/kg PO with or without co-administration of a Ras pathway inhibitor in the H358 KRas$^{G12C}$ model of human non-small cell lung cancer. FIG. 21A shows the efficacy of Compound C and Trametinib (MEK inhibitor), alone or in combination, and FIG. 21B shows percent body weight changes in these mice; FIG. 21C shows the efficacy of Compound C and Cobimetinib (MEK inhibitor) alone or in combination, and FIG. 21D shows percent body weight changes in these mice; FIG. 21E the efficacy of Compound C and Ulixertinib (ERK1/2 inhibitor), alone or in combination, and FIG. 21F shows percent body weight changes in these mice. Control is vehicle only for all groups.

FIG. 22A shows the efficacy of Compound C and Abemaciclib, alone or in combination, and FIG. 22B shows percent body weight changes in these mice.

DETAILED DESCRIPTION OF THE INVENTION

Figure 2:
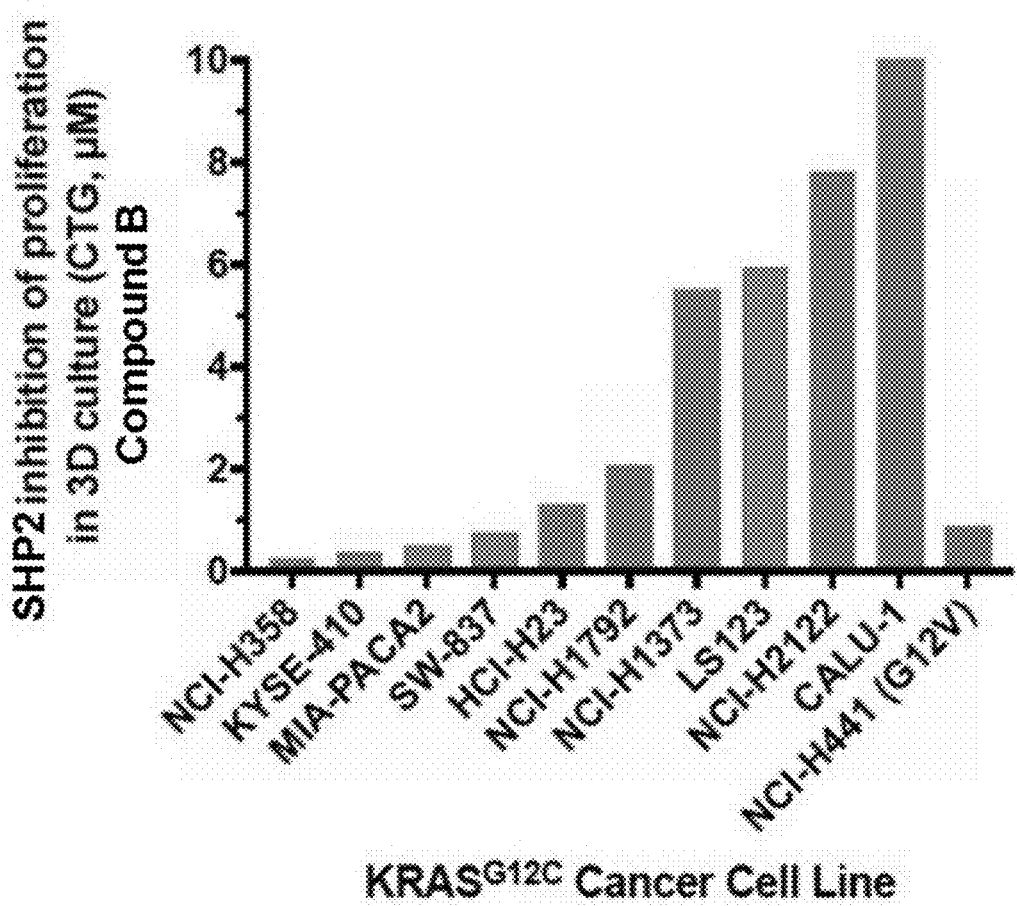
FIG. 2 shows inhibitory potency (IC50 values) of SHP2 allosteric inhibitor Compound B (Compound B) on cell viability (as measured using CTG) in a panel of $KRAS^{G12C}$ mutant cell lines and H441 ($KRAS^{G12V}$) grown in 3D culture.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

General Methods

The practice of the present invention will employ, unless otherwise indicated, conventional techniques of cell culturing, molecular biology (including recombinant techniques), microbiology, cell biology, biochemistry and immunology, which are within the skill of the art. Such techniques are explained fully in the literature, such as, *Molecular Cloning: A Laboratory Manual*, third edition (Sambrook et al., 2001) Cold Spring Harbor Press; *Oligonucleotide Synthesis* (P. Herdewijn, ed., 2004); Animal Cell Culture (R. I. Freshney), ed., 1987); *Methods in Enzymology* (Academic Press, Inc.); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Manual of Clinical Laboratory Immunology* (B. Detrick, N. R. Rose, and J. D. Folds eds., 2006); *Immunochemical Protocols* (J. Pound, ed., 2003); *Lab Manual in Biochemistry: Immunology and Biotechnology* (A. Nigam and A. Ayyagari, eds. 2007); *Immunology Methods Manual: The Comprehensive Sourcebook of Techniques* (Ivan Lefkovits, ed., 1996); Using Antibodies: A Laboratory Manual (E. Harlow and D. Lane, eds., 1988); and others.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "e.g." is used herein to mean "for example," and will be understood to imply the inclusion of a stated step or element or group of steps or elements but not the exclusion of any other step or element or group of steps or elements.

By "optional" or "optionally," it is meant that the subsequently described event or circumstance may or may not occur, and that the description includes instances where the event or circumstance occurs and instances in which it does not. For example, "optionally substituted aryl" encompasses both "aryl" and "substituted aryl" as defined herein. It will be understood by those ordinarily skilled in the art, with respect to any group containing one or more substituents, that such groups are not intended to introduce any substitution or substitution patterns that are sterically impractical, synthetically non-feasible, and/or inherently unstable.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "carrier", as used in this disclosure, encompasses excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The terms "Compound A" and "Cmp A" are used interchangeably herein to refer to a SHP2 inhibitor compound having the following structure:

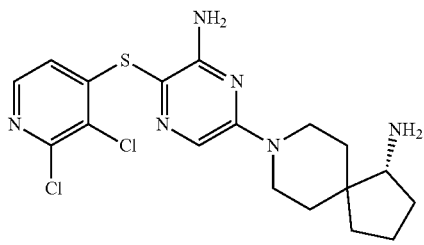 [SMILES: Nc1nc(N2CCC3(CCC[C@H]3N)CC2)cnc1Sc1ccnc(Cl)c1Cl]

The terms "Compound B" and "Cmp B" are used interchangeably herein to refer to a SHP2 inhibitor compound having the following structure:

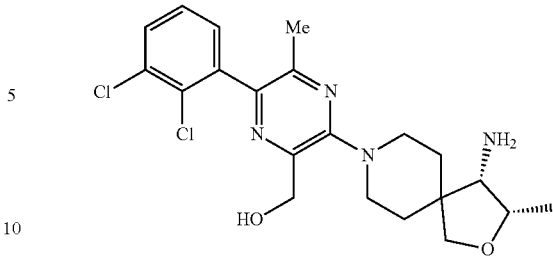

The term "Compound C" and "Cmp C" are used interchangeably herein to refer to an allosteric SHP2 inhibitor compound of similar structure to Compounds A and B. Compound C is disclosed in PCT/US2017/041577 (WO 2018/013597), incorporated herein by reference in its entirety.

The term SHP099 refers to a SHP2 inhibitor having the following structure:

The terms "Class III BRAF mutation"; "Class 3 BRAF mutation"; "BRAF Class 3 mutation"; "BRAF Class III mutation"; "BRAF$^{Class\ 3}$ mutation" and "BRAF$^{Class\ III}$ mutation" are used interchangeably herein to refer to a kinase-dead or lower activity BRAF mutation (as compared to wildtype BRAF) including, but not limited to any of the Class 3 BRAF mutations disclosed in Yao, Z. et al., Nature, 2017 Aug. 10; 548(7666):234-238 or Nieto, P. et al., Nature. 2017 Aug. 10; 548(7666):239-243, each of which are incorporated herein by reference in their entirety. Class 3 BRAF mutations include, without limitation, the following amino acid substitutions in human BRAF: D287H; P367R; V459L; G466V; G466E; G466A; S467L; G469E; N581S; N581I; D594N; D594G; D594A; D594H; F595L; G596D; G596R and A762E.

The terms "Class I MEK1 mutation" or "Class 1 MEK1 mutation" are used herein to refer to a MEK1 mutation that causes the MEK1 kinase to be dependent on and hyperactivated by phosphorylation of S218 and S222 by RAF. In some embodiments, Class I MEK1 mutations include, but are not limited to any of the Class I MEK1 mutations disclosed in Gao Y., et al., Cancer Discov. 2018 May; 8(5):648-661, incorporated herein by reference in its entirety. For example, in some embodiments, the term "Class I MEK1 mutation" includes, without limitation, the following amino acid substitutions in human MEK1: D67N; P124L; P124S; and L177V.

The terms "Class II MEK1 mutation" and "Class 2 MEK1 mutation" are used herein to refer to a MEK1 mutation that causes the MEK1 kinase to have some level of basal, RAF-independent activity, but to be further activated by RAF. In some embodiments, Class II MEK1 mutations include, but are not limited to any of the Class II MEK1 mutations disclosed in Gao Y., et al., Cancer Discov. 2018 May; 8(5):648-661, incorporated herein by reference in its entirety. For example, in some embodiments, the term "Class II MEK1 mutation" includes, without limitation, the following amino acid substitutions in human MEK1: ΔE51-Q58; ΔF53-Q58; E203K; L177M; C121S; F53L; K57E; Q56P; and K57N.

The term "combination therapy" refers to a method of treatment comprising administering to a subject at least two therapeutic agents, optionally as one or more pharmaceutical compositions. For example, a combination therapy may comprise administration of a single pharmaceutical composition comprising at least two therapeutic agents and one or more pharmaceutically acceptable carrier, excipient, diluent, and/or surfactant. A combination therapy may comprise administration of two or more pharmaceutical compositions, each composition comprising one or more therapeutic agent and one or more pharmaceutically acceptable carrier, excipient, diluent, and/or surfactant. In various embodiments, at least one of the therapeutic agents is a SHP2 inhibitor. The two agents may optionally be administered simultaneously (as a single or as separate compositions) or sequentially (as separate compositions). The therapeutic agents may be administered in an effective amount. The therapeutic agent may be administered in a therapeutically effective amount. In some embodiments, the effective amount of one or more of the therapeutic agents may be lower when used in a combination therapy than the therapeutic amount of the same therapeutic agent when it is used as a monotherapy, e.g., due an additive or synergistic effect of combining the two or more therapeutics.

Reference to "determining," in relation to the methods disclosed herein for "determining" whether a subject that has disease or disorder (e.g., a tumor) will be responsive to SHP2 inhibition and in relation to "determining" whether a sample (e.g., a tumor) is classified as a certain subtype (e.g., an $NF1^{LOF}$ or $KRAS^{G12C}$ subtype), comprises both empirically determining (e.g., via an experimental method known in the art or disclosed herein) and mere reference to a record comprising information suitable for such a determining. For example, in some embodiments, "determining" may comprise analysis of a subject's medical or other record, which record indicates that the subject comprises a tumor comprising a cell with a $KRAS^{G12C}$ mutation. In some embodiments, "determining" may comprise analysis of a subject's medical or other record, which record indicates that the subject comprises a tumor comprising a cell with an $NF1^{LOF}$ mutation. In some embodiments, "determining" may comprise analysis of a subject's medical or other record, which record indicates that the subject comprises a tumor comprising a cell with a $KRAS^{G12D}$, $KRAS^{G12S}$ or a $KRAS^{G12V}$ mutation. In some embodiments, "determining" may comprise experimentally testing a sample (e.g., a tissue sample comprising one or more cell such as a tumor cell) from a subject having, or suspected of having, a disease or disorder (e.g., a tumor) that is treatable with a SHP2 inhibitor to determine whether the sample comprises an indicator that the cell might be sensitive to SHP2 inhibition. In some such embodiments, the indicator that the cell might be sensitive to SHP2 inhibition comprises the presence of a $NF1^{LOF}$ mutation, a RAS mutation, an NRAS mutation, an HRAS mutation, a KRAS mutation, a KRAS mutation with a substitution at amino acid 12, a $KRAS^{G12A}$ mutation, a $KRAS^{G12C}$ mutation, a $KRAS^{G12D}$ mutation, a $KRAS^{G12F}$ mutation, a $KRAS^{G12I}$ mutation, a $KRAS^{G12L}$ mutation, a $KRAS^{G12R}$ mutation, a $KRAS^{G12S}$ mutation, a $KRAS^{G12V}$ mutation, a $KRAS^{G12Y}$ mutation, a Class III BRAF mutation, or a combination of two or more such mutations. Suitable methods for experimentally determining the presence of such mutations are disclosed herein and known in the art (e.g., Domagala et al., Pol J Pathol 2012; 3: 145-164, incorporated herein by reference in its entirety).

The term "disorder" is used in this disclosure to mean, and is used interchangeably with, the terms disease, condition, or illness, unless otherwise indicated.

An "effective amount" when used in connection with a compound is an amount effective for treating or preventing a disease or disorder in a subject as described herein.

The term "inhibitor" means a compound that prevents a biomolecule, (e.g., a protein, nucleic acid) from completing or initiating a reaction. An inhibitor can inhibit a reaction by competitive, uncompetitive, or non-competitive means. Exemplary inhibitors include, but are not limited to, nucleic acids, DNA, RNA, shRNA, siRNA, proteins, protein mimetics, peptides, peptidomimetics, antibodies, small molecules, chemicals, analogs that mimic the binding site of an enzyme, receptor, or other protein, e.g., that is involved in signal transduction, therapeutic agents, pharmaceutical compositions, drugs, and combinations of these. In some embodiments, the inhibitor can be nucleic acid molecules including, but not limited to, siRNA that reduce the amount of functional protein in a cell. Accordingly, compounds said to be "capable of inhibiting" a particular protein, e.g., SHP2, comprise any such inhibitor.

The term "monotherapy" refers to a method of treatment comprising administering to a subject a single therapeutic agent, optionally as a pharmaceutical composition. For example, a monotherapy may comprise administration of a pharmaceutical composition comprising a therapeutic agent and one or more pharmaceutically acceptable carrier, excipient, diluent, and/or surfactant. The therapeutic agent may be administered in an effective amount. The therapeutic agent may be administered in a therapeutically effective amount.

The term "mutation" as used herein indicates any modification of a nucleic acid and/or polypeptide which results in an altered nucleic acid or polypeptide. The term "mutation" may include, for example, point mutations, deletions or insertions of single or multiple residues in a polynucleotide, which includes alterations arising within a protein-encoding region of a gene as well as alterations in regions outside of a protein-encoding sequence, such as, but not limited to, regulatory or promoter sequences, as well as amplifications and/or chromosomal breaks or translocations.

The terms "NF1 loss of function" and "$NF1^{LOF}$" are used interchangeably herein to refer to any mutation that renders the NF1 enzyme catalytically inactive or that results in little or no production of NF1 transcript or protein. More than 2600 different mutations in NF1 are known to be inherited, and more than 80% of all constitutional NF1 mutations are inactivating (i.e., $NF1^{LOF}$ mutations)(Philpott et al., Human Genomics (2017) 11:13, incorporated herein by reference in its entirety).

A "patient" or "subject" is a mammal, e.g., a human, mouse, rat, guinea pig, dog, cat, horse, cow, pig, or non-human primate, such as a monkey, chimpanzee, baboon or rhesus.

The term "prevent" or "preventing" with regard to a subject refers to keeping a disease or disorder from afflicting the subject. Preventing includes prophylactic treatment. For instance, preventing can include administering to the subject a compound disclosed herein before a subject is afflicted with a disease and the administration will keep the subject from being afflicted with the disease.

The term "providing to a/the subject" a therapeutic agent, e.g., a SHP2 inhibitor, includes administering such an agent.

The terms "RAS pathway" and "RAS/MAPK pathway" are used interchangeably herein to refer to a signal transduction cascade downstream of various cell surface growth factor receptors in which activation of RAS (and its various isoforms and alleotypes) is a central event that drives a variety of cellular effector events that determine the proliferation, activation, differentiation, mobilization, and other functional properties of the cell. SHP2 conveys positive signals from growth factor receptors to the RAS activation/deactivation cycle, which is modulated by guanine nucleotide exchange factors (GEFs, such as SOS1) that load GTP onto RAS to produce functionally active GTP-bound RAS as well as GTP-accelerating proteins (GAPs, such as NF1) that facilitate termination of the signals by conversion of GTP to GDP. GTP-bound RAS produced by this cycle conveys essential positive signals to a series of serine/threonine kinases including RAF and MAP kinases, from which emanate additional signals to various cellular effector functions.

The terms "RAS pathway mutation" and "RAS/MAPK pathway activating mutation" are used interchangeably herein to refer to a mutation in a gene encoding a protein directly involved in the signaling processes of the RAS/MAPK signaling pathway and/or regulating (either positively or negatively) this signaling pathway that renders the pathway active, wherein such mutation may increase, change or decrease the activity level of said protein. Such proteins include but are not limited to Ras, Raf, NF1, SOS, and specific isoforms or alleotypes thereof.

The term "RTK-driven tumor" refers to a tumor comprising a cell with one or more oncogenic mutation of an RTK, or a protein that is part of the RTK signaling complex, that causes high levels RTK signaling. Some such cells may be considered "addicted" to the RTK, and inhibition of RTK signaling leads to simultaneous suppression of downstream pathways, often resulting in cell growth, arrest, and death. RTK-driven tumors include, but are not limited to, non-small cell lung cancers (NSCLCs) with mutations in EGFR or ALK.

The term "SHP2" means "Src Homolgy-2 phosphatase" and is also known as SH-PTP2, SH-PTP3, Syp, PTP1D, PTP2C, SAP-2 or PTPN11.

The terms "SHP2 inhibitor" and "inhibitor of SHP2" are used interchangeably.

The term "SOS" (e.g., a "SOS mutation") refers to SOS genes, which are known in the art to include RAS guanine nucleotide exchange factor proteins that are activated by receptor tyrosine kinases to promote GTP loading of RAS and signaling. The term SOS includes all SOS homologs that promotes the exchange of Ras-bound GDP by GTP. In particular embodiments, SOS refers specifically to "son of sevenless homolog 1" ("SOS1").

Reference to a "subtype" of a cell, (e.g., an $NF1^{LOF}$ subtype, a $KRAS^{G12C}$ subtype, a $KRAS^{G12S}$ subtype, a $KRAS^{G12D}$ subtype, a $KRAS^{G12V}$ subtype) means that the cell contains a gene mutation encoding a change in the protein of the type indicated. For example, a cell classified as an "$NF1^{LOF}$ subtype" contains a mutation that results in NF1 loss of function; a cell classified as a "$KRAS^{G12C}$ subtype" contains at least one KRAS allele that encodes an amino acid substitution of cysteine for glycine at position 12 (G12C); and, similarly, other cells of a particular subtype (e.g., KRASG12D $KRAS^{G12S}$ and $KRAS^{G12V}$ subtypes) contain at least one allele with the indicated mutation (e.g., a $KRAS^{G12D}$ mutation, a $KRAS^{G12S}$ mutation or a $KRAS^{G12V}$ mutation, respectively). Unless otherwise noted, all amino acid position substitutions referenced herein (such as, e.g., "G12C" in $KRAS^{G12C}$) correspond to substitutions in the human version of the referenced protein, i.e., $KRAS^{G12C}$ refers to a G→C substitution in position 12 of human KRAS.

A "therapeutic agent" is any substance, e.g., a compound or composition, capable of treating a disease or disorder. In some embodiments, therapeutic agents that are useful in connection with the present disclosure include without limitation SHP2 inhibitors, ALK inhibitors, MEK inhibitors, RTK inhibitors (TKIs), and cancer chemotherapeutics. Many such inhibitors are known in the art and are disclosed herein.

The terms "therapeutically effective amount", "therapeutic dose", "prophylactically effective amount", or "diagnostically effective amount" is the amount of the drug, e.g., a SHP2 inhibitor, needed to elicit the desired biological response following administration.

The term "treatment" or "treating" with regard to a subject, refers to improving at least one symptom, pathology or marker of the subject's disease or disorder, either directly or by enhancing the effect of another treatment. Treating includes curing, improving, or at least partially ameliorating the disorder, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

Overview

The present disclosure relates to, inter alia, compositions, methods, and kits for treating or preventing a disease or disorder (e.g., cancer) with a SHP2 inhibitor alone or in combination with another suitable therapeutic agent.

SHP2 is an important signaling effector molecule for a variety of receptor tyrosine kinases (RTKs), including the receptors of platelet-derived growth factor (PDGFR), fibroblast growth factor (FGFR), and epidermal growth factor (EGFR). SHP2 is also an important signaling molecule that regulates the activation of the mitogen activated protein (MAP) kinase pathway which can lead to cell transformation, a prerequisite for the development of cancer. For example, SHP2 is involved in signaling through the Ras-mitogen-activated protein kinase, the JAK-STAT and/or the phosphoinositol 3-kinase-AKT pathways. SHP2 mediates activation of Erk1 and Erk2 (Erk1/2, Erk) MAP kinases by receptor tyrosine kinases such as ErbB1, ErbB2 and c-Met by modulating RAS activation.

SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive conformation, inhibiting its own activity via a binding network involving residues from both the N-SH2 and PTP domains. In response to growth factor stimulation, SHP2 associates with the RTK signaling apparatus, and this induces a conformational change that results in SHP2 activation.

Activating mutations of SHP2 have been associated with developmental pathologies such as Noonan syndrome and Leopard Syndrome and may also be found in multiple cancer types, including most RTK-driven tumors, leukemia, lung and breast cancer, gastric carcinoma, anaplastic large-cell lymphoma, glioblastoma and neuroblastoma.[1]

Grossmann, K S, Rosário, M., Birchmeier, C. & Birchmeier, W. The tyrosine phosphatase Shp2 in development and cancer. Adv. Cancer Res. 106, 53-89 (2010). Chan, R. J. & Feng, G. S. PTPN11 is the first identified proto-oncogene that encodes a tyrosine phosphatase Blood 109, 862-867 (2007). Matozaki, T., Murata, Y., Saito, Y., Okazawa, H. & Ohnishi, H. Protein tyrosine phosphatase SHP-2: a proto-oncogene product that promotes Ras activation. Cancer Sci. 100, 1786-1793 (2009). Mohi, M. G. & Neel, B. G. The role of Shpt (PTPN11) in cancer. Curr. Opin. Genet. Dev. 17, 23-30 (2007). Östman, A, Hellberg, C. & Böhmer, F. D. Protein-tyrosine phosphatases and cancer. Nat. Rev. Cancer 6, 307-320 (2006).

In addition, SHP2 plays a role in transducing signals originating from immune checkpoint molecules, including but not limited to programmed cell death protein 1 (PD-1) and cytotoxic T-lymphocyte-associated protein 4 (CTLA-4). In this context, inhibition of SHP2 function may promote activation of immune cells expressing checkpoint molecules, including anti-cancer immune responses.

It has been disclosed previously that either the knockdown of SHP2 expression using RNAi technology or inhibition of SHP2 by an allosteric small molecule inhibitor interferes with signaling from various RTKs involved in driving cancer cell growth. However, this work also concluded that such approaches would be ineffective at blocking growth signaling in cells in which growth is driven by mutations in proteins that act downstream of RTKs, such as those containing activating mutations in Ras or Raf proteins (Chen, Ying-Nan P. 148 Nature Vol 535 7 Jul. 2016 at pg. 151).

Accordingly, in some embodiments, the present disclosure relates to the unexpected discovery that, contrary to the teachings of the prior art, certain subsets of cells carrying certain oncogenic Ras pathway mutations (e.g., $KRAS^{G12C}$ mutations) are sensitive to SHP2 inhibition and may be effectively treated with SHIP2 inhibitors (see, e.g., Example 1). For example, the present disclosure demonstrates that certain subsets of cancer cells carrying particular KRAS mutations (e.g., $KRAS^{G12C}$ mutations) or $NF1^{LOF}$ mutations are sensitive to SHP2 inhibition and that SHP2 inhibition is an effective means for preventing and delaying the emergence of tumor resistance to various therapeutic agents including cancer therapies (e.g., MAPK inhibitors) and an effective means for re-sensitizing a tumor that is resistant to a cancer therapy (e.g., a MAPK inhibitor) to that inhibitor, particularly in the context of Ras pathway mutations. Similarly, the present disclosure demonstrates that certain subsets of cancer cells carrying particular BRAF mutations (e.g., Class 3 BRAF mutations) or MEK mutations (e.g., Class 1 MEK1 mutations) are sensitive to SHP2 inhibition and that SHP2 inhibition is an effective means for preventing and delaying the emergence of tumor resistance to various therapeutic agents including cancer therapies (e.g., MAPK inhibitors, MEK inhibitors, Erk inhibitors, etc.) and an effective means for re-sensitizing a tumor that is resistant to a cancer therapy (e.g., a MAPK inhibitor) to that inhibitor, particularly in the context of Ras pathway mutations.

The observation that a SHP2 inhibitor can inhibit some, but not all, KRAS mutant cells may be a function of the nucleotide cycling features of a particular KRAS mutation and its corresponding dependence on signaling inputs to maintain high levels of the active, GTP-bound state. Indeed Patricelli and coworkers have demonstrated that $KRAS^{G12C}$ is not a constitutively and fully active protein but rather the nucleotide state of $KRAS^{G12C}$ is in a state of dynamic flux that can be modulated by upstream signaling factors (Patricelli et al., Cancer Discov. 2016 March; 6(3):316-29, incorporated herein by reference in its entirety). Similarly, in cells which have lost function of the GTPase activating protein (GAP), e.g. $NF1^{LOF}$ there is a shift towards the active, GTP-bound state of RAS, which drives signaling to RAS effectors and growth addiction. In these cells, the wildtype RAS undergoes nucleotide cycling which, as for $KRAS^{G12C}$ makes it sensitive to upstream signaling inputs to maintain a highly active state. In the present disclosure, the sensitivity of $KRAS^{G12C}$ and $NF1^{LOF}$ lines to a SHP2 allosteric inhibitor reflects modulation of these upstream factors, and hence the nucleotide state of mutant/WT RAS, by the inhibitor.

Thus the present disclosure provides at least in part, compositions, methods, and kits for the identification, assessment and/or treatment of a disease or condition (e.g., a cancer or tumor such as, for example an oncogene-associated cancer or tumor) responsive to a treatment that includes a SHP2 inhibitor alone or in combination with another cancer therapeutic agent (e.g., an inhibitor of a MAP kinase pathway).

Figures 5A, 5B, 5C:
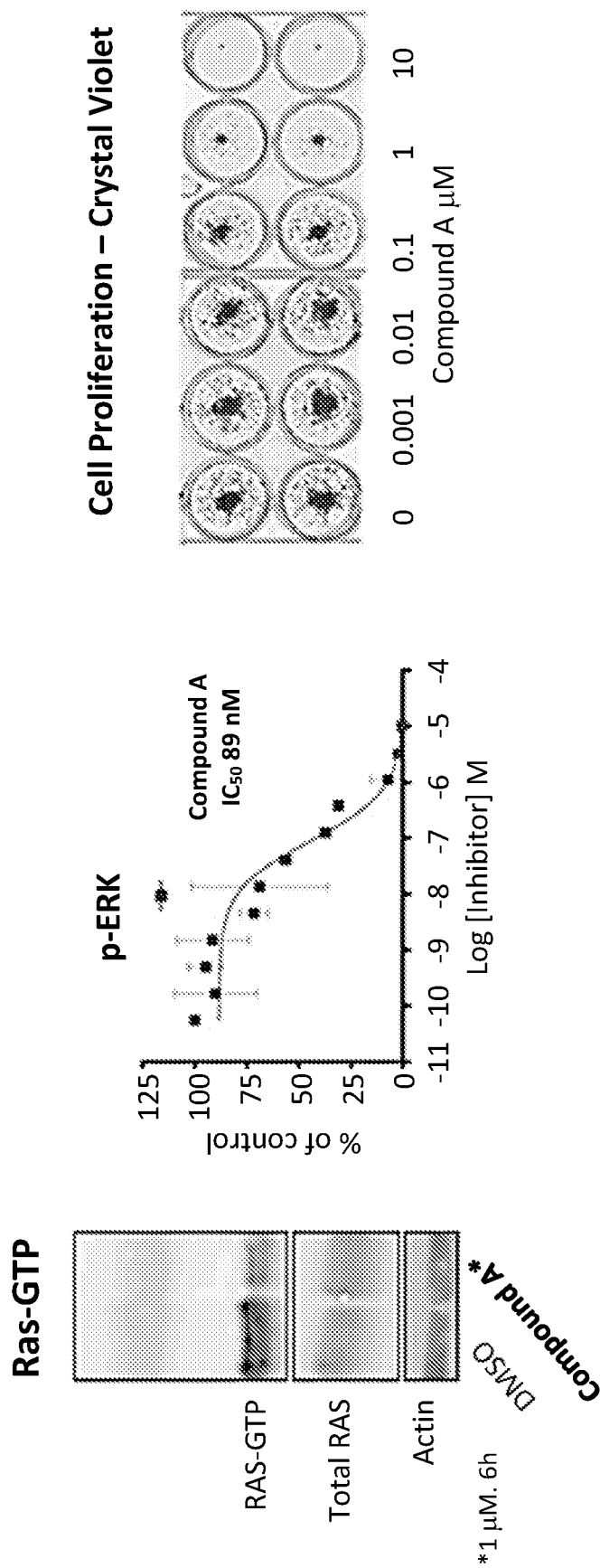
FIG. 5A shows Compound A (Compound A) reduces RAS-GTP.
FIG. 5B shows Compound A (Compound A) inhibits p-ERK1/2.
FIG. 5C shows Compound A (Compound A) inhibits H1838 NF1$^{LOF}$ cell growth.

In some embodiments, the present disclosure provides a method for patient stratification based upon the presence or absence of a RAS pathway mutation or based upon the particular subtype of such a mutation. As used herein, "patient stratification" means classifying one or more patient as having a disease or disorder (e.g., cancer) that is either likely or unlikely to be treatable with a SHP2 inhibitor. Patient stratification may comprise classifying a patient as having a tumor that is sensitive to treatment with a SHP2 inhibitor. The patient stratification may be based on the presence or absence of a tumor comprising one or more cell containing a RAS pathway mutation that renders the mutated protein dependent on signaling flux through SHP2. As used herein, the term "at least partially dependent on signaling flux through SHP2" when used in relation to a mutation, e.g., a RAS pathway mutation, refers to a mutation that renders the function of the mutated protein susceptible to modulation by SHP2 and the effects of inhibitors thereof. The RAS pathway mutation may occur in one or more protein selected from KRAS, NRAS, HRAS, ARAF, BRAF, CRAF, SOS, MEK (e.g., MEK1), and NFL The RAS pathway mutation may occur in one or more protein selected from KRAS, NRAS, HRAS, BRAF, SOS, and NH. In particular embodiments, the mutation in KRAS, NRAS, HRAS, BRAF, SOS, MEK (e.g., MEK1) or NF1 renders the mutated protein sensitive to upstream signaling inputs to maintain a highly active state. The upstream signaling inputs may require SHP2. As used herein, the term "sensitive to upstream signaling inputs to maintain a highly active state" means that maintenance of the active state of a protein (e.g., GTP-RAS) requires upstream signaling inputs (e.g., signaling via SHP2), and modulation of these inputs (e.g., by SHP2 inhibition) results in a change of the active state of the protein (e.g., as shown herein, inhibition of SHP2 results in decreased RAS-GTP levels (FIGS. 4-5); thus RAS is sensitive to upstream signaling inputs to maintain a highly active state). Such mutations may include, without limitation one or more of the following mutations: $KRAS^{G12A}$; $KRAS^{G12C}$; $KRAS^{G12D}$; $KRAS^{G12S}$; $KRAS^{G12V}$; an $NF1^{LOF}$ mutation; an $NF1^{LOF}$ mutation; a Class 3 BRAF mutation; a Class 1 MEK1 mutation; a Class 2 MEK1 mutation, and mutations in SOS. Such mutations may include, without limitation one or more of the following mutations: $KRAS^{G12A}$; $KRAS^{G12C}$; $KRAS^{G12D}$; $KRAS^{G12S}$; $KRAS^{G12V}$; an $NF1^{LOF}$ mutation; an $NF1^{LOF}$ mutation; a Class 3 BRAF mutation; and mutations in SOS.

In some embodiments, the present invention provides a method for subject stratification comprising (a) determining whether a cell from the subject comprises a RAS pathway mutation selected from the group consisting of $KRAS^{G12A}$; $KRAS^{G12C}$; $KRAS^{G12D}$; $KRAS^{G12S}$; $KRAS^{12V}$; an $NF1^{LOF}$ mutation; a Class 3 BRAF mutation; a Class 1 MEK 1 mutation; a Class 2 MEK1 mutation; and a SOS mutation/amplification; (b) administering to the subject SHP2 inhibitor; (c) optionally, administering to the subject an additional therapeutic agent (e.g., an anti-cancer therapeutic agent).

In some embodiments, the present invention provides a method for subject stratification comprising (a) determining whether a cell from the subject comprises a RAS pathway mutation selected from the group consisting of $KRAS^{G12A}$; $KRAS^{G12C}$; $KRAS^{G12D}$; $KRAS^{G12S}$; $KRAS^{12V}$, an $NF1^{LOF}$ mutation; a Class 3 BRAF mutation; and a SOS mutation/amplification; (b) administering to the subject SHP2 inhibitor; (c) optionally, administering to the subject an additional therapeutic agent (e.g., an anti-cancer therapeutic agent).

Any disease or condition associated with a RAS pathway mutation may be identified, assessed, and/or treated according to the present disclosure. In particular embodiments, the RAS pathway mutation renders the mutated protein dependent on signaling flux through SHP2. Several such diseases or conditions comprising RAS pathway mutations are known in the art. For example, in certain embodiments, the present disclosure provides methods for treating a disease or condition selected from, but not limited to, Noonan Syndrome (e.g., Noonan syndrome caused by a mechanism other than a SHP2 mutation), Leopard Syndrome (e.g., Leopard Syndrome caused by a mechanism other than a SHP2 mutation); tumors of hemopoietic and lymphoid system including myeloproliferative syndromes, myelodysplastic syndromes, and leukemia, e.g., acute myeloid leukemia, and juvenile myelomonocytic leukemias; esophageal cancer; breast cancer; lung cancer; colon cancer; gastric cancer, neuroblastoma, bladder cancer, prostate cancer; glioblastoma; urothelial carcinoma, uterine carcinoma, adenoid and ovarian sereous cystadenocarcinoma, paraganglioma, phaeochromocytoma, pancreatic cancer, adrenocortical carcinoma, stomach adenocarcinoma, sarcoma, rhabdomyosarcoma, lymphoma, head and neck cancer, skin cancer, peritoneum cancer, intestinal cancer (small and large intestine), thyroid cancer, endometrial cancer, cancer of the biliary tract, soft tissue cancer, ovarian cancer, central nervous system cancer (e.g., primary CNS lymphoma), stomach cancer, pituitary cancer, genital tract cancer, urinary tract cancer, salivary gland cancer, cervical cancer, liver cancer, eye cancer, cancer of the adrenal gland, cancer of autonomic ganglia, cancer of the upper aerodigestive tract, bone cancer, testicular cancer, pleura cancer, kidney cancer, penis cancer, parathyroid cancer, cancer of the meninges, vulvar cancer and melanoma comprising a method disclosed herein, such as, e.g., a monotherapy or combination therapy disclosed herein.

In various embodiments, the methods for treating such diseases or disorders involve administering to a subject an effective amount of a SHP2 inhibitor or a composition (e.g., a pharmaceutical composition) comprising a SHP2 inhibitor. Any compound or substance capable of inhibiting SHP2 may be utilized in application with the present disclosure to inhibit SHP2. Non-limiting examples of such SHP2 inhibitors are known in the art and are disclosed herein. For example, the compositions and methods described herein may utilize one or more SHP2 inhibitor selected from, but not limited to, any SHP2 inhibitor disclosed in Chen, Ying-Nan P et al., 148 Nature Vol 535 7 Jul. 2016, incorporated herein by reference in its entirety, including SHP099, disclosed therein. The compositions and methods described herein may utilize one or more SHP2 inhibitor selected from, but not limited to any SHP2 inhibitor disclosed in PCT application PCT/US2017/041577 (WO2018013597), which is incorporated herein by reference in its entirety. The compositions and methods described herein may utilize one or more SHP2 inhibitor selected from, but not limited to any SHP2 inhibitor disclosed in PCT applications PCT/IB2015/050343 (WO2015107493); PCT/IB2015/050344 (WO2015107494); PCT/IB2015/050345 (WO201507495); PCT/IB2016/053548 (WO2016/203404); PCT/IB2016/053549 (WO2016203405); PCT/IB2016/053550 (WO2016203406); PCT/US2010/045817 (WO2011022440); PCT/US2017/021784 (WO2017156397); and PCT/US2016/060787 (WO2017079723); and PCT/CN2017/087471 (WO 2017211303), each of which is incorporated herein by reference in its entirety. The compositions and methods described herein may utilize one or more SHP2 inhibitor selected from, but not limited to any SHP2 inhibitor disclosed in Chen L, et al., Mol Pharmacol. 2006 August; 70(2):562-70, incorporated herein by reference in its entirety, including NSC-87877 disclosed therein. The compositions and methods described herein may utilize TNO155, described under ClinicalTrials.gov Identifier: NCT03114319, available at world wide web address: clinicaltrials.gov/ct2/show/NCT03114319, incorporated herein by reference in its entirety. The compositions and methods described herein may utilize one or more SHP2 inhibitor selected from, but not limited to Compound A, disclosed herein; Compound B, disclosed herein; Compound C, disclosed herein; a SHP2 inhibitor compound of Formula I, Formula II, Formula III, Formula I-V1, Formula I-V2, Formula I-W, Formula I-X, Formula I-Y, Formula I-Z, Formula IV, Formula V, Formula VI, Formula IV-X, Formula IV-Y, Formula IV-Z, Formula VII, Formula VIII, Formula IX, and Formula X, disclosed herein; a compound from Table 1, disclosed herein; and a compound from Table 2, disclosed herein.

One aspect of the disclosure relates to compounds of Formula I:

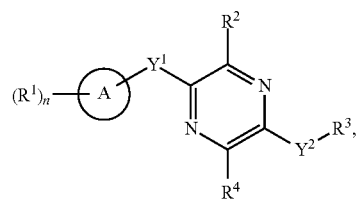

and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^1$ is S or a direct bond;

$Y^2$ is —$NR^a$—, —$(CR^a_2)_m$—, —C(O)—, —$C(R^a)_2$NH—, —$(CR^a_2)_m$O—, —C(O)N($R^a$)—, —N($R^a$)C(O)—, —S(O)$_2$N($R^a$)—, —N($R^a$)S(O)$_2$—, —N($R^a$)C(O)N($R^a$)—, —N($R^a$)C(S)N($R^a$)—, —C(O)O—, —OC(O)—, —OC(O)N($R^a$)—, —N($R^a$)C(O)O—, —C(O)N($R^a$)O—, —N($R^a$)C(S)—, —C(S)N($R^a$)—, or —OC(O)O—; wherein the bond on the left side of $Y^2$, as drawn, is bound to the pyrazine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —NO$_2$, —CN, —$NR^5R^6$, —$SR^5$, —S(O)$_2NR^5R^6$, —S(O)$_2R^5$, —$NR^5$S(O)$_2NR^5R^6$, —$NR^5$S(O)$_2R^6$, —S(O)$NR^5R^6$, —S(O)$R^5$, —$NR^5$S(O)$NR^5R^6$, —$NR^5$S(O)$R^6$, —C(O)$R^5$, or —CO$_2R^5$, wherein each alkyl, alkenyl, cycloalkenyl, alkynyl, or cycloalkyl is optionally substituted with one or more —OH, halogen, —NO$_2$, oxo, —CN, —$R^5$, —$OR^5$, —$NR^5R^6$, —$SR^5$, —S(O)$_2NR^5R^6$, —S(O)$_2R^5$, —$NR^5$S(O)$_2NR^5R^6$, —$NR^5$S(O)$_2R^6$, —S(O)$NR^5R^6$, —S(O)$R^5$, —$NR^5$S(O)$NR^5R^6$, —$NR^5$S(O)$R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is independently —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, or —$NH_2$;

$R^4$ is independently —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Another aspect of the disclosure relates to compounds of Formula II:

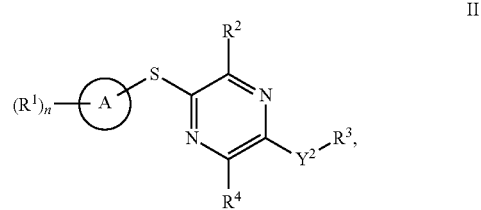

and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^2$ is —$NR^a$—, —$(CR^a_2)_m$—, —C(O)—, —$C(R^a)_2NH$—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —$OC(O)N(R^a)$—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyrazine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^3$ is independently —C$_1$-C$_6$alkyl or a 3- to 12-membered monocyclic or polycyclic heterocycle, wherein each alkyl or heterocycle is optionally substituted with one or more —C$_1$-C$_6$alkyl, —OH, or —NH$_2$; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, or —NH$_2$;

R$^4$ is independently —H, -D, or —C$_1$-C$_6$alkyl, wherein each alkyl is optionally substituted with one or more —OH, —NH$_2$, halogen, or oxo; or R$^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR', —SW, halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Another aspect of the disclosure relates to compounds of Formula III:

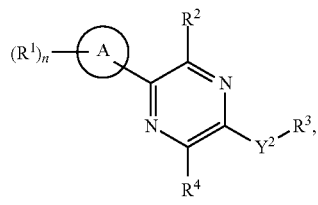

III and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

Y$^2$ is —NR$^a$—, —(CR$^a{}_2$)$_m$—, —C(O)—, —C(R$^a$)$_2$NH—, —(CR$^a{}_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y$^2$, as drawn, is bound to the pyrazine ring and the bond on the right side of the Y$^2$ moiety is bound to R$^3$;

R$^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^2$ is independently —OR$^b$, —CN, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

R$^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^3$ is independently —C$_1$-C$_6$alkyl or a 3- to 12-membered monocyclic or polycyclic heterocycle, wherein each alkyl or heterocycle is optionally substituted with one or more —C$_1$-C$_6$alkyl, —OH, or —NH$_2$; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, or —NH$_2$;

R$^4$ is independently —H, -D, or —C$_1$-C$_6$alkyl, wherein each alkyl is optionally substituted with one or more —OH, —NH$_2$, halogen, or oxo; or R$^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

One aspect of the disclosure related to compounds of Formula I-V1:

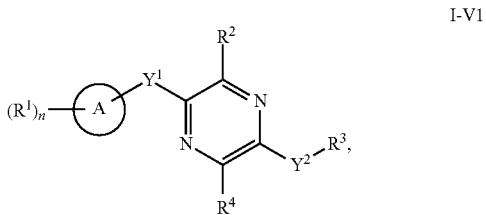

and pharmaceutically acceptable salts, prodrugs, solvates, hydrates, tautomers, or isomers thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$Y^1$ is —S—, a direct bond, —NH—, —S(O)$_2$—, —S(O)$_2$—NH—, —C(=CH$_2$)—, —CH—, or —S(O)—;

$Y^2$ is —NR$^a$—, wherein the bond on the left side of $Y^2$, as drawn, is bound to the pyrazine ring and the bond on the right side of the $Y^2$ moiety, as drawn, is bound to $R^3$;

$R^a$ and $R^4$, together with the atom or atoms to which they are attached, are combined to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

$R^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO$_2$, oxo, =O, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O) NR$^5$R$^6$, —NR$^5$S(O)R$^6$, heterocycle, aryl, or heteroaryl;

$R^2$ is independently —NH$_2$, —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

$R^b$ is independently, at each occurrence, —H, -D, —OH, —C$_1$-C$_6$alkyl, —C$_3$-C$_8$cycloalkyl, —C$_2$-C$_6$alkenyl, —(CH$_2$)$_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O) NR$^5$R$^6$, —NR$^5$C(O)R$^6$, heterocycle, aryl, heteroaryl, —(CH$_2$)$_n$OH, —C$_1$-C$_6$alkyl, —CF$_3$, —CHF$_2$, or —CH$_2$F;

$R^3$ is independently —H, —C$_1$-C$_6$alkyl, a 3- to 12-membered monocyclic or polycyclic heterocycle, a 5- to 12-membered spiroheterocycle, C$_3$-C$_8$cycloalkyl, or —(CH$_2$)$_n$—R$^b$, wherein each alkyl, spiroheterocycle, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl;

$R^5$ and $R^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, —CF$_3$, or —CN;

$R^7$ and $R^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN; and n is independently, at each occurrence, 0, 1, 2, 3, 4, 5, 6, 7, 8, 9, or 10.

One aspect of the disclosure related to compounds of Formula I-V2:

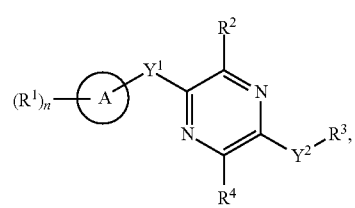

and pharmaceutically acceptable salts, prodrugs, solvates, hydrates, tautomers, and isomers thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$Y^1$ is —S—, a direct bond, —NH—, —S(O)$_2$—, —S(O)$_2$—NH—, —C(=CH$_2$)—, —CH—, or —S(O)—;

$Y^2$ is —NR$^a$—, wherein the bond on the left side of $Y^2$, as drawn, is bound to the pyrazine ring and the bond on the right side of the $Y^2$ moiety, as drawn, is bound to $R^3$;

$R^3$ is combined with $R^a$ to form a 3- to 12-membered polycyclic heterocycle or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —$NO_2$, oxo, =O, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$NH_2$, —$OR^b$, —CN, —$C_1$-$C_6$alkyl, —$C_2$-$C_6$alkenyl, —$C_4$-$C_8$cycloalkenyl, —$C_2$-$C_6$alkynyl, halogen, —$C(O)OR^b$, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^b$ is independently, at each occurrence, —H, -D, —OH, —$C_1$-$C_6$alkyl, —$C_3$-$C_8$cycloalkyl, —$C_2$-$C_6$alkenyl, —$(CH_2)_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$, —$NR^5C(O)R^6$, heterocycle, aryl, heteroaryl, —$(CH_2)_nOH$, —$C_1$-$C_6$alkyl, —$CF_3$, —$CHF_2$, or —$CH_2F$;

$R^4$ is independently —H, -D, —$C_1$-$C_6$alkyl, —$C_1$-$C_6$haloalkyl, —$C_1$-$C_6$hydroxyalkyl, —$CF_2OH$, —CHFOH, —NH—$NHR^5$, —NH—$OR^5$, —O—$NR^5R^6$, —$NHR^5$, —$OR^5$, —$NHC(O)R^5$, —$NHC(O)NHR^5$, —$NHS(O)_2R^5$, —$NHS(O)_2NHR^5$, —$S(O)_2OH$, —$C(O)OR^5$, —$NH(CH_2)_nOH$, —$C(O)NH(CH_2)_nOH$, —$C(O)NH(CH_2)_nR^b$, —$C(O)R^b$, —$NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —OR', —SW, halogen, —$NR^7R^8$, —$NO_2$, —$CF_3$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$OR^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN; and n is independently, at each occurrence, 0, 1, 2, 3, 4, 5, 6, 7, 8, 9, or 10.

One aspect of the disclosure relates to compounds of Formula I-W:

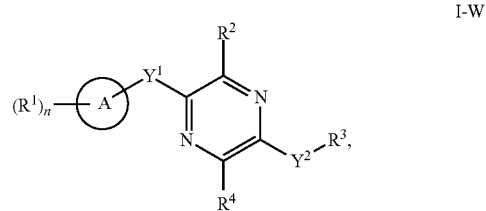

I-W and pharmaceutically acceptable salts, prodrugs, solvates, hydrates, tautomers, and isomers thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$Y^1$ is —S—, a direct bond, —NH—, —$S(O)_2$—, —$S(O)_2$—NH—, —$C(=CH_2)$—, —CH—, or —$S(O)$—;

$Y^2$ is —$NR^a$—, —$(CR^a_2)_m$—, —$C(O)$—, —$C(R^a)_2NH$—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —$C(O)O$—, —$OC(O)$—, —$OC(O)N(R^a)$—, —$N(R^a)C(O)O$—, —$C(O)N(R^a)O$—, —$N(R^a)C(S)$—, —$C(S)N(R^a)$—, or —$OC(O)O$—; wherein the bond on the left side of $Y^2$, as drawn, is bound to the pyrazine ring and the bond on the right side of the $Y^2$ moiety, as drawn, is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —$NO_2$, oxo, =O, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, halogen, —$C(O)OR^b$, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl; and wherein the heterocyclyl or heteroaryl is not attached via a nitrogen atom;

R¹ is independently, at each occurrence, —H, -D, —OH, —C₃-C₈cycloalkyl, —C₁-C₆alkyl, 3- to 12-membered heterocyclyl, or —(CH₂)ₙ-aryl, wherein each alkyl or cycloalkyl is optionally substituted with one or more —NH₂, or wherein 2 Rᵃ, together with the carbon atom to which they are both attached, can combine to form a 3- to 8-membered cycloalkyl;

Rᵇ is independently, at each occurrence, —H, -D, —OH, —C₁-C₆alkyl, —C₃-C₈cycloalkyl, —C₂-C₆alkenyl, —(CH₂)ₙ-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —(CH₂)ₙ-aryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)NR⁵R⁶, —NR⁵C(O)R⁶, heterocycle, aryl, heteroaryl, —(CH₂)ₙOH, —C₁-C₆alkyl, —CF₃, —CHF₂, or —CH₂F;

R³ is independently —H, —C₁-C₆alkyl, a 3- to 12-membered monocyclic or polycyclic heterocycle, a 5- to 12-membered spiroheterocycle, C₃-C₈cycloalkyl, or —(CH₂)ₙ—Rᵇ, wherein each alkyl, spiroheterocycle, heterocycle, or cycloalkyl is optionally substituted with one or more —C₁-C₆alkyl, —OH, —NH₂, —ORᵇ, —NHRᵇ, —(CH₂)ₙOH, heterocyclyl, or spiroheterocyclyl; or R³ can combine with Rᵃ to form a 3- to 12-membered monocyclic or polycyclic heterocycle or a 5- to 12-membered spiroheterocycle, wherein each heterocycle or spiroheterocycle is optionally substituted with one or more —C₁-C₆alkyl, halogen, —OH, —ORᵇ, —NH₂, —NHRᵇ, heteroaryl, heterocyclyl, —(CH₂)ₙNH₂, —(CH₂)ₙOH, —COORᵇ, —CONHRᵇ, —CONH(CH₂)ₙCOORᵇ, —NHCOORᵇ, —CF₃, —CHF₂, —CH₂F, or =O;

R⁴ is independently —H, -D, —C₁-C₆alkyl, —C₁-C₆haloalkyl, —C₁-C₆hydroxyalkyl —CF₂OH, —CHFOH —NH—NHR⁵, —NH—OR⁵, —O—NR⁵R⁶, —NHR⁵, —OR⁵, —NHC(O)R⁵, —NHC(O)NHR⁵, —NHS(O)₂R⁵, —NHS(O)₂NHR⁵, —S(O)₂OH, —C(O)OR⁵, —NH(CH₂)ₙOH, —C(O)NH(CH₂)ₙOH, —C(O)NH(CH₂)ₙRᵇ, —C(O)Rᵇ, —NH₂, —OH, —CN, —C(O)NR⁵R⁶, —S(O)₂NR⁵R⁶, C₃-C₈cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH₂, —ORᵇ, halogen, or oxo; wherein each aryl or heteroaryl is optionally substituted with one or more —OH, —NH₂, or halogen; or Rᵃ and R⁴, together with the atom or atoms to which they are attached, can combine to form a monocyclic or polycyclic C₃-C₁₂cycloalkyl or a monocyclic or polycyclic 3- to 12-membered heterocycle, wherein the cycloalkyl or heterocycle is optionally substituted with oxo; wherein the heterocycle optionally comprises —S(O)₂— in the heterocycle;

R⁵ and R⁶ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, —CF₃, or —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, —ORᵇ, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

m is independently, at each occurrence, 1, 2, 3, 4, 5 or 6; and n is independently, at each occurrence, 0, 1, 2, 3, 4, 5, 6, 7, 8, 9, or 10.

One aspect of the disclosure relates to compounds of Formula I-X:

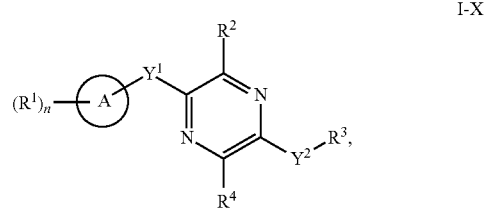

and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

Y¹ is —S— or a direct bond;

Y² is —NRᵃ—, —(CRᵃ₂)ₘ—, —C(O)—, —C(Rᵃ)₂NH—, —(CRᵃ₂)ₘO—, —C(O)N(Rᵃ)—, —N(Rᵃ)C(O)—, —S(O)₂N(Rᵃ)—, —N(Rᵃ)S(O)₂—, —N(Rᵃ)C(O)N(Rᵃ)—, —N(Rᵃ)C(S)N(Rᵃ)—, —C(O)O—, —OC(O)—, —OC(O)N(Rᵃ)—, —N(Rᵃ)C(O)O—, —C(O)N(Rᵃ)O—, —N(Rᵃ)C(S)—, —C(S)N(Rᵃ)—, or —OC(O)O—; wherein the bond on the left side of Y², as drawn, is bound to the pyrazine ring and the bond on the right side of the Y² moiety, as drawn, is bound to R³;

R¹ is independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, —OH, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, or —CO₂R⁵, wherein each alkyl, alkenyl, cycloalkenyl, alkynyl, or cycloalkyl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R² is independently —ORᵇ, —CN, —C₁-C₆alkyl, —C₂-C₆alkenyl, —C₄-C₈cycloalkenyl, —C₂-C₆alkynyl, —C₃-C₈cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl; and wherein the heterocyclyl or heteroaryl is not attached via a nitrogen atom;

R$^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^3$ is independently —H, —C$_1$-C$_6$alkyl, or a 3- to 12-membered monocyclic or polycyclic heterocycle, wherein each alkyl or heterocycle is optionally substituted with one or more —C$_1$-C$_6$alkyl, —OH, or —NH$_2$; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, or —NH$_2$;

R$^4$ is independently —H, -D, —C$_1$-C$_6$alkyl, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, halogen, or oxo; wherein each aryl or heteroaryl is optionally substituted with one or more —OH, —NH$_2$, or halogen; or R$^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

One aspect of the disclosure relates to compounds of Formula I-Y:

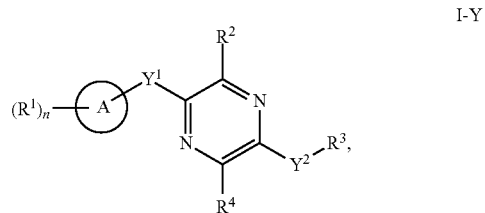

I-Y and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

Y$^1$ is —S— or a direct bond;

Y$^2$ is —NR$^a$—, —(CR$^a_2$)$_m$—, —C(O)—, —C(R$^a$)$_2$NH—, —(CR$^a_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y$^2$, as drawn, is bound to the pyrazine ring and the bond on the right side of the Y$^2$ moiety, as drawn, is bound to R$^3$;

R$^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^2$ is independently —OR$^b$, —CN, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

R$^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^3$ is independently —H, —C$_1$-C$_6$alkyl, a 3- to 12-membered monocyclic or polycyclic heterocycle, C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

R$^4$ is independently —H, -D, —C$_1$-C$_6$alkyl, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —CN, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, halogen, or oxo; wherein each aryl or heteroaryl is optionally substituted with one or more —OH, —NH$_2$, or halogen; or R$^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

One aspect of the disclosure relates to compounds of Formula I-Z:

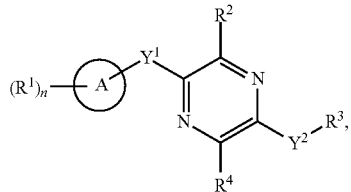

I-Z and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

Y$^1$ is —S—, a direct bond, —NH—, —S(O)$_2$—, —S(O)$_2$—NH—, —C(=CH$_2$)—, —CH—, or —S(O)—;

Y$^2$ is —NR$^a$—, —(CR$^a_2$)$_m$—, —C(R$^a$)$_2$NH—, —(CR$^a_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —OC(O)N(R$^a$)—, —N(R$^a$)C(O)O—, —C(O)N(R$^a$)O—, —N(R$^a$)C(S)—, or —C(S)N(R$^a$)—; where in the bond on the left side of Y$^2$, as drawn, is bound to the pyrazine ring and the bond on the right side of the Y$^2$ moiety, as drawn, is bound to R$^3$;

R$^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^2$ is independently —OR$^b$, —NH$_2$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

R$^a$ is independently, at each occurrence —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^3$ is independently —H, —C$_1$-C$_6$alkyl, a 3- to 12-membered monocyclic or polycyclic heterocycle, C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

R$^4$ is independently —C$_1$-C$_6$alkyl, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, halogen, or oxo; wherein each aryl or heteroaryl is optionally substituted with one or more —OH, —NH$_2$, or halogen;

R$^a$ and R$^4$, together with the atom or atoms to which they are attached, are combined to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR', —SR', halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

One aspect of the invention relates to compounds of Formula IV:

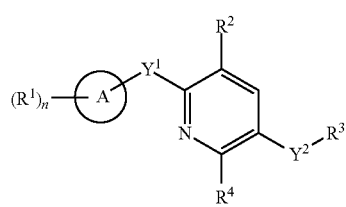

IV and pharmaceutically acceptable salts, prodrugs, solvates, hydrates, tautomers, or isomers thereof, wherein:

A is selected from the group consisting of 5- to 12-membered monocyclic or polycyclic cycloalkyl, heterocycloalkyl, aryl, or heteroaryl;

Y$^1$ is —S— or a direct bond;

Y$^2$ is selected from the group consisting of: —NR$^a$—, —(CR$^a_2$)$_m$—, —C(O)—, —C(R$^a$)$_2$NH—, —(CR$^a_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, and —OC(O)O—; wherein the bond on the left side of Y$^2$, as drawn, is bound to the pyridine ring and the bond on the right side of the Y$^2$ moiety is bound to R$^3$;

R$^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^2$ is independently —OR$^b$, —CN, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, aryl, heterocyclyl containing 1-5 heteroatoms selected from the group consisting of N, S, P, or O, or heteroaryl containing 1-5 heteroatoms selected from the group consisting of N, S, P, or O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

R$^a$ is independently, at each occurrence, selected from the group consisting of —H, -D, —OH, —C$_3$-C$_8$cycloalkyl, and —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^b$ is independently —H, -D, —C$_1$-C$_6$alkyl, —C$_1$-C$_6$cycloalkyl, —C$_2$-C$_6$alkenyl, or heterocyclyl containing 1-5 heteroatoms selected from the group consisting of N, S, P, or O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^3$ is independently, at each occurrence, selected from the group consisting of —C$_1$-C$_6$alkyl, or a 3-to 12-membered monocyclic or polycyclic heterocycle, wherein each alkyl or heterocycle is optionally substituted with one or more —C$_1$-C$_6$alkyl, —OH, or —NH$_2$; or R$^3$ can combine with R$^a$ to form a 3-to 12-membered monocyclic or polycyclic heterocycle, or a 5-to 12-membered spiroheterocycle, wherein each heterocycle or spiroheterocycle is optionally substituted with —C$_1$-C$_6$alkyl, —OH, or —NH$_2$;

R⁴ is independently, at each occurrence, —H, -D, or —C₁-C₆alkyl, wherein each alkyl is optionally substituted with one or more —OH, —NH₂, halogen, or oxo; or Rᵃ and R⁴, together with the atom or atoms to which they are attached, can combine to form a monocyclic or polycyclic C₃-C₁₂cycloalkyl, or a monocyclic or polycyclic 3-to 12-membered heterocycle, wherein the cycloalkyl or heterocycle is optionally substituted with oxo;

R⁵ and R⁶ are each independently, at each occurrence, selected from the group consisting of —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3-to 12-membered heterocycle, —OR⁷, —SR⁷, halogen, —NR⁷R⁸, —NO₂, and —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3-to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

m is independently 1, 2, 3, 4, 5 or 6; and n is independently 0, 1, 2, 3, 4, 5, 6, 7, 8, 9, or 10.

Another aspect of the invention relates to compounds of Formula V:

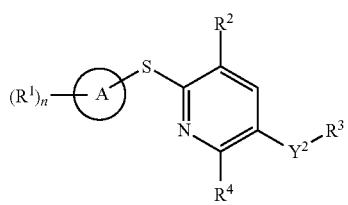

V and pharmaceutically acceptable salts, prodrugs, solvates, hydrates, tautomers, or isomers thereof, wherein:

A is selected from the group consisting of 5- to 12-membered monocyclic or polycyclic cycloalkyl, heterocycloalkyl, aryl, or heteroaryl;

Y² is selected from the group consisting of: —NRᵃ—, —(CRᵃ₂)ₘ—, —C(O)—, —C(Rᵃ)₂NH—, —(CRᵃ₂)ₘO—, —C(O)N(Rᵃ)—, —N(Rᵃ)C(O)—, —S(O)₂N(Rᵃ)—, —N(Rᵃ)S(O)₂—, —N(Rᵃ)C(O)N(Rᵃ)—, —N(Rᵃ)C(S)N(Rᵃ)—, —C(O)O—, —OC(O)—, —OC(O)N(Rᵃ)—, —N(Rᵃ)C(O)O—, —C(O)N(Rᵃ)O—, —N(Rᵃ)C(S)—, —C(S)N(Rᵃ)—, and —OC(O)O—; wherein the bond on the left side of Y², as drawn, is bound to the pyridine ring and the bond on the right side of the Y² moiety is bound to R³;

R¹ is independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, —OH, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, or —CO₂R⁵, wherein each alkyl, alkenyl, cycloalkenyl, alkynyl, or cycloalkyl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R² is independently —ORᵇ, —CN, —C₁-C₆alkyl, —C₂-C₆alkenyl, —C₄-C₈cycloalkenyl, —C₂-C₆alkynyl, —C₃-C₈cycloalkyl, aryl, heterocyclyl containing 1-5 heteroatoms selected from the group consisting of N, S, P, or O, or heteroaryl containing 1-5 heteroatoms selected from the group consisting of N, S, P, or O; wherein each alkyl, alkenyl, cycloalkenyl, alkynyl, cycloalkyl, heterocyclyl, aryl, or heteroaryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl; and wherein the heterocyclyl or heteroaryl is not attached via a nitrogen atom;

Rᵃ is independently, at each occurrence, selected from the group consisting of —H, -D, —OH, —C₃-C₈cycloalkyl, and —C₁-C₆alkyl, wherein each alkyl or cycloalkyl is optionally substituted with one or more —NH₂, wherein 2 Rᵃ, together with the carbon atom to which they are both attached, can combine to form a 3- to 8-membered cycloalkyl;

Rᵇ is independently —H, -D, —C₁-C₆alkyl, —C₁-C₆cycloalkyl, —C₂-C₆alkenyl, or heterocyclyl containing 1-5 heteroatoms selected from the group consisting of N, S, P, or O; wherein each alkyl, cycloalkyl, alkenyl, or heterocycle is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R³ is independently, at each occurrence, selected from the group consisting of —C₁-C₆alkyl, or a 3-to 12-membered monocyclic or polycyclic heterocycle, wherein each alkyl or heterocycle is optionally substituted with one or more —C₁-C₆alkyl, —OH, or —NH₂; or R³ can combine with Rᵃ to form a 3-to 12-membered monocyclic or polycyclic heterocycle, or a 5-to 12-membered spiroheterocycle, wherein each heterocycle or spiroheterocycle is optionally substituted with —C₁-C₆alkyl, —OH, or —NH₂;

R⁴ is independently, at each occurrence, —H, -D, or —C₁-C₆alkyl, wherein each alkyl is optionally substituted with one or more —OH, —NH₂, halogen, or oxo; or Rᵃ and R⁴, together with the atom or atoms to which they are attached, can combine to form a monocyclic or polycyclic C₃-C₁₂cycloalkyl, or a monocyclic or polycyclic 3-to 12-membered heterocycle, wherein the cycloalkyl or heterocycle is optionally substituted with oxo;

R⁵ and R⁶ are each independently, at each occurrence, selected from the group consisting of —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3-to 12-membered heterocycle, —OR⁷, —SR⁷, halogen, —NR⁷R⁸, —NO₂, and —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3-to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

m is independently 1, 2, 3, 4, 5 or 6; and n is independently 0, 1, 2, 3, 4, 5, 6, 7, 8, 9, or 10.

Another aspect of the invention relates to compounds of Formula VI:

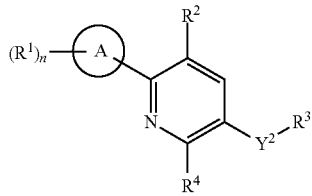

and pharmaceutically acceptable salts, prodrugs, solvates, hydrates, tautomers, or isomers thereof, wherein:

A is selected from the group consisting of 5- to 12-membered monocyclic or polycyclic cycloalkyl, heterocycloalkyl, aryl, or heteroaryl;

$Y^2$ is selected from the group consisting of: $-NR^a-$, $-(CR^a{}_2)_m-$, $-C(O)-$, $-C(R^a)_2NH-$, $-(CR^a{}_2)_mO-$, $-C(O)N(R^a)-$, $-N(R^a)C(O)-$, $-S(O)_2N(R^a)-$, $-N(R^a)S(O)_2-$, $-N(R^a)C(O)N(R^a)-$, $-N(R^a)C(S)N(R^a)-$, $-C(O)O-$, $-OC(O)-$, $-OC(O)N(R^a)-$, $-N(R^a)C(O)O-$, $-C(O)N(R^a)O-$, $-N(R^a)C(S)-$, $-C(S)N(R^a)-$, and $-OC(O)O-$; wherein the bond on the left side of $Y^2$, as drawn, is bound to the pyridine ring and the bond on the right side of the $Y^2$ moiety is bound to $R^3$;

$R^1$ is independently, at each occurrence, $-H$, $-D$, $-C_1$-$C_6$alkyl, $-C_2$-$C_6$alkenyl, $-C_4$-$C_8$cycloalkenyl, $-C_2$-$C_6$alkynyl, $-C_3$-$C_8$cycloalkyl, $-OH$, halogen, $-NO_2$, $-CN$, $-NR^5R^6$, $-SR^5$, $-S(O)_2NR^5R^6$, $-S(O)_2R^5$, $-NR^5S(O)_2NR^5R^6$, $-NR^5S(O)_2R^6$, $-S(O)NR^5R^6$, $-S(O)R^5$, $-NR^5S(O)NR^5R^6$, $-NR^5S(O)R^6$, $-C(O)R^5$, or $-CO_2R^5$, wherein each alkyl, alkenyl, cycloalkenyl, alkynyl, or cycloalkyl is optionally substituted with one or more $-OH$, halogen, $-NO_2$, oxo, $-CN$, $-R^5$, $-OR^5$, $-NR^5R^6$, $-SR^5$, $-S(O)_2NR^5R^6$, $-S(O)_2R^5$, $-NR^5S(O)_2NR^5R^6$, $-NR^5S(O)_2R^6$, $-S(O)NR^5R^6$, $-S(O)R^5$, $-NR^5S(O)NR^5R^6$, $-NR^5S(O)R^6$, heterocycle, aryl, or heteroaryl;

$R^2$ is independently $-OR^b$, $-CN$, $-C_1$-$C_6$alkyl, $-C_2$-$C_6$alkenyl, $-C_4$-$C_8$cycloalkenyl, $-C_2$-$C_6$alkynyl, $-C_3$-$C_8$cycloalkyl, aryl, heterocyclyl containing 1-5 heteroatoms selected from the group consisting of N, S, P, or O, or heteroaryl containing 1-5 heteroatoms selected from the group consisting of N, S, P, or O; wherein each alkyl, alkenyl, cycloalkenyl, alkynyl, cycloalkyl, heterocyclyl, aryl, or heteroaryl is optionally substituted with one or more $-OH$, halogen, $-NO_2$, oxo, $-CN$, $-R^5$, $-OR^5$, $-NR^5R^6$, $-SR^5$, $-S(O)_2NR^5R^6$, $-S(O)_2R^5$, $-NR^5S(O)_2NR^5R^6$, $-NR^5S(O)_2R^6$, $-S(O)NR^5R^6$, $-S(O)R^5$, $-NR^5S(O)NR^5R^6$, $-NR^5S(O)R^6$, heterocycle, aryl, or heteroaryl; and wherein the heterocyclyl or heteroaryl is not attached via a nitrogen atom;

$R^a$ is independently, at each occurrence, selected from the group consisting of $-H$, $-D$, $-OH$, $-C_3$-$C_8$cycloalkyl, and $-C_1$-$C_6$alkyl, wherein each alkyl or cycloalkyl is optionally substituted with one or more $-NH_2$, wherein 2 $R^a$, together with the carbon atom to which they are both attached, can combine to form a 3- to 8-membered cycloalkyl;

$R^b$ is independently $-H$, $-D$, $-C_1$-$C_6$alkyl, $-C_1$-$C_6$cycloalkyl, $-C_2$-$C_6$alkenyl, or heterocyclyl containing 1-5 heteroatoms selected from the group consisting of N, S, P, or O; wherein each alkyl, cycloalkyl, alkenyl, or heterocycle is optionally substituted with one or more $-OH$, halogen, $-NO_2$, oxo, $-CN$, $-R^5$, $-OR^5$, $-NR^5R^6$, $-SR^5$, $-S(O)_2NR^5R^6$, $-S(O)_2R^5$, $-NR^5S(O)_2NR^5R^6$, $-NR^5S(O)_2R^6$, $-S(O)NR^5R^6$, $-S(O)R^5$, $-NR^5S(O)NR^5R^6$, $-NR^5S(O)R^6$, heterocycle, aryl, or heteroaryl;

$R^3$ is independently, at each occurrence, selected from the group consisting of $-C_1$-$C_6$alkyl, or a 3-to 12-membered monocyclic or polycyclic heterocycle, wherein each alkyl or heterocycle is optionally substituted with one or more $-C_1$-$C_6$alkyl, $-OH$, or $-NH_2$; or $R^3$ can combine with $R^a$ to form a 3-to 12-membered monocyclic or polycyclic heterocycle, or a 5-to 12-membered spiroheterocycle, wherein each heterocycle or spiroheterocycle is optionally substituted with $-C_1$-$C_6$alkyl, $-OH$, or $-NH_2$;

$R^4$ is independently, at each occurrence, $-H$, $-D$, or $-C_1$-$C_6$alkyl, wherein each alkyl is optionally substituted with one or more $-OH$, $-NH_2$, halogen, or oxo; or $R^a$ and $R^4$, together with the atom or atoms to which they are attached, can combine to form a monocyclic or polycyclic $C_3$-$C_{12}$cycloalkyl, or a monocyclic or polycyclic 3-to 12-membered heterocycle, wherein the cycloalkyl or heterocycle is optionally substituted with oxo;

$R^5$ and $R^6$ are each independently, at each occurrence, selected from the group consisting of $-H$, $-D$, $-C_1$-$C_6$alkyl, $-C_2$-$C_6$alkenyl, $-C_4$-$C_8$cycloalkenyl, $-C_2$-$C_6$alkynyl, $-C_3$-$C_8$cycloalkyl, a monocyclic or polycyclic 3-to 12-membered heterocycle, $-OR^7$, $-SR^7$, halogen, $-NR^7R^8$, $-NO_2$, and $-CN$;

$R^7$ and $R^8$ are independently, at each occurrence, $-H$, $-D$, $-C_1$-$C_6$alkyl, $-C_2$-$C_6$alkenyl, $-C_4$-$C_8$cycloalkenyl, $-C_2$-$C_6$alkynyl, $-C_3$-$C_8$cycloalkyl, a monocyclic or polycyclic 3-to 12-membered heterocycle, wherein each alkyl, alkenyl, cycloalkenyl, alkynyl, cycloalkyl, or heterocycle is optionally substituted with one or more $-OH$, $-SH$, $-NH_2$, $-NO_2$, or $-CN$;

m is independently 1, 2, 3, 4, 5 or 6; and n is independently 0, 1, 2, 3, 4, 5, 6, 7, 8, 9, or 10.

One aspect of the invention relates to compounds of Formula IV-Y:

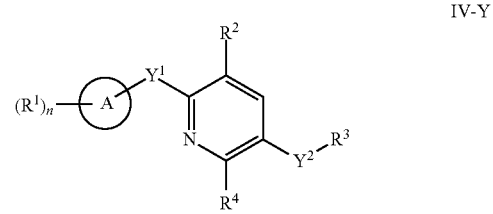

or a pharmaceutically acceptable salt, prodrug, solvate, hydrate, tautomer, or isomer thereof, wherein:

A is selected from the group consisting of 5- to 12-membered monocyclic or polycyclic cycloalkyl, heterocycloalkyl, aryl, or heteroaryl;

$Y^1$ is $-S-$ or a direct bond;

$Y^2$ is selected from the group consisting of: $-NR^a-$, $-(CR^a{}_2)_m-$, $-C(O)-$, $-C(R^a)_2NH-$, $-(CR^a{}_2)_mO-$, $-C(O)N(R^a)-$, $-N(R^a)C(O)-$, $-S(O)_2N(R^a)-$, $-N(R^a)S(O)_2-$, $-N(R^a)C(O)N(R^a)-$, $-N(R^a)C(S)N(R^a)-$, $-C(O)O-$, $-OC(O)-$, $-OC(O)N(R^a)-$, $-N(R^a)C(O)O-$, $-C(O)N(R^a)O-$, $-N(R^a)C(S)-$, $-C(S)N(R^a)-$, and $-OC(O)O-$; wherein the bond on the left side of $Y^2$, as drawn, is bound to the pyridine ring and the bond on the right side of the $Y^2$ moiety, as drawn, is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, or O, or heteroaryl containing 1-5 heteroatoms selected from the group consisting of N, S, P, or O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, selected from the group consisting of —H, -D, —OH, —$C_3$-$C_8$cycloalkyl, and —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently —H, -D, —$C_1$-$C_6$alkyl, —$C_1$-$C_6$cycloalkyl, —$C_2$-$C_6$alkenyl, or heterocyclyl containing 1-5 heteroatoms selected from the group consisting of N, S, P, or O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, heteroaryl, —$(CH_2)_nOH$, —$C_1$-$C_6$alkyl, $CF_3$, $CHF_2$, or $CH_2F$;

$R^3$ is independently, at each occurrence, selected from the group consisting of —H, —$C_1$-$C_6$alkyl, a 3-to 12-membered monocyclic or polycyclic heterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^a$, —$NHR^a$, —$(CH_2)_nOH$, heterocyclyl, or spiroheterocyclyl; or $R^3$ can combine with $R^a$ to form a 3-to 12-membered monocyclic or polycyclic heterocycle, or a 5-to 12-membered spiroheterocycle, wherein each heterocycle or spiroheterocycle is optionally substituted with —$C_1$-$C_6$alkyl, —OH, —$NH_2$, heteroaryl, heterocyclyl, —$(CH_2)_nNH_2$, —$COOR^a$, —$CONHR^b$, —$CONH(CH_2)_nCOOR^a$, —$NHCOOR^a$, —$CF_3$, $CHF_2$, or $CH_2F$;

$R^4$ is independently, at each occurrence, —H, -D, —$C_1$-$C_6$alkyl, —NH—$NHR^5$, —NH—$OR^5$, —O—$NR^5R^6$, —$NHR^5$, —$OR^5$, —$NHC(O)R^5$, —$NHC(O)NHR^5$, —$NHS(O)_2R^5$, —$NHS(O)_2NHR^5$, —$S(O)_2OH$, —$C(O)OR^5$, —NH($CH_2$)$_n$OH, —$C(O)NH(CH_2)_nOH$, —$C(O)NH(CH_2)_nR^b$, —$C(O)R^b$, $NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, or O, heteroaryl containing 1-5 heteroatoms selected from the group consisting of N, S, P, or O, wherein each alkyl, cycloalkyl, or heterocyclyl is optionally substituted with one or more —OH, —$NH_2$, halogen, or oxo; wherein each aryl or heteroaryl is optionally substituted with one or more —OH, —$NH_2$, or halogen; or $R^a$ and $R^4$, together with the atom or atoms to which they are attached, can combine to form a monocyclic or polycyclic $C_3$-$C_{12}$cycloalkyl, or a monocyclic or polycyclic 3-to 12-membered heterocycle, wherein the cycloalkyl or heterocycle is optionally substituted with oxo; wherein the heterocycle optionally comprises —$S(O)_2$— in the heterocycle;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3-to 12-membered heterocycle, —$OR^7$, —$SR^7$, halogen, —$NR^7R^8$, —$NO_2$, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3-to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently 1, 2, 3, 4, 5 or 6; and n is independently 0, 1, 2, 3, 4, 5, 6, 7, 8, 9, or 10.

One aspect of the invention relates to compounds of Formula IV-Z:

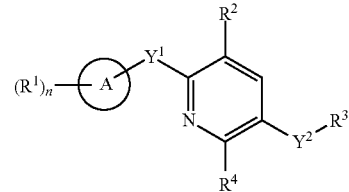

IV-Z or a pharmaceutically acceptable salt, prodrug, solvate, hydrate, tautomer, or isomer thereof, wherein:

A is selected from the group consisting of 5- to 12-membered monocyclic or polycyclic cycloalkyl, heterocycloalkyl, aryl, or heteroaryl;

$Y^1$ is —S—, a direct bond, —NH—, —$S(O)_2$—, —$S(O)_2$—NH—, —$C(=CH_2)$—, —CH—, or —$S(O)$—;

$Y^2$ is selected from the group consisting of: —$NR^a$—, —$(CR^a_2)_m$—, —C(O)—, —$C(R^a)_2NH$—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —$C(O)O$—, —$OC(O)$—, —$OC(O)N(R^a)$—, —$N(R^a)C(O)O$—, —$C(O)N(R^a)O$—, —$N(R^a)C(S)$—, —$C(S)N(R^a)$—, and —$OC(O)O$—; wherein the bond on the left side of $Y^2$, as drawn, is bound to the pyridine ring and the bond on the right side of the $Y^2$ moiety, as drawn, is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R² is independently —OR^b, —CN, —C₁-C₆alkyl, —C₂-C₆alkenyl, —C₄-C₈cycloalkenyl, —C₂-C₆alkynyl, —NH₂, halogen, —C(O)OR^a, —C₃-C₈cycloalkyl, aryl, heterocyclyl containing 1-5 heteroatoms selected from the group consisting of N, S, P, or O, or heteroaryl containing 1-5 heteroatoms selected from the group consisting of N, S, P, or O; wherein each alkyl, alkenyl, cycloalkenyl, alkynyl, cycloalkyl, heterocyclyl, aryl, or heteroaryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl; and wherein the heterocyclyl or heteroaryl is not attached via a nitrogen atom;

R^a is independently, at each occurrence, selected from the group consisting of —H, -D, —OH, —C₃-C₈cycloalkyl, and —C₁-C₆alkyl, wherein each alkyl or cycloalkyl is optionally substituted with one or more —NH₂, wherein 2 R^a, together with the carbon atom to which they are both attached, can combine to form a 3- to 8-membered cycloalkyl;

R^b is independently —H, -D, —C₁-C₆alkyl, —C₁-C₆cycloalkyl, —C₂-C₆alkenyl, or heterocyclyl containing 1-5 heteroatoms selected from the group consisting of N, S, P, or O; wherein each alkyl, cycloalkyl, alkenyl, or heterocycle is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, heteroaryl, —(CH₂)ₙOH, —C₁-C₆alkyl, CF₃, CHF₂, or CH₂F;

R³ is independently, at each occurrence, selected from the group consisting of —H, —C₁-C₆alkyl, a 3-to 12-membered monocyclic or polycyclic heterocycle, C₃-C₈cycloalkyl, or —(CH₂)ₙ—R^b, wherein each alkyl, heterocycle, or cycloalkyl is optionally substituted with one or more —C₁-C₆alkyl, —OH, —NH₂, —OR^a, —NHR^a, —(CH₂)ₙOH, heterocyclyl, or spiroheterocyclyl; or R³ can combine with R^a to form a 3-to 12-membered monocyclic or polycyclic heterocycle, or a 5-to 12-membered spiroheterocycle, wherein each heterocycle or spiroheterocycle is optionally substituted with —C₁-C₆alkyl, —OH, —NH₂, heteroaryl, heterocyclyl, —(CH₂)ₙNH₂, —COOR^a, —CONHR^b, —CONH(CH₂)ₙCOOR^a, —NHCOOR^a, —CF₃, CHF₂, or CH₂F;

R⁴ is independently, at each occurrence, —H, -D, —C₁-C₆alkyl, —NH—NHR⁵, —NH—OR⁵, —O—NR⁵R⁶, —NHR⁵, —OR⁵, —NHC(O)R⁵, —NHC(O)NHR⁵, —NHS(O)₂R⁵, —NHS(O)₂NHR⁵, —S(O)₂OH, —C(O)OR⁵, —NH(CH₂)ₙOH, —C(O)NH(CH₂)ₙOH, —C(O)NH(CH₂)ₙR^b, —C(O)R^b, NH₂, —OH, —CN, —C(O)NR⁵R⁶, —S(O)₂NR⁵R⁶, C₃-C₈cycloalkyl, aryl, heterocyclyl containing 1-5 heteroatoms selected from the group consisting of N, S, P, or O, heteroaryl containing 1-5 heteroatoms selected from the group consisting of N, S, P, or O, wherein each alkyl, cycloalkyl, or heterocyclyl is optionally substituted with one or more —OH, —NH₂, halogen, or oxo; wherein each aryl or heteroaryl is optionally substituted with one or more —OH, —NH₂, or halogen; or R^a and R⁴, together with the atom or atoms to which they are attached, can combine to form a monocyclic or polycyclic C₃-C₁₂cycloalkyl, or a monocyclic or polycyclic 3-to 12-membered heterocycle, wherein the cycloalkyl or heterocycle is optionally substituted with oxo; wherein the heterocycle optionally comprises —S(O)₂— in the heterocycle;

R⁵ and R⁶ are each independently, at each occurrence, selected from the group consisting of —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3-to 12-membered heterocycle, —OR⁷, —SR⁷, halogen, —NR⁷R⁸, —NO₂, and —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3-to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

m is independently 1, 2, 3, 4, 5 or 6; and n is independently 0, 1, 2, 3, 4, 5, 6, 7, 8, 9, or 10.

One aspect of the invention relates to compounds of Formula VII:

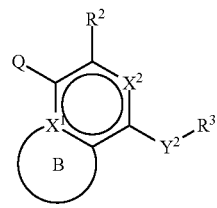

VII and pharmaceutically acceptable salts, prodrugs, solvates, hydrates, tautomers, or isomers thereof, wherein:

Q is H or

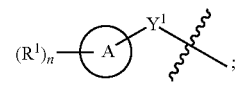

;

A is selected from the group consisting of 5- to 12-membered monocyclic or polycyclic cycloalkyl, heterocycloalkyl, aryl, or heteroaryl;

R¹ is independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, —OH, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, or —CO₂R⁵, wherein each alkyl, alkenyl, cycloalkenyl, alkynyl, or cycloalkyl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

Y¹ is —S—, a direct bond, —NH—, —S(O)₂—, —S(O)₂—NH—, —C(=CH₂)—, —CH—, or —S(O)—;

X¹ is N or C;

X² is N or CH;

B, including the atoms at the points of attachment, is a monocyclic or polycyclic 5-to 12-membered heterocycle or a monocyclic or polycyclic 5-to 12-membered heteroaryl;

R² is independently H, —OR^b, —NR⁵R⁶, —CN, —C₁-C₆alkyl, —C₂-C₆alkenyl, —C₄-C₈cycloalkenyl, —C₂-

C$_6$alkynyl, —NH$_2$, halogen, —C(O)OR$^a$, —C$_3$-C$_8$cycloalkyl, heterocyclyl containing 1-5 heteroatoms selected from the group consisting of N, S, P, or O, or heteroaryl containing 1-5 heteroatoms selected from the group consisting of N, S, P, or O; wherein each alkyl, alkenyl, cycloalkenyl, alkynyl, cycloalkyl, heterocyclyl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

Y$^2$ is selected from the group consisting of: —NR$^a$—, —(CR$^a$$_2$)$_m$—, —C(O)—, —C(R$^a$)$_2$NH—, —(CR$^a$$_2$)$_n$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, and —OC(O)O—; wherein the bond on the left side of Y$^2$, as drawn, is bound to the ring and the bond on the right side of the Y$^2$ moiety, as drawn, is bound to R$^3$;

R$^a$ is independently, at each occurrence, selected from the group consisting of —H, -D, —OH, —C$_3$-C$_8$cycloalkyl, and —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^b$ is independently —H, -D, —C$_1$-C$_6$alkyl, —C$_1$-C$_6$cycloalkyl, —C$_2$-C$_6$alkenyl, or heterocyclyl containing 1-5 heteroatoms selected from the group consisting of N, S, P, or O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, heteroaryl, —(CH$_2$)$_n$OH, —C$_1$-C$_6$alkyl, CF$_3$, CHF$_2$, or CH$_2$F;

R$^3$ is independently, at each occurrence, selected from the group consisting of —H, —C$_1$-C$_6$alkyl, a 3-to 12-membered monocyclic or polycyclic heterocycle, C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^a$, —NHR$^a$, —(CH$_2$)$_n$OH, heterocyclyl, or spiroheterocyclyl; or R$^3$ can combine with R$^a$ to form a 3-to 12-membered monocyclic or polycyclic heterocycle, or a 5-to 12-membered spiroheterocycle, wherein each heterocycle or spiroheterocycle is optionally substituted with —C$_1$-C$_6$alkyl, —OH, —NH$_2$, heteroaryl, heterocyclyl, —(CH$_2$)$_n$NH$_2$, —COOR$^a$, —CONHR$^b$, —CONH(CH$_2$)$_n$COOR$^a$, —NHCOOR$^a$, —CF$_3$, CHF$_2$, or CH$_2$F;

R$^5$ and R$^6$ are each independently, at each occurrence, selected from the group consisting of —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3-to 12-membered heterocycle, —OR$^7$, —SR$^7$, halogen, —NR$^7$R$^8$, —NO$_2$, and —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3-to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently 1, 2, 3, 4, 5 or 6; and n is independently 0, 1, 2, 3, 4, 5, 6, 7, 8, 9, or 10.

Another aspect of the invention relates to compounds of Formula VIII:

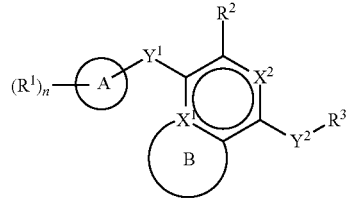

VIII and pharmaceutically acceptable salts, prodrugs, solvates, hydrates, tautomers, or isomers thereof, wherein:

A is selected from the group consisting of 5- to 12-membered monocyclic or polycyclic cycloalkyl, heterocycloalkyl, aryl, or heteroaryl;

R$^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

Y$^1$ is —S—, a direct bond, —NH—, —S(O)$_2$—, —S(O)$_2$—NH—, —C(=CH$_2$)—, —CH—, or —S(O)—;

X$^1$ is N or C;

X$^2$ is N or CH;

B, including the atoms at the points of attachment, is a monocyclic or polycyclic 5-to 12-membered heterocycle or a monocyclic or polycyclic 5-to 12-membered heteroaryl;

R$^2$ is independently H, —OR$^b$, —NR$^5$R$^6$, —CN, —C$_1$-C$_6$alkyl, —C$_2$-C$_6$alkenyl, —C$_4$-C$_8$cycloalkenyl, —C$_2$-C$_6$alkynyl, —NH$_2$, halogen, —C(O)OR$^a$, —C$_3$-C$_8$cycloalkyl, heterocyclyl containing 1-5 heteroatoms selected from the group consisting of N, S, P, or O, or heteroaryl containing 1-5 heteroatoms selected from the group consisting of N, S, P, or O; wherein each alkyl, alkenyl, cycloalkenyl, alkynyl, cycloalkyl, heterocyclyl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

Y$^2$ is selected from the group consisting of: —NR$^a$—, —(CR$^a$$_2$)$_m$—, —C(O)—, —C(R$^a$)$_2$NH—, —(CR$^a$$_2$)$_n$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, and —OC(O)O—; wherein the bond on the left side of Y$^2$, as drawn, is bound to the ring and the bond on the right side of the Y$^2$ moiety, as drawn, is bound to R$^3$;

R$^a$ is independently, at each occurrence, selected from the group consisting of —H, -D, —OH, —C$_3$-C$_8$cycloalkyl, and —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

$R^b$ is independently —H, -D, —$C_1$-$C_6$alkyl, —$C_1$-$C_6$cycloalkyl, —$C_2$-$C_6$alkenyl, or heterocyclyl containing 1-5 heteroatoms selected from the group consisting of N, S, P, or O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, heteroaryl, —$(CH_2)_nOH$, —$C_1$-$C_6$alkyl, $CF_3$, $CHF_2$, or $CH_2F$;

$R^3$ is independently, at each occurrence, selected from the group consisting of —H, —$C_1$-$C_6$alkyl, a 3- to 12-membered monocyclic or polycyclic heterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^a$, —$NHR^a$, —$(CH_2)_nOH$, heterocyclyl, or spiroheterocyclyl; or $R^3$ can combine with $R^a$ to form a 3- to 12-membered monocyclic or polycyclic heterocycle, or a 5- to 12-membered spiroheterocycle, wherein each heterocycle or spiroheterocycle is optionally substituted with —$C_1$-$C_6$alkyl, —OH, —$NH_2$, heteroaryl, heterocyclyl, —$(CH_2)_nNH_2$, —$COOR^a$, —$CONHR^b$, —$CONH(CH_2)_nCOOR^a$, —$NHCOOR^a$, —$CF_3$, $CHF_2$, or $CH_2F$;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently 1, 2, 3, 4, 5 or 6; and n is independently 0, 1, 2, 3, 4, 5, 6, 7, 8, 9, or 10.

Another aspect of the invention relates to compounds of Formula IX:

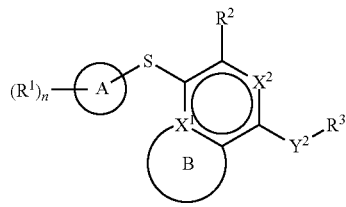

IX and pharmaceutically acceptable salts, prodrugs, solvates, hydrates, tautomers, or isomers thereof, wherein:

A is selected from the group consisting of 5- to 12-membered monocyclic or polycyclic cycloalkyl, heterocycloalkyl, aryl, or heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$X^1$ is N or C;

$X^2$ is N or CH;

B, including the atoms at the points of attachment, is a monocyclic or polycyclic 5- to 12-membered heterocycle or a monocyclic or polycyclic 5- to 12-membered heteroaryl;

$R^2$ is independently H, —$OR^b$, —$NR^5R^6$, —CN, —$C_1$-$C_6$alkyl, —$C_2$-$C_6$alkenyl, —$C_4$-$C_8$cycloalkenyl, —$C_2$-$C_6$alkynyl, —$NH_2$, halogen, —$C(O)OR^a$, —$C_3$-$C_8$cycloalkyl, aryl, heterocyclyl containing 1-5 heteroatoms selected from the group consisting of N, S, P, or O, or heteroaryl containing 1-5 heteroatoms selected from the group consisting of N, S, P, or O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$Y^2$ is selected from the group consisting of: —$NR^a$—, —$(CR^a_2)_m$—, —$C(O)$—, —$C(R^a)_2NH$—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —$C(O)O$—, —$OC(O)$—, —$OC(O)N(R^a)$—, —$N(R^a)C(O)O$—, —$C(O)N(R^a)O$—, —$N(R^a)C(S)$—, —$C(S)N(R^a)$—, and —$OC(O)O$—; wherein the bond on the left side of $Y^2$, as drawn, is bound to the ring and the bond on the right side of the $Y^2$ moiety, as drawn, is bound to $R^3$;

$R^a$ is independently, at each occurrence, selected from the group consisting of —H, -D, —OH, —$C_3$-$C_8$cycloalkyl, and —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently —H, -D, —$C_1$-$C_6$alkyl, —$C_1$-$C_6$cycloalkyl, —$C_2$-$C_6$alkenyl, or heterocyclyl containing 1-5 heteroatoms selected from the group consisting of N, S, P, or O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, heteroaryl, —$(CH_2)_nOH$, —$C_1$-$C_6$alkyl, $CF_3$, $CHF_2$, or $CH_2F$;

$R^3$ is independently, at each occurrence, selected from the group consisting of —H, —$C_1$-$C_6$alkyl, a 3- to 12-membered monocyclic or polycyclic heterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^a$, —$NHR^a$, —$(CH_2)_nOH$, heterocyclyl, or spiroheterocyclyl; or $R^3$ can combine with $R^a$ to form a 3- to 12-membered monocyclic or polycyclic heterocycle, or a 5- to 12-membered spiroheterocycle, wherein each heterocycle or spiroheterocycle is optionally substituted with —$C_1$-$C_6$alkyl, —OH, —$NH_2$, heteroaryl, heterocyclyl, —$(CH_2)_nNH_2$, —$COOR^a$, —$CONHR^b$, —$CONH(CH_2)_nCOOR^a$, —$NHCOOR^a$, —$CF_3$, $CHF_2$, or $CH_2F$;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3-to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently 1, 2, 3, 4, 5 or 6; and n is independently 0, 1, 2, 3, 4, 5, 6, 7, 8, 9, or 10.

Another aspect of the invention relates to compounds of Formula X:

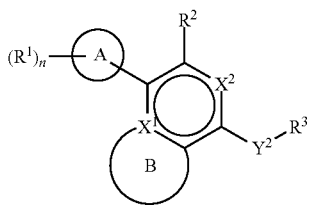

X and pharmaceutically acceptable salts, prodrugs, solvates, hydrates, tautomers, or isomers thereof, wherein:

A is selected from the group consisting of 5- to 12-membered monocyclic or polycyclic cycloalkyl, heterocycloalkyl, aryl, or heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5$—$S(O)NR^5R^6$, —$NR^5S(O)R^6$, heterocycle, aryl, or heteroaryl;

$X^1$ is N or C;

$X^2$ is N or CH;

B, including the atoms at the points of attachment, is a monocyclic or polycyclic 5-to 12-membered heterocycle or a monocyclic or polycyclic 5-to 12-membered heteroaryl;

$R^2$ is independently H, —$OR^b$, —$NR^5R^6$, —CN, —$C_1$-$C_6$alkyl, —$C_2$-$C_6$alkenyl, —$C_4$-$C_8$cycloalkenyl, —$C_2$-$C_6$alkynyl, —$NH_2$, halogen, —$C(O)OR^a$, —$C_3$-$C_8$cycloalkyl, heterocyclyl containing 1-5 heteroatoms selected from the group consisting of N, S, P, or O, or heteroaryl containing 1-5 heteroatoms selected from the group consisting of N, S, P, or O; wherein each alkyl, alkenyl, cycloalkenyl, alkynyl, cycloalkyl, heterocyclyl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$Y^2$ is selected from the group consisting of: —$NR^a$—, —$(CR^a_2)_m$—, —C(O)—, —$C(R^a)_2NH$—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —$OC(O)N(R^a)$—, —$N(R^a)C(O)O$—, —$C(O)N(R^a)O$—, —$N(R^a)C(S)$—, —$C(S)N(R^a)$—, and —OC(O)O—; wherein the bond on the left side of $Y^2$, as drawn, is bound to the ring and the bond on the right side of the $Y^2$ moiety, as drawn, is bound to $R^3$;

$R^a$ is independently, at each occurrence, selected from the group consisting of —H, -D, —OH, —$C_3$-$C_8$cycloalkyl, and —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently —H, -D, —$C_1$-$C_6$alkyl, —$C_1$-$C_6$cycloalkyl, —$C_2$-$C_6$alkenyl, or heterocyclyl containing 1-5 heteroatoms selected from the group consisting of N, S, P, or O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, heteroaryl, —$(CH_2)_nOH$, —$C_1$-$C_6$alkyl, $CF_3$, $CHF_2$, or $CH_2F$;

$R^3$ is independently, at each occurrence, selected from the group consisting of —H, —$C_1$-$C_6$alkyl, a 3-to 12-membered monocyclic or polycyclic heterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^a$, —$NHR^a$, —$(CH_2)_nOH$, heterocyclyl, or spiroheterocyclyl; or $R^3$ can combine with $R^a$ to form a 3-to 12-membered monocyclic or polycyclic heterocycle, or a 5-to 12-membered spiroheterocycle, wherein each heterocycle or spiroheterocycle is optionally substituted with —$C_1$-$C_6$alkyl, —OH, —$NH_2$, heteroaryl, heterocyclyl, —$(CH_2)_nNH_2$, —$COOR^a$, —$CONHR^b$, —$CONH(CH_2)_nCOOR^a$, —$NHCOOR^a$, —$CF_3$, $CHF_2$, or $CH_2F$;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3-to 12-membered heterocycle, —$OR^7$, —$SR^7$, halogen, —$NR^7R^8$, —$NO_2$, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3-to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently 1, 2, 3, 4, 5 or 6; and n is independently 0, 1, 2, 3, 4, 5, 6, 7, 8, 9, or 10.

Another aspect of the present disclosure relates to compounds, and pharmaceutically acceptable salts, prodrugs, solvates, hydrates, tautomers, or isomers thereof, in Table 1.

TABLE 1

| Cmpd # | Structure |
|---|---|
| 1 | 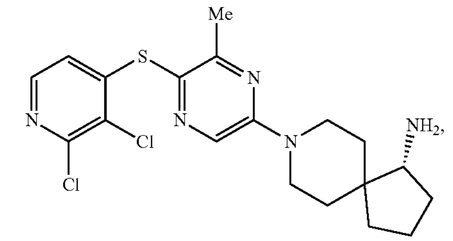 |
| 2 | 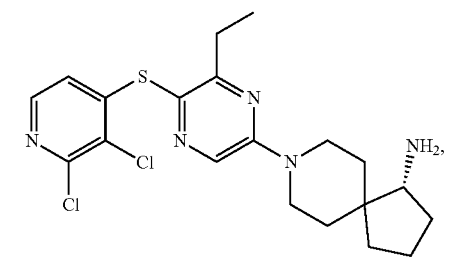 [SMILES: CCc1nc(N2CCC3(CCC[C@H]3N)CC2)cnc1Sc1ccnc(Cl)c1Cl] |
| 3 | 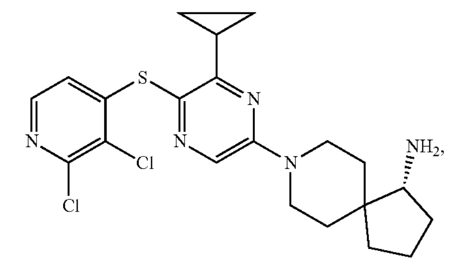 [SMILES: N[C@@H]1CCCC12CCN(c1cnc(Sc3ccnc(Cl)c3Cl)c(C3CC3)n1)CC2] |
| 4 | 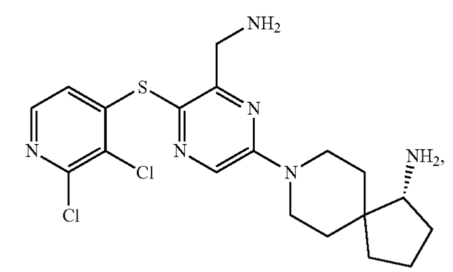 [SMILES: NCc1nc(N2CCC3(CCC[C@H]3N)CC2)cnc1Sc1ccnc(Cl)c1Cl] |
| 5 | 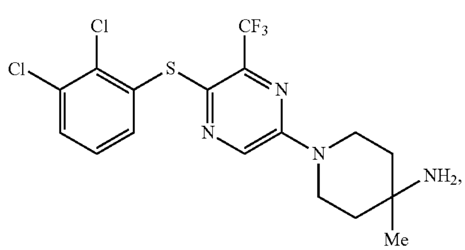 |
| 6 | 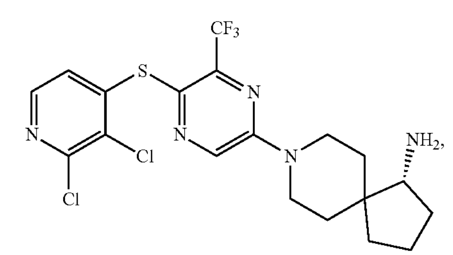 [SMILES: N[C@@H]1CCCC12CCN(c1cnc(Sc3ccnc(Cl)c3Cl)c(C(F)(F)F)n1)CC2] |
| 7 | |
| 8 | |
| 9 | |
| 10 | |
| 11 | |
| 12 | |

TABLE 1-continued

| Cmpd # | Structure |
|---|---|
| 13 | 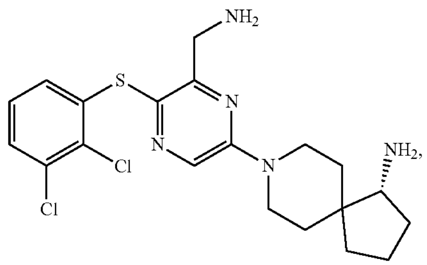 [SMILES: NCc1nc(N2CCC3(CCC[C@H]3N)CC2)cnc1Sc1cccc(Cl)c1Cl] |
| 14 | 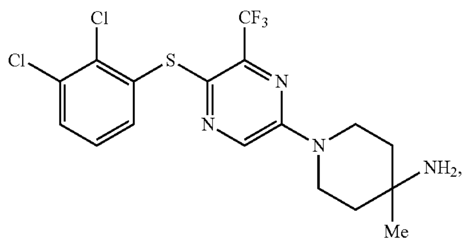 [SMILES: CC1(N)CCN(c2cnc(Sc3cccc(Cl)c3Cl)c(C(F)(F)F)n2)CC1] |
| 15 | 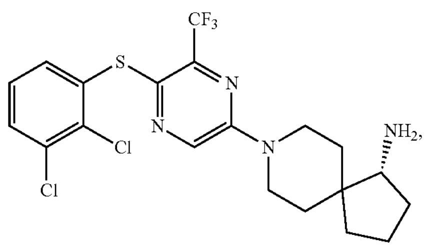 |
| 16 | 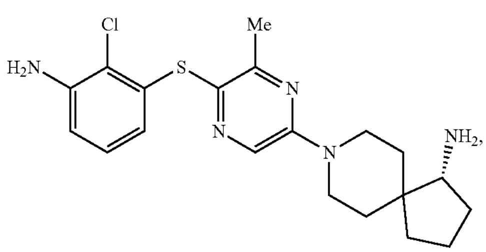 [SMILES: Cc1nc(N2CCC3(CCC[C@H]3N)CC2)cnc1Sc1cccc(N)c1Cl] |
| 17 | 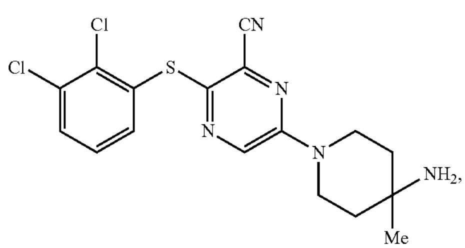 [SMILES: CC1(N)CCN(c2cnc(Sc3cccc(Cl)c3Cl)c(C#N)n2)CC1] |
| 18 | 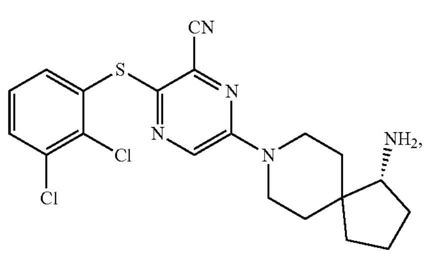 [SMILES: N#Cc1nc(N2CCC3(CCC[C@H]3N)CC2)cnc1Sc1cccc(Cl)c1Cl] |
| 19 | |
| 20 | |
| 21 | |
| 22 | |
| 23 | |
| 24 | |

TABLE 1-continued

| Cmpd # | Structure |
|---|---|
| 25 | (structure) |
| 26 | (structure) |
| 27 | (structure) |
| 28 | (structure) |
| 29 | (structure) |
| 30 | (structure) |
| 31 | (structure) |
| 32 | (structure) |
| 33 | (structure) |
| 34 | (structure) |
| 35 | (structure) |
| 36 | (structure) |

TABLE 1-continued
| Cmpd # | Structure |
|---|---|
| 37 | 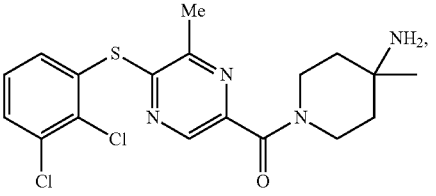 [SMILES: Cc1nc(C(=O)N2CCC(C)(N)CC2)cnc1Sc1cccc(Cl)c1Cl] |
| 38 | 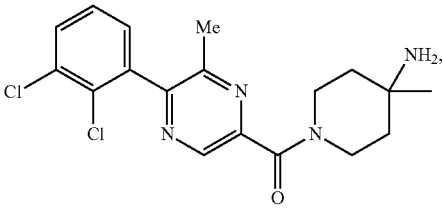 [SMILES: Cc1nc(C(=O)N2CCC(C)(N)CC2)cnc1-c1cccc(Cl)c1Cl] |
| 39 | 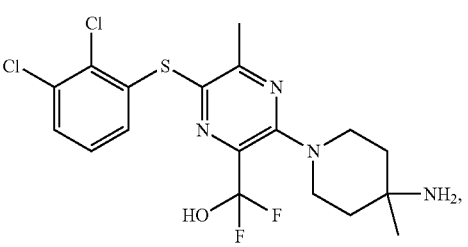 [SMILES: Cc1nc(N2CCC(C)(N)CC2)c(C(O)(F)F)nc1Sc1cccc(Cl)c1Cl] |
| 40 | 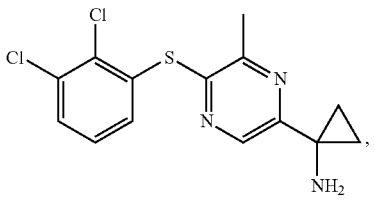 [SMILES: Cc1nc(C2(N)CC2)cnc1Sc1cccc(Cl)c1Cl] |
| 41 | 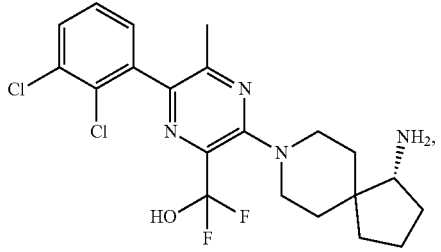 [SMILES: Cc1nc(N2CCC3(CCC[C@H]3N)CC2)c(C(O)(F)F)nc1-c1cccc(Cl)c1Cl] |
| A-1 | 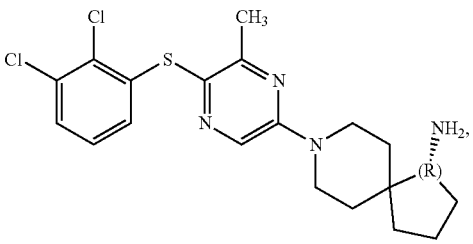 |
| A-2 | 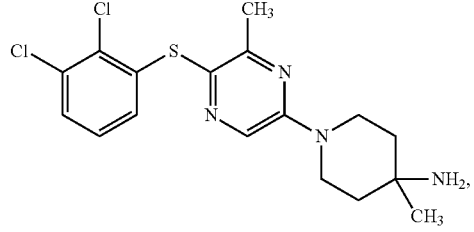 [SMILES: Cc1nc(N2CCC(C)(N)CC2)cnc1Sc1cccc(Cl)c1Cl] |
| A-3 | 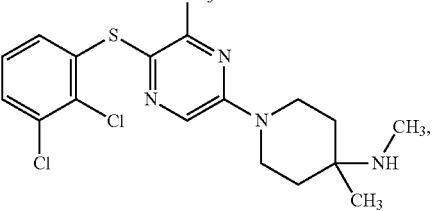 |
| A-4 | 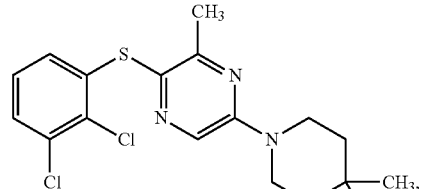 |
| A-5 | 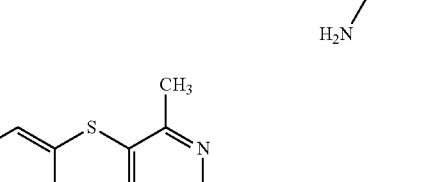 |
| A-6 | 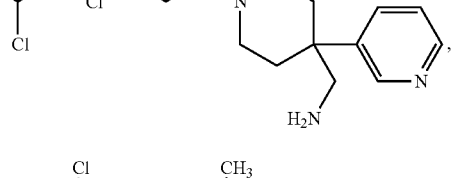 |
| A-7 | 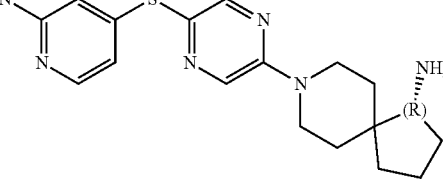 |

TABLE 1-continued

| Cmpd # | Structure |
|---|---|
| A-8 | (structure) |
| A-9 | (structure) |
| A-10 | (structure) |
| A-11 | (structure) |
| A-12 | (structure) |
| A-13 | (structure) |
| A-14 | (structure) |
| A-15 | (structure) |
| A-16 | (structure) |
| A-17 | (structure) |
| A-18 | (structure) |

TABLE 1-continued

| Cmpd # | Structure |
|---|---|
| A-19 | [structure: 2,3-dichlorophenyl-S-pyrazine(CN)-piperidine-4-NH2,4-CH3] |
| A-20 | [structure: 2,3-dichlorophenyl-S-pyrazine(CN)-(R)-2-amino-8-azaspiro[4.5]decane] |
| A-21 | [structure: 2,3-dichlorophenyl-S-pyrazine(OH)-(R)-2-amino-8-azaspiro[4.5]decane] |
| A-22 | [structure: 2,3-dichlorophenyl-S-pyrazine(OH)-piperidine-4-CH3,4-NH2] |
| A-23 | [structure: 2,3-dichlorophenyl-pyrazine(CH3)-(R)-2-amino-8-azaspiro[4.5]decane] |
| A-24 | [structure: 2,3-dichlorophenyl-pyrazine(CH3)-piperidine-4-NH2,4-CH3] |
| A-25 | [structure: 2,3-dichlorophenyl-pyrazine(CH3)-azetidine-3-NH2,3-CH3] |
| A-26 | [structure: 2,3-dichlorophenyl-pyrazine(CN)-piperidine-4-NH2,4-CH3] |
| A-27 | [structure: 2,3-dichlorophenyl-pyrazine(CN)-(R)-2-amino-8-azaspiro[4.5]decane] |
| A-28 | [structure: 2,3-dichlorophenyl-pyrazine(CH3)-piperidine-4-CH3,4-CH2NH2] |
| A-29 | [structure: 2,3-dichlorophenyl-pyrazine(CH3)(OH)-(R)-2-amino-8-azaspiro[4.5]decane] |
| A-30 | [structure: 2,3-dichlorophenyl-pyrazine(CH3)(CONH2)-(R)-2-amino-8-azaspiro[4.5]decane] |

TABLE 1-continued

| Cmpd # | Structure |
|---|---|
| A-31 | (structure) |
| A-32 | (structure) |
| A-33 | (structure) |
| A-34 | (structure) |
| A-35 | (structure) |
| A-36 | (structure) |
| A-37 | (structure) |
| A-38 | (structure) |
| A-39 | (structure) |
| A-40 | (structure) |
| A-41 | (structure) |

TABLE 1-continued
| Cmpd # | Structure |
|---|---|
| A-42 | 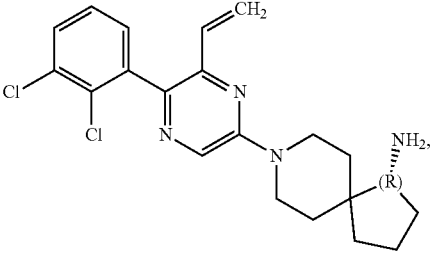 |
| A-43 | 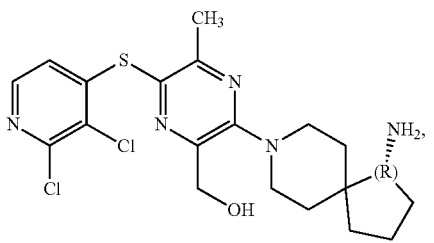 |
| A-44 | 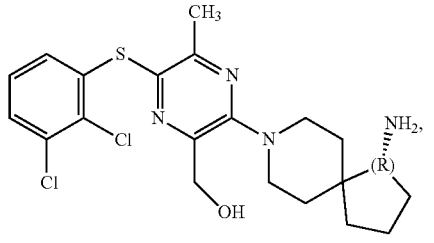 |
| A-45 | 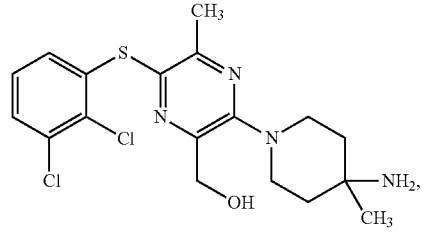 [SMILES: Cc1nc(N2CCC(C)(N)CC2)c(CO)nc1Sc1cccc(Cl)c1Cl] |
| A-46 | 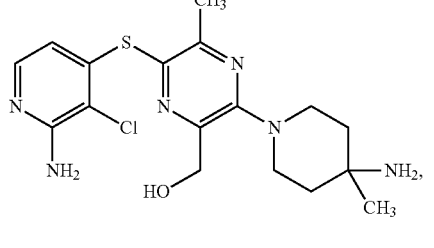 |
| A-47 | 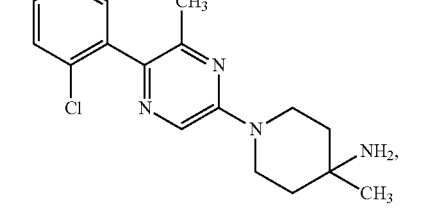 |
| A-48 | 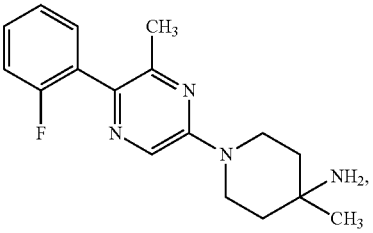 [SMILES: Cc1nc(N2CCC(C)(N)CC2)cnc1-c1ccccc1F] |
| A-49 | 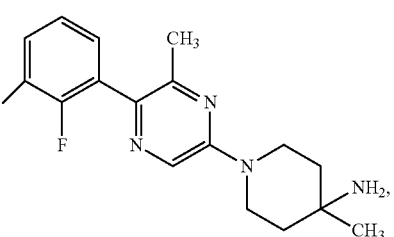 |
| A-50 | 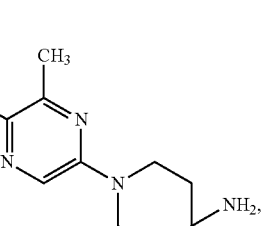 |
| A-51 | 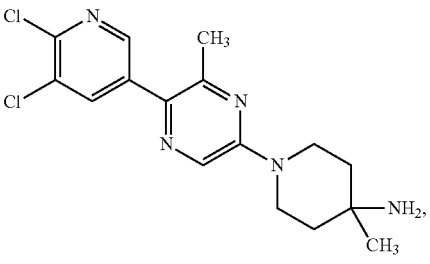 [SMILES: Cc1nc(N2CCC(C)(N)CC2)cnc1-c1cnc(Cl)c(Cl)c1] |
| A-52 | 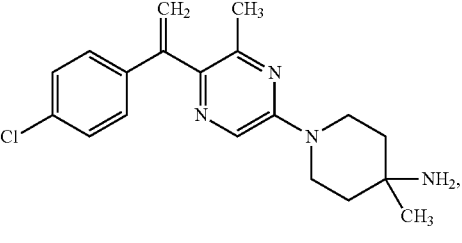 [SMILES: C=C(c1ccc(Cl)cc1)c1ncc(N2CCC(C)(N)CC2)nc1C] |
| A-53 | 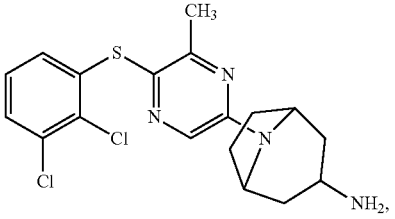 [SMILES: Cc1nc(N2C3CCC2CC(N)C3)cnc1Sc1cccc(Cl)c1Cl] |

TABLE 1-continued

| Cmpd # | Structure |
|---|---|
| A-54 | (structure) |
| A-55 | (structure) |
| A-56 | (structure) |
| A-57 | (structure) |
| A-58 | (structure) |
| A-59 | (structure) |
| A-60 | (structure) |
| A-61 | (structure) |
| A-62 | (structure) |
| A-63 | (structure) |
| A-64 | (structure) |
| A-65 | (structure) |
| A-66 | (structure) |
| A-67 | (structure) |

TABLE 1-continued

| Cmpd # | Structure |
|---|---|
| A-68 | *(structure)* |
| A-69 | *(structure)* |
| A-70 | *(structure)* |
| A-71 | *(structure)* |
| A-72 | *(structure)* |
| A-73 | *(structure)* |
| A-74 | *(structure)* |
| A-75 | *(structure)* |
| A-76 | *(structure)* |
| A-77 | *(structure)* |
| A-78 | *(structure)* |
| A-79 | *(structure)* |

TABLE 1-continued

| Cmpd # | Structure |
|---|---|
| A-80 | (structure) |
| A-81 | (structure) |
| A-82 | (structure) |
| A-83 | (structure) |
| A-84 | (structure) |
| A-85 | (structure) |
| A-86 | (structure) |
| A-87 | (structure) |
| A-88 | (structure) |
| A-89 | (structure) |

TABLE 1-continued

| Cmpd # | Structure |
|---|---|
| A-90 | [structure] |
| A-91 | [structure] |
| A-92 | [structure] |
| A-93 | [structure] |
| A-94 | [structure] |
| A-95 | [structure] |
| A-96 | [structure] |
| A-97 | [structure] |
| A-98 | [structure] |
| A-99 | [structure] |

TABLE 1-continued

| Cmpd # | Structure |
|---|---|
| A-100 | 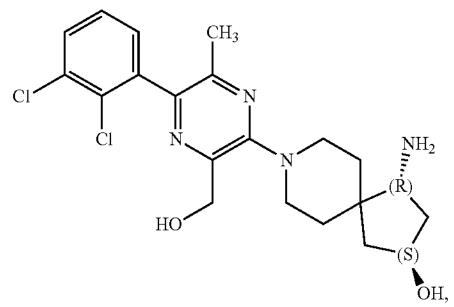 |
| A-101 | 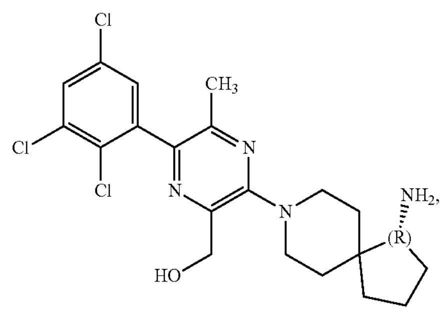 |
| A-102 | 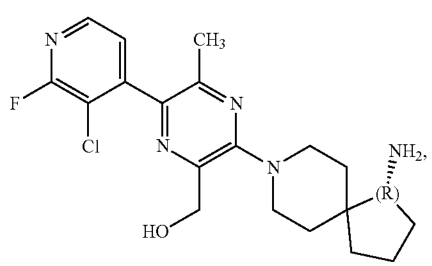 |
| A-103 | 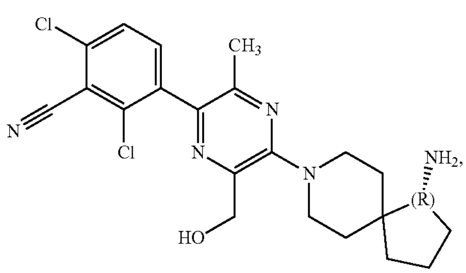 |
| A-104 | 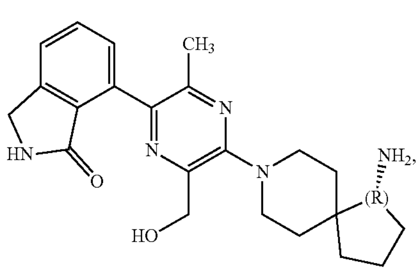 |
| A-105 | |
| A-106 | |
| A-107 | |
| A-108 | |
| A-109 | |

TABLE 1-continued

| Cmpd # | Structure |
|---|---|
| A-110 | 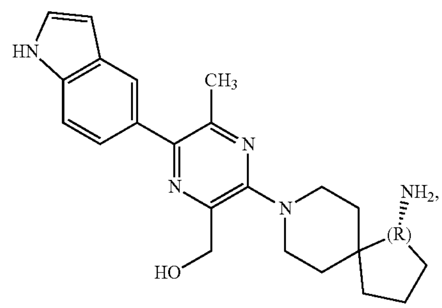 |
| A-111 | 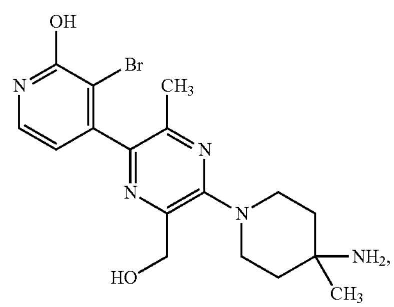 [SMILES: Cc1nc(N2CCC(C)(N)CC2)c(CO)nc1-c1ccnc(O)c1Br] |
| A-112 | 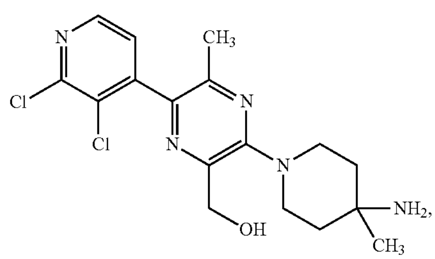 [SMILES: Cc1nc(N2CCC(C)(N)CC2)c(CO)nc1-c1ccnc(Cl)c1Cl] |
| A-113 | 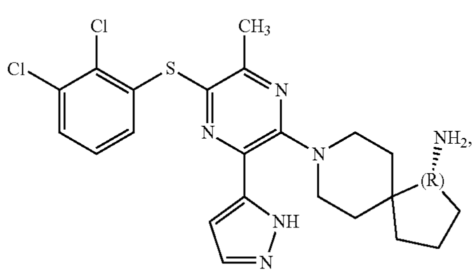 |
| A-114 | 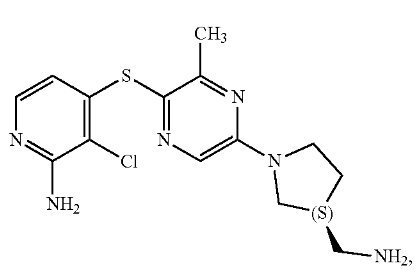 |
| A-115 | 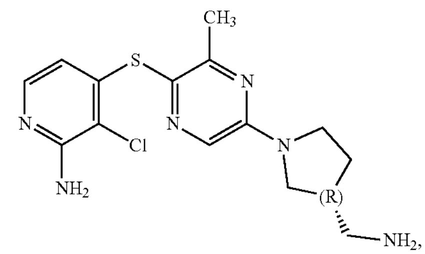 |
| A-116 | 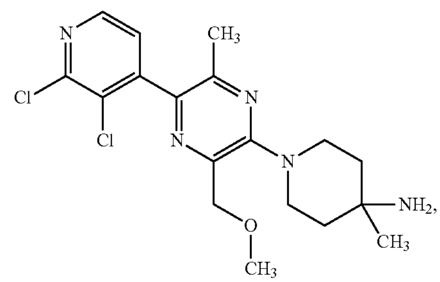 [SMILES: COCc1nc(-c2ccnc(Cl)c2Cl)c(C)nc1N1CCC(C)(N)CC1] |
| A-117 | 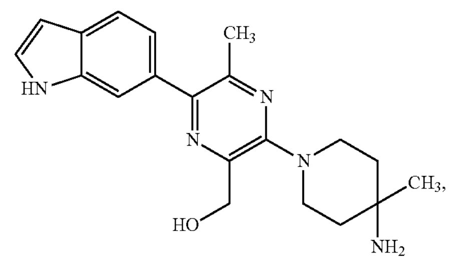 [SMILES: Cc1nc(N2CCC(C)(N)CC2)c(CO)nc1-c1ccc2cc[nH]c2c1] |
| A-118 | 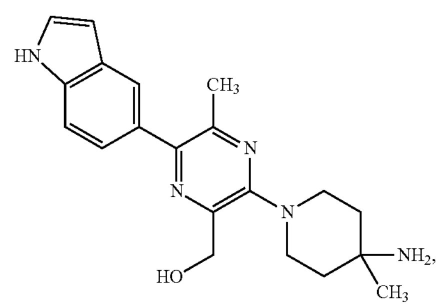 [SMILES: Cc1nc(N2CCC(C)(N)CC2)c(CO)nc1-c1ccc2[nH]ccc2c1] |
| A-119 | 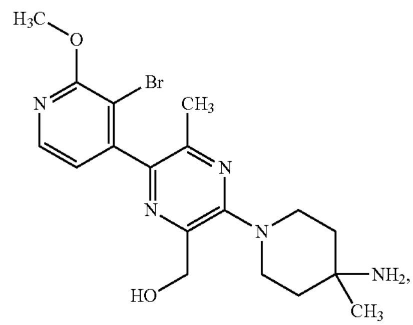 [SMILES: COc1nccc(-c2nc(CO)c(N3CCC(C)(N)CC3)nc2C)c1Br] |

TABLE 1-continued

| Cmpd # | Structure |
|---|---|
| A-120 | [structure] |
| A-121 | [structure] |
| A-122 | [structure] |
| A-123 | [structure] |
| A-124 | [structure] |
| A-125 | [structure] |
| A-126 | [structure] |
| A-127 | [structure] |
| A-128 | [structure] |
| A-129 | [structure] |
| A-130 | [structure] |

TABLE 1-continued

| Cmpd # | Structure |
|---|---|
| A-131 | 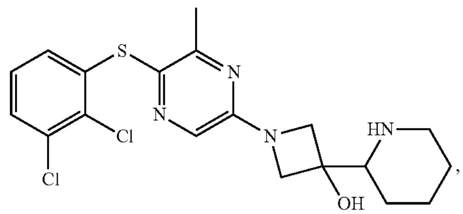 [SMILES: Cc1nc(N2CC(O)(C3CCCCN3)C2)cnc1Sc1cccc(Cl)c1Cl] |
| A-132 | 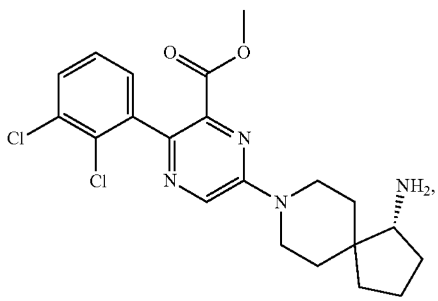 [SMILES: COC(=O)c1nc(N2CCC3(CCC[C@H]3N)CC2)cnc1-c1cccc(Cl)c1Cl] |
| A-133 | 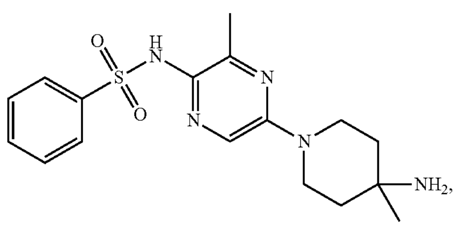 [SMILES: Cc1nc(N2CCC(C)(N)CC2)cnc1NS(=O)(=O)c1ccccc1] |
| A-134 | 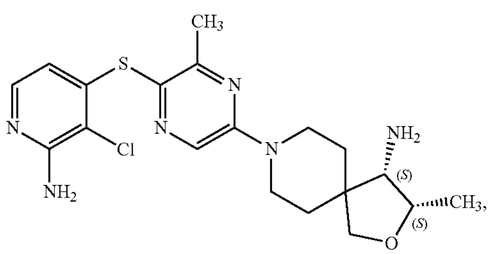 |
| A-135 | 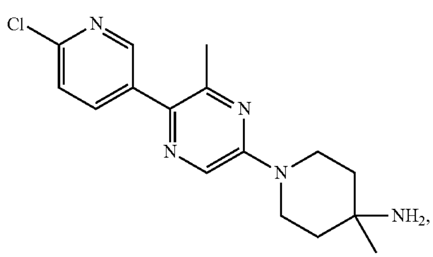 [SMILES: Cc1nc(N2CCC(C)(N)CC2)cnc1-c1ccc(Cl)nc1] |
| A-136 | 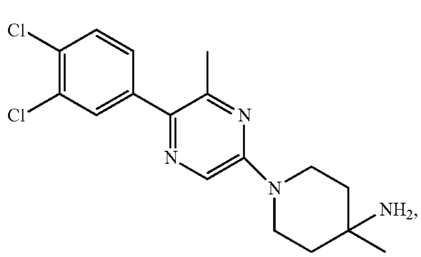 [SMILES: Cc1nc(N2CCC(C)(N)CC2)cnc1-c1ccc(Cl)c(Cl)c1] |
| A-137 | 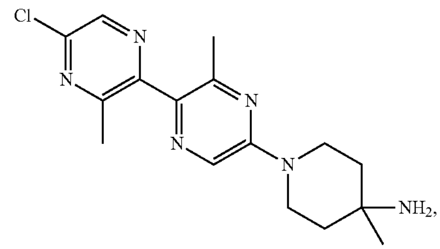 [SMILES: Cc1nc(Cl)cnc1-c1ncc(N2CCC(C)(N)CC2)nc1C] |
| A-138 | 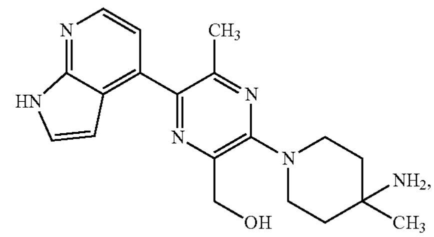 [SMILES: Cc1nc(N2CCC(C)(N)CC2)c(CO)nc1-c1ccnc2[nH]ccc12] |
| A-139 | 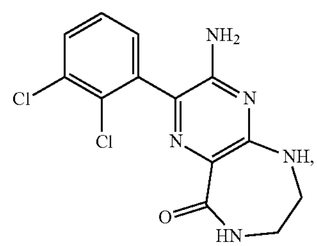 [SMILES: Nc1nc2c(nc1-c1cccc(Cl)c1Cl)C(=O)NCCN2] |
| A-140 | 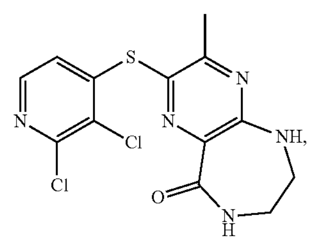 [SMILES: Cc1nc2c(nc1Sc1ccnc(Cl)c1Cl)C(=O)NCCN2] |
| A-141 | 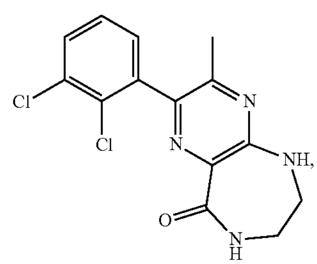 [SMILES: Cc1nc2c(nc1-c1cccc(Cl)c1Cl)C(=O)NCCN2] |
| A-142 | 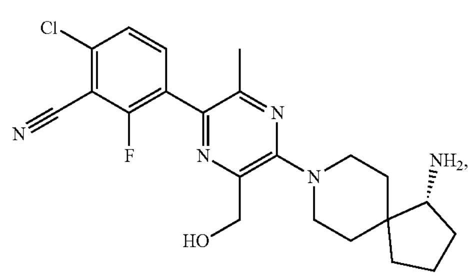 [SMILES: Cc1nc(N2CCC3(CCC[C@H]3N)CC2)c(CO)nc1-c1ccc(Cl)c(C#N)c1F] |

TABLE 1-continued

| Cmpd # | Structure |
|---|---|
| A-143 | 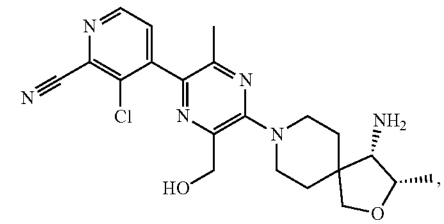 [SMILES: Cc1nc(N2CCC3(CC2)CO[C@@H](C)[C@H]3N)c(CO)nc1-c1ccnc(C#N)c1Cl] |
| A-144 | 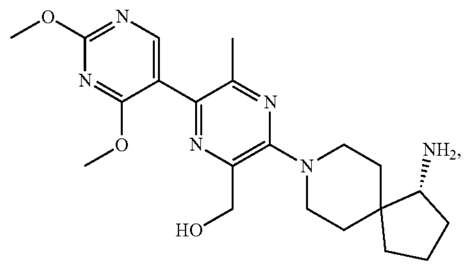 [SMILES: COc1ncc(-c2nc(CO)c(N3CCC4(CCC[C@H]4N)CC3)nc2C)c(OC)n1] |
| A-145 | 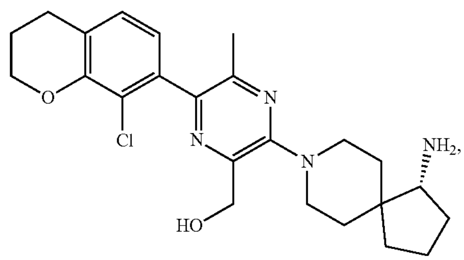 [SMILES: Cc1nc(N2CCC3(CCC[C@H]3N)CC2)c(CO)nc1-c1ccc2c(c1Cl)OCCC2] |
| A-146 | 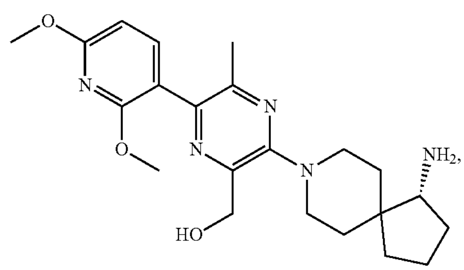 [SMILES: COc1ccc(-c2nc(CO)c(N3CCC4(CCC[C@H]4N)CC3)nc2C)c(OC)n1] |
| A-147 | 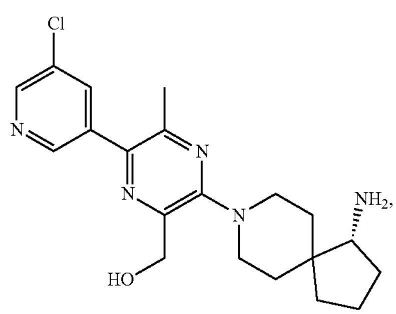 [SMILES: Cc1nc(N2CCC3(CCC[C@H]3N)CC2)c(CO)nc1-c1cncc(Cl)c1] |
| A-148 | 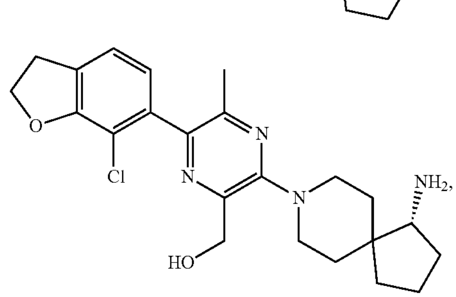 |
| A-149 | |
| A-150 | |
| A-151 | |
| A-152 | |
| A-153 | |

TABLE 1-continued

| Cmpd # | Structure |
|---|---|
| A-154 | |
| A-155 | |
| A-156 | |
| A-157 | |
| A-158 | |
| A-159 | 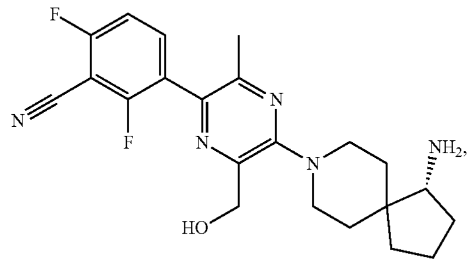 [SMILES: Cc1nc(N2CCC3(CCC[C@H]3N)CC2)c(CO)nc1-c1ccc(F)c(C#N)c1F] |
| A-160 | 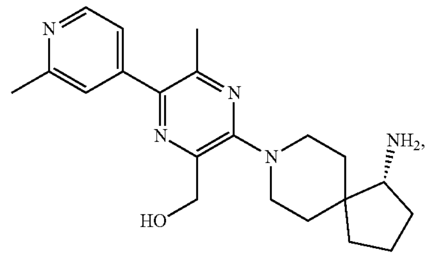 [SMILES: Cc1cc(-c2nc(CO)c(N3CCC4(CCC[C@H]4N)CC3)nc2C)ccn1] |
| A-161 | 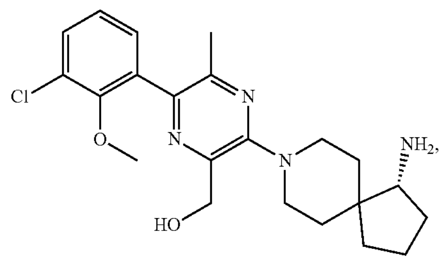 [SMILES: COc1c(Cl)cccc1-c1nc(CO)c(N2CCC3(CCC[C@H]3N)CC2)nc1C] |
| A-162 | 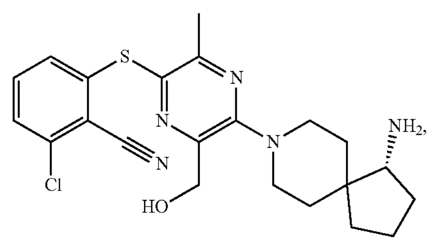 [SMILES: Cc1nc(N2CCC3(CCC[C@H]3N)CC2)c(CO)nc1Sc1cccc(Cl)c1C#N] |
| A-163 | 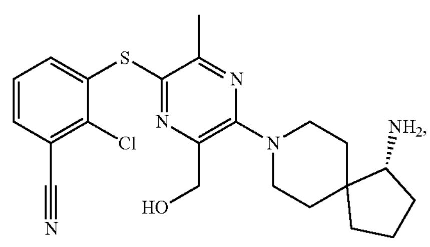 [SMILES: Cc1nc(N2CCC3(CCC[C@H]3N)CC2)c(CO)nc1Sc1cccc(C#N)c1Cl] |
| A-164 | 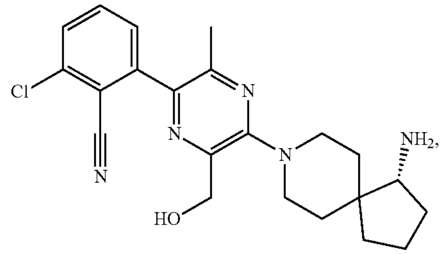 [SMILES: Cc1nc(N2CCC3(CCC[C@H]3N)CC2)c(CO)nc1-c1cccc(Cl)c1C#N] |

TABLE 1-continued
| Cmpd # | Structure |
|---|---|
| A-165 | 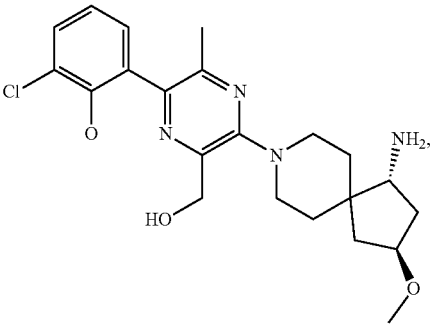 [SMILES: CO[C@@H]1C[C@@H](N)C2(CCN(c3nc(C)c(-c4cccc(Cl)c4O)nc3CO)CC2)C1] |
| A-166 | 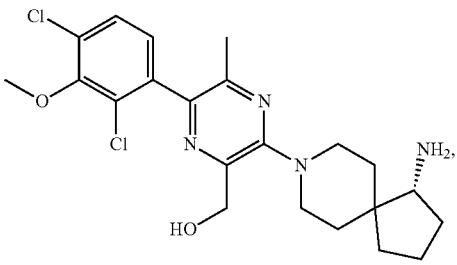 [SMILES: COc1c(Cl)ccc(-c2nc(CO)c(N3CCC4(CCC[C@H]4N)CC3)nc2C)c1Cl] |
| A-167 | 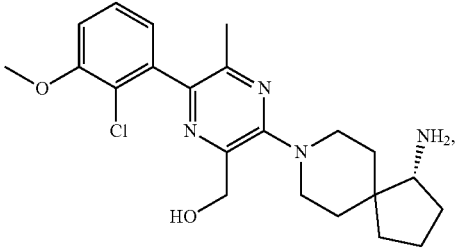 [SMILES: COc1cccc(-c2nc(CO)c(N3CCC4(CCC[C@H]4N)CC3)nc2C)c1Cl] |
| A-168 | 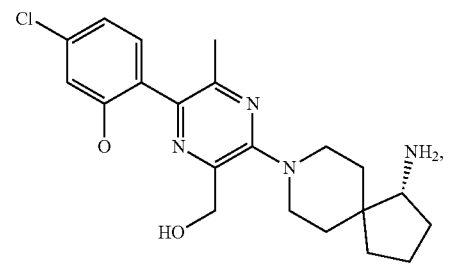 [SMILES: Cc1nc(N2CCC3(CCC[C@H]3N)CC2)c(CO)nc1-c1ccc(Cl)cc1O] |
| A-169 | 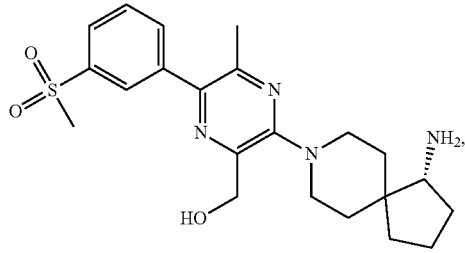 [SMILES: Cc1nc(N2CCC3(CCC[C@H]3N)CC2)c(CO)nc1-c1cccc(S(C)(=O)=O)c1] |
| A-170 | 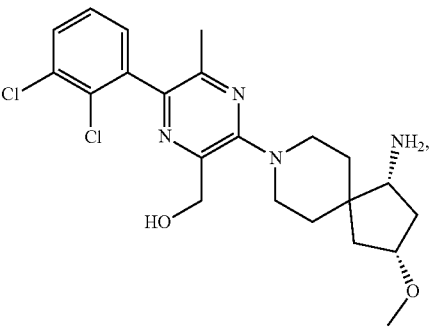 [SMILES: CO[C@H]1C[C@@H](N)C2(CCN(c3nc(C)c(-c4cccc(Cl)c4Cl)nc3CO)CC2)C1] |
| A-171 | 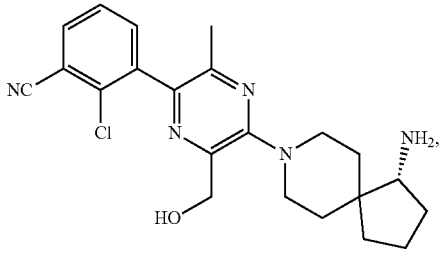 [SMILES: Cc1nc(N2CCC3(CCC[C@H]3N)CC2)c(CO)nc1-c1cccc(C#N)c1Cl] |
| A-172 | 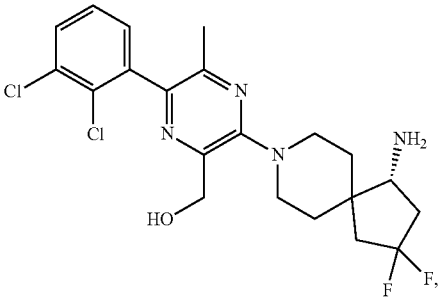 [SMILES: Cc1nc(N2CCC3(CC2)CC(F)(F)C[C@H]3N)c(CO)nc1-c1cccc(Cl)c1Cl] |
| A-173 | 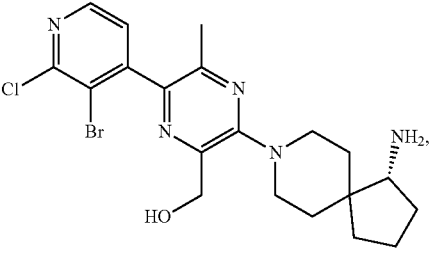 [SMILES: Cc1nc(N2CCC3(CCC[C@H]3N)CC2)c(CO)nc1-c1ccnc(Cl)c1Br] |
| A-174 | 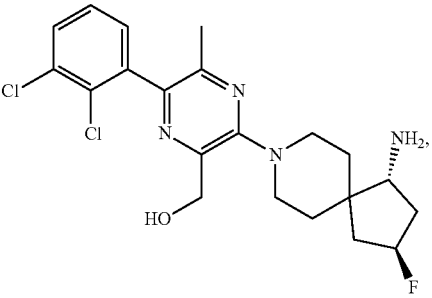 [SMILES: Cc1nc(N2CCC3(CC2)C[C@H](F)C[C@H]3N)c(CO)nc1-c1cccc(Cl)c1Cl] |

TABLE 1-continued

| Cmpd # | Structure |
|---|---|
| A-175 | 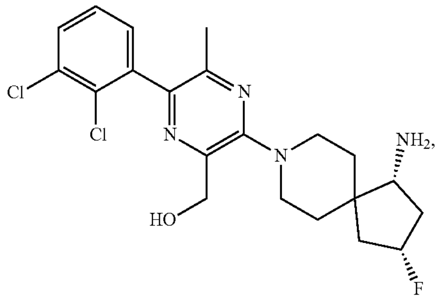 [SMILES: Cc1nc(N2CCC3(CC2)C[C@@H](F)C[C@H]3N)c(CO)nc1-c1cccc(Cl)c1Cl] |
| A-176 | 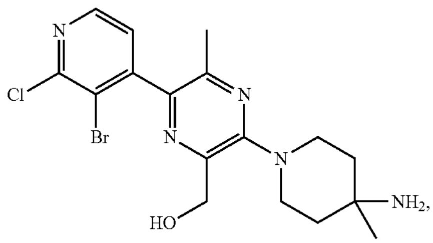 [SMILES: Cc1nc(N2CCC(C)(N)CC2)c(CO)nc1-c1ccnc(Cl)c1Br] |
| A-177 | 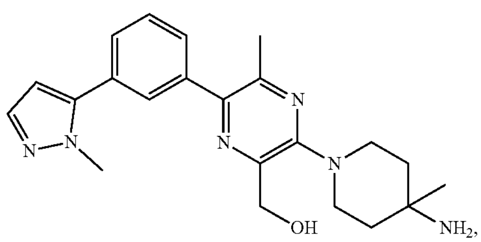 [SMILES: Cc1nc(N2CCC(C)(N)CC2)c(CO)nc1-c1cccc(-c2ccnn2C)c1] |
| A-178 | 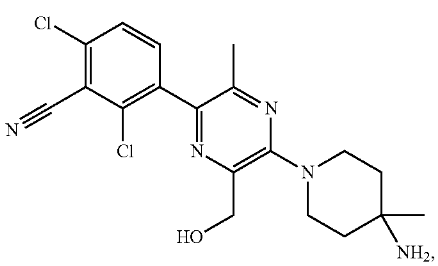 [SMILES: Cc1nc(N2CCC(C)(N)CC2)c(CO)nc1-c1ccc(Cl)c(C#N)c1Cl] |
| A-179 | 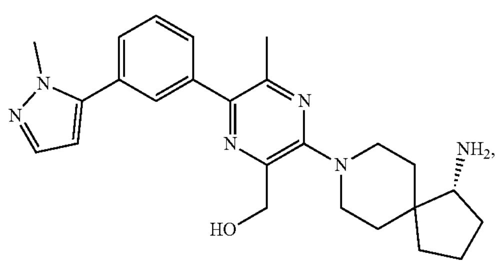 [SMILES: Cc1nc(N2CCC3(CCC[C@H]3N)CC2)c(CO)nc1-c1cccc(-c2ccnn2C)c1] |
| A-180 | 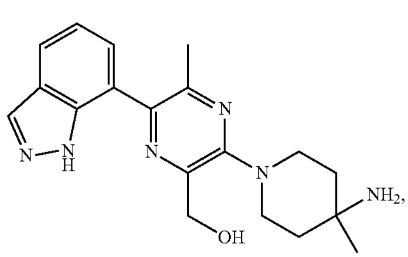 [SMILES: Cc1nc(N2CCC(C)(N)CC2)c(CO)nc1-c1cccc2cn[nH]c12] |
| A-181 | 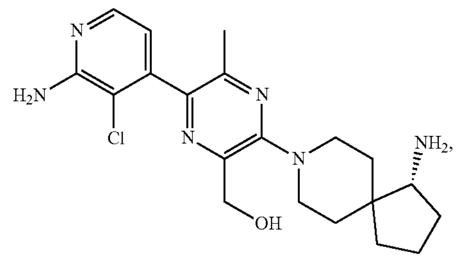 [SMILES: Cc1nc(N2CCC3(CCC[C@H]3N)CC2)c(CO)nc1-c1ccnc(N)c1Cl] |
| A-182 | 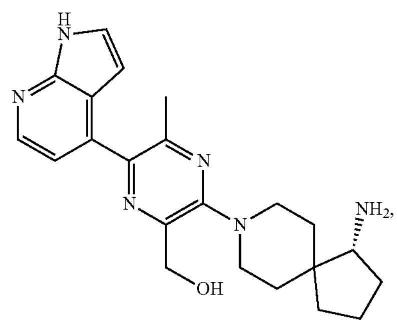 [SMILES: Cc1nc(N2CCC3(CCC[C@H]3N)CC2)c(CO)nc1-c1ccnc2[nH]ccc12] |
| A-183 | 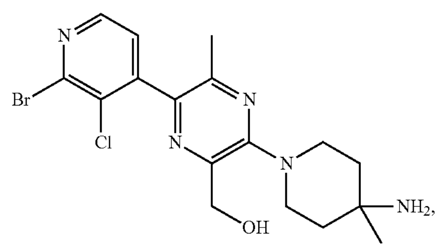 [SMILES: Cc1nc(N2CCC(C)(N)CC2)c(CO)nc1-c1ccnc(Br)c1Cl] |
| A-184 | 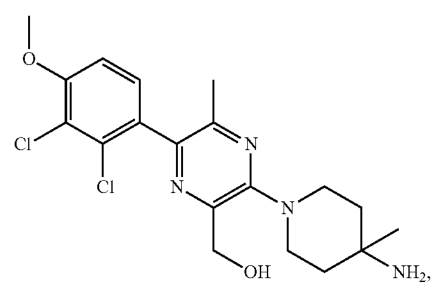 [SMILES: COc1ccc(-c2nc(CO)c(N3CCC(C)(N)CC3)nc2C)c(Cl)c1Cl] |
| A-185 | 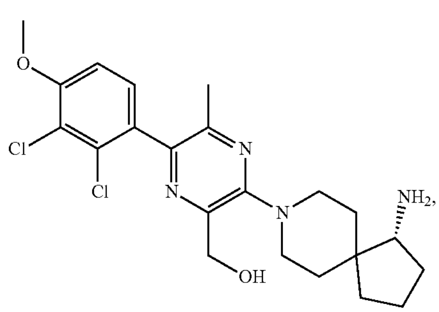 [SMILES: COc1ccc(-c2nc(CO)c(N3CCC4(CCC[C@H]4N)CC3)nc2C)c(Cl)c1Cl] |

TABLE 1-continued

| Cmpd # | Structure |
|---|---|
| A-186 | (structure) |
| A-187 | (structure) |
| A-188 | (structure) |
| A-189 | (structure) |
| A-190 | (structure) |
| A-191 | (structure) |
| A-192 | (structure) |
| A-193 | (structure) |
| A-194 | (structure) |
| A-195 | (structure) |

TABLE 1-continued

| Cmpd # | Structure |
|---|---|
| A-196 | 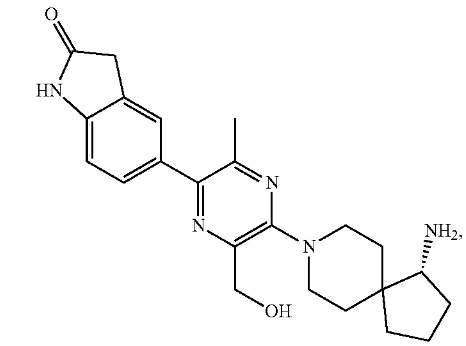 [SMILES: Cc1nc(N2CCC3(CCC[C@H]3N)CC2)c(CO)nc1-c1ccc2c(c1)CC(=O)N2] |
| A-197 | 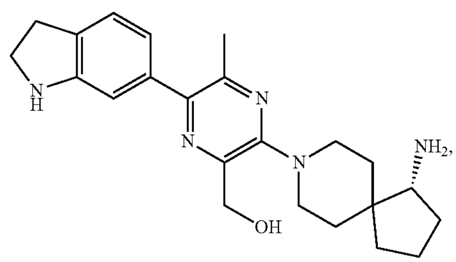 [SMILES: Cc1nc(N2CCC3(CCC[C@H]3N)CC2)c(CO)nc1-c1ccc2c(c1)NCC2] |
| A-198 | 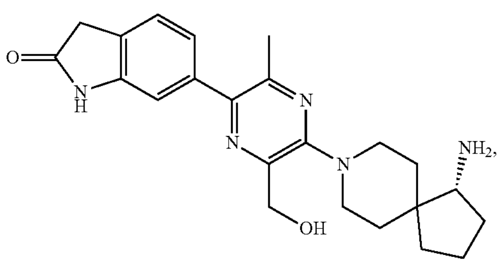 [SMILES: Cc1nc(N2CCC3(CCC[C@H]3N)CC2)c(CO)nc1-c1ccc2c(c1)NC(=O)C2] |
| A-199 | 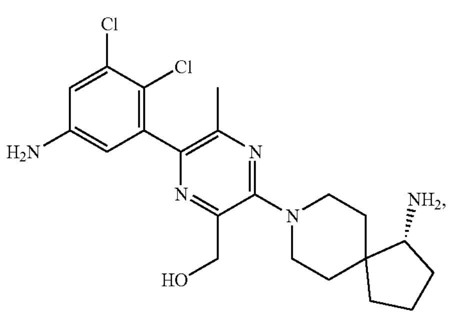 [SMILES: Cc1nc(N2CCC3(CCC[C@H]3N)CC2)c(CO)nc1-c1cc(N)cc(Cl)c1Cl] |
| A-200 | 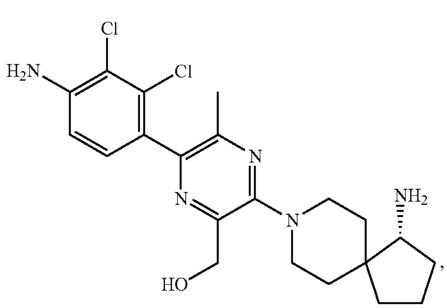 [SMILES: Cc1nc(N2CCC3(CCC[C@H]3N)CC2)c(CO)nc1-c1ccc(N)c(Cl)c1Cl] |
| A-201 | |
| A-202 | |
| A-203 | |
| A-204 | |
| A-205 | |

TABLE 1-continued
| Cmpd # | Structure |
|---|---|
| A-206 | 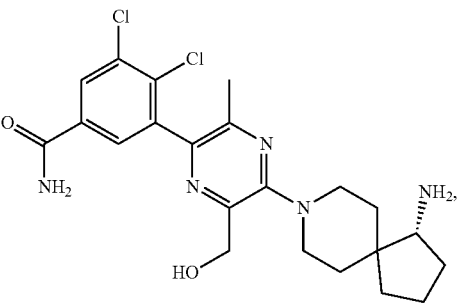 [SMILES: Cc1nc(N2CCC3(CCC[C@H]3N)CC2)c(CO)nc1-c1cc(C(N)=O)cc(Cl)c1Cl] |
| A-207 | 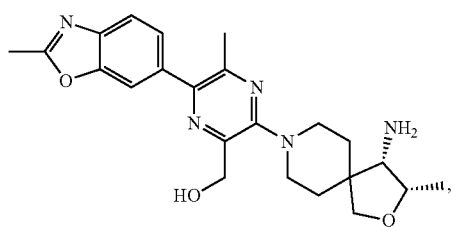 |
| A-208 | 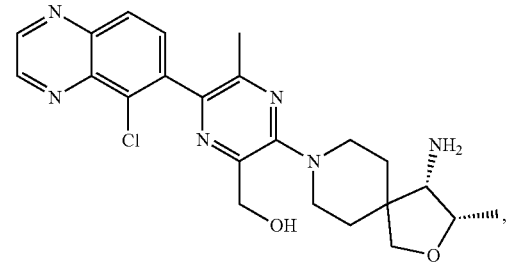 [SMILES: Cc1nc(N2CCC3(CC2)CO[C@@H](C)[C@H]3N)c(CO)nc1-c1ccc2nccnc2c1Cl] |
| A-209 | 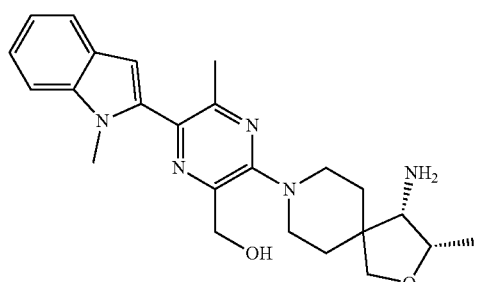 |
| A-210 | 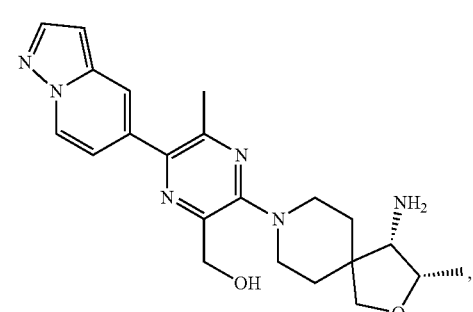 |
| A-211 | 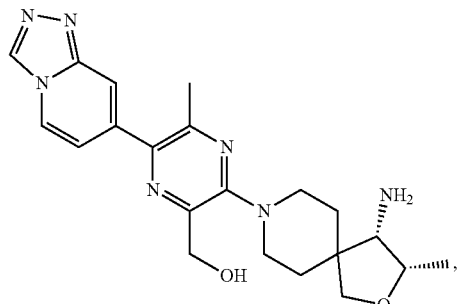 |
| A-212 | 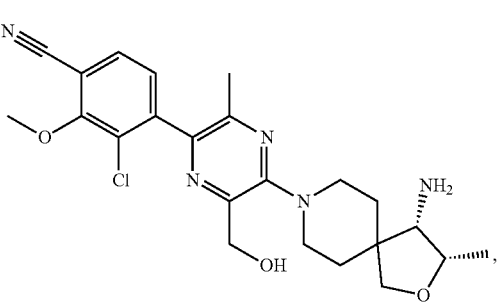 |
| A-213 | 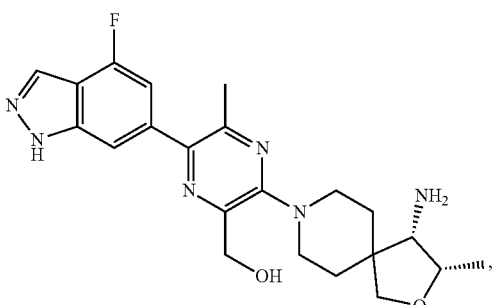 |
| A-214 | 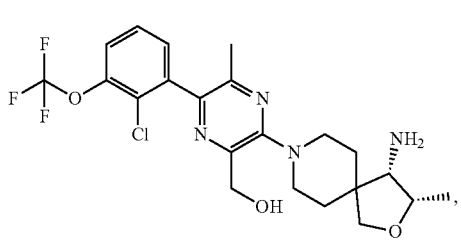 [SMILES: Cc1nc(N2CCC3(CC2)CO[C@@H](C)[C@H]3N)c(CO)nc1-c1cccc(OC(F)(F)F)c1Cl] |
| A-215 | 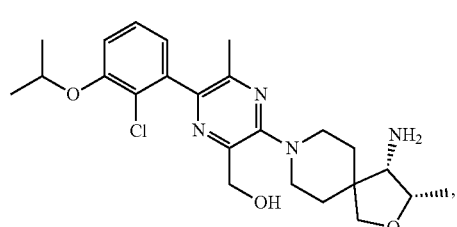 |

TABLE 1-continued

| Cmpd # | Structure |
|---|---|
| A-216 | (structure) |
| A-217 | (structure) |
| A-218 | (structure) |
| A-219 | (structure) |
| A-220 | (structure) |
| A-221 | (structure) |
| A-222 | (structure) |
| A-223 | (structure) |
| A-224 | (structure) |
| A-225 | (structure) |
| A-226 | (structure) |
| A-227 | (structure) |

TABLE 1-continued

| Cmpd # | Structure |
|---|---|
| A-228 | (structure) |
| A-229 | (structure) |
| A-230 | (structure) |
| A-231 | (structure) |
| A-232 | (structure) |
| A-233 | (structure) |
| A-234 | (structure) |
| A-235 | (structure) |
| A-236 | (structure) |
| A-237 | (structure) |

TABLE 1-continued

| Cmpd # | Structure |
|---|---|
| A-238 | 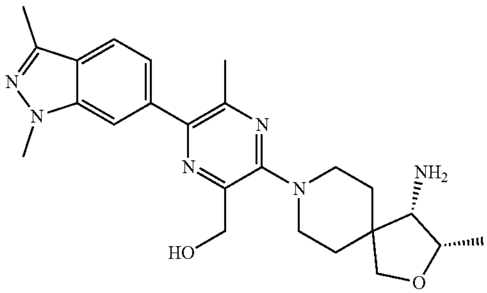 |
| A-239 | 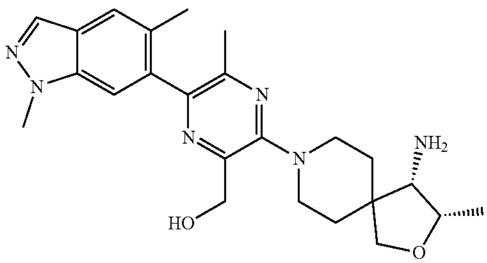 |
| A-240 | 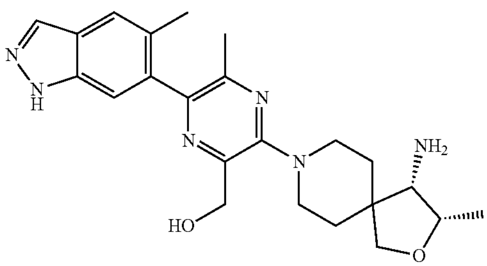 |
| A-241 | 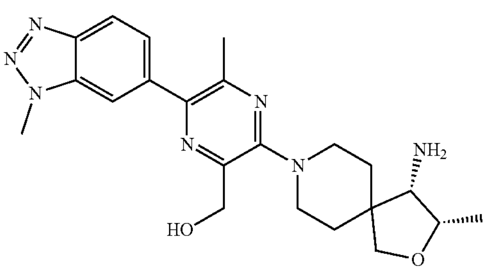 |
| A-242 | 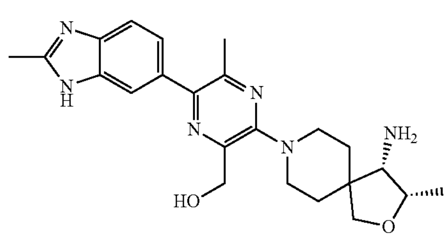 |
| A-243 | |
| A-244 | |
| A-245 | |
| A-246 | |
| A-247 | |

TABLE 1-continued
| Cmpd # | Structure |
|---|---|
| A-248 | 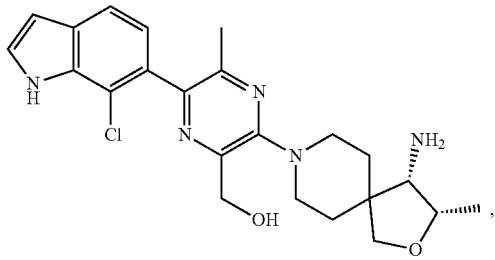 |
| A-249 | 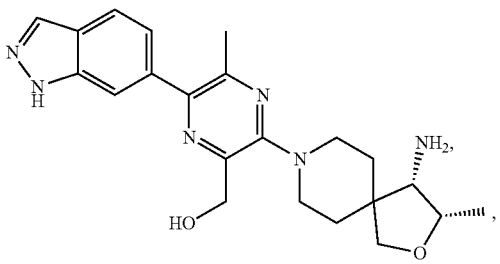 [SMILES: Cc1nc(N2CCC3(CC2)CO[C@@H](C)[C@H]3N)c(CO)nc1-c1ccc2nn[nH]c2c1] |
| A-250 | 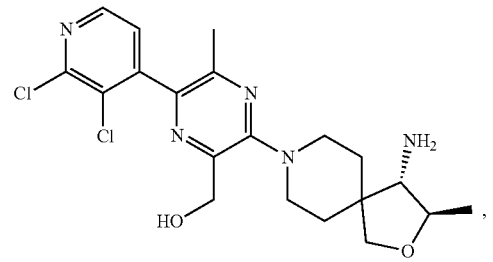 [SMILES: Cc1nc(N2CCC3(CC2)CO[C@H](C)[C@H]3N)c(CO)nc1-c1ccnc(Cl)c1Cl] |
| A-251 | 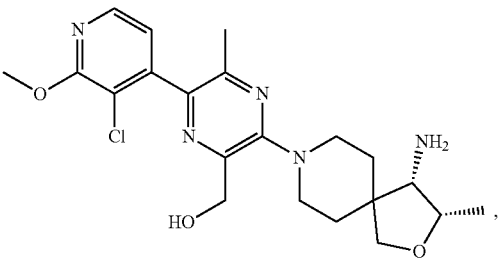 |
| A-252 | 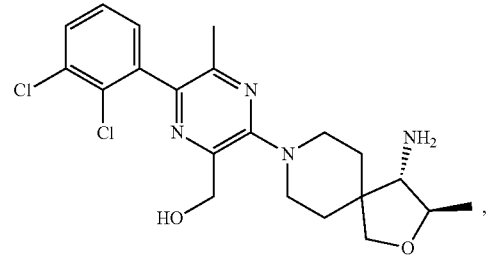 [SMILES: Cc1nc(N2CCC3(CC2)CO[C@H](C)[C@H]3N)c(CO)nc1-c1cccc(Cl)c1Cl] |
| A-253 | 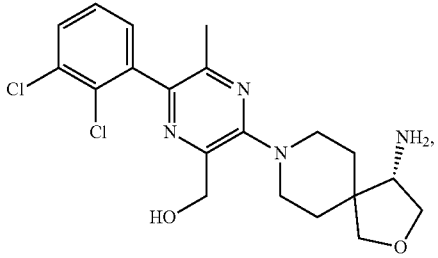 [SMILES: Cc1nc(N2CCC3(CC2)COC[C@H]3N)c(CO)nc1-c1cccc(Cl)c1Cl] |
| A-254 | 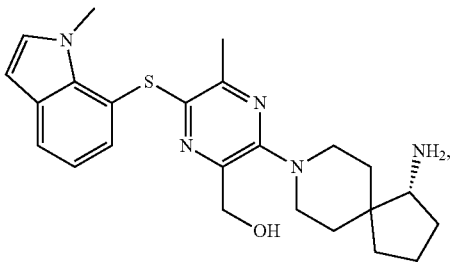 [SMILES: Cc1nc(N2CCC3(CCC[C@H]3N)CC2)c(CO)nc1Sc1cccc2ccn(C)c12] |
| A-255 | 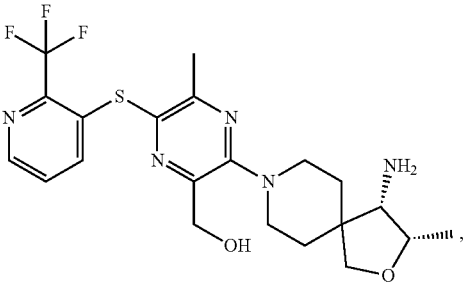 [SMILES: Cc1nc(N2CCC3(CC2)CO[C@@H](C)[C@H]3N)c(CO)nc1Sc1cccnc1C(F)(F)F] |
| A-256 | 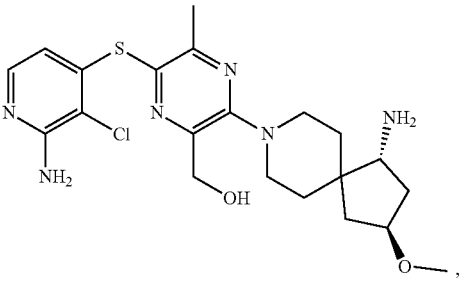 [SMILES: CO[C@@H]1C[C@@H](N)C2(CCN(c3nc(C)c(Sc4ccnc(N)c4Cl)nc3CO)CC2)C1] |
| A-257 | 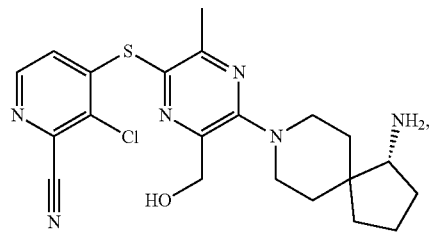 [SMILES: Cc1nc(N2CCC3(CCC[C@H]3N)CC2)c(CO)nc1Sc1ccnc(C#N)c1Cl] |

TABLE 1-continued
| Cmpd # | Structure |
|---|---|
| A-258 | 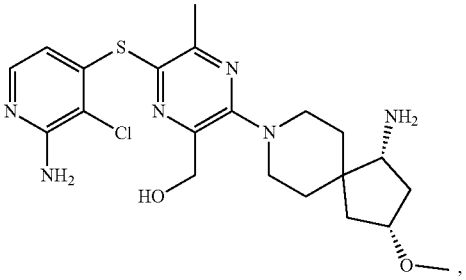 [SMILES: CO[C@H]1C[C@@H](N)C2(CCN(c3nc(C)c(Sc4ccnc(N)c4Cl)nc3CO)CC2)C1] |
| A-259 | 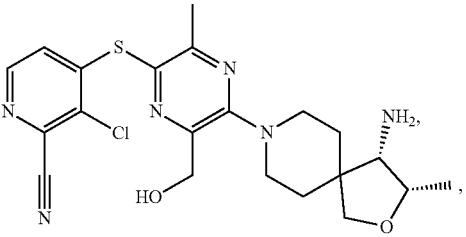 [SMILES: Cc1nc(N2CCC3(CC2)CO[C@@H](C)[C@H]3N)c(CO)nc1Sc1ccnc(C#N)c1Cl] |
| A-260 | 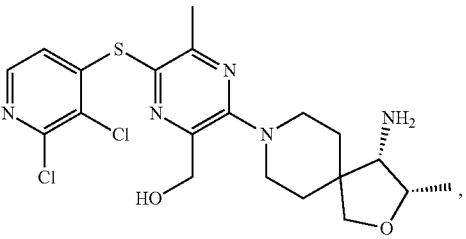 |
| A-261 | 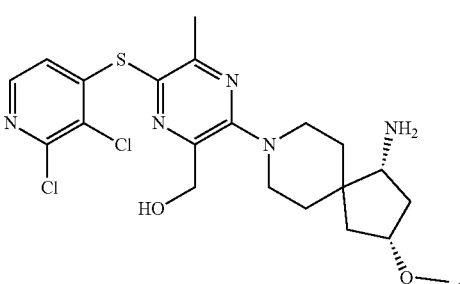 |
| A-262 | 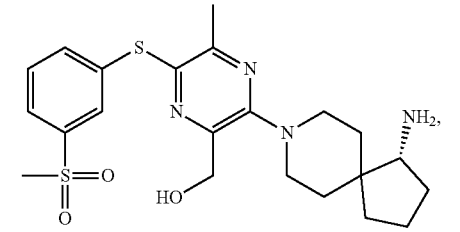 [SMILES: Cc1nc(N2CCC3(CCC[C@H]3N)CC2)c(CO)nc1Sc1cccc(S(C)(=O)=O)c1] |
| A-263 | 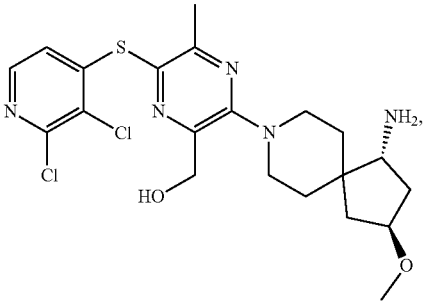 [SMILES: CO[C@@H]1C[C@@H](N)C2(CCN(c3nc(C)c(Sc4ccnc(Cl)c4Cl)nc3CO)CC2)C1] |
| A-264 | 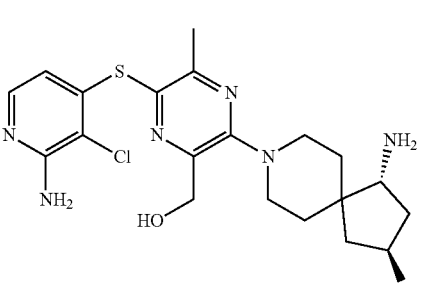 |
| A-265 | 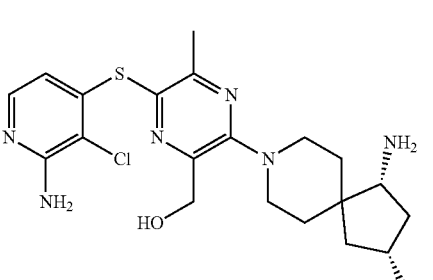 |
| A-266 | 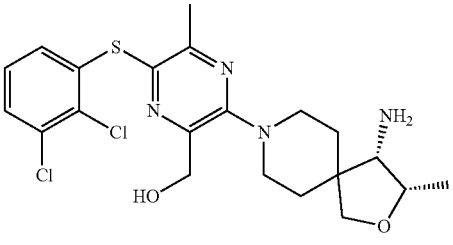 |
| A-267 | 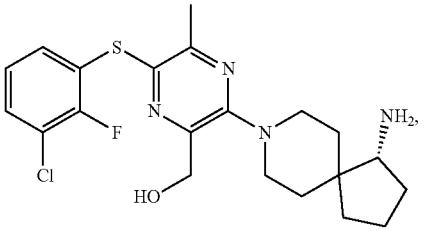 [SMILES: Cc1nc(N2CCC3(CCC[C@H]3N)CC2)c(CO)nc1Sc1cccc(Cl)c1F] |

TABLE 1-continued

| Cmpd # | Structure |
|---|---|
| A-268 | |
| A-269 | |
| A-270 | |
| A-271 | |
| A-272 | |
| A-273 | 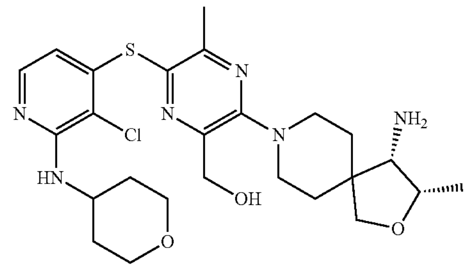 |
| A-274 | 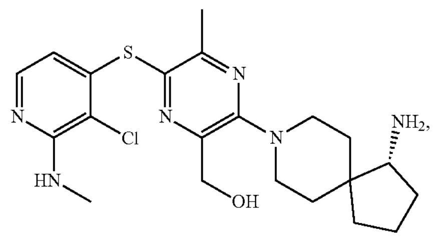 [SMILES: CNc1nccc(Sc2nc(CO)c(N3CCC4(CCC[C@H]4N)CC3)nc2C)c1Cl] |
| A-275 | 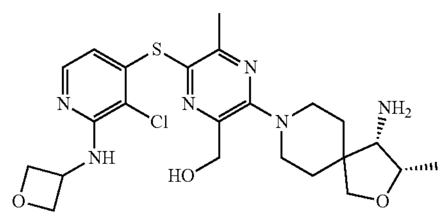 |
| A-276 | 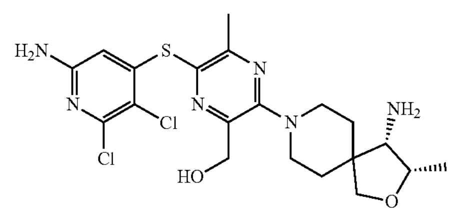 |
| A-277 | 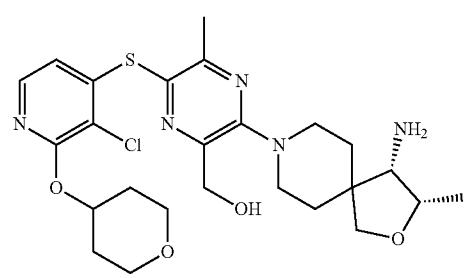 |
| A-278 | 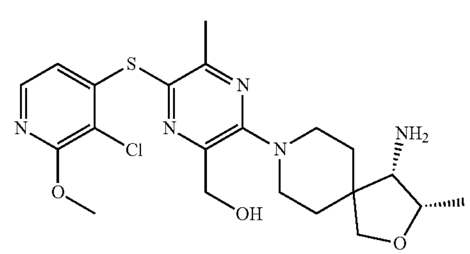 |

TABLE 1-continued

| Cmpd # | Structure |
|---|---|
| A-279 | (structure) |
| A-280 | (structure) |
| A-281 | (structure) |
| A-282 | (structure) |
| A-283 | (structure) |
| A-284 | (structure) |
| A-285 | (structure) |
| A-286 | (structure) |
| A-287 | (structure) |
| A-288 | (structure) |

TABLE 1-continued

| Cmpd # | Structure |
|---|---|
| A-289 | (structure) |
| A-290 | (structure) |
| A-291 | (structure) |
| A-292 | (structure) |
| A-293 | (structure) |
| A-294 | (structure) |
| A-295 | (structure) |
| A-296 | (structure) |
| A-297 | (structure) |
| A-298 | (structure) |
| A-299 | (structure) |

TABLE 1-continued
| Cmpd # | Structure |
|---|---|
| A-300 | 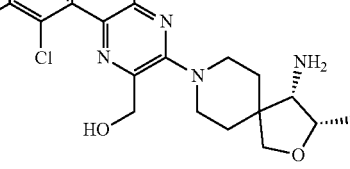 |
| A-301 | 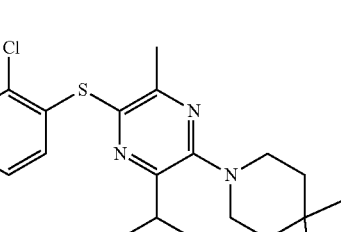 |
| A-302 | 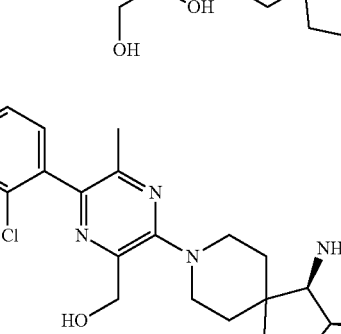 |
| A-303 | 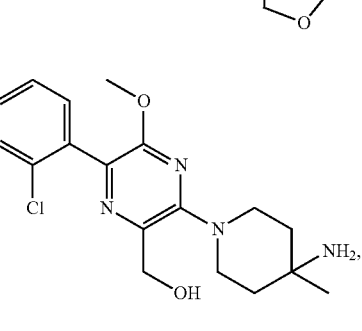 |
| A-304 | 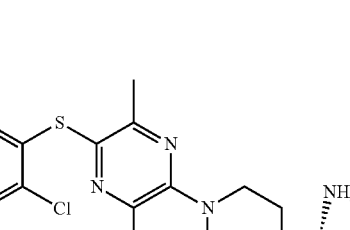 |
| A-305 | 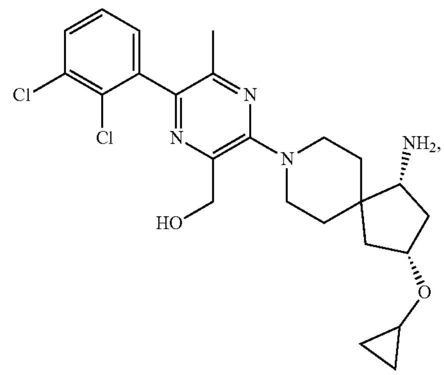 [SMILES: Cc1nc(N2CCC3(CC2)C[C@@H](OC2CC2)C[C@H]3N)c(CO)nc1-c1cccc(Cl)c1Cl] |
| A-306 | 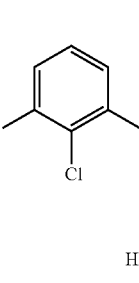 |
| A-307 | 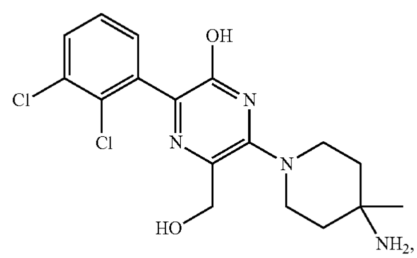 [SMILES: CC1(N)CCN(c2nc(O)c(-c3cccc(Cl)c3Cl)nc2CO)CC1] |
| A-308 | 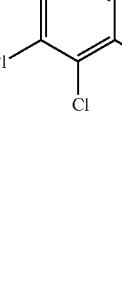 |
Another aspect of the present disclosure relates to compounds, and pharmaceutically acceptable salts, prodrugs, solvates, hydrates, tautomers, or isomers thereof, in Table 2.

TABLE 2
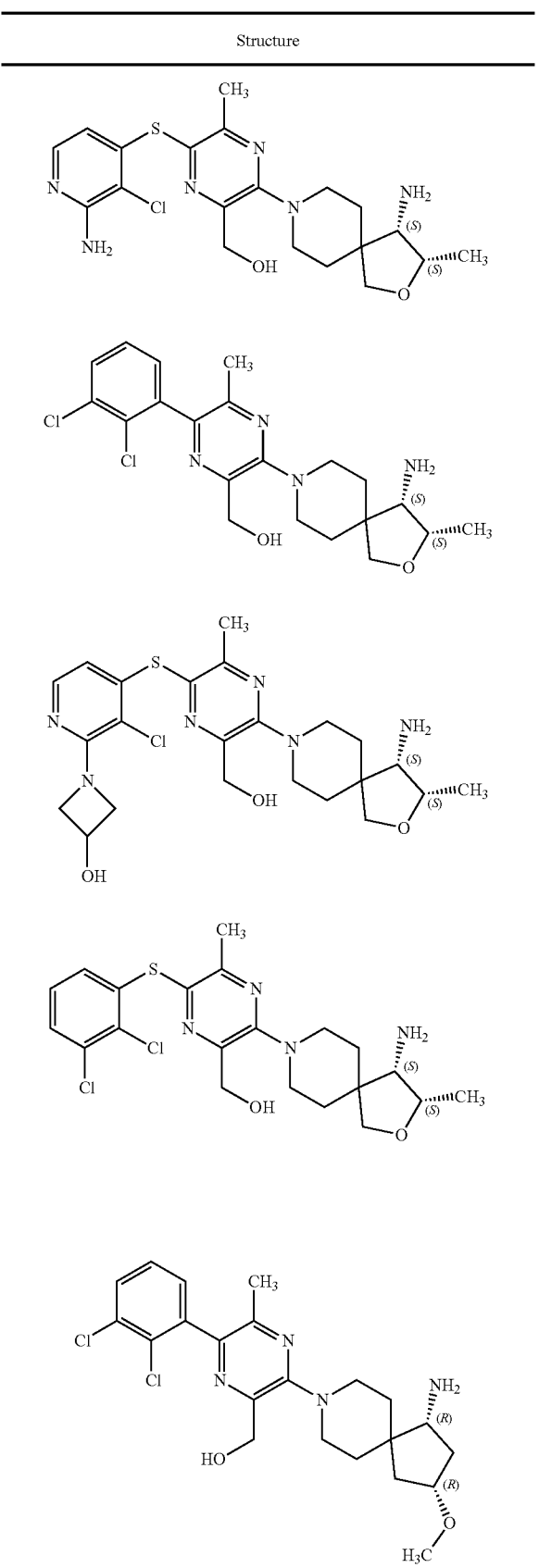
TABLE 2-continued
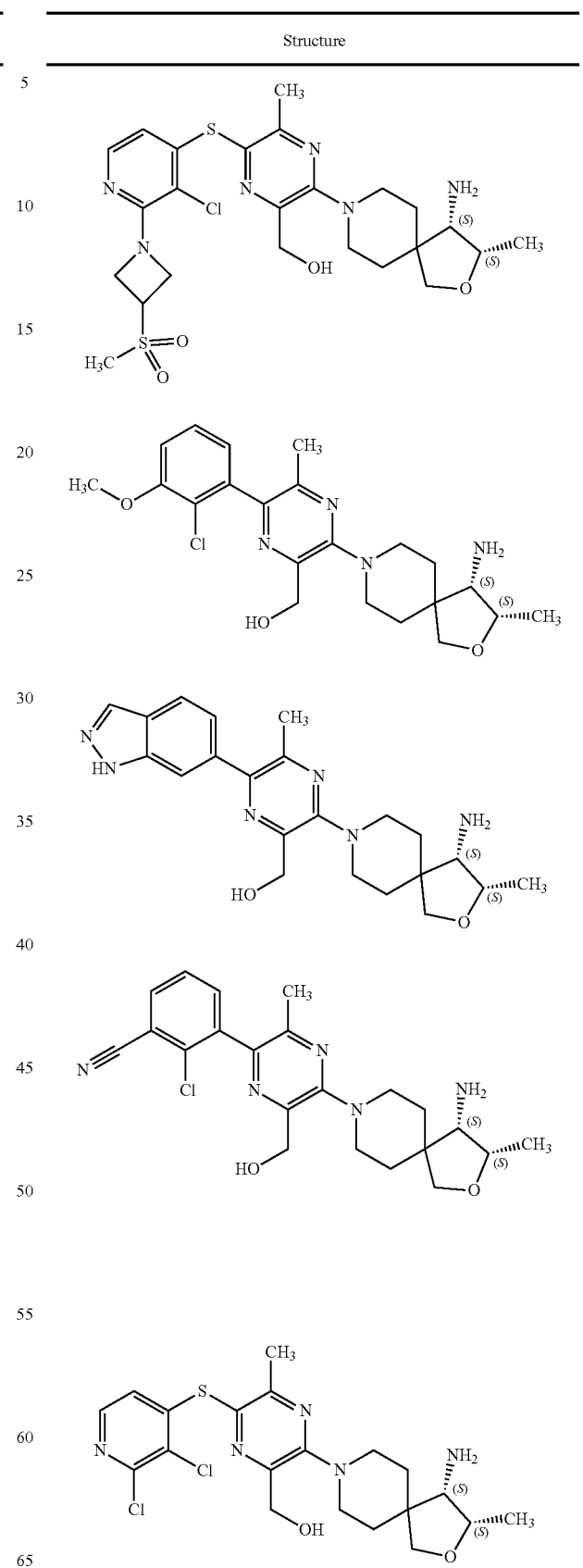

TABLE 2-continued

Structure

[Chemical structures shown]

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, halogen, —O—C$_1$-C$_6$alkyl, —C$_1$-C$_6$alkyl, —OC$_2$-C$_6$alkenyl, —OC$_2$-C$_6$alkynyl, —C$_2$-C$_6$alkenyl, —C$_2$-C$_6$alkynyl, —OH, —OP(O)(OH)$_2$, —OC(O)C$_1$-C$_6$alkyl, —C(O)C$_1$-C$_6$alkyl, —OC(O)OC$_1$-C$_6$alkyl, —NH$_2$, —NH(C$_1$-C$_6$alkyl), —N(C$_1$-C$_6$alkyl)$_2$, —S(O)$_2$—C$_1$-C$_6$alkyl, —S(O)NHC$_1$-C$_6$alkyl, and —S(O)N(C$_1$-C$_6$alkyl)$_2$. The substituents can themselves be optionally substituted.

Unless otherwise specifically defined, "heteroaryl" means a monovalent or multivalent monocyclic aromatic radical or a polycyclic aromatic radical of 5 to 24 ring atoms, containing one or more ring heteroatoms selected from N, S, P, and O, the remaining ring atoms being C. Heteroaryl as herein defined also means a bicyclic heteroaromatic group wherein the heteroatom is selected from N, S, P, and O. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazolyl, benzo[d]imidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, 1-methyl-1H-indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, isoindolin-1-one, indolin-2-one, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo [1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, 2-methylbenzo[d]oxazolyl, 1,2,3,4-tetrahydropyrrolo[1,2-a]pyrimidyl, 2,3-dihydrobenzofuranyl, benzooxazolyl, benzoisoxazolyl, benzo[d]isoxazolyl, benzo[d]oxazolyl, furo[2,3-b]pyridinyl, benzothiophenyl, 1,5-naphthyridinyl, furo[3,2-b]pyridinyl, [1,2,4]triazolo[1,5-a]pyridinyl, benzo[1,2,3]triazolyl, 1-methyl-1H-benzo[d][1,2,3]triazolyl, imidazo[1,2-a]pyrimidinyl, [1,2,4] triazolo[4,3-b]pyridazinyl, quinoxalinyl, benzo[c][1,2,5]thiadiazolyl, benzo[c] [1,2,5]oxadiazolyl, 1,3-dihydro-2H-benzo[d]imidazol-2-one, 3,4-dihydro-2H-pyrazolo[1,5-b][1,2]oxazinyl, 3,4-dihydro-2H-benzo[b][1,4]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, benzo[d][1,3]dioxolyl, pyrazolo[1,5-a]pyridinyl, and derivatives thereof.

"Alkyl" refers to a straight or branched chain saturated hydrocarbon. C$_1$-C$_6$alkyl groups contain 1 to 6 carbon atoms. Examples of a C$_1$-C$_6$alkyl group include, but are not limited to, methyl, ethyl, propyl, butyl, pentyl, isopropyl, isobutyl, sec-butyl and tert-butyl, isopentyl and neopentyl.

The term "alkenyl" means an aliphatic hydrocarbon group containing a carbon carbon double bond and which may be straight or branched having about 2 to about 6 carbon atoms in the chain. Certain alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A C$_2$-C$_6$ alkenyl group is an alkenyl group containing between 2 and 6 carbon atoms.

The term "alkynyl" means an aliphatic hydrocarbon group containing a carbon carbon triple bond and which may be straight or branched having about 2 to about 6 carbon atoms in the chain. Certain alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

The term "cycloalkenyl" means monocyclic, non-aromatic unsaturated carbon rings containing 4-18 carbon atoms. Examples of cycloalkenyl groups include, without limitation, cyclopentenyl, cyclohexenyl, cycloheptenyl, cyclooctenyl, and norborenyl. A $C_4$-$C_8$ cycloalkenyl is a cycloalkenyl group containing between 4 and 8 carbon atoms.

In some embodiments, the terms "heterocyclyl" or "heterocycloalkyl" or "heterocycle" refer to monocyclic or polycyclic 3 to 24-membered rings containing carbon and heteroatoms selected from oxygen, phosphorus, nitrogen, and sulfur and wherein there are no delocalized π electrons (aromaticity) shared among the ring carbon or heteroatoms. Heterocyclyl rings include, but are not limited to, oxetanyl, azetidinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heteroycyclyl or heterocycloalkyl ring can also be fused or bridged, e.g., can be a bicyclic ring.

In some embodiments "heterocyclyl" or "heterocycloalkyl" or "heterocycle" is a saturated, partially saturated or unsaturated, mono or bicyclic ring containing 3-24 atoms of which at least one atom is chosen from nitrogen, sulfur or oxygen, which may, unless otherwise specified, be carbon or nitrogen linked, wherein a —$CH_2$— group can optionally be replaced by a —C(O)— or a ring sulfur atom may be optionally oxidised to form the S-oxides. "Heterocyclyl" can be a saturated, partially saturated or unsaturated, mono or bicyclic ring containing 5 or 6 atoms of which at least one atom is chosen from nitrogen, sulfur or oxygen, which may, unless otherwise specified, be carbon or nitrogen linked, wherein a —$CH_2$— group can optionally be replaced by a —C(O)— or a ring sulfur atom may be optionally oxidised to form S-oxide(s). Non-limiting examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydro thienyl, 2,4-dioxoimidazolidinyl, 2-oxo-1,3,4-(4-triazolinyl), 2-oxazolidinonyl, 5,6-dihydro uracilyl, 1,3-benzodioxolyl, 1,2,4-oxadiazolyl, 2-azabicyclo[2.2.1]heptyl, 4-thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrimidyl, thiazolyl, pyrazinyl, pyridazinyl, pyridyl, 4-pyridonyl, quinolyl and 1-isoquinolonyl.

As used herein, the term "halo" or "halogen" means a fluoro, chloro, bromo, or iodo group.

The term "carbonyl" refers to a functional group comprising a carbon atom double-bonded to an oxygen atom. It can be abbreviated herein as "oxo," as C(O), or as C=O.

"Spirocycle" or "spirocyclic" means carbogenic bicyclic ring systems with both rings connected through a single atom. The ring can be different in size and nature, or identical in size and nature. Examples include spiropentane, spirohexane, spiroheptane, spirooctane, spirononane, or spirodecane. One or both of the rings in a spirocycle can be fused to another carbocyclic, heterocyclic, aromatic, or heteroaromatic ring. One or more of the carbon atoms in the spirocycle can be substituted with a heteroatom (e.g., O, N, S, or P). A $C_5$-$C_{12}$ spirocycle is a spirocycle containing between 5 and 12 carbon atoms. In some embodiments, a $C_5$-$C_{12}$ spirocycle is a spirocycle containing from 5 to 12 carbon atoms. One or more of the carbon atoms can be substituted with a heteroatom.

The term "spirocyclic heterocycle," "spiroheterocyclyl," or "spiroheterocycle" is understood to mean a spirocycle wherein at least one of the rings is a heterocycle (e.g., at least one of the rings is furanyl, morpholinyl, or piperadinyl). A spirocyclic heterocycle can contain between 5 and 12 atoms, at least one of which is a heteroatom selected from N, O, S and P. In some embodiments, a spirocyclic heterocycle can contain from 5 to 12 atoms, at least one of which is a heteroatom selected from N, O, S and P.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the disclosure.

The SHP2 inhibitor may be administered alone as a monotherapy or in combination with one or more other therapeutic agent (e.g., an inhibitor of a MAP kinase pathway or an anti-cancer therapeutic agent) as a combination therapy. The SHP2 inhibitor may be administered as a pharmaceutical composition. The SHP2 inhibitor may be administered before, after, and/or concurrently with the one or more other therapeutic agent (e.g., an inhibitor of a MAP kinase pathway or an anti-cancer therapeutic agent). If administered concurrently with the one or more other therapeutic agent, such administration may be simultaneous (e.g., in a single composition) or may be via two or more separate compositions, optionally via the same or different modes of administration (e.g., local, systemic, oral, intravenous, etc.).

The SHP2 inhibitor may be administered in combination with one or more MEK inhibitor as a combination therapy. The SHP2 inhibitor may be administered as a pharmaceutical composition in combination with one or more MEK inhibitor as a combination therapy. The SHP2 inhibitor may be administered before, after, and/or concurrently with the one or more MEK inhibitor. If administered concurrently with the one or more MEK inhibitor, such administration may be simultaneous (e.g., in a single composition) or may be via two or more separate compositions, optionally via the same or different modes of administration (e.g., local, systemic, oral, intravenous, etc.).

In some embodiments, the SHP2 inhibitor is administered to the subject as a monotherapy for the treatment of a tumor. The tumor may contain a RAS pathway activating mutation.

In various embodiments, the RAS pathway activating mutation confers cellular dependence on SHP2 (e.g., for reloading of GTP onto RAS).

In certain embodiments, the SHP2 inhibitor is administered to the subject as a monotherapy for the treatment of a tumor comprising a cell that contains an NF1$^{LOF}$ mutation. NF1 is a GAP protein that modulates RAS activation by facilitating hydrolysis of GTP from GTP from active RAS-GTP, thereby inactivating RAS. RAS oscillates between GDP-bound "off" and GTP-bound "on." Loss of function mutations in NF1 reduce GTP hydrolysis by RAS, and shift the equilibrium toward activated RAS, thereby resulting in cancerous growth/proliferation and possibly oncogene addiction. NF1 mutations occur frequently in NSCLC (e.g., 8.3% per Cancer Genome Atlas Research Network "Comprehensive molecular profiling of lung adenocarcinoma." Nature 511, 533-550 (2014)), and more than 80% of all constitutional NF1 mutations are NF1$^{LOF}$ (Philpott, 2017), yet no targeted therapies are available for treating NF1$^{LOF}$ subtype tumors. As shown herein, SHP2 inhibition in NF1$^{LOF}$ cells resulted in dose dependent suppression of p-ERK signaling and proliferation (Example 1, FIGS. 6A and 6B).

In certain embodiments, the SHP2 inhibitor is administered to the subject as a monotherapy for the treatment of a tumor comprising a cell that contains a mutation in a RAS gene. In certain embodiments, the RAS gene mutation renders the RAS pathway dependent on signaling flux through SHP2. The RAS pathway mutation may be a KRAS, NRAS, or HRAS mutation. Oncogenic RAS mutations, such as KRAS mutations, shift the RAS equilibrium to the GTP-bound "on" state, driving signaling to RAS effectors and oncogene addiction. As used herein, "oncogene addiction" refers to the phenomenon whereby a tumor cell exhibits apparent dependence on a single oncogenic pathway or protein for sustained proliferation and/or survival, despite its myriad of genetic alterations. Treatment of KRAS cell line panels identified certain mutations as biomarkers of growth sensitivity to SHP2 inhibition (Example 1, Table 3). In certain embodiments, the SHP2 inhibitor is administered to the subject as a monotherapy for the treatment of a tumor comprising a cell that contains a KRAS$^{G12C}$ mutation. In certain embodiments, the SHP2 inhibitor is administered to the subject as a monotherapy for the treatment of an tumor comprising a cell that contains a KRAS$^{G12A}$; a KRAS$^{G12D}$ a KRAS$^{G12S}$, or a KRAS$^{G12V}$ mutation.

In certain embodiments, the SHP2 inhibitor is administered to the subject as a monotherapy for the treatment of a tumor comprising a cell containing a RAF gene mutation. The RAF gene mutation may render the RAS pathway dependent on signaling flux through SHP2. In certain embodiments, the mutation is a Class III BRAF mutation. In some embodiments, the Class III BRAF mutation may be selected from the group consisting of: D287H; P367R; V459L; G466V; G466E; G466A; S467L; G469E; N581S; N581I; D594N; D594G; D594A; D594H; F595L; G596D; G596R and A762E. In certain embodiments, the mutation is an ARAF or CRAF mutation.

In certain embodiments, the SHP2 inhibitor is administered to the subject as a monotherapy for the treatment of a tumor comprising a cell containing a MEK gene mutation. The MEK gene mutation may render the RAS pathway dependent on signaling flux through SHP2. In certain embodiments, the MEK gene mutation is a Class I MEK1 mutation. In some embodiments, the Class I MEK1 mutation may be selected from the group consisting of D67N; P124L; P124S; and L177V. In certain embodiments, the MEK gene mutation is a Class II MEK1 mutation. In some embodiments, the Class II MEK1 mutation may be selected from the group consisting of ΔE51-Q58; ΔF53-Q58; E203K; L177M; C121S; F53L; K57E; Q56P; and K57N.

In certain embodiments, the SHP2 inhibitor is administered to the subject in combination with one or more other therapeutic agent (e.g., an inhibitor of a MAP kinase pathway) as a combination therapy for the treatment of a tumor comprising a cell containing a RAS pathway mutation that renders the mutated protein dependent on signaling flux through SHP2. The mutation may comprise one or more of an NF1$^{LOF}$ mutation; a RAS/RAF mutation; a KRAS mutation; a KRAS mutation selected from a KRAS$^{G12A}$ mutation; a KRAS$^{G12C}$ mutation; a KRAS$^{G12D}$ mutation; a KRAS$^{G12S}$ mutation; a KRAS$^{G12V}$ mutation; a Class III BRAF mutation; a BRAF mutation selected from D287H; P367R; V459L; G466V; G466E; G466A; S467L; G469E; N581S; N581I; D594N; D594G; D594A; D594H; F595L; G596D; G596R and A762E; a Class I MEK1 mutation; a MEK1 mutation selected from D67N; P124L; P124S; and L177V; a Class II MEK1 mutation; and a MEK1 mutation selected from ΔE51-Q58; ΔF53-Q58; E203K; L177M; C121S; F53L; K57E; Q56P; and K57N. The mutation may comprise one or more of an ARAF or CRAF mutation. The combination therapy may comprise administration of a SHP2 inhibitor and any other anti-cancer therapeutic agent known in the art or disclosed herein. For example, the SHP2 inhibitor may be administered to the subject in combination with an anti-cancer agent selected from, e.g., but not limited to, mitotic inhibitors such as a taxane, a vinca alkaloid, paclitaxel, docetaxel, vincristine, vinblastine, vinorelbine or vinflunine, and other anticancer agents, e.g. cisplatin, 5-fluorouracil or 5-fluoro-2-4(1H,3H)-pyrimidinedione (5FU), flutamide, gemcitabine, a checkpoint inhibitor (e.g., a checkpoint inhibitor antibody) such as, e.g., a PD-1 antibody, such as, e.g., pembrolizumab (or "Keytruda", Merck) nivolumab (or "Opdivo", BMS), PDR001 (NVS), REGN2810 (Sanofi/Regeneron), a PD-L1 antibody such as, e.g., avelumab (or "MSB0010718C" or "Bavencio", PFE & Merck Kga), durvalumab (or "Imfinzi" or "MEDI-4736", Medimmune & Celgene), atezolizumab (or "Tecentriq" or "MPDL-3280A", Genentech & Roche), Pidilizumab (or "CT-001", Medivation—Now Pfizer), JNJ-63723283 (JNJ), BGB-A317 (BeiGene & Celgene) or a checkpoint inhibitor disclosed in Preusser, M. et al. (2015) Nat. Rev. Neurol. (incorporated herein by reference in its entirety), including, without limitation, Ipilimumab, Tremelimumab, Nivolumab, Pembrolizumab, Pidilizumab, AMP224, AMP514/MEDI0680, BMS936559, MED14736, MPDL3280A, MSB0010718C, BMS986016, IMP321, Lirilumab, IPH2101, 1-7F9, and KW-6002; an RTK inhibitor, an EGFR inhibitor, an ALK inhibitor, a PI3K/AKT pathway inhibitor, an inhibitor of a MAP kinase pathway, and a MEK inhibitor. The RTK inhibitor (TKI) may inhibit, e.g., one or more RTK selected from epidermal growth factor receptor (EGFR), platelet derived growth factor receptor (PDGFR), erbB2, erbB4, vascular endothelial growth factor receptor (VEGFR), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, hepatocyte growth factor receptors (HGFR), the RET protooncogene, and ALK. The TKI may include, but is not limited to, one or more TKI described in Cancers (Basel). 2015 September; 7(3): 1758-1784, incorporated herein by reference in its entirety. The TKI may include, but is not limited to, an EGFR inhibitor or an Alk inhibitor. The TKI may include, but is not limited to trastuzumab (Herceptin); cetuximab (Erbitux); panitumumab (vectibix); gefitinib (iressa); erlotinib (tarceva); lapatinib (tykerb); afatinib; sorafenib (nexavar); sunitinib (sutent); bevacizumab (avastin); soratinib; pazopanib; nilotinib; brivanib (BMS-540215); CHIR-258 (TKI-258); SGX523; and imatinib (gleevec). Other TKIs that may be used according to the present disclosure in combination with a SHP2 inhibitor may include, but are not limited to the growth factor receptor inhibitor agents described in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London, incorporated herein by reference in its entirety. The combination therapy may comprise a SHP2 inhibitor in combination with an inhibitor of the PI3K/AKT pathway ("PI3K/AKT inhibitor") known in the art or disclosed herein. The PI3K/AKT inhibitor may include, but is not limited to, one or more PI3K/AKT inhibitor described in Cancers (Basel). 2015 September; 7(3): 1758-1784, incorporated herein by reference in its entirety. For example, the PI3K/AKT inhibitor may be selected from one or more of NVP-BEZ235; BGT226; XL765/SAR245409; SF1126; GDC-0980; PI-103; PF-04691502; PKI-587; GSK2126458. The ALK inhibitor may include, but is not limited to, ceritinib, TAE-684 (also referred to herein as "NVP-TAE694"), PF02341066 (also referred to herein as "crizotinib" or "1066"), alectinib; brigatinib; entrectinib; Ensartinib (X-396); lorlatinib; ASP3026; CEP-37440; 4SC-203; TL-398; PLB1003; TSR-011; CT-707; TPX-0005, and AP26113. Additional examples of ALK kinase inhibitors are described in example 3-39 of WO 2005016894, incorporated herein by reference in its entirety. The SHP2 inhibitor may be administered before, after, or concurrently with one or more of such anti-cancer agents. In some embodiments, such combinations may offer significant advantages, including additive or synergistic activity in therapy.

In some particular embodiments, the present disclosure provides for method for treating a disease or disorder, e.g., a cancer, with a combination therapy comprising a SHP2 inhibitor known in the art or disclosed herein in combination with an inhibitor of the MAP kinase (MAPK) pathway (or "MAPK inhibitor") known in the art or disclosed herein. The MAPK inhibitor may be a MEK inhibitor. MAPK inhibitors for use in the methods disclosed herein may include, but are not limited to, one or more MAPK inhibitor described in Cancers (Basel). 2015 September; 7(3): 1758-1784, incorporated herein by reference in its entirety. For example, the MAPK inhibitor may be selected from one or more of Trametinib, Binimetinib, Selumetinib, Cobimetinib, LErafAON (NeoPharm), ISIS 5132; Vemurafenib, Pimasertib, TAK733, RO4987655 (CH4987655); CI-1040; PD-0325901; CH5126766; MAP855; AZD6244; Refametinib (RDEA 119/BAY 86-9766); GDC-0973/XL581; AZD8330 (ARRY-424704/ARRY-704); RO5126766 (Roche, described in PLoS One. 2014 Nov. 25; 9(11), incorporated herein by reference in its entirety); and GSK1120212 (or "JTP-74057", described in Clin Cancer Res. 2011 Mar. 1; 17(5):989-1000, incorporated herein by reference in its entirety). The SHP2 inhibitor may be administered before, after, or concurrently with one or more of such MAPK inhibitor. In some embodiments, such combinations may offer significant advantages, including additive or synergistic activity in therapy.

In some embodiments, the present disclosure provides for method for treating a disease or disorder, e.g., a cancer, with a combination therapy comprising a SHP2 inhibitor known in the art or disclosed herein in combination with an inhibitor of a RAS protein (or "RAS inhibitor") known in the art or disclosed herein. The RAS inhibitor may inhibit KRAS, NRAS, or HRAS. The RAS inhibitor may inhibit a specific KRAS, NRAS, or HRAS mutation. The RAS inhibitor may be a $KRAS^{G12C}$ specific inhibitor. For example, the RAS inhibitor may be ARS-853 (Patricelli et al., 2016), which binds selectively to the cysteine residue of $KRAS^{G12C}$ in the GDP bound state.

Figure 9:
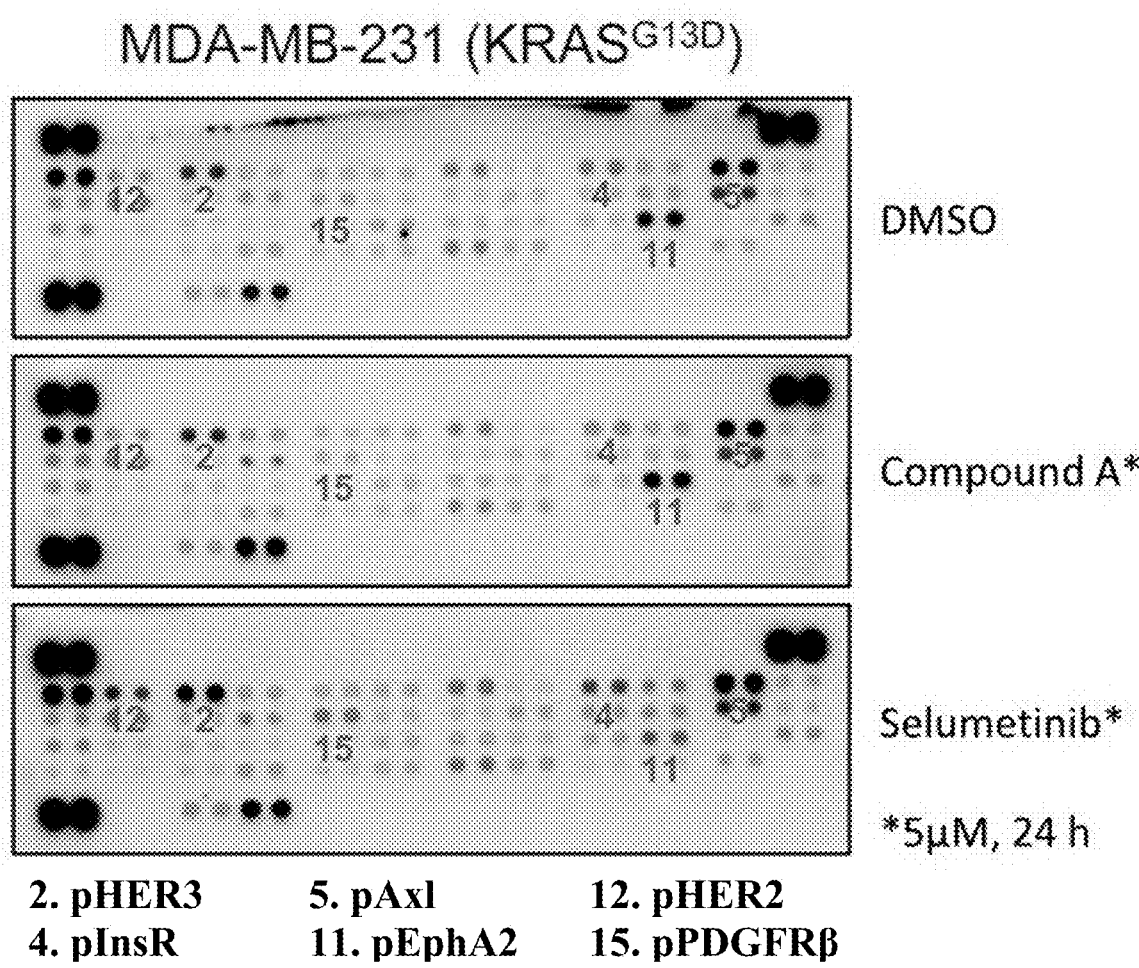
FIG. 9 shows that MEK inhibition by selumetinib caused feedback-driven p-RTK hyperactivation in MDA-MB-231 (KRAS$^{G13D}$) cell line whereas Compound A (Compound A) did not.
Figure 10:
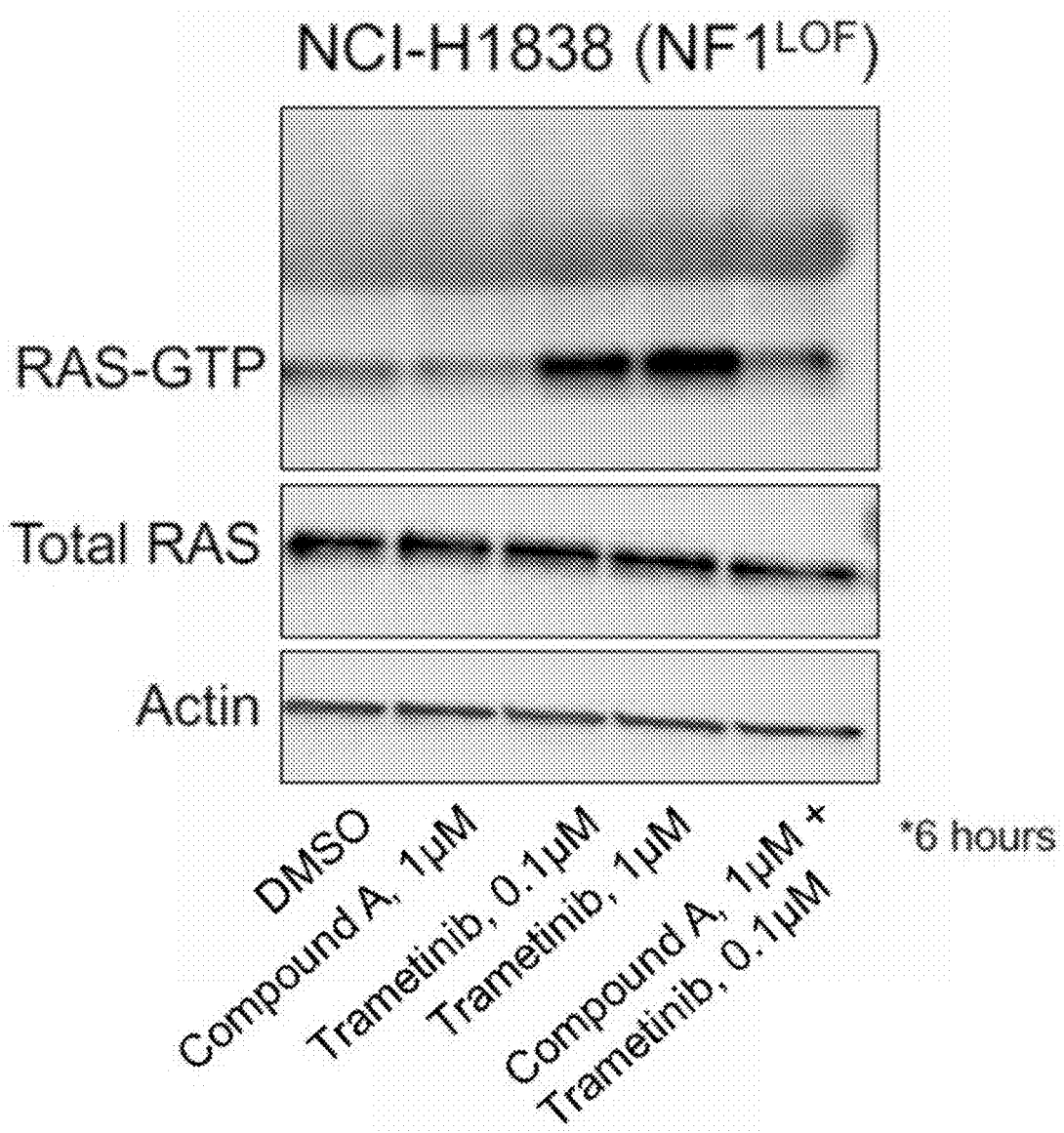
FIG. 10 shows that MEK inhibition by trametinib in NCI-H1838 (NF1$^{LOF}$) caused feedback-driven RAS-GTP accumulation and Compound A (Compound A) suppressed this effect.
Figures 12, 12A:
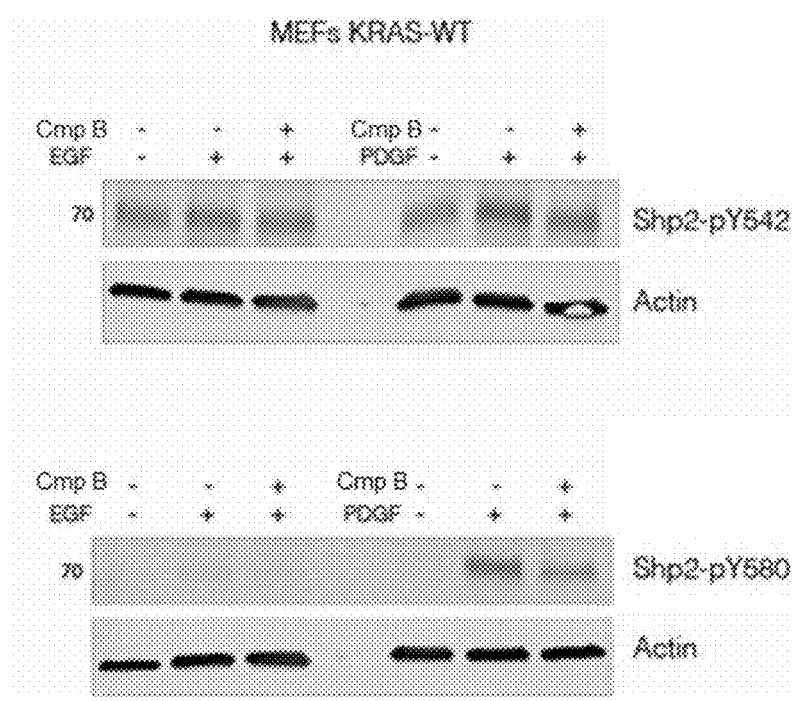
FIG. 12 shows phosphorylation of Tyr-542 and Tyr-580 measured in response to both EGF and PDGF in various cell lines.
FIG. 12A shows Tyr phosphorylation in mouse embryonic fibroblasts (MEFs).
Figures 12, 12B:
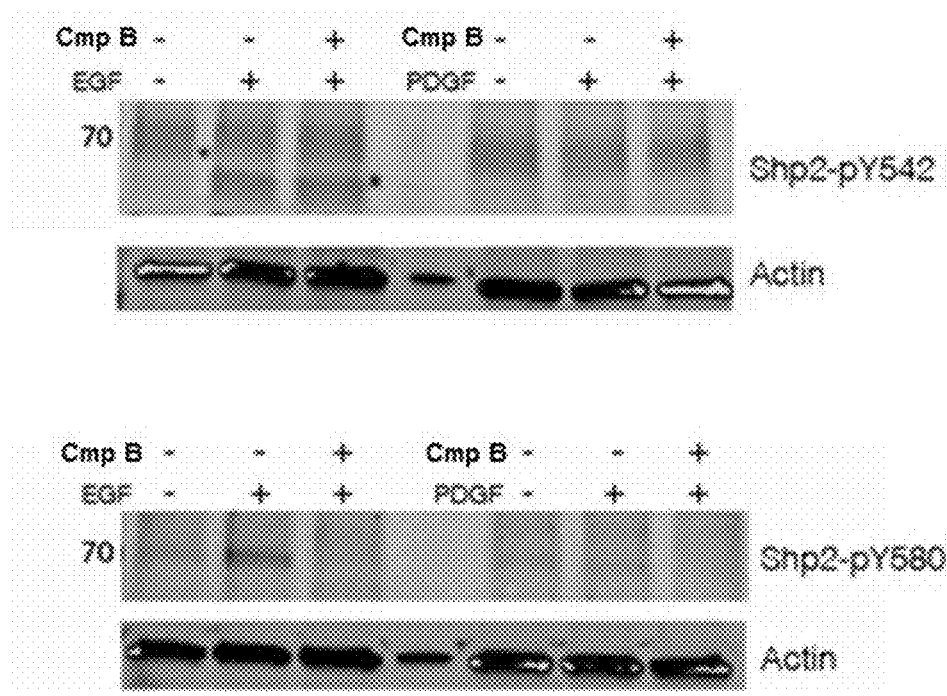
FIG. 12B shows Tyr phosphorylation in H358 cells.
Figures 12, 12C:
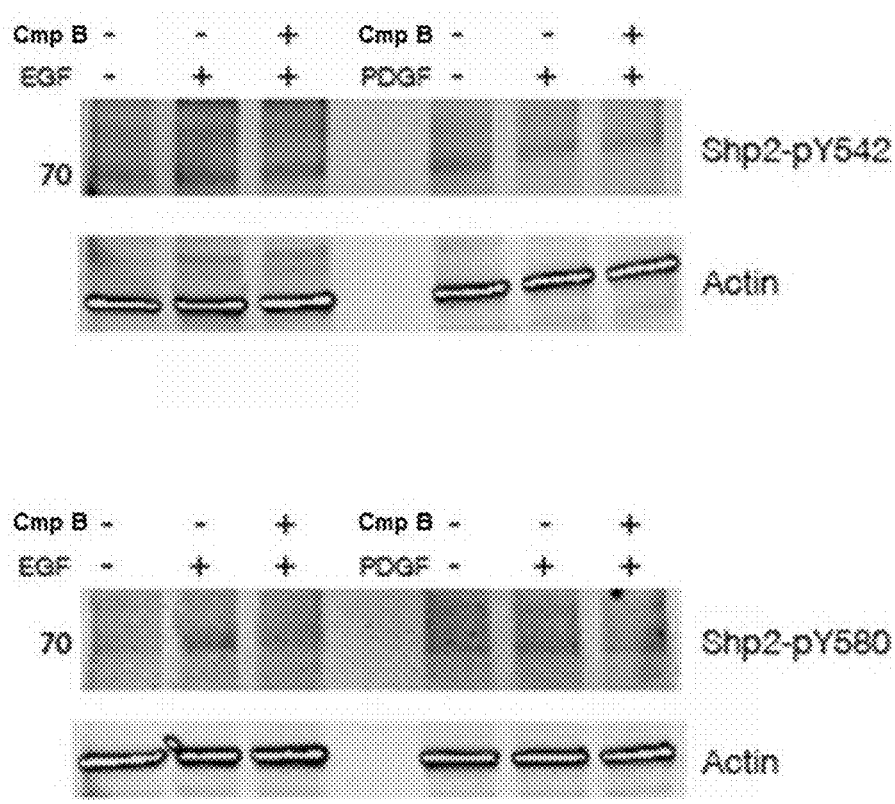
FIG. 12C shows Tyr phosphorylation in HEK 293 (C) cells. "Cmp B" stands for Compound B.

The present disclosure also demonstrates the unexpected discovery that inhibition of SHP2 does not result in feedback driven activation RAS pathway signaling (FIG. 9), even though SHP2 inhibition does result in decreased ERK phosphorylation (FIG. 5B) and might, therefore, be expected to induce such feedback activation in the same manner as MEK inhibition does (FIG. 10). Further, SHP2 inhibition counteracted MEK inhibitor-induced activation of RAS (FIG. 11). Thus, unlike MAPK inhibitors, which may induce resistance, SHP2 inhibitors do not cause hyperactivation of RAS, and they are able to attenuate hyperactivation of RAS in response to MEK inhibitor treatment that may contribute to MEK inhibitor drug resistance.

Accordingly, in some embodiments, the present disclosure provides a method for preventing or delaying the emergence of resistance in a cell (e.g., a tumor cell) to a therapeutic agent (e.g., an anti-cancer agent) targeting a RAS pathway signal transducer, the method comprising administering the therapeutic agent in combination with a SHP2 inhibitor. The SHP2 inhibitor may be administered before, after, or concurrently with the therapeutic agent. In particular embodiments, the therapeutic agent is a MAPK inhibitor (e.g., MEK inhibitor). MEK inhibitors induce feedback activation of RAS, which, as shown herein, may be blocked with a SHP2 inhibitor. The administering may be in vivo, e.g., to a subject (such as a mammal, preferably a human). Thus, the method for preventing or delaying the emergence of resistance in a cell (e.g., a tumor cell) to a therapeutic agent (e.g., an anti-cancer agent) targeting a RAS pathway signal transducer, may comprise administering a SHP2 inhibitor and a MEK inhibitor selected from one or more of Trametinib (GSK1120212); Selumetinib (AZD6244); Cobimetinib (GDC-0973/XL581), Binimetinib, Vemurafenib, Pimasertib, TAK733, RO4987655 (CH4987655); CI-1040; PD-0325901; CH5126766; MAP855; Refametinib (RDEA 119/BAY 86-9766); RO5126766, AZD8330 (ARRY-424704/ARRY-704); and GSK1120212. In some embodiments, the RAS pathway inhibitor is Abemaciclib or Ulixertinib. The method for preventing or delaying the emergence of resistance in a cell (e.g., a tumor cell) to a therapeutic agent (e.g., an anti-cancer agent) targeting a RAS pathway signal transducer, may comprise administering a MEK inhibitor and a SHP2 inhibitor selected from (i) Compound A; (ii) Compound B; (iii) SHP099; (iv)NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof. The method for preventing or delaying the emergence of resistance in a cell (e.g., a tumor cell) to a therapeutic agent (e.g., an anti-cancer agent) targeting a RAS pathway signal transducer, may comprise administering Compound B and a MEK inhibitor selected from one or more of Trametinib (GSK1120212); Selumetinib (AZD6244); Cobimetinib (GDC-0973/XL581), Binimetinib, Vemurafenib, Pimasertib, TAK733, RO4987655 (CH4987655); CI-1040; PD-0325901; CH5126766; MAP855; Refametinib (RDEA 119/BAY 86-9766); RO5126766, AZD8330 (ARRY-424704/ARRY-704); and GSK1120212. In some embodiments, the RAS pathway inhibitor is Abemaciclib or Ulixertinib. The method for preventing or delaying the emergence of resistance in a cell (e.g., a tumor cell) to a therapeutic agent (e.g., an anti-cancer agent) targeting a RAS pathway signal transducer, may comprise administering Trametinib and a SHP2 inhibitor selected from (i) Compound A; (ii) Compound B; (iii) SHP099; (iv)NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof. The method for preventing or delaying the emergence of resistance in a cell (e.g., a tumor cell) to a therapeutic agent (e.g., an anti-cancer agent) targeting a RAS pathway signal transducer, may comprise administering Trametinib (GSK1120212) and Compound B. The method for preventing or delaying the emergence of resistance in a cell (e.g., a tumor cell) to a therapeutic agent (e.g., an anti-cancer agent) targeting a RAS pathway signal transducer, may comprise administering Trametinib (GSK1120212) and Compound A. The method for preventing or delaying the emergence of resistance in a cell (e.g., a tumor cell) to a therapeutic agent (e.g., an anti-cancer agent) targeting a RAS pathway signal transducer, may comprise administering Trametinib (GSK1120212) and Compound C. The method for preventing or delaying the emergence of resistance in a cell (e.g., a tumor cell) to a therapeutic agent (e.g., an anti-cancer agent) targeting a RAS pathway signal transducer, may comprise administering Trametinib (GSK1120212) and a compound selected from Table 1. The method for preventing or delaying the emergence of resistance in a cell (e.g., a tumor cell) to a therapeutic agent (e.g., an anti-cancer agent) targeting a RAS pathway signal transducer, may comprise administering Trametinib (GSK1120212) and a compound selected from Table 2. The method for preventing or delaying the emergence of resistance in a cell (e.g., a tumor cell) to a therapeutic agent (e.g., an anti-cancer agent) targeting a RAS pathway signal transducer, may comprise administering Trametinib (GSK1120212) and SHP099. The method for preventing or delaying the emergence of resistance in a cell (e.g., a tumor cell) to a therapeutic agent (e.g., an anti-cancer agent) targeting a RAS pathway signal transducer, may comprise administering Trametinib (GSK1120212) and NSC-87877. The method for preventing or delaying the emergence of resistance in a cell (e.g., a tumor cell) to a therapeutic agent (e.g., an anti-cancer agent) targeting a RAS pathway signal transducer, may comprise administering Trametinib (GSK1120212) and a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155, and; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof.

In some embodiments, the present disclosure provides a method for re-sensitizing a tumor that is resistant to a therapeutic agent targeting a RAS pathway signal transducer, the method comprising administering a SHP2 inhibitor. In particular embodiments, the therapeutic agent is a MAPK inhibitor (e.g., MEK inhibitor or an ERK inhibitor). Suitable MAPK inhibitors are known in the art, are disclosed herein, and include, without limitation: MEK inhibitors, one or more MAPK inhibitor described in Cancers (Basel). 2015 September; 7(3): 1758-1784, incorporated herein by reference in its entirety, one or more of Trametinib, Binimetinib, Selumetinib, Cobimetinib, LErafAON (NeoPharm), ISIS 5132; Vemurafenib, Pimasertib, TAK733, RO4987655 (CH4987655); CI-1040; PD-0325901; CH5126766; MAP855; AZD6244; Refametinib (RDEA 119/BAY 86-9766); GDC-0973/XL581; AZD8330 (ARRY-424704/ARRY-704); RO5126766 (Roche, described in PLoS One. 2014 Nov. 25; 9(11), incorporated herein by reference in its entirety); and GSK1120212 (or "JTP-74057", described in Clin Cancer Res. 2011 Mar. 1; 17(5):989-1000, incorporated herein by reference in its entirety.

In some embodiments, the present disclosure provides a method for treating cells (e.g., cancer cells) with a SHP2 inhibitor, wherein the cells have been rendered dependent on SHP2 by treatment with a therapeutic agent (e.g., a MAPK inhibitor). The therapeutic agent may be a MAPK inhibitor selected from a MEK inhibitor and an ERK inhibitor. The therapeutic agent may induce overactivation of the RAS pathway via relief of a natural RAS pathway negative feedback mechanism, wherein the overactivated RAS pathway is dependent on SHP2 signaling (e.g., for priming the reloading of GTP onto RAS). Administration of a SHP2 inhibitor in combination with the therapeutic agent (e.g., a MAPK inhibitor) may prevents such overactivation of the RAS pathway by the therapeutic agent. Such cells may, but need not comprise a RAS pathway mutation that confers cellular dependence on SHP2 (e.g., for reloading of GTP onto RAS). Treatment with a SHP2 inhibitor in combination with a MAPK inhibitor (e.g., a MEK or ERK inhibitor) may prevent MAPK inhibitor-induced feedback activation of the RAS pathway.

The present invention also provides methods for determining whether a subject has tumor that will be responsive to SHP2 inhibition. The method may comprise determining whether the tumor is classified as an $NF1^{LOF}$ subtype and administering to the subject an inhibitor of SHP2 if the tumor is classified as an $NF1^{LOF}$ subtype. In some embodiments, the determining may comprise empirical determining, e.g., via experimentation. Such methods for determining a subtype of a tumor are known in the art and may include genotyping, measuring NF1 protein levels, determining the size of NF1 (e.g., via any suitable method such as western blot, mass spectrometry, size exclusion chromatography), or measuring by a functional assay such as, a RAS-GTP accumulation assay.

In one embodiment, the present invention provides a method for determining whether a subject that has cancer will be responsive to SHP2 inhibition, the method comprising determining whether the cancer is classified as a $KRAS^{G12C}$ subtype and administering to the subject an inhibitor of SHP2 if the biological sample is classified as a $KRAS^{G12C}$ subtype. Methods for determining KRAS subtypes are known in the art and are suitable for use according to the present disclosure including, but not limited to direct sequencing, next generation sequencing, and utilization of a high-sensitivity diagnostic assay (with CE-IVD mark), e.g., as described in Domagala, et al., Pol J Pathol 3: 145-164 (2012), incorporated herein by reference in its entirety, including TheraScreen PCR; AmoyDx; PNAClamp; Real-Quality; EntroGen; LightMix; StripAssay; Hybcell plexA; Devyser; Surveyor; Cobas; and TheraScreen Pyro.

In one embodiment, the present invention provides a method for determining whether a subject that has cancer will be responsive to SHP2 inhibition, the method comprising determining whether the cancer is classified as a $KRAS^{G12D}$ subtype and administering to the subject an inhibitor of SHP2 if the biological sample is classified as a $KRAS^{G12D}$ subtype.

In one embodiment, the present invention provides a method for determining whether a subject that has cancer will be responsive to SHP2 inhibition, the method comprising determining whether the cancer is classified as a $KRAS^{G12S}$ subtype and administering to the subject an inhibitor of SHP2 if the biological sample is classified as a $KRAS^{G12S}$ subtype.

In one embodiment, the present invention provides a method for determining whether a subject that has cancer will be responsive to SHP2 inhibition, the method comprising determining whether the cancer is classified as a $KRAS^{G12V}$ subtype and administering to the subject an inhibitor of SHP2 if the biological sample is classified as a $KRAS^{G12V}$ subtype.

In one embodiment, the present disclosure provides methods of determining whether a treatment comprising a SHP2 inhibitor is optimal for administration to a patient suffering from a SHP2 related disease or disorder. In some aspects, the disease or disorder is a cancer. In some aspects, determining whether a patient should receive a treatment including a SHP2 inhibitor includes determining whether the cancer is classified as an $NF1^{LOF}$ subtype and, if so, determining that the patient should receive a SHP2 inhibitor treatment. In some aspects, determining whether a patient should receive a treatment including a SHP2 inhibitor includes determining whether the cancer is classified as a $KRAS^{G12C}$ subtype and, if so, determining that the patient should receive a SHP2 inhibitor treatment. In some aspects, determining whether a patient should receive a treatment including a SHP2 inhibitor includes determining whether the cancer is classified as a $KRAS^{G12A}$ subtype and, if so, determining that the patient should receive a SHP2 inhibitor treatment. In some aspects, determining whether a patient should receive a treatment including a SHP2 inhibitor includes determining whether the cancer is classified as a $KRAS^{G12S}$ subtype and, if so, determining that the patient should receive a SHP2 inhibitor treatment. In some aspects, determining whether a patient should receive a treatment including a SHP2 inhibitor includes determining whether the cancer is classified as a $KRAS^{G12V}$ subtype and, if so, determining that the patient should receive a SHP2 inhibitor treatment. The present disclosure accordingly also provides methods of treating such a patient comprising an $NF1^{LOF}$ subtype, a $KRAS^{G12A}$, a $KRAS^{G12C}$ subtype, a $KRAS^{G12V}$ subtype and/or a $KRAS^{G12S}$ subtype with a SHP2 inhibitor.

As one of ordinary skill in the art will appreciate, in various embodiments, all of the therapeutic agents disclosed herein, i.e., the specific TKI inhibitors, MEK inhibitors, ALK inhibitors, SHP2 inhibitors, EGFR inhibitors, etc., may be used in any one or more of the embodiments disclosed herein that call for such an inhibitor, generally. Thus, for example, an embodiment comprising treatment with, e.g., a "SHP2 inhibitor," generally, or a "TKI inhibitor," generally, may comprise treatment with any one or more SHP2 inhibitor or TKI inhibitor, respectively, that is disclosed herein (unless context requires otherwise).

Administration of the disclosed compositions and compounds (e.g., SHP2 inhibitors and/or other therapeutic agents) can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compounds or pharmaceutical compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts. Pharmaceutical compositions suitable for the delivery of a SHP2 inhibitor (alone or, e.g., in combination with another therapeutic agent according to the present disclosure) and methods for their preparation will be readily apparent to those skilled in the art. Such compositions and methods for their preparation may be found, e.g., in Remington's Pharmaceutical Sciences, 19th Edition (Mack Publishing Company, 1995), incorporated herein in its entirety.

Illustrative pharmaceutical compositions are tablets and gelatin capsules comprising a SHP2 inhibitor alone or in combination with another therapeutic agent according to the disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, a SHP2 inhibitor (alone or in combination with another therapeutic agent according to the disclosure) is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the SHP2 inhibitor (alone or in combination with another therapeutic agent according to the disclosure).

The SHP2 inhibitor can be also formulated as a suppository, alone or in combination with another therapeutic agent according to the disclosure, which can be prepared from fatty emulsions or suspensions; using polyalkylene glycols such as propylene glycol, as the carrier.

The SHP2 inhibitor can also be administered in the form of liposome delivery systems, such as small unilamellar vesicles, large unilamellar vesicles and multilamellar vesicles, either alone or in combination with another therapeutic agent according to the disclosure. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described for instance in U.S. Pat. No. 5,262,564, the contents of which are hereby incorporated by reference.

SHP2 inhibitors can also be delivered by the use of monoclonal antibodies as individual carriers to which the disclosed compounds are coupled. SHP2 inhibitors can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, a SHP2 inhibitor can be coupled to a class of biodegradable polymers useful in achieving controlled release of a drug, for example, polylactic acid, poly epsilon caprolactone, polyhydroxy butyric acid, poly orthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention relates to a pharmaceutical composition comprising a SHP2 inhibitor (alone or in combination with another therapeutic agent according to the present disclosure) and a pharmaceutically acceptable carrier. The pharmaceutically acceptable carrier can further include an excipient, diluent, or surfactant.

Thus, the present disclosure provides compositions (e.g., pharmaceutical compositions) comprising one or more SHP2 inhibitor for use in a method disclosed herein, e.g., a SHP2 monotherapy. Such compositions may comprise a SHP2 inhibitor and, e.g., one or more carrier, excipient, diluent, and/or surfactant.

The present disclosure provides compositions (e.g., pharmaceutical compositions) comprising one or more SHP2 inhibitor and one or more additional therapeutic agent for use in a method disclosed herein, e.g., a SHP2 combination therapy. Such compositions may comprise a SHP2 inhibitor, an additional therapeutic agent (e.g., a TKI, a MAPK pathway inhibitor, an EGFR inhibitor, an ALK inhibitor, a MEK inhibitor) and, e.g., one or more carrier, excipient, diluent, and/or surfactant.

The present disclosure provides compositions (e.g., pharmaceutical compositions) comprising one or more SHP2 inhibitor and one or more MEK inhibitor for use in a method disclosed herein, e.g., a SHP2 combination therapy. Such compositions may comprise a SHP2 inhibitor, a MEK inhibitor and, e.g., one or more carrier, excipient, diluent, and/or surfactant. Such compositions may consist essentially of a SHP2 inhibitor, a MEK inhibitor and, e.g., one or more carrier, excipient, diluent, and/or surfactant. Such compositions may consist of a SHP2 inhibitor, a MEK inhibitor and, e.g., one or more carrier, excipient, diluent, and/or surfactant. For example, one non-limiting example of a composition of the present disclosure may comprise, consist essentially of, or consist of (a) a SHP2 inhibitor; (b) a MEK inhibitor selected from one or more of Trametinib (GSK1120212); Selumetinib (AZD6244); Cobimetinib (GDC-0973/XL581), Binimetinib, Vemurafenib, Pimasertib, TAK733, RO4987655 (CH4987655); CI-1040; PD-0325901; CH5126766; MAP855; Refametinib (RDEA 119/BAY 86-9766); RO5126766, AZD8330 (ARRY-424704/ARRY-704); and GSK1120212; and (c) one or more carrier, excipient, diluent, and/or surfactant. Another non-limiting example of a composition of the present disclosure may comprise, consist essentially of, or consist of (a) a MEK inhibitor; (b) a SHP2 inhibitor selected from (i) Compound A; (ii) Compound B; (iii) SHP099; (iv)NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof; and (c) one or more carrier, excipient, diluent, and/or surfactant.

Another non-limiting example of a composition of the present disclosure may comprise, consist essentially of, or consist of (a) Compound B; (b) a MEK inhibitor selected from one or more of Trametinib (GSK1120212); Selumetinib (AZD6244); Cobimetinib (GDC-0973/XL581), Binimetinib, Vemurafenib, Pimasertib, TAK733, RO4987655 (CH4987655); CI-1040; PD-0325901; CH5126766; MAP855; Refametinib (RDEA 119/BAY 86-9766); RO5126766, AZD8330 (ARRY-424704/ARRY-704); and GSK1120212; and (c) one or more carrier, excipient, diluent, and/or surfactant. Another non-limiting example of a composition of the present disclosure may comprise, consist essentially of, or consist of (a) Trametinib; (b) a SHP2 inhibitor selected from (i) Compound A; (ii) Compound B; (iii) SHP099; (iv)NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof; and (c) one or more carrier, excipient, diluent, and/or surfactant.

Another non-limiting example of a composition of the present disclosure may comprise, consist essentially of, or consist of (a) Compound B; (b) Trametinib (GSK1120212); and (c) one or more carrier, excipient, diluent, and/or surfactant.

Another non-limiting example of a composition of the present disclosure may comprise, consist essentially of, or consist of (a) Compound A; (b) Trametinib (GSK1120212); and (c) one or more carrier, excipient, diluent, and/or surfactant.

Another non-limiting example of a composition of the present disclosure may comprise, consist essentially of, or consist of (a) Compound C; (b) Trametinib (GSK1120212); and (c) one or more carrier, excipient, diluent, and/or surfactant.

Another non-limiting example of a composition of the present disclosure may comprise, consist essentially of, or consist of (a) a compound selected from the compounds in Table 1; (b) Trametinib (GSK1120212); and (c) one or more carrier, excipient, diluent, and/or surfactant.

Another non-limiting example of a composition of the present disclosure may comprise, consist essentially of, or consist of (a) a compound selected from the compounds in Table 2; (b) Trametinib (GSK1120212); and (c) one or more carrier, excipient, diluent, and/or surfactant.

Another non-limiting example of a composition of the present disclosure may comprise, consist essentially of, or consist of (a) SHP099; (b) Trametinib (GSK1120212); and (c) one or more carrier, excipient, diluent, and/or surfactant.

Another non-limiting example of a composition of the present disclosure may comprise, consist essentially of, or consist of (a) Trametinib (GSK1120212); (b) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X and (c) one or more carrier, excipient, diluent, and/or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed Compound By weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of a SHP2 inhibitor, when used for the indicated effects, range from about 0.5 mg to about 5000 mg as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Effective dosage amounts of an ALK inhibitor, when used for the indicated effects, range from about 0.5 mg to about 5000 mg as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Effective dosage amounts of an EGFR inhibitor, when used for the indicated effects, range from about 0.5 mg to about 5000 mg as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Effective dosage amounts of an MEK inhibitor, when used for the indicated effects, range from about 0.05 mg to about 5000 mg as needed to treat the condition. Compositions for in vivo or in vitro use can contain about 0.05, 0.1, 0.2, 0.3, 0.4, 0.5, 0.6, 0.7, 0.8, 0.9, 1, 2, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

The present invention also provides kits for treating a disease or disorder with a SHP2 inhibitor, one or more carrier, excipient, diluent, and/or surfactant, and a means for determining whether a sample from a subject (e.g., a tumor sample) is likely to be sensitive to SHP2 treatment. In some embodiments, the means for determine comprises a means for determining whether the sample comprises an $NF1^{LOF}$ mutation, a $KRAS^{G12C}$ mutation, a $KRAS^{G12D}$ mutation, a $KRAS^{G12S}$ mutation, and/or a $KRAS^{G12V}$ mutation. Such means include, but are not limited to direct sequencing, and utilization of a high-sensitivity diagnostic assay (with CE-IVD mark), e.g., as described in Domagala, et al., Pol J Pathol 3: 145-164 (2012), incorporated herein by reference in its entirety, including TheraScreen PCR; AmoyDx; PNA-Clamp; RealQuality; EntroGen; LightMix; StripAssay; Hybcell plexA; Devyser; Surveyor; Cobas; and TheraScreen Pyro.

All of the U.S. patents, U.S. patent application publications, U.S. patent applications, PCT patent application, PCT patent application publications, foreign patents, foreign patent applications and non-patent publications referred to in this specification or listed in any Application Data Sheet are incorporated herein by reference in their entirety. From the foregoing it will be appreciated that, although specific embodiments of the invention have been described herein for purposes of illustration, various modifications may be made without deviating from the spirit and scope of the invention.

EXAMPLE EMBODIMENTS

Some embodiments of this disclosure are Embodiment I, as follows:

Embodiment I-1. A method of treating a subject having a disease or disorder comprising a cell containing a mutation encoding the KRAS$^{G12C}$ variant, comprising providing to the subject an inhibitor of SHP2.

Embodiment I-1a. An inhibitor of SHP2 for use in a method of treating a disease or disorder comprising a cell containing a mutation encoding the KRAS$^{G12C}$ variant.

Embodiment I-1b. Use of an inhibitor of SHP2 for the manufacture of a medicament for treating a disease or disorder comprising a cell containing a mutation encoding the KRAS$^{G12C}$ variant.

Embodiment I-2. A method of treating a subject having a disease or disorder comprising a cell with a mutation encoding an NF1 loss of function (NF1$^{LOF}$) variant, comprising providing to the subject an inhibitor of SHP2.

Embodiment I-2a. An inhibitor of SHP2 for use in a method of treating a disease or disorder comprising a cell with a mutation encoding an NF1 loss of function (NF1$^{LOF}$) variant.

Embodiment I-2b. Use of an inhibitor of SHP2 for the manufacture of a medicament for treating a disease or disorder comprising a cell with a mutation encoding an NF1 loss of function (NF1$^{LOF}$) variant.

Embodiment I-3. A method of treating a subject having a disease or disorder associated with a RAS pathway mutation in a cell of the subject that renders the cell at least partially dependent on signaling flux through SHP2, comprising providing to the subject an inhibitor of SHP2.

Embodiment I-3a. An inhibitor of SHP2 for use in a method of treating a disease or disorder associated with a RAS pathway mutation in a cell that renders the cell at least partially dependent on signaling flux through SHP2.

Embodiment I-3b. Use of an inhibitor of SHP2 for the manufacture of a medicament for treating a disease or disorder associated with a RAS pathway mutation in a cell that renders the cell at least partially dependent on signaling flux through SHP2.

Embodiment I-4. The method of Embodiment I-3, wherein the RAS pathway mutation is a RAS mutation selected from a KRAS mutation, an NRAS mutation, a SOS mutation, a BRAF Class III mutation, a Class I MEK1 mutation, a Class II MEK1 mutation, and an NF1 mutation.

Embodiment I-5. The method of Embodiment I-4, wherein the KRAS mutation is selected from a KRAS$^{G12A}$ mutation, a KRAS$^{G12C}$ mutation, a KRAS$^{G12D}$ mutation, a KRAS$^{G12F}$ mutation, a KRAS$^{G12I}$ mutation, a KRAS$^{G12L}$ mutation, a KRAS$^{G12R}$ mutation, a KRAS$^{G12S}$ mutation, a KRAS$^{G12V}$ mutation, and a KRAS$^{G12Y}$ mutation.

Embodiment I-6. The method of Embodiment I-4, wherein the KRAS mutation is KRAS$^{G12C}$.

Embodiment I-7. The method of Embodiment I-4, wherein the KRAS mutation is KRAS$^{G12A}$.

Embodiment I-8. The method of Embodiment I-4, wherein the BRAF Class III mutation is selected from one or more of the following amino acid substitutions in human BRAF: D287H; P367R; V459L; G466V; G466E; G466A; S467L; G469E; N581S; N581I; D594N; D594G; D594A; D594H; F595L; G596D; G596R and A762E.

Embodiment I-9. The method of Embodiment I-4, wherein the NF1 mutation is a loss of function mutation.

Embodiment I-10. The method of Embodiment I-4, wherein the Class I MEK1 mutation is selected from one or more of the following amino acid substitutions in human MEK1: D67N; P124L; P124S; and L177V.

Embodiment I-11. The method of Embodiment I-4, wherein the Class II MEK1 mutation is selected from one or more of the following amino acid substitutions in human MEK1: ΔE51-Q58; ΔF53-Q58; E203K; L177M; C121S; F53L; K57E; Q56P; and K57N.

Embodiment I-12. The method of any one of Embodiments I-1 to I-11, further comprising providing to the subject an inhibitor of the RAS pathway.

Embodiment I-13. The method of Embodiment I-12, wherein the inhibitor of the RAS pathway is a MAPK inhibitor.

Embodiment I-14. The method of Embodiment I-13, wherein the inhibitor of the RAS pathway is a MEK inhibitor or ERK inhibitor.

Embodiment I-15. The method of Embodiment I-12, wherein the inhibitor of the Ras pathway is selected from one or more of Trametinib, Binimetinib, Selumetinib, Cobimetinib, LErafAON (NeoPharm), ISIS 5132; Vemurafenib, Pimasertib, TAK733, RO4987655 (CH4987655); CI-1040; PD-0325901; CH5126766; MAP855; AZD6244; Refametinib (RDEA 119/BAY 86-9766); GDC-0973/XL581; AZD8330 (ARRY-424704/ARRY-704); RO5126766; ARS-853; LY3214996; BVD523; GSK1120212; Ulixertinib, and Abemaciclib.

Embodiment I-16. The method of any one of Embodiments I-1 to I-15, wherein the disease or condition is a tumor.

Embodiment I-17. The method of Embodiment I-16, wherein the tumor is selected from an NSCLC, a colon cancer, an oesophageal cancer, a rectal cancer, JMML, breast cancer, melanoma, Scwannoma, and a pancreatic cancer.

Embodiment I-18. A method of treating a subject having a disease associated with an NF1 loss of function mutation, comprising providing to the subject an inhibitor of SHP2.

Embodiment I-18a. An inhibitor of SHP2 for use in a method of treating a disease associated with an NF1 loss of function mutation.

Embodiment I-18b. Use of an inhibitor of SHP2 for the manufacture of a medicament for treating a disease associated with an NF1 loss of function mutation.

Embodiment I-19. The method of Embodiment I-18, wherein the disease is a tumor comprising cells with an NF1 loss of function mutation.

Embodiment I-20. The method of Embodiment I-19, wherein the tumor is an NSCLC or melanoma tumor.

Embodiment I-21. The method of Embodiment I-18, wherein the disease is selected from neurofibromatosis type I, neurofibromatosis type II, schwannomatosis, and Watson syndrome.

Embodiment I-22. The method of any one of Embodiments I-18 to I-21, further comprising providing to the subject an inhibitor of the RAS pathway.

Embodiment I-23. The method of Embodiment I-22, wherein the RAS pathway inhibitor is selected from one or more of Trametinib, Binimetinib, Selumetinib, Cobimetinib, LErafAON (NeoPharm), ISIS 5132; Vemurafenib, Pimasertib, TAK733, RO4987655 (CH4987655); CI-1040; PD-0325901; CH5126766; MAP855; AZD6244; Refametinib (RDEA 119/BAY 86-9766); GDC-0973/XL581; AZD8330 (ARRY-424704/ARRY-704); RO5126766; ARS-853; LY3214996; BVD523; GSK1120212; Ulixertinib, and Abemaciclib.

Embodiment I-24. A method for treating a subject having a tumor comprising:

(a) determining whether a biological sample obtained from the subject is classified as a KRAS mutant; and (b) administering to the subject an inhibitor of SHP2 if the biological sample is classified as a $KRAS^{G12C}$ mutant, a $KRAS^{G12D}$ mutant, a $KRAS^{G12S}$ mutant, or a $KRAS^{G12V}$ mutant.

Embodiment I-24a. An inhibitor of SHP2 for use in a method of treating a subject having a tumor, wherein the tumor comprises a $KRAS^{G12C}$ mutation, a $KRAS^{G12D}$ mutation, a $KRAS^{G12S}$ mutation, or a $KRAS^{G12V}$ mutation.

Embodiment I-24b. A method of selecting a subject having a tumor for treatment:

wherein the method comprises determining in vitro whether a biological sample obtained from the subject is classified as a KRAS mutant; and wherein the subject is selected for treatment if the biological sample is classified as a $KRAS^{G12C}$ mutant, a $KRAS^{G12D}$ mutant, a $KRAS^{G12S}$ mutant, or a $KRAS^{G12V}$ mutant.

Embodiment I-24c. An inhibitor of SHP2 for use in a method for treating a tumor, wherein the method comprises:

(a) determining whether a biological sample obtained from the subject is classified as a KRAS mutant; and (b) administering to the subject an inhibitor of SHP2 if the biological sample is classified as a $KRAS^{G12C}$ mutant, a $KRAS^{G12D}$ mutant, a $KRAS^{G12S}$ mutant, or a $KRAS^{G12V}$ mutant.

Embodiment I-25. A method for treating a subject having a tumor comprising:

(a) determining whether a biological sample obtained from the subject is classified as an $NF1^{LOF}$ mutant; and (b) administering to the subject an inhibitor of SHP2 if the biological sample is classified as an $NF1^{LOF}$ mutant.

Embodiment I-25a. An inhibitor of SHP2 for use in a method of treating a subject having a tumor, wherein the tumor comprises a $NF1^{LOF}$ mutation.

Embodiment I-25b. A method of selecting a subject having a tumor for treatment:

wherein the method comprises determining in vitro whether a biological sample obtained from the subject is classified as a $NF1^{LOF}$ mutant; and wherein the subject is selected for treatment if the biological sample is classified as a $NF1^{LOF}$ mutant.

Embodiment I-25c. An inhibitor of SHP2 for use in a method for treating a tumor, wherein the method comprises:

(a) determining whether a biological sample obtained from the subject is classified as a $NF1^{LOF}$ mutant; and (b) administering to the subject an inhibitor of SHP2 if the biological sample is classified as a $NF1^{LOF}$ mutant.

Embodiment I-26. A method for treating a subject having a tumor comprising:

(a) determining whether a biological sample obtained from the subject is classified as an Class 3 BRAF mutant; and (b) administering to the subject an inhibitor of SHP2 if the biological sample is classified as an Class 3 BRAF mutant.

Embodiment I-26a. An inhibitor of SHP2 for use in a method of treating a subject having a tumor, wherein the tumor comprises Class 3 BRAF mutation.

Embodiment I-26b. A method of selecting a subject having a tumor for treatment:

wherein the method comprises determining in vitro whether a biological sample obtained from the subject is classified as a Class 3 BRAF mutant; and wherein the subject is selected for treatment if the biological sample is classified as a Class 3 BRAF mutant.

Embodiment I-26c. An inhibitor of SHP2 for use in a method for treating a tumor, wherein the method comprises:

(a) determining whether a biological sample obtained from the subject is classified as a Class 3 BRAF mutant; and (b) administering to the subject an inhibitor of SHP2 if the biological sample is classified as a Class 3 BRAF mutant.

Embodiment I-27. A method for treating a subject having a tumor comprising:

(a) determining whether a biological sample obtained from the subject is classified as an Class I MEK1 mutant; and (b) administering to the subject an inhibitor of SHP2 if the biological sample is classified as an Class I MEK1 mutant.

Embodiment I-27a. An inhibitor of SHP2 for use in a method of treating a subject having a tumor, wherein the tumor comprises a Class I MEK1 mutation.

Embodiment I-27b. A method of selecting a subject having a tumor for treatment:

wherein the method comprises determining in vitro whether a biological sample obtained from the subject is classified as a Class I MEK1 mutant; and wherein the subject is selected for treatment if the biological sample is classified as a Class I MEK1 mutant.

Embodiment I-27c. An inhibitor of SHP2 for use in a method for treating a tumor, wherein the method comprises:

(a) determining whether a biological sample obtained from the subject is classified as a Class I MEK1 mutant; and (b) administering to the subject an inhibitor of SHP2 if the biological sample is classified as a Class I MEK1 mutant.

Embodiment I-28. A method for treating a subject having a tumor comprising:

(a) determining whether a biological sample obtained from the subject is classified as an Class II MEK1 mutant; and (b) administering to the subject an inhibitor of SHP2 if the biological sample is classified as an Class II MEK1 mutant.

Embodiment I-28a. An inhibitor of SHP2 for use in a method of treating a subject having a tumor, wherein the tumor comprises a Class II MEK1 mutation.

Embodiment I-28b. A method of selecting a subject having a tumor for treatment:

wherein the method comprises determining in vitro whether a biological sample obtained from the subject is classified as a Class II MEK1 mutant; and wherein the subject is selected for treatment if the biological sample is classified as a Class II MEK1 mutant.

Embodiment I-28c. An inhibitor of SHP2 for use in a method for treating a tumor, wherein the method comprises:

(a) determining whether a biological sample obtained from the subject is classified as a Class II MEK1 mutant; and (b) administering to the subject an inhibitor of SHP2 if the biological sample is classified as a Class II MEK1 mutant.

Embodiment I-29. A method for treating or preventing drug resistance in a subject receiving administration of a RAS pathway inhibitor, comprising administering to the subject an inhibitor of SHP2.

Embodiment I-29a. An inhibitor of SHP2 for use in a method for treating or preventing drug resistance in a subject receiving administration of a RAS pathway inhibitor.

Embodiment I-29b. Use of an inhibitor of SHP2 for the manufacture of a medicament for treating or preventing drug resistance in a subject receiving administration of a RAS pathway inhibitor.

Embodiment I-30. The method of Embodiment I-29, wherein the subject comprises a tumor containing cells with an NF1$^{LOF}$ mutation.

Embodiment I-31. The method of Embodiment I-29 or I-30, wherein the subject comprises a tumor containing a KRAS$^{G12C}$ mutation, a KRAS$^{G12D}$ mutation, a KRAS$^{G12A}$ mutation, a KRAS$^{G12S}$ mutation, or a KRAS$^{G12V}$ mutation.

Embodiment I-32. The method of any one of Embodiments I-29 to I-31, wherein the RAS pathway inhibitor is a MEK inhibitor.

Embodiment I-33. The method Embodiment I-32, wherein the MEK inhibitor is selected from one or more of Trametinib (GSK1120212), Selumetinib (AZD6244), Cobimetinib (GDC-0973/XL581), Binimetinib, Vemurafenib, Pimasertib, TAK733, RO4987655 (CH4987655), Vemurafenib, Pimasertib, TAK733, RO4987655 (CH4987655); CI-1040; PD-0325901, Refametinib (RDEA 119/BAY 86-9766), RO5126766, AZD8330 (ARRY-424704/ARRY-704), CH5126766, MAP855, and GSK1120212.

Embodiment I-34. The method of any one of Embodiments I-29 to I-31, wherein the RAS pathway inhibitor is an ERK inhibitor.

Embodiment I-35. The method of Embodiment I-34, wherein the ERK inhibitor is selected from any ERK inhibitor known in the art; LY3214996; Ulixertinib; and BVD523.

Embodiment I-36. The method of any one of the preceding embodiments, wherein the inhibitor of SHP2 is selected from (i) Compound A; (ii) Compound B; (iii) SHP099; (iv) NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof.

Embodiment I-37. A combination therapy comprising a RAS pathway inhibitor and an inhibitor of SHP2.

Embodiment I-38. The combination therapy of Embodiment I-37, wherein the RAS pathway inhibitor is a MEK inhibitor.

Embodiment I-39. The combination therapy of Embodiment I-38, wherein the MEK inhibitor is selected from one or more of Trametinib (GSK1120212), Selumetinib (AZD6244), Cobimetinib (GDC-0973/XL581), Binimetinib, Vemurafenib, Pimasertib, TAK733, RO4987655 (CH4987655), CI-1040; PD-0325901, Refametinib (RDEA 119/BAY 86-9766), RO5126766, AZD8330 (ARRY-424704/ARRY-704), CH5126766, MAP855, and GSK1120212.

Embodiment I-40. The combination therapy of Embodiment I-37, wherein the RAS pathway inhibitor is the KRAS$^{G12C}$-specific inhibitor ARS-853.

Embodiment I-41. The combination therapy of any one of Embodiments I-37 to I-40, wherein the inhibitor of SHP2 is selected from (i) Compound A; (ii) Compound B; (iii) SHP099; (iv)NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof.

Embodiment I-42. The combination therapy of any one of Embodiments I-37 to I-41, for use in the treatment of a tumor.

Embodiment I-43. The combination therapy of Embodiment I-42, wherein the tumor is selected from tumors of hemopoietic and lymphoid system; a myeloproliferative syndrome; a myelodysplastic syndromes; leukemia; acute myeloid leukemia; juvenile myelomonocytic leukemia; esophageal cancer; breast cancer; lung cancer; colon cancer; gastric cancer; neuroblastoma; bladder cancer; prostate cancer; glioblastoma; urothelial carcinoma; uterine carcinoma; adenoid and ovarian sereous cystadenocarcinoma; paraganglioma; phaeochromocytoma; pancreatic cancer; adrenocortical carcinoma; stomach adenocarcinoma; sarcoma; rhabdomyosarcoma; lymphoma; head and neck cancer; skin cancer; peritoneum cancer; intestinal cancer (small and large intestine); thyroid cancer; endometrial cancer; cancer of the biliary tract; soft tissue cancer; ovarian cancer; central nervous system cancer (e.g.; primary CNS lymphoma); stomach cancer; pituitary cancer; genital tract cancer; urinary tract cancer; salivary gland cancer; cervical cancer; liver cancer; eye cancer; cancer of the adrenal gland; cancer of autonomic ganglia; cancer of the upper aerodigestive tract; bone cancer; testicular cancer; pleura cancer; kidney cancer; penis cancer; parathyroid cancer; cancer of the meninges; vulvar cancer and melanoma.

Embodiment I-44. A pharmaceutical composition comprising a RAS pathway inhibitor, a SHP2 inhibitor, and one or more pharmaceutically acceptable carrier, excipient, diluent, and/or surfactant.

Embodiment I-45. The pharmaceutical composition of Embodiment I-44, wherein the SHP2 inhibitor is selected from (i) Compound A; (ii) Compound B; (iii) SHP099; (iv)NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof.

Embodiment I-46. The pharmaceutical composition of Embodiment I-44 or 1-45, wherein the RAS pathway inhibitor is selected from one or more of Trametinib (GSK1120212) Selumetinib (AZD6244); Cobimetinib (GDC-0973/XL581), Binimetinib, Vemurafenib, Pimasertib, TAK733, RO4987655 (CH4987655); CI-1040; PD-0325901; CH5126766; MAP855; Refametinib (RDEA 119/BAY 86-9766); RO5126766, AZD8330 (ARRY-424704/ARRY-704); GSK1120212, Ulixertinib; and Abemaciclib.

Embodiment I-47. The pharmaceutical composition of any one of Embodiments I-44 to I-46, for use in the treatment of a tumor.

Embodiment I-48. The pharmaceutical composition of Embodiment I-47, wherein the tumor is selected from tumors of hemopoietic and lymphoid system; a myeloproliferative syndrome; a myelodysplastic syndromes; leukemia; acute myeloid leukemia; juvenile myelomonocytic leukemia; esophageal cancer; breast cancer; lung cancer; colon cancer; gastric cancer; neuroblastoma; bladder cancer; prostate cancer; glioblastoma; urothelial carcinoma; uterine carcinoma; adenoid and ovarian sereous cystadenocarcinoma; paraganglioma; phaeochromocytoma; pancreatic cancer; adrenocortical carcinoma; stomach adenocarcinoma; sarcoma; rhabdomyosarcoma; lymphoma; head and neck cancer; skin cancer; peritoneum cancer; intestinal cancer (small and large intestine); thyroid cancer; endometrial cancer; cancer of the biliary tract; soft tissue cancer; ovarian cancer; central nervous system cancer (e.g.; primary CNS lymphoma); stomach cancer; pituitary cancer; genital tract cancer; urinary tract cancer; salivary gland cancer; cervical cancer; liver cancer; eye cancer; cancer of the adrenal gland; cancer of autonomic ganglia; cancer of the upper aerodigestive tract; bone cancer; testicular cancer; pleura cancer; kidney cancer; penis cancer; parathyroid cancer; cancer of the meninges; vulvar cancer and melanoma.

Embodiment I-49. The method of any one of Embodiment I-16, I-18, I-19, I-24 to I-28, and I-30 to I-36, wherein the tumor is selected from tumors of hemopoietic and lymphoid system; a myeloproliferative syndrome; a myelodysplastic syndromes; leukemia; acute myeloid leukemia; juvenile myelomonocytic leukemia; esophageal cancer; breast cancer; lung cancer; colon cancer; gastric cancer; neuroblastoma; bladder cancer; prostate cancer; glioblastoma; urothelial carcinoma; uterine carcinoma; adenoid and ovarian sereous cystadenocarcinoma; paraganglioma; phaeochromocytoma; pancreatic cancer; adrenocortical carcinoma; stomach adenocarcinoma; sarcoma; rhabdomyosarcoma; lymphoma; head and neck cancer; skin cancer; peritoneum cancer; intestinal cancer (small and large intestine); thyroid cancer; endometrial cancer; cancer of the biliary tract; soft tissue cancer; ovarian cancer; central nervous system cancer (e.g.; primary CNS lymphoma); stomach cancer; pituitary cancer; genital tract cancer; urinary tract cancer; salivary gland cancer; cervical cancer; liver cancer; eye cancer; cancer of the adrenal gland; cancer of autonomic ganglia; cancer of the upper aerodigestive tract; bone cancer; testicular cancer; pleura cancer; kidney cancer; penis cancer; parathyroid cancer; cancer of the meninges; vulvar cancer and melanoma.

Embodiment I-50. A method of inhibiting the growth or proliferation of a cell containing a RAS pathway mutation, wherein the RAS pathway mutation renders the cell at least partially dependent on signaling flux through SHP2, the method comprising contacting the cell with an inhibitor of SHP2.

Embodiment I-50a. An inhibitor of SHP2 for use in a method of inhibiting the growth or proliferation of a cell containing a RAS pathway mutation, wherein the RAS pathway mutation renders the cell at least partially dependent on signaling flux through SHP2.

Embodiment I-50b. Use of an inhibitor of SHP2 for the manufacture of a medicament for inhibiting the growth or proliferation of a cell containing a RAS pathway mutation, wherein the RAS pathway mutation renders the cell at least partially dependent on signaling flux through SHP2.

Embodiment I-51. A method of inhibiting RAS-GTP accumulation in a cell containing a RAS pathway mutation, wherein the RAS pathway mutation renders the cell at least partially dependent on signaling flux through SHP2, the method comprising contacting the cell with an inhibitor of SHP2.

Embodiment I-51a. An inhibitor of SHP2 for use in a method of inhibiting RAS-GTP accumulation in a cell containing a RAS pathway mutation, wherein the RAS pathway mutation renders the cell at least partially dependent on signaling flux through SHP2.

Embodiment I-51b. Use of an inhibitor of SHP2 for the manufacture of a medicament for inhibiting RAS-GTP accumulation in a cell containing a RAS pathway mutation, wherein the RAS pathway mutation renders the cell at least partially dependent on signaling flux through SHP2.

Embodiment I-52. A method of killing a cell containing a RAS pathway mutation, wherein the RAS pathway mutation renders the cell at least partially dependent on signaling flux through SHP2, the method comprising contacting the cell with an inhibitor of SHP2.

Embodiment I-52a. An inhibitor of SHP2 for use in a method of killing a cell containing a RAS pathway mutation, wherein the RAS pathway mutation renders the cell at least partially dependent on signaling flux through SHP2.

Embodiment I-52b. Use of an inhibitor of SHP2 for the manufacture of a medicament for killing a cell containing a RAS pathway mutation, wherein the RAS pathway mutation renders the cell at least partially dependent on signaling flux through SHP2.

Embodiment I-53. The method of any one of Embodiments I-50 to I-52, wherein the SHP2 inhibitor is selected from (i) Compound A; (ii) Compound B; (iii) SHP099; (iv)NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof.

Embodiment I-54. The method of any one of Embodiments I-50 to I-53, wherein the RAS pathway mutation is selected from a KRAS mutation, an NRAS mutation, an HRAS mutation, a SOS mutation, a Class III BRAF mutation, and an NF1 loss of function mutation.

Embodiment I-55. The method of Embodiment I-54, wherein the KRAS mutation is selected from a $KRAS^{G12A}$ mutation, a $KRAS^{G12C}$ mutation, a $KRAS^{G12D}$ mutation, a $KRAS^{G12F}$ mutation, a $KRAS^{G12I}$ mutation, a $KRAS^{G12L}$ mutation, a $KRAS^{G12R}$ mutation, a $KRAS^{G12S}$ mutation, a $KRAS^{G12V}$ mutation, and a $KRAS^{G12Y}$ mutation.

Embodiment I-56. The method of Embodiment I-54, wherein the KRAS mutation is $KRAS^{G12C}$.

Embodiment I-57. The method of Embodiment I-54, wherein the KRAS mutation is $KRAS^{G12A}$.

Embodiment I-58. The method of Embodiment I-54, wherein the Class 3 BRAF mutation is selected from one or more of the following amino acid substitutions in human BRAF: D287H; P367R; V459L; G466V; G466E; G466A; S467L; G469E; N581S; N581I; D594N; D594G; D594A; D594H; F595L; G596D; G596R and A762E.

Embodiment I-59. The method of any one of Embodiments I-50 to I-58, further comprising contacting the cell with an inhibitor of the RAS pathway.

Embodiment I-60. The method of Embodiment I-59, wherein the inhibitor of the RAS pathway is a MAPK inhibitor.

Embodiment I-61. The method of Embodiment I-60, wherein the inhibitor of the RAS pathway is a MEK inhibitor or ERK inhibitor.

Embodiment I-62. The method of Embodiment I-61, wherein the inhibitor of the Ras pathway is selected from one or more of Trametinib, Binimetinib, Selumetinib, Cobimetinib, LErafAON (NeoPharm), ISIS 5132; Vemurafenib, Pimasertib, TAK733, RO4987655 (CH4987655); CI-1040; PD-0325901; CH5126766; MAP855; AZD6244; Refametinib (RDEA 119/BAY 86-9766); GDC-0973/XL581; AZD8330 (ARRY-424704/ARRY-704); RO5126766; ARS-853; LY3214996; BVD523; GSK1120212; Ulixertinib; and Abemaciclib.

Embodiment I-63. The method of any one of Embodiment I-1 to I-36, I-49 to I-62 further comprising contacting the cell with a SOS inhibitor.

Embodiment I-64. The method of Embodiment I-63, wherein the SOS inhibitor is administered to a cell comprising higher than normal SOS levels or SOS activity.

Embodiment I-65. The method of Embodiment I-16, wherein the tumor is from a NSCLC tumor.

Embodiment I-66. The method of Embodiment I-16, wherein the tumor is a colon cancer tumor.

Embodiment I-67. The method of Embodiment I-16, wherein the tumor is an oesophageal cancer tumor.

Embodiment I-68. The method of Embodiment I-16, wherein the tumor is a rectal cancer tumor.

Embodiment I-69. The method of Embodiment I-16, wherein the tumor is a JMML tumor.

Embodiment I-70. The method of Embodiment I-16, wherein the tumor is a breast cancer tumor.

Embodiment I-71. The method of Embodiment I-16, wherein the tumor is a melanoma tumor.

Embodiment I-72. The method of Embodiment I-16, wherein the tumor is a Scwannoma tumor.

Embodiment I-73. The method of Embodiment I-16, wherein the tumor is a pancreatic cancer tumor.

Embodiment I-74. The method of any one of the preceding embodiments, wherein the SHP2 inhibitor is selected from (i) Compound A; (ii) Compound B; (iii) SHP099; (iv)NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof.

Embodiment I-75. A method of inhibiting the growth of a tumor cell, comprising contacting the tumor cell a combination therapy comprising a MEK inhibitor and a SHP2 inhibitor.

Embodiment I-75a. A combination therapy comprising a MEK inhibitor and a SHP2 inhibitor for use in a method of inhibiting the growth of a tumor cell.

Embodiment I-75b. Use of a combination therapy comprising a MEK inhibitor and a SHP2 inhibitor for the manufacture of a medicament for inhibiting the growth of a tumor cell.

Embodiment I-76. The method of Embodiment I-75, wherein the MEK inhibitor is selected from one or more of Trametinib (GSK1120212), Selumetinib (AZD6244), Cobimetinib (GDC-0973/XL581), Binimetinib, Vemurafenib, Pimasertib, TAK733, RO4987655 ($CH_{4987655}$), CI-1040; PD-0325901, $CH_{5126766}$, MAP855, Refametinib (RDEA 119/BAY 86-9766), RO5126766, AZD8330 (ARRY-424704/ARRY-704), and GSK1120212.

Embodiment I-77. The method of Embodiment I-75 or I-76, wherein the SHP2 inhibitor is selected from (i) Compound A; (ii) Compound B; (iii) SHP099; (iv)NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof.

Embodiment I-78. The method of any one of Embodiments I-75 to I-77, wherein the MEK inhibitor is Trametinib (GSK1120212).

Embodiment I-79. The method of any one of Embodiments I-75 to I-78, wherein the SHP2 inhibitor is Compound B.

Embodiment I-80. The method of Embodiment I-75, wherein the MEK inhibitor is Trametinib (GSK1120212) and the SHP2 inhibitor is Compound B.

Embodiment I-81. The method of any one of Embodiment I-75 to I-80, wherein the tumor cell is a cell from a tumor selected from tumors of hemopoietic and lymphoid system; a myeloproliferative syndrome; a myelodysplastic syndromes; leukemia; acute myeloid leukemia; juvenile myelomonocytic leukemia; esophageal cancer; breast cancer; lung cancer; colon cancer; gastric cancer; neuroblastoma; bladder cancer; prostate cancer; glioblastoma; urothelial carcinoma; uterine carcinoma; adenoid and ovarian sereous cystadenocarcinoma; paraganglioma; phaeochromocytoma; pancreatic cancer; adrenocortical carcinoma; stomach adenocarcinoma; sarcoma; rhabdomyosarcoma; lymphoma; head and neck cancer; skin cancer; peritoneum cancer; intestinal cancer (small and large intestine); thyroid cancer; endometrial cancer; cancer of the biliary tract; soft tissue cancer; ovarian cancer; central nervous system cancer (e.g.; primary CNS lymphoma); stomach cancer; pituitary cancer; genital tract cancer; urinary tract cancer; salivary gland cancer; cervical cancer; liver cancer; eye cancer; cancer of the adrenal gland; cancer of autonomic ganglia; cancer of the upper aerodigestive tract; bone cancer; testicular cancer; pleura cancer; kidney cancer; penis cancer; parathyroid cancer; cancer of the meninges; vulvar cancer and melanoma.

Embodiment I-82. The method of any one of Embodiments I-75 to I-80, wherein the tumor is from a NSCLC tumor.

Embodiment I-83. The method of any one of Embodiments I-75 to I-82, wherein the contacting occurs in vivo in a subject.

Embodiment I-84. The method of Embodiment I-83, wherein the subject is a human.

Embodiment I-85. The method of any one of Embodiments I-75 to I-84, wherein the contacting of the tumor cell with the combination therapy comprising the MEK inhibitor and the SHP2 inhibitor results in an inhibition of tumor growth that is more than merely additive with respect to the amount of tumor growth inhibition achievable by contacting the tumor cell with each of the respective MEK and SHP2 inhibitors separately.

Embodiment I-86. The method of any one of Embodiments I-75 to I-85, wherein the MEK inhibitor and the SHP2 inhibitor do not contact the tumor cell simultaneously.

Embodiment I-87. The method of any one of Embodiments I-75 to I-85, wherein the MEK inhibitor and the SHP2 inhibitor contact the tumor cell simultaneously.

Embodiment I-88. The method of any one of Embodiments I-85 to I-87, wherein the contacting is via administration of the MEK inhibitor and the SHP2 inhibitor to the subject.

Embodiment I-89. The method of Embodiment I-88, wherein the administration of the MEK inhibitor precedes the administration of the SHP2 inhibitor.

Embodiment I-90. The method of Embodiment I-88, wherein the administration of the SHP2 inhibitor precedes the administration of the MEK inhibitor.

Embodiment I-91. The method of Embodiment I-88, wherein the administration of the SHP2 inhibitor and the administration of the MEK inhibitor occurs simultaneously.

Embodiment I-92. The method of Embodiment I-91, wherein the SHP2 inhibitor and the MEK inhibitor are administered as a single pharmaceutical composition.

Embodiment I-93. The method of Embodiment I-91, wherein the SHP2 inhibitor and the MEK inhibitor are administered as separate pharmaceutical compositions.

Embodiment I-94. The method of any one of Embodiments I-75 to I-93, wherein the growth of the tumor cell is inhibited enough to case partial or complete regression of the tumor.

Embodiment I-95. A method of inhibiting the growth of a tumor cell, comprising contacting the tumor cell a combination therapy comprising trametinib (GSK1120212) and Compound B.

Embodiment I-95a. A combination therapy comprising trametinib (GSK1120212) and Compound B for use in a method of inhibiting the growth of a tumor cell.

Embodiment I-95b. Use of a combination therapy comprising trametinib (GSK1120212) and Compound B for the manufacture of medicament for inhibiting the growth of a tumor cell.

Embodiment I-96. The method of Embodiment I-95, wherein the tumor cell is from a NSCLC tumor.

Embodiment I-97. The method of Embodiment I-95 or I-96, wherein the contacting occurs in vivo in a subject.

Embodiment I-98. The method of Embodiment I-97, wherein the subject is a human.

Embodiment I-99. The method of any one of Embodiments I-95 to I-98, wherein the contacting of the tumor cell with the combination therapy comprising trametinib (GSK1120212) and Compound B results in an inhibition of tumor growth that is more than merely additive with respect to the amount of tumor growth inhibition achievable by contacting the tumor cell with each of trametinib (GSK1120212) and Compound B separately.

Embodiment I-100. The method of any one of Embodiments I-95 to I-99, wherein the growth of the tumor cell is inhibited enough to case partial or complete regression of the tumor.

Embodiment I-101. A method of treating a subject having a tumor, comprising contacting a tumor cell in the tumor in the subject with a combination therapy comprising a MEK inhibitor and a SHP2 inhibitor.

Embodiment I-101a. A combination therapy comprising a MEK inhibitor and a SHP2 inhibitor for use in a method of treating a subject having a tumor.

Embodiment I-101b. Use of a combination therapy comprising a MEK inhibitor and a SHP2 inhibitor for the manufacture of medicament for treating a subject having a tumor.

Embodiment I-102. The method of Embodiment I-101, wherein the MEK inhibitor is selected from one or more of Trametinib (GSK1120212); Selumetinib (AZD6244); Cobimetinib (GDC-0973/XL581), Binimetinib, Vemurafenib, Pimasertib, TAK733, RO4987655 (CH4987655), CI-1040; PD-0325901; CH5126766; MAP855; Refametinib (RDEA 119/BAY 86-9766); RO5126766, AZD8330 (ARRY-424704/ARRY-704); and GSK1120212.

Embodiment I-103. The method of Embodiment I-101 or I-102, wherein the SHP2 inhibitor is selected from (i) Compound A; (ii) Compound B; (iii) SHP099; (iv)NSC-87877; (v) a SHP2 inhibitor compound of any one of Formula I, of Formula II, of Formula III, of Formula I-V1, of Formula I-V2, of Formula I-W, of Formula I-X, of Formula I-Y, of Formula I-Z, of Formula IV, of Formula V, of Formula VI, of Formula IV-X, of Formula IV-Y, of Formula IV-Z, of Formula VII, of Formula VIII, of Formula IX, and of Formula X; (vi) TNO155; (vii) a SHP2 inhibitor disclosed in international PCT application PCT/US2017/041577 (WO2018013597), incorporated herein by reference in its entirety; (viii) Compound C; (ix) a compound from Table 1, disclosed herein; (x) a compound from Table 2, disclosed herein; and (xi) a combination thereof.

Embodiment I-104. The method of Embodiment I-101, wherein the MEK inhibitor is Trametinib (GSK1120212).

Embodiment I-105. The method of any one of Embodiments I-101 to I-104, wherein the SHP2 inhibitor is Compound B.

Embodiment I-106. The method of Embodiment I-101, wherein the MEK inhibitor is Trametinib (GSK1120212) and the SHP2 inhibitor is Compound B.

Embodiment I-107. The method of any one of Embodiments I-101 to I-106, wherein the tumor cell is a cell from a tumor selected from tumors of hemopoietic and lymphoid system; a myeloproliferative syndrome; a myelodysplastic syndromes; leukemia; acute myeloid leukemia; juvenile myelomonocytic leukemia; esophageal cancer; breast cancer; lung cancer; colon cancer; gastric cancer; neuroblastoma; bladder cancer; prostate cancer; glioblastoma; urothelial carcinoma; uterine carcinoma; adenoid and ovarian sereous cystadenocarcinoma; paraganglioma; phaeochromocytoma; pancreatic cancer; adrenocortical carcinoma; stomach adenocarcinoma; sarcoma; rhabdomyosarcoma; lymphoma; head and neck cancer; skin cancer; peritoneum cancer; intestinal cancer (small and large intestine); thyroid cancer; endometrial cancer; cancer of the biliary tract; soft tissue cancer; ovarian cancer; central nervous system cancer (e.g.; primary CNS lymphoma); stomach cancer; pituitary cancer; genital tract cancer; urinary tract cancer; salivary gland cancer; cervical cancer; liver cancer; eye cancer; cancer of the adrenal gland; cancer of autonomic ganglia; cancer of the upper aerodigestive tract; bone cancer; testicular cancer; pleura cancer; kidney cancer; penis cancer; parathyroid cancer; cancer of the meninges; vulvar cancer and melanoma.

Embodiment I-108. The method of any one of Embodiments I-101 to I-107, wherein the tumor cell is from a NSCLC tumor.

Embodiment I-109. The method of any one of Embodiments I-101 to I-108, wherein the contacting occurs in vivo in a subject.

Embodiment I-110. The method of Embodiment I-109, wherein the subject is a human.

Embodiment I-111. The method of any one of Embodiments I-101 to I-110, wherein the contacting of the tumor cell with the combination therapy comprising the MEK inhibitor and the SHP2 inhibitor results in an inhibition of tumor growth that is more than merely additive with respect to the amount of tumor growth inhibition achievable by contacting the tumor cell with each of the respective MEK and SHP2 inhibitors separately.

Embodiment I-112. The method of any one of Embodiments I-101 to I-111, wherein the MEK inhibitor and the SHP2 inhibitor do not contact the tumor cell simultaneously.

Embodiment I-113. The method of any one of Embodiments I-101 to I-111, wherein the MEK inhibitor and the SHP2 inhibitor contact the tumor cell simultaneously.

Embodiment I-114. The method of any one of Embodiments I-111 to I-113, wherein the contacting is via administration of the MEK inhibitor and the SHP2 inhibitor to the subject.

Embodiment I-115. The method of Embodiment I-114, wherein the administration of the MEK inhibitor precedes the administration of the SHP2 inhibitor.

Embodiment I-116. The method of Embodiment I-114, wherein the administration of the SHP2 inhibitor precedes the administration of the MEK inhibitor.

Embodiment I-117. The method of Embodiment I-114, wherein the administration of the SHP2 inhibitor and the administration of the MEK inhibitor occurs simultaneously.

Embodiment I-118. The method of Embodiment I-117, wherein the SHP2 inhibitor and the MEK inhibitor are administered as a single pharmaceutical composition.

Embodiment I-119. The method of Embodiment I-117, wherein the SHP2 inhibitor and the MEK inhibitor are administered as separate pharmaceutical compositions.

Embodiment I-120. The method of any one of Embodiments I-101 to I-119, wherein the treatment inhibits the growth of the tumor cell.

Embodiment I-121. The method of Embodiment I-120, wherein the growth of the tumor cell is inhibited enough to case partial or complete regression of the tumor.

Embodiment I-122. A method of treating a subject having a tumor, comprising contacting a tumor cell of the tumor in the subject with a combination therapy comprising trametinib (GSK1120212) and Compound B.

Embodiment I-122a. A combination therapy comprising trametinib (GSK1120212) and Compound B for use in a method of treating a subject having a tumor.

Embodiment I-122b. Use of a combination therapy comprising trametinib (GSK1120212) and Compound B for the manufacture of a medicament for treating a subject having a tumor.

Embodiment I-123. The method of Embodiment I-122, wherein the tumor cell is from a NSCLC tumor.

Embodiment I-124. The method of Embodiment I-122 or I-123, wherein the contacting occurs in vivo in a subject.

Embodiment I-125. The method of Embodiment I-124, wherein the subject is a human.

Embodiment I-126. The method of any one of Embodiments I-122 to I-125, wherein the contacting of the tumor cell with the combination therapy comprising trametinib (GSK1120212) and Compound B results in an inhibition of tumor growth that is more than merely additive with respect to the amount of tumor growth inhibition achievable by contacting the tumor cell with each of trametinib (GSK1120212) and Compound B separately.

Embodiment I-127. The method of any one of Embodiments I-122 to I-126, wherein the growth of the tumor cell is inhibited enough to case partial or complete regression of the tumor.

Embodiment I-128. The method of any one of Embodiments I-1 to I-36, I-49 to I-78, I-80 to I-94, I-101 to I-104, I-107 to I-121, wherein the SHP2 inhibitor is Compound C.

Embodiment I-129. The combination therapy of any one of Embodiments I-37 to I-43, wherein the SHP2 inhibitor is Compound C.

Embodiment I-130. The pharmaceutical composition of any one of Embodiments I-44 to I-48, wherein the SHP2 inhibitor is Compound C.

Embodiment I-131. A method of inhibiting the growth of a tumor cell, comprising contacting the tumor cell with a combination therapy comprising trametinib (GSK1120212) and Compound C.

Embodiment I-131a. A combination therapy comprising trametinib (GSK1120212) and Compound C for use in a method of inhibiting the growth of a tumor cell.

Embodiment I-131 b. Use of a combination therapy comprising trametinib (GSK1120212) and Compound C for the manufacture of a medicament for inhibiting the growth of a tumor cell.

Embodiment I-132. The method of Embodiment I-131, wherein the tumor cell is from a NSCLC tumor.

Embodiment I-133. The method of Embodiment I-131 or I-132, wherein the contacting occurs in vivo in a subject.

Embodiment I-134. The method of Embodiment I-133, wherein the subject is a human.

Embodiment I-135. The method of any one of Embodiments I-131 to I-134, wherein the contacting of the tumor cell with the combination therapy comprising trametinib (GSK1120212) and Compound C results in an inhibition of tumor growth that is more than merely additive with respect to the amount of tumor growth inhibition achievable by contacting the tumor cell with each of trametinib (GSK1120212) and Compound C separately.

Embodiment I-136. The method of any one of Embodiments I-131 to I-135, wherein the growth of the tumor cell is inhibited enough to case partial or complete regression of the tumor.

Embodiment I-137. A method of treating a subject having a tumor, comprising contacting a tumor cell of the tumor in the subject with a combination therapy comprising trametinib (GSK1120212) and Compound C.

Embodiment I-137a. A combination therapy comprising trametinib (GSK1120212) and Compound C for use in a method of treating a subject having a tumor.

Embodiment I-137b. Use of a combination therapy comprising trametinib (GSK1120212) and Compound C for the manufacture of a medicament for treating a subject having a tumor.

Embodiment I-138. The method of Embodiment I-137, wherein the tumor cell is from a NSCLC tumor.

Embodiment I-139. The method of Embodiment I-137 or I-138, wherein the contacting occurs in vivo in a subject.

Embodiment I-140. The method of Embodiment I-139, wherein the subject is a human.

Embodiment I-141. The method of any one of Embodiments I-137 to I-140, wherein the contacting of the tumor cell with the combination therapy comprising trametinib (GSK1120212) and Compound C results in an inhibition of tumor growth that is more than merely additive with respect to the amount of tumor growth inhibition achievable by contacting the tumor cell with each of trametinib (GSK1120212) and Compound C separately.

Embodiment I-142. The method of any one of Embodiment I-137 to I-141, wherein the growth of the tumor cell is inhibited enough to case partial or complete regression of the tumor.

Embodiment I-143. The method of any one of Embodiments I-1 to I-36 and 1-49, comprising administering an effective amount of the inhibitor of SHP2.

Embodiment I-144. The method of any one of Embodiments I-50 to I-128 and 1-131 to I-142, comprising contacting the cell with an effective amount of the inhibitor of SHP2.

Embodiment I-145. The combination therapy of any one of Embodiments I-37 to I-43, I-75a, I-95a, I-101a, I-122a, 1-129, I-131a, and I-137a, comprising an effective amount of the inhibitor of SHP2.

Embodiment I-146. The pharmaceutical composition of any one of Embodiments I-44 to I-48 and I-130, comprising an effective amount of the inhibitor of SHP2.

Embodiment I-147. The inhibitor of SHP2 for use in a method according to any one of Embodiments I-1a, I-2a, I-3a, I-18a, I-24a, I-24c, I-25a, I-25c, I-26a, I-26c, I-27a, I-27c, I-28a, I-28c, I-29a, I-50a, I-51a, and I-52a, wherein the inhibitor of SHP2 is used in an effective amount.

Embodiment I-148. The use of an inhibitor of SHP2 according to any one of Embodiments I-1b, I-2b, I-3b, I-18b, I-29b, I-50b, I-51b, I-52b, I-, wherein the inhibitor of SHP2 is used in an effective amount.

Embodiment I-149. The method of any one of Embodiments I-1 to I-36 and 1-49, comprising administering a therapeutically effective amount of the inhibitor of SHP2.

Embodiment I-150. The method of any one of Embodiments I-50 to I-128 and 1-131 to I-142, comprising contacting the cell with a therapeutically effective amount of the inhibitor of SHP2.

Embodiment I-151. The combination therapy of any one of Embodiments I-37 to I-43, I-75a, I-95a, I-101a, I-122a, 1-129, I-131a, and I-137a, comprising a therapeutically effective amount of the inhibitor of SHP2.

Embodiment I-152. The pharmaceutical composition of any one of Embodiments I-44 to I-48 and I-130, comprising a therapeutically effective amount of the inhibitor of SHP2.

Embodiment I-153. The inhibitor of SHP2 for use in a method according to any one of Embodiments I-1a, I-2a, I-3a, I-18a, I-24a, I-24c, I-25a, I-25c, I-26a, I-26c, I-27a, I-27c, I-28a, I-28c, I-29a, I-50a, I-51a, and I-52a, wherein the inhibitor of SHP2 is used in a therapeutically effective amount.

Embodiment I-154. The use of an inhibitor of SHP2 according to any one of Embodiments I-1b, I-2b, I-3b, I-18b, I-29b, I-50b, I-51b, I-52b, I-, wherein the inhibitor of SHP2 is used in a therapeutically effective amount.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Effect of SHP2 Allosteric Inhibitors on Cancer Cells Containing Ras Pathway Mutations and Dependent Upon Reloading of GTP onto KRAS Objective:

The effect of SHP2 allosteric inhibitors, Compound A or Compound B on RAS pathway activation and tumor cell growth in vitro, and in vivo, was evaluated in cancer cell lines with Ras pathway mutations, including distinct mutations in KRAS, NF1, and BRAF that confer cellular dependence on reloading of GTP onto RAS.

Methods:

To evaluate cell viability in 3D culture, cells in logarithmic growth phase were plated in growth medium containing 0.65% methylcellulose at an optimum seeding density. Cells were incubated overnight prior to treatment with different concentrations of the test article. Cells were cultured for an additional seven days and cell viability assessed using the CellTiterGlo™ (CTG) reagent, according to the manufacturer's instructions. In some instances, cells were grown in 3D culture as spheroids. Briefly, 2500 cells/well were seeded in round bottom ultra-low attachment 96-well plates (Corning) in growth media supplemented with 10% fetal bovine serum and 1% penicillin/streptomycin, and allowed to form spheroids for 72 hours at 37° C. in 5% CO2. Spheroid formation was confirmed visually, and spheroids were treated in duplicate with serial 3-fold dilutions of Compound B in complete growth media (final DMSO concentration=0.1%). Following drug exposure for five days, cell viability in spheroids was determined using the CellTiter-Glo assay kit. H1838 cells were seeded at $5 \times 10^3$ cells per well of a 12-well plate. After one day in culture, cells were treated with the test article, which was then replenished every three days. Cells were maintained in culture for 10 days until the control wells reached confluency at which time the cells were fixed and stained with crystal violet.

To determine the potency of test articles to inhibit phosphorylation of extracellular signal-related kinase 1 and 2 (ERK1/2) at Thr202/Tyr204 (p-ERK), respective cell lines were cultured under standard 2D culture conditions. Cells were plated at ~$20 \times 10^3$ cells per well and following overnight incubation were washed with serum-free media. Cells were then incubated for one hour with increasing concentrations of the test article in serum-free media containing 0.2% BSA prior to termination of the assay and measurement of pERK levels in cellular lysates by AlphaLisa SureFire Ultra kit conducted according to the manufacturer's instructions.

To determine the effects of small molecules on levels of activated RAS-GTPase, cell lines of interest were cultured under standard 2D culture conditions. Cells were seeded and following overnight incubation incubated at 37° C. with vehicle (DMSO) or test article(s). After an appropriate incubation period, cells were washed and cell lysis buffer added to prepare a cell lysate. The levels of Ras-GTP in the lysates were determined using affinity purification of a Raf-RBD (Ras binding domain of Raf)/GTP-Ras complex. In one approach, the Pierce Active Ras Pulldown and Detection Kit was used. Briefly, clarified lysates (500 µg total protein, quantified by BCA) were mixed with glutathione resin, which had been preincubated with GST-Raf-RBD. The mixture was vortexed and incubated at 4° C. for 1 hour with gentle rocking. The resin was washed three times with lysis buffer and bound Ras-GTP eluted by addition of 2× reducing sample buffer. Eluted proteins were separated by SDS-PAGE using a 4-15% Tris-glycine gel (BioRad). Proteins were transferred to a nitrocellulose membrane for western blot using an anti-Ras antibody (Thermofisher, 1:200) and a Licor IRDye-800 anti-mouse secondary antibody (1:20,000). The Licor Odyssey CLx was used for visualization.

The effects of a SHP2 inhibitor on tumor cell growth in vivo were evaluated in the NSCLC H358 KRas$^{G12C}$ xenograft model using female CB.17 SCID (8-12 weeks old) or Balb/c (6-8 weeks old). Mice were implanted with H358 tumor cells in 50% Matrigel (1×10$^7$ and 5×10$^6$ for SCID and Balb/c mice, respectively) subcutaneously in the flank. Once tumors reached an average size of ~200 mm$^3$ mice were randomized to treatment groups and administration of test article or vehicle (50 mM acetate buffer, pH 4.6 containing 10% captisol, unless otherwise indicated) initiated. Body weight and tumor volume (using calipers) was measured biweekly until study endpoint. Compound A or Compound B were administered by oral gavage daily. The positive control, paclitaxel (30 mg/kg iv) in 5% ethanol, 5% cremophor EL, in 5% dextrose in deionized water was administered once every five days. Trametinib (1 mg/kg PO in 0.5% Methylcellulose+0.5% Tween 80) was administered by oral gavage daily. The study endpoint was defined as a mean tumor volume of 2000 mm$^3$ in the control group or 22 days, whichever came first. Mean tumor volume data are reported for all animals that remained on study.

Similar methods were used to evaluate efficacy of test articles in the pancreatic MiaPaca-2 KRas$^{G12C}$ xenograft model. Balb/c nude mice (6-8 weeks old) were implanted with 1.35×10$^9$ MiaPaca-2 tumor cells in 50% Matrigel subcutaneously in the flank. Once tumors reached an average size of ~100-200 mm$^3$ mice were randomized to treatment groups. Administration of test articles and study design are as described above for H358 xenograft model.

Results:

Across a small panel of KRAS mutant cell lines, presence of a KRAS$^{G12C}$ mutation enriched for sensitivity to 3D growth inhibition (defined as a CTG IC$_{50}$<10 μM) by a SHP2 inhibitor (Compound A) (Table 3; Ref #1 Crown Bio Project #E3105-U1609).

TABLE 3

Inhibitory potency (IC$_{50}$ values) of SHP2 allosteric inhibitor Compound A on cell viability (as measured using CTG) of a panel of KRAS mutant cell lines grown in 3D culture.

| Cell Line | KRAS Mutation | IC$_{50}$ (μM) |
| --- | --- | --- |
| NCI-H1573 | G12A | 0.2 |
| NCI-H2009 | G12A | 0.3 |
| NCI-H358 | G12C | 0.1 |
| KYSE-410 | G12C | 0.1 |
| SW837 | G12C | 0.3 |
| MIAPaCa-2 | G12C | 0.3 |
| NCI-H23 | G12C | 0.7 |
| NCI-H1792 | G12C | 1.2 |
| NCI-H1373 | G12C | 1.3 |
| NCI-H2122 | G12C | 5.9 |
| Calu-1 | G12C | >10 |
| LS513 | G12D | 0.1 |
| SNU-601 | G12D | 2.9 |
| HPAC | G12D | >10 |
| LS180 | G12D | >10 |
| SK-LU-1 | G12D | >10 |
| A549 | G12S | >10 |
| NCI-H441 | G12V | 0.1 |
| NCI-H727 | G12V | 0.3 |
| Capan-1 | G12V | >10 |
| SHP-77 | G12V | >10 |
| SW480 | G12V | >10 |
| SW620 | G12V | >10 |
| SW900 | G12V | >10 |
| HCT116 | G13D | >10 |
| LoVo | G13D | >10 |
| NCI-H1944 | G13D | >10 |
| T84 | G13D | >10 |
| NCI-H1155 | Q61H | >10 |
| NCI-H460 | Q61H | >10 |
| Calu-6 | Q61K | >10 |
| SNU-668 | Q61K | >10 |
| SW948 | Q61L | >10 |
| ASPC-1 | G12D | >10 |
| MDA-MB-231 | G13D | >10 |

Figures 3, 3C:
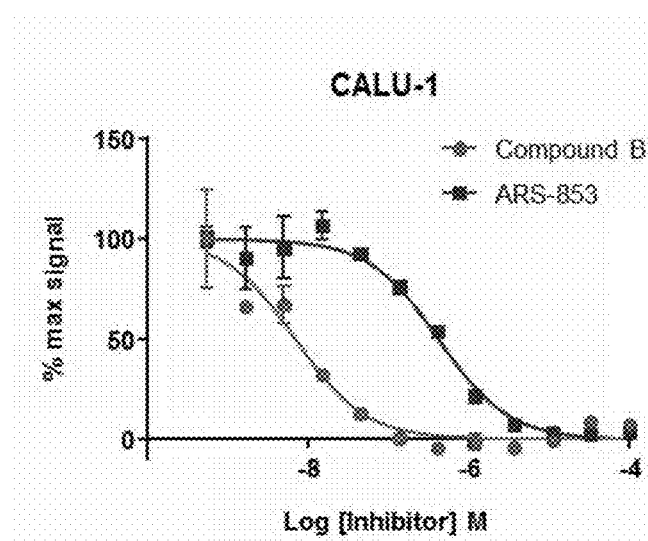
FIG. 3 shows Compound B (Compound B) (allosteric SHP2 inhibitor) and ARS-853 (covalent $KRAS^{G12C}$-selective inhibitor) caused concentration-dependent inhibition of cellular p-ERK1/2 levels in NSCLC KRAS$^{G12C}$ cell lines.
FIG. 3C shows inhibition of pERK1/2 levels in CALU-1 cells.

Consistent with and extending these observations, Compound B, was a potent inhibitor of growth (CTG IC$_{50}$ range 0.4 to 7.87 μM) in 9/10 KRAS$^{G12C}$ lines, 2/2 KRAS$^{G12A}$ lines, 2/5 KRAS$^{G12D}$ lines, and also two KRAS$^{G12V}$ lines, H441 (FIG. 2; Ref #2 Crown Bio Project #E3105-U1703). In a subset of the KRAS$^{G12C}$ mutant cell lines, the effect of the SHP2 inhibitor on activation of the RAS-MAPK pathway was evaluated (see FIG. 3). Compound B produced a concentration-dependent inhibition of p-ERK1/2 levels in H358, H1792 and Calu-1 cells. Consistent with their genetic characterization as containing a mutant gene encoding KRAS$^{G12C}$, these cells were also sensitive to the KRAS-specific covalent inhibitor ARS-853 (Patricelli et al., 2016), which binds selectively to the cysteine residue of KRAS$^{G12C}$ in the GDP bound state. The effect of a SHP2 inhibitor on Ras activation in H358 cells was demonstrated with Compound A (FIG. 4). Compound A inhibited Ras activation, as assessed by levels of Ras-GTP, with an associated concentration-dependent inhibition of p-ERK levels and cell viability. Based on these data, which demonstrate that certain oncogenic G12 variants of KRAS are dependent on SHP2-mediated GTP-loading to maintain signal transduction and cell growth, we posited that other oncogenic mutations in signal transducers of the RAS pathway might also be dependent on such upstream SHP2 signaling and, thus, sensitive to SHP2 inhibition.

One such protein involved in the RAS Pathway that might confer sensitivity to SHP2 signaling by its absence or reduced function is NF1 NF1 is a RAS-GAP protein that facilitates the hydrolysis of RAS-GTP into its inactive RAS-GTP form, thereby inactivating RAS. NF1 is a tumor suppressor, and loss of function mutations in this gene result RAS-GTP accumulation and downstream signaling leading to cell growth in various human cancers (Nissan, Krauthammer, Redig). Therefore, we tested whether SHP2 inhibition might effectively prevent RAS pathway signaling and cell growth in NF1$^{LOF}$ models.

Figure 19:
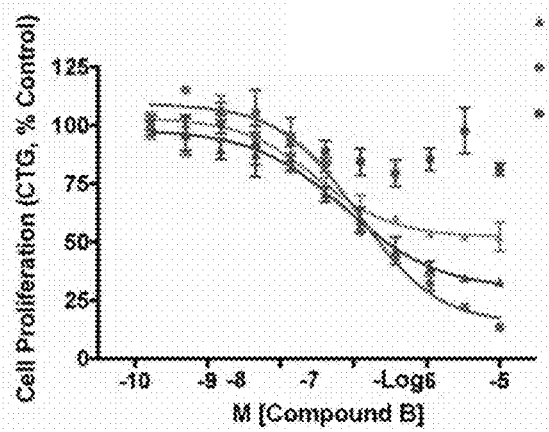
FIG. 19 shows SHP2 inhibition suppresses growth and RAS/MAPK signaling in cancer cell lines driven by NF1$^{LOF}$ mutation.
Figure 19:
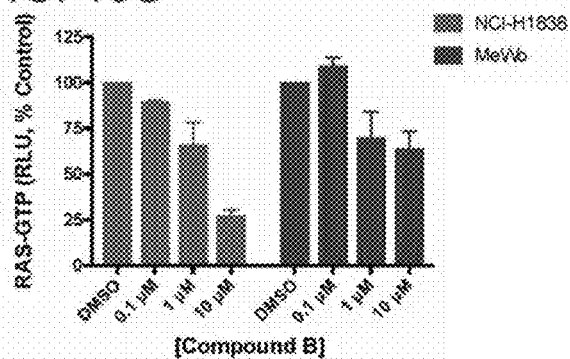
Figure 19:
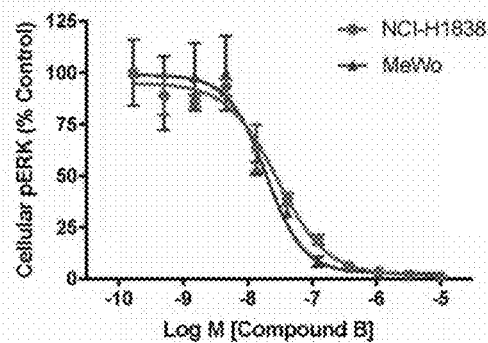

Similar to the observations in the KRAS$^{G12C}$ line, Compound A also inhibited Ras-GTP and potently inhibited p-ERK and cell growth (crystal violet stain) in H1838 NF1$^{LOF}$ NSCLC cells in vitro (FIG. 5). Furthermore, consistent with this, proliferation of 3/4 NF1$^{LOF}$ cell lines exhibited sensitivity to Compound B (FIG. 19A-B). NF1$^{LOF}$ cell lines were prepared and treated with experimental or control agents as describe above in this Example and RAS-GTP and pERK levels were measured as previously described above. Treatment of the sensitive NF1$^{LOF}$ cell lines NCI-H1838 (lung, NF1N184fs) and MeWo (melanoma, NF1Q1336*) with Compound B led to downregulation of RAS-GTP levels and suppression of pERK (FIG. 19C-D), demonstrating that SHP2 inhibition can attenuate the accumulation of RAS-GTP, and consequent RAS/MAPK pathway activation resulting from NF1 loss. Collectively, these data indicate that loss of NF1 is a second class of downstream oncogenic mutation that can be targeted through inhibition of RAS-GTP loading via SHP2 inhibition. No effect of SHP2 inhibition was observed in the YUHEF (NF1Q853*/FS-indel), melanoma cell line (FIG. 19A-B). The genomic landscape of this line mirrors that of clinical melanoma populations in that NF1$^{LOF}$ mutations frequently co-occur in cancers that contain co-occurring mutations in RAS/MAPK pathway genes, some of which may confer resistance to SHP2 inhibition {Krauthammer, 2015 #2476; Nissan, 2014 #2426}. Specifically, YUHEF carries three SOS1 mutations and RAF1P261L, a previously described MAPK pathway-activating Noonan Syndrome mutation {Kobayashi, 2010 #2532; Krauthammer, 2015 #2476}.

Taken together, these results suggest that a SHP2 inhibitor can attenuate RAS-MAPK signaling in KRAS$^{G12C}$ mutant cell lines and NF1 loss of function cell lines, while differential sensitivity to growth inhibition may be observed, which likely reflects the intrinsic variation in dependence of each cell line on signaling via the Ras pathway.

Figure 6:
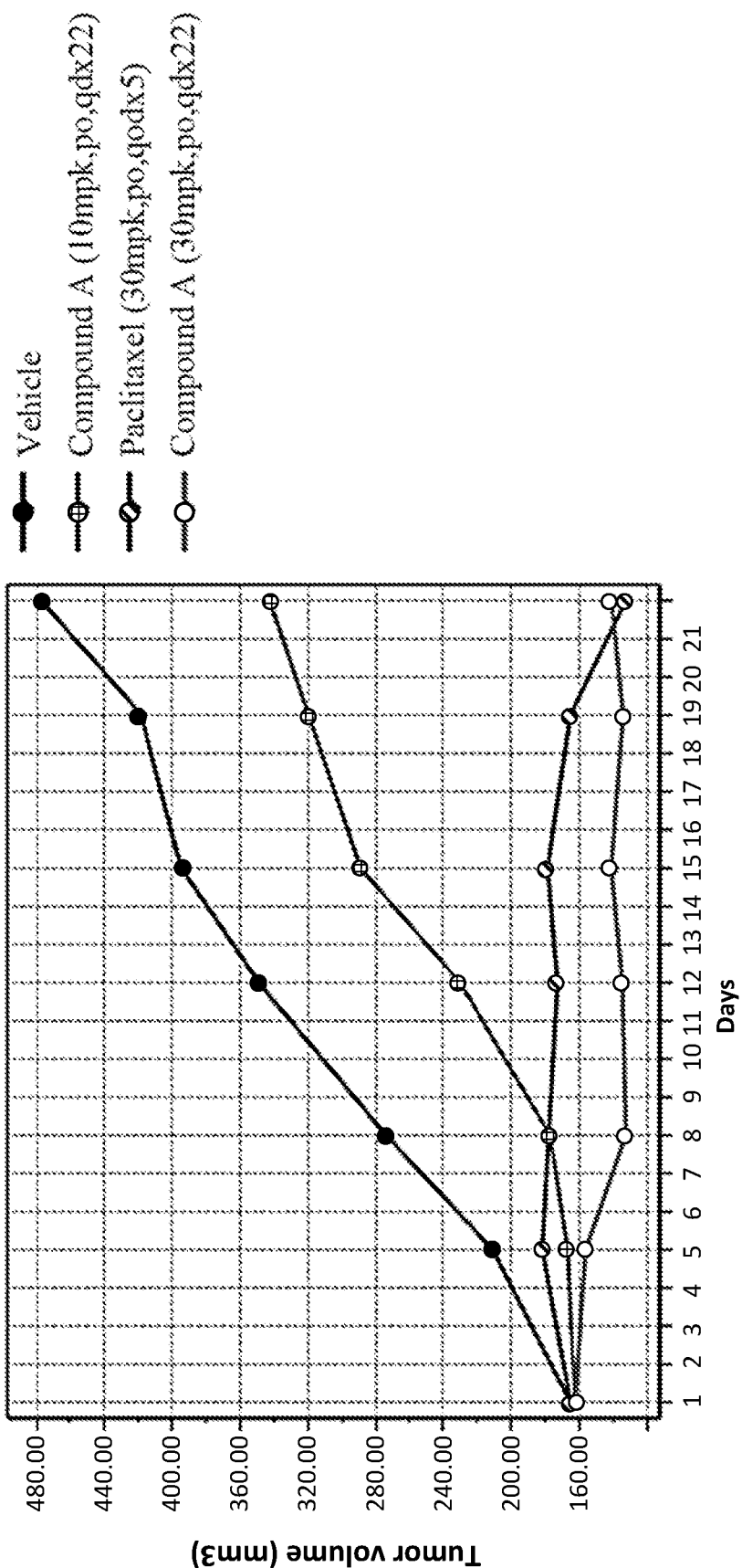
FIG. 6 shows dose-dependent inhibition of tumor cell growth in the NSCLC H358 xenograft model in female CB.17 SCID mice following oral administration of Compound A (Compound A).
Figure 7:
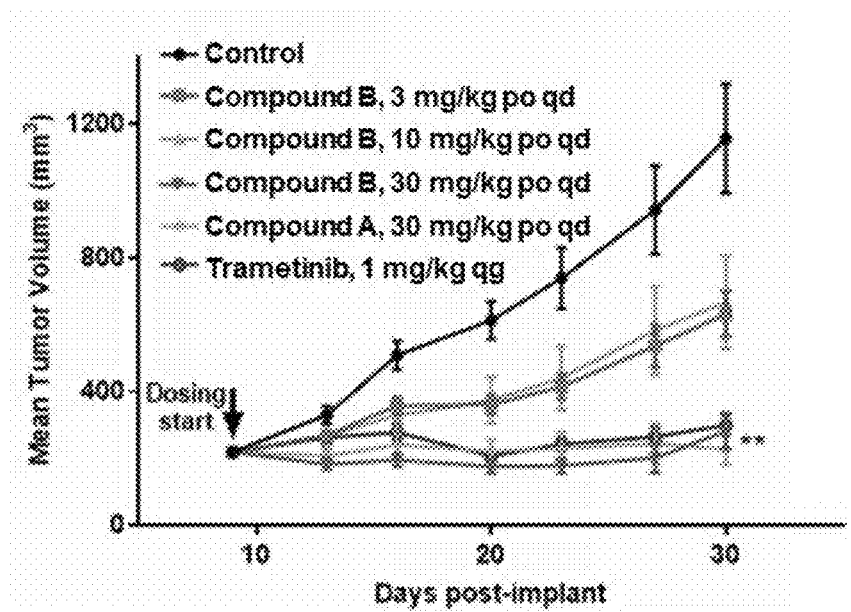
FIG. 7 shows dose-dependent inhibition of tumor cell growth in the NSCLC H358 xenograft model in female athymic nude mice following oral administration of the SHP2 allosteric inhibitor Compound B (Compound B) (**p<0.01 ANOVA with multiple comparisons)
Figure 8:
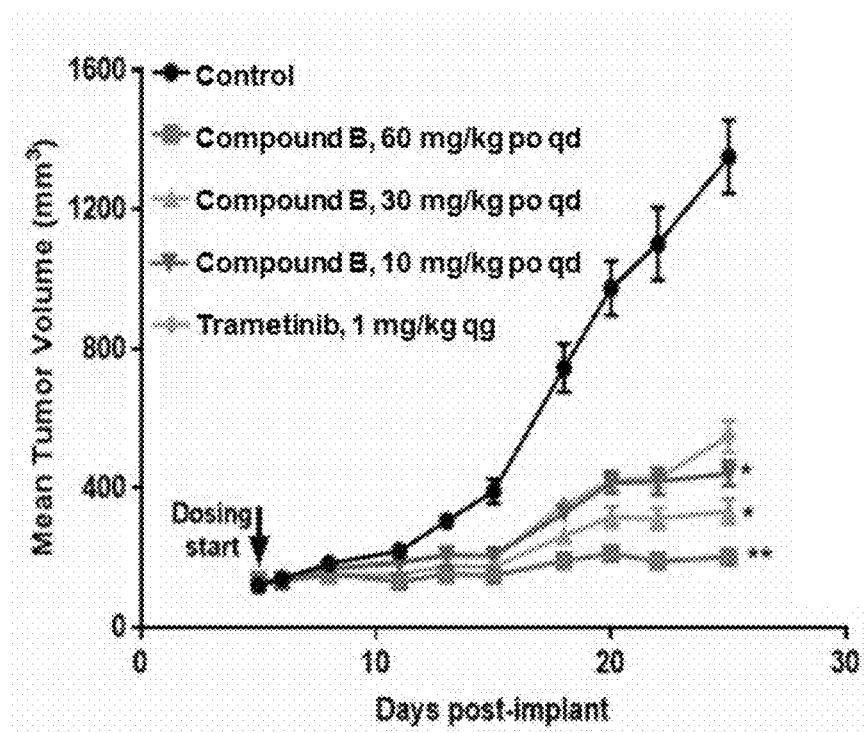
FIG. 8 shows dose-dependent inhibition of tumor cell growth in the pancreatic cancer MiaPaca-2 xenograft model in female athymic nude mice following oral administration of the SHP2 allosteric inhibitor Compound B (Compound B) (*p<0.05, **p<0.01 ANOVA with multiple comparisons).

The effect of a SHP2 inhibitor on KRAS$^{G12C}$ tumor cell growth in vivo was evaluated in the NSCLC H358 and pancreatic MiaPaca-2 xenograft models. Oral administration of Compound A or Compound B, respectively, produced a dose-dependent decrease in tumor volume in vivo in the H358 xenograft model (FIGS. 6 and 7). At a dose of 30 mg/kg PO qd Compound A the reduction in tumor volume was of a similar order of magnitude to that of the comparator paclitaxel, a well-known non-targeted chemotherapeutic agent. Similarly, the SHP2 inhibitor Compound B produced a dose-dependent decrease in tumor volume in both the H358 KRAS$^{G12C}$ and MiaPaca-2 KRAS$^{G12C}$ xenograft models (FIGS. 7 and 8). At a dose of 30 mg/kg PO qd Compound B the reduction in tumor volume was of a similar order of magnitude to that of the MEK inhibitor trametinib (1 m/kg PO) in the H358 model but was greater than trametinib (1 m/kg PO) in the MiaPaca-2 model.

Similarly, Compound A was also a potent inhibitor of p-ERK (FIG. 5B) and cell growth (crystal violet stain)(FIG. 5C) in H1838 NF1$^{LOF}$ NSCLC cells in vitro.

Another protein that is involved in signaling via the RAS Pathway is the serine/threonine kinase BRAF, and mutations in BRAF are commonly present in human cancer, and such mutations are oncogenic because of their resultant hyperactivation of pERK signaling. Three classes of oncogenic BRAF mutations have been reported. Class I mutations occur at V600 and result in constitutively active BRAF monomers that are active regardless of their RAS-GTP state (Poulikakos, 2011). Class II mutations are dependent on dimerization, but also are active regardless of their RAS-GTP state (Yao, 2015). Class III mutations of BRAF are both RAF dimer and RAS-GTP dependent (Yao, 2017). Accordingly, we posited that Class I and Class I mutations might be refractory to SHP2 inhibition because they signal independent of GTP, whereas, in contrast Class III mutations might be dependent on SHP2 signaling to promote adequate GTP loading, and cells containing these mutations might, therefore, be sensitive to SHP2 inhibition.

We screened a representative panel of cell lines bearing oncogenic BRAF mutations in these three classes for sensitivity to SHP2 inhibition.

Figure 13:
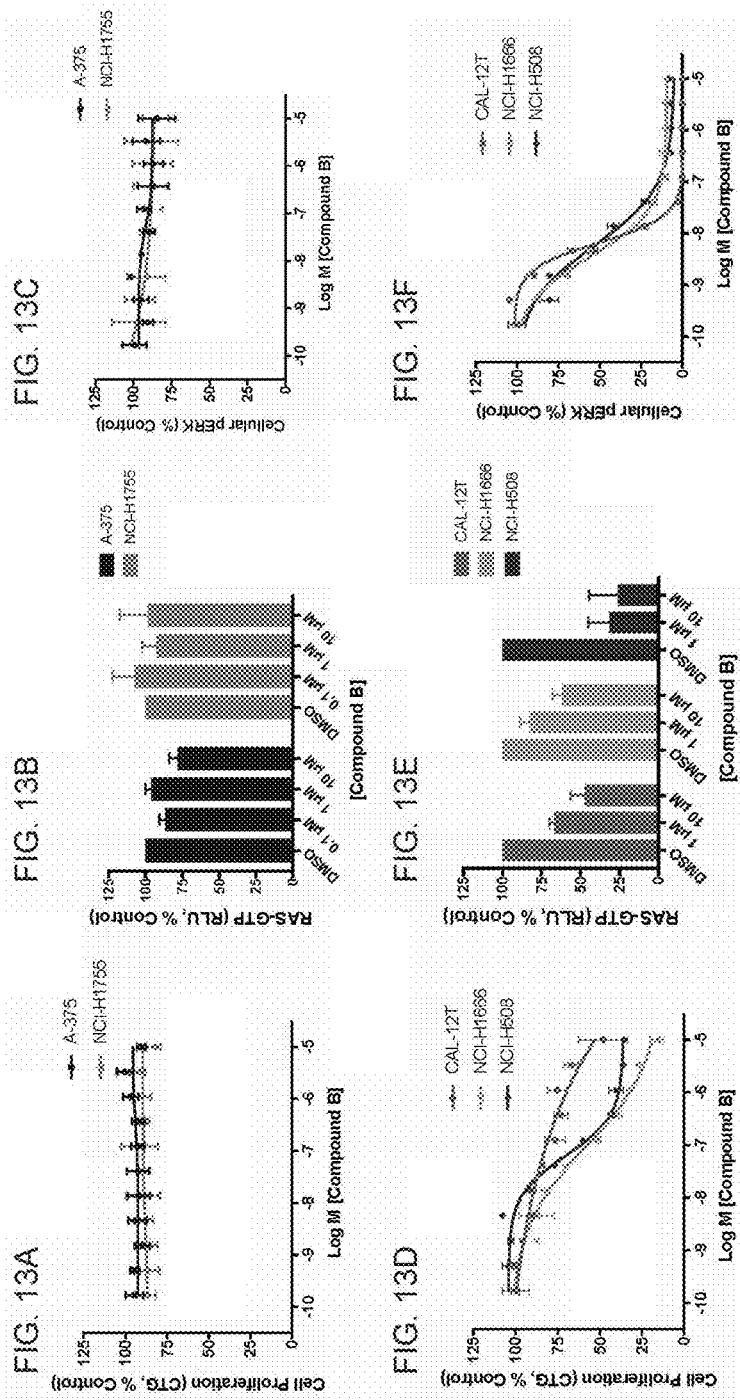
FIG. 13 shows SHP2 inhibition suppresses growth and RAS/MAPK signaling in cancer cell lines with BRAF Class III mutations.

First, we confirmed that Class I BRAF mutations were refractory to SHP2 inhibition. Consistent with the mechanistic framework, we observed that Compound B failed to suppress proliferation and RAS-GTP and pERK levels in A375 cells (FIG. 13A-C). Similar results were observed in a cell line carrying a Class II BRAF mutation, NCI-H1755 (lung, BRAFG469A), which exhibits RAS-independent homodimer formation and signaling (Yao 2015) (FIG. 13A-C). Notably, Compound B did not inhibit RAS-GTP levels in these cell lines. Class I and Class II BRAF mutant oncoproteins function downstream of RAS but drive strong, ERK-dependent negative feedback, leading to RAS-GTP suppression upstream of RAS. Our data suggest this suppression is either insensitive to SHP2 inhibition, for example if suppression occurs via direct inhibition of SOS1 (Corbalan-Garcia, 1996; Kamioka, 2011), or sufficiently strong that the remaining low levels of RAS-GTP cannot be reliably quantified with our assay.

However, in three cell lines carrying Class III BRAF mutations, NCI-H1666 (BRAFG466V/+), NCI-H508 (BRAFG596R/+), and Cal-12T (BRAFG466V/+), treatment with Compound B led to concordant suppression of both pERK levels (FIG. 13F and of RAS-GTP levels (FIG. 13E), and, proliferation (FIG. 13D). These results are consistent with recent reports that Class III BRAF mutations are bona fide cancer drivers that remain sensitive to modulation of upstream signaling and RAS-GTP levels (Yao, 2017). Therefore, Class III BRAF mutations are a third category of downstream oncogenic mutation that can be targeted through blockade of upstream SHP2-mediated RAS-GTP loading.

To more fully define the cellular effects of Compound B, we examined biomarkers of cell cycle and apoptosis. Activated Caspase 3/7 Assay in Spheroids. NCI-H358 cells (Lung, KRAS$^{G12C}$) were grown into spheroids by seeding 5,000 cells/well in round bottom ultra-low attachment 96-well plates (Corning) in RPMI media (Gibco) supplemented with 10% fetal bovine serum and 1% penicillin/streptomycin. Immediately after seeding, cells were spun down at 1000 RPM for 5 minutes, and incubated at 37° C. in 5% CO2 for five days to allow for spheroid formation. Spheroid formation was confirmed visually. Spheroids were treated in triplicate with Compound B, staurosporine (Sigma), or DMSO (Sigma) (0.1% final), diluted in RPMI media supplemented with 10% fetal bovine serum and 1% penicillin/streptomycin, and incubated at 37° C. in 5% CO2 for 20 hours. Caspase 3/7 activity was measured using the Caspase-Glo 3/7 Assay System (Promega), following the manufacturer's instructions. After addition of Caspase-Glo reagent, the well contents were pipetted several times and incubated at room temperature in the dark for 45 minutes to allow thorough cell lysis. 50 µL of the lysate/reaction was transferred to an opaque white 96-well ½ area plates (Perkin Elmer). Luminescence was read in an EnVision Multilabel Plate Reader (Perkin Elmer). Assay data was plotted using Prism 7 (GraphPad) software.

In NCI-H358 cells (Lung, KRAS$^{G12C}$), treatment of spheroid cultures with Compound B led to robust caspase 3/7 activation, indicating a pro-apoptotic effect (FIG. 15).

Figure 20:
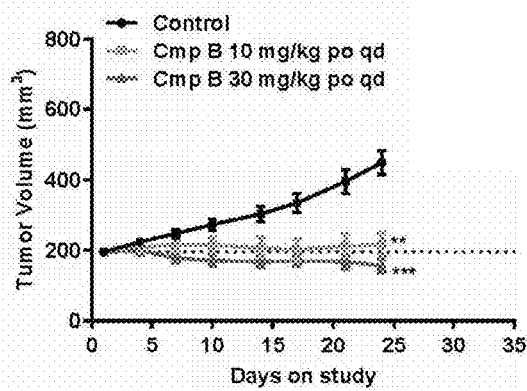
FIG. 20 shows SHP2 inhibition suppresses growth and RAS/MAPK signaling in cancer cell lines driven by NF1$^{LOF}$ mutation.
Figure 20:
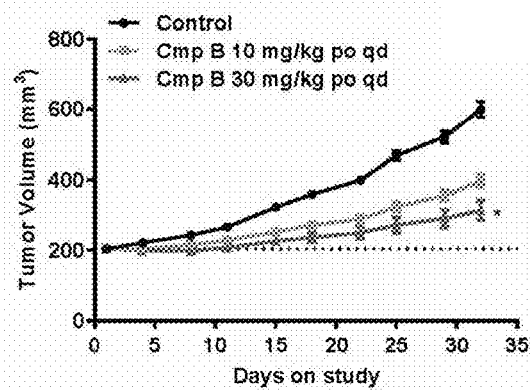
Figure 20:
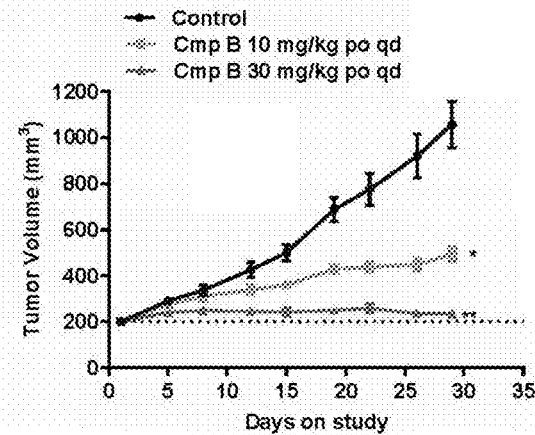
Figure 20:
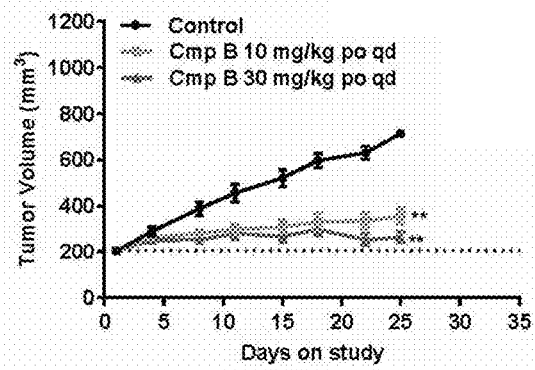

To extend our studies into additional clinically-relevant in vivo models, we evaluated the response to Compound B mediated SHP2 inhibition in patient-derived xenograft (PDX) models. Two PDX models of BRAF mutant NSCLC, LUN023 and LUN037, were tested. LUN023 carries the previously described class 3 mutation BRAF$^{D594N}$ {Yao, 2017 #2432}, while LUN037 carries BRAF$^{N581D}$, a known class 3 residue and established RASopathy substitution {Niihori, 2006 #2538}. As predicted for this class of semi-autonomous driver of RAS/MAPK signaling, we observed dose-dependent tumor growth inhibition upon repeated daily oral dosing of Compound B in both models (FIGS. 20A and 20B). Further, we tested Compound B in two additional PDX models of NSCLC and confirmed KRAS$^{G12C}$ mutations as genotypic biomarkers of sensitivity to SHP2 inhibition in these PDXs, validating our in vitro and cell-line based in vivo findings (FIGS. 20C-20D).

Summary:

The observation that a SHP2 inhibitor can inhibit some, but not all, KRAS mutant cells is likely a function of the nucleotide cycling features of a particular KRAS mutation and its corresponding dependence on signaling inputs to maintain high levels of the active, GTP-bound state. Indeed Patricelli and coworkers have demonstrated that KRAS$^{G12C}$ is not a constitutively and fully active protein but rather the nucleotide state of KRAS$^{G12C}$ is in a state of dynamic flux that can be modulated by upstream signaling factors (Patricelli et al., 2016). Similarly, in cells which have lost function of the GTPase activating protein (GAP), e.g. NF1$^{LOF}$ there is a shift towards the active, GTP-bound state of RAS which drives signaling to RAS effectors and growth addiction. In these cells, the wild type RAS undergoes nucleotide cycling which, as for KRAS$^{G12C}$ makes it sensitive to upstream signaling inputs to maintain a highly active state. In addition, cells which have acquired a Class 3 mutation in BRAF drive high pERK signaling in a manner that remains dependent on RAS-GTP, and therefore on upstream signaling factors. The sensitivity of KRAS$^{G12C}$; NF1$^{LOF}$; and BRAF Class 3 cell lines to a SHP2 allosteric inhibitor reflects modulation of these upstream factors, and hence the nucleotide state of mutant/WT RAS, by the inhibitor.

Example 2

Effect of SHP2 Allosteric Inhibitors on the Treatment or Prevention of Tumor Resistance to MAPK-Pathway Inhibitors Objective: The effect of SHP2 allosteric inhibitors, Compound A or Compound B, on feedback-driven RAS pathway activation resulting from MEK inhibition was evaluated in various cancer cell lines comprising distinct mutations in KRAS and other mutations that modulate nucleotide cycling of RAS, such as NF1$^{LOF}$.

Methods:

To determine the effects of test article(s) on levels of phosphorylated RTKs, MDA-MB231 cells were seeded in 6-well plates and incubated overnight in full growth medium. Cells were treated for 24 hours with selumetinib (5 μM) or Compound A (1 and 5 μM) or left untreated (DMSO control). Lysates were generated using the lysis buffer provided with the kit (Phospho-RTK Array; R&D systems) with inclusion of a protease inhibitor cocktail. To control for protein concentration, total protein levels were quantified using BCA reagent kit. The levels of phospho-RTK were determined according to the manufacturer's instructions.

To determine the effects of small molecules on levels of activated RAS-GTPase, cell lines of interest were cultured under standard 2D culture conditions. Cells were seeded and following overnight incubation incubated at 37° C. with vehicle (DMSO) or test article(s). After an appropriate incubation period, cells were washed and cell lysis buffer added to prepare a cell lysate. The levels of Ras-GTP in the lysates were determined using affinity purification of a Raf-RBD (Ras binding domain of Raf)/GTP-Ras complex. In one approach, the Pierce Active Ras Pulldown and Detection Kit was used. Briefly, clarified lysates (500 μg total protein, quantified by BCA) were mixed with glutathione resin which had been preincubated with GST-Raf-RBD. The mixture was vortexed and incubated at 4° C. for 1 hour with gentle rocking. The resin was washed three times with lysis buffer and bound Ras-GTP eluted by addition of 2× reducing sample buffer. Eluted proteins were separated by SDS-PAGE using a 4-15% Tris-glycine gel (BioRad). Proteins were transferred to a nitrocellulose membrane for western blot using an anti-Ras antibody (Thermofisher, 1:200) and a Licor IRDye-800 anti-mouse secondary antibody (1:20,000). The Licor Odyssey CLx was used for visualization.

Results:

The observation that a SHP2 inhibitor can prevent the feedback reactivation of RTKs, as read out by their phosphorylation status (FIG. 9), demonstrates that inhibition of SHP2 upstream of RAS does not disrupt homeostatic regulation of the RAS/MAPK pathway in the same way as inhibition of MEK downstream of RAS. Consistent with this principle, the addition of a SHP2 inhibitor with a MEK inhibitor suppressed the feedback-driven accumulation of RAS-GTP that is triggered by MEK inhibitor treatment (FIGS. 10-11). As accumulation of RAS-GTP is hypothesized to prime cancer cells to develop resistance to targeted therapies (i.e. MEK inhibitors), these data support the concept that a SHP2 inhibitor may be deployed in cancer patients to treat or prevent tumor resistance to RAS/MAPK pathway inhibitors.

Example 3

Effect of SHP2 Inhibitor (Compound B) on SHP2 Phosphorylation

Objective: To determine whether inhibition of SHP2 with an allosteric inhibitor prevents tyrosine phosphorylation of the C-terminal tail (Tyr-542 and Tyr-580) of SHP2.

Background:

Tyrosine phosphorylation of the C-terminal tail (Tyr-542 and Tyr-580) of SHP2 has been proposed to have both regulatory and functional consequences. Early work proposed that SHP2 acts as a scaffolding protein to link PDGFRβ to Ras by interactions with Grb2-SOS (Bennett, 1994) via tyrosine phosphorylation after growth factor stimulation. However, it remains controversial whether Grb2 binds to pY542 or pY580 in a cellular context, and whether this interaction is the main functional consequence of Y542/580 phosphorylation. Lu et. al (2001) used phosphotyrosine mimics at these sites to show that phosphorylation increases SHP2 PTPase activity, presumably through intramolecular interactions with the SH2 domains. This suggests that phosphorylation of these residues may contribute significantly towards enzyme activity rather than scaffolding. Subsequent work identified a growth factor specificity for tyrosine phosphorylation in murine fibroblasts (PDGF, FGF, but not EGF) and also concluded that Y580 phosphorylation occurs after, and is dependent on, phosphorylation of Y542 (Araki et al., 2003). This observation led the authors to hypothesize that in a "closed state" Y580 is inaccessible to phosphorylation until a conformational change evoked by phosphorylation of Y542 occurs. They also proposed that p-Y542 is the main Grb2 binding site in fibroblasts. A comprehensive study using FRET corroborated that p-Y542/580 interact with the SHP2 SH2 domains, and that Y580 phosphorylation is dependent on phosphorylation of Y542 (Sun et al, 2013). This study identified Y580 as the likely major binding site for Grb2 in MEFs. Based on these observations, SHP2 pY542 has been used as a biomarker to identify RTK-driven resistance to BRAF inhibitors (Prahallad, 2015), since phosphorylation of this residue occurs in response to RTK signaling.

Methods:

Cells (MEFs, HEK 293E, H358) were plated in 6-well plates at a density of 750,000 cells/well in low serum (0.1% FBS) media and allowed to grow overnight. Cells were incubated with either DMSO (0.05%), or Compound B (5 µM) for 1 hour. Cells were stimulated with 50 ng/mL of EGF or PDGF for 5 minutes, washed with cold PBS, and 150 µL of lysis buffer (Thermo #1862301) with Halt Protease/Phosphatase inhibitor (Thermo #78440) was added. Cells were scraped, transferred to a cold Eppendorf tube and vortexed for 10 seconds. Lysates were spun at 4 C for 15 min at 13,000 rpm and transferred to a new tube. Lysate protein concentration was assessed using the BCA assay. Lysates (30 µg/lane) were run on a 4-15% Tris glycine gel and transferred to a nitrocellulose membrane using the iBlot2. Western blots were performed using phospho-SHP2 antibodies from Cell Signaling Technologies; pY542 (#3751) and pY580 (#3703) were both used at 1:1000 dilution in 5% BSA in TBS. Membranes were incubated with primary antibody overnight with gentle shaking at 4 C. Beta actin antibody (Cell Signaling Technologies #8457, 1:2000) was used as a loading control. The secondary antibody (Licor IRDye 800 CW anti-rabbit) was used at a 1:20000 dilution in 5% BSA in TBS for 1 hour shaking at room temperature. Blots were visualized using the Licor Odyssey Clx Imager.

Results

These experiments show an increase in phosphorylation of Tyr-542 and Tyr-580 in response to growth factors. In agreement with the literature, this phosphorylation is stimulated by PDGF in MEFs, but not EGF. Conversely, in HEK293 and H358 cells, where MAPK signaling is predominantly EGF stimulated (data not shown), we observe phosphorylation with EGF, but not PDGF. These results suggest that the growth factor specificity of SHP2 Y542/Y580 phosphorylation is cell line dependent. Treatment of these cells with Compound B, an allosteric inhibitor which stabilizes the auto-inhibited, closed conformation of SHP2, decreases the overall phosphorylation levels of Y580, but not Y542. This observation agrees with the hypothesis proposed by Araki et al. (2003); Y580 is occluded from phosphorylation in a "closed state". We postulate that Compound B stabilizes this "closed state", preventing phosphorylation at this site. It is currently unclear whether the cellular functional consequences of Compound B inhibition of phosphorylation of Y580 are linked to attenuation of Grb2 binding or to a reduction in SHP2 PTPase activity. However, taken collectively, the present observations suggest that inhibition of phosphorylation of Y580 may serve as a marker of Compound B, or other allosteric SHP2 inhibitor, target engagement in a cell. Furthermore, the present observations suggest that pY580 levels/dependence may be predictive of sensitivity to Compound B or another SHP2 inhibitor.

EXAMPLE 3 REFERENCES

Araki, T, Nawa, H, and Neel, B G. (2003) J. Biol. Chem. 278, 41677-41684.

Bennet, A M, Tang, T L, Sugimoto, S, Walsh, C T, and Neel B G. (1994). PNAS, 91, 7335-7339.

Lu, W, Gong, D, Bar-Sagi, D, and Cole, P A. (2001). Mol. Cell, 8, 759-769.

Prahallad, A., Bernards, R. et al. (2015). Cell Rep., 12, 1978-1985.

Sun, J., Lu, S., Lin, L., Zhuo, Y., Liu, B., Chien, S., Neel, B. G., and Wang, Y. (2013). Nat. Comm. 4:2037, DOI10.1038/ncomms3037.

Example 4

SHP2 Allosteric Inhibition Assay

Objective: To demonstrate the inhibition of SHP2 activity with Compounds A, B, and C.

Without wishing to be bound by theory, SHP is allosterically activated through binding of bis-tyrosyl-phosphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 was monitored using the surrogate substrate DiFMUP in a prompt fluorescence assay format.

The phosphatase reactions were performed at room temperature in 96-well black polystyrene plate, flat bottom, non-binding surface (Corning, Cat #3650) using a final reaction volume of 100 µL and the following assay buffer conditions: 50 mM HEPES, pH 7.2, 100 mM NaCl, 0.5 mM EDTA, 0.05% P-20, 1 mM DTT.

The inhibition of SHP2 by Compound A, Compound B, and Compound C was monitored using an assay in which 0.2 nM of SHP2 was incubated with 0.5 µM of Activating Peptide 1 (sequence: H$_2$N-LN(pY)IDLDLV(dPEG8)LST(pY)ASINFQK-amide) (SEQ ID NO: 4) or Activating Peptide 2 (sequence: H2N-LN(pY)AQLWHA(dPEG8)LTI(pY)ATIRRF-amide) (SEQ ID NO: 5). After 30-60 minutes incubation at 25° C., the surrogate substrate DiFMUP (Invitrogen, Cat #D6567) was added to the reaction and activity was determined by a kinetic read using a microplate reader (Envision, Perkin-Elmer or Spectramax M5, Molecular Devices). The excitation and emission wavelengths were 340 nm and 450 nm, respectively. Initial rates were determined from a linear fit of the data, and the inhibitor dose response curves were analyzed using normalized IC$_{50}$ regression curve fitting with control based normalization.

Using the above-protocol, SHP2 inhibition by Compound A, Compound B, and Compound C is shown in Table 4.

TABLE 4

SHP2 Inhibition by Compounds A, B, and C

| Compound | SHP2 IC$_{50}$, nM |
|---|---|
| Compound A | 2.19 |
| Compound B | 1.55 |
| Compound C | 1.29 |

Example 5

Inhibition of SHP2-Dependent RAS-GTP Loading can be Rescued by Constitutive Activation of SOS1

Objective:

In light of our findings that multiple classes of RAS/MAPK pathway oncoproteins that remain dependent upon RAS-GTP loading can be targeted via SHP2 inhibition, we asked whether SHP2-dependent modulation of RAS-GTP was due to disruption of core RAS-regulatory processes.

Methods:

SOS-WT and SOS-F Expression Constructs

N-terminally HA-tagged SOS-WT and SOS-F constructs were synthesized (Atum) and subcloned into the pcDNA5/FRT/TO vector (ThermoFisher) using the following primers: SOS1-HA-F or 5'-ACAGGTAAGCTTATGTACCCATAC-GATGTTCCAGATTAC-3' (SEQ ID NO: 1), SOS1-HA-REV 5'-AGACTAGCGGCCGCTCAGGAAGAATGGG-CATTCTCCAA-3' (SEQ ID NO: 2), and SOS-F-HA-REV 5'-GATCGAGCGGCCGCTCAG-GAGAGCACACACTTGCAG-3' (SEQ ID NO: 3). SOS-WT and SOS-F plasmids were co-transfected with the pOG44 Flp-recombinase expression vector (ThermoFisher) into the HEK Flp-In T-Rex 293 cell line according to the manufacturer's protocol. Transfected cells were selected in drug media (200 µg/mL hygromycin B, 15 µg/mL blastidicin) and expression of SOS constructs was verified by western blot (SOS-1: Cell Signaling Technologies #5890; HA: Sigma 11867423001).

pERK Analysis of HEK-293 SOS-WT and SOS-F 30,000 HEK-293 cells per well were plated in 96-well plates in Biotin-free RPMI (Hyclone) supplemented with 0.1% fetal bovine serum, 0.02% bovine serum albumin and 1% penicillin/streptomycin. Expression of SOS1 constructs was induced by the addition 0.1 µg/mL doxycycline (Sigma) for 24 hours. Cells were treated with serial 3-fold dilutions of Compound B diluted in biotin-free media supplemented with 0.02% bovine serum albumin and 1% penicillin/streptomycin (final DMSO concentration equivalent to 0.1%) for one hour. For the final 5 minutes of drug treatment, cells were stimulated with 50 ng/mL EGF (Sigma), lysed and subjected to ERK1/2 phosphorylation analysis as described above.

Results

Figures 14, 14A, 14B:
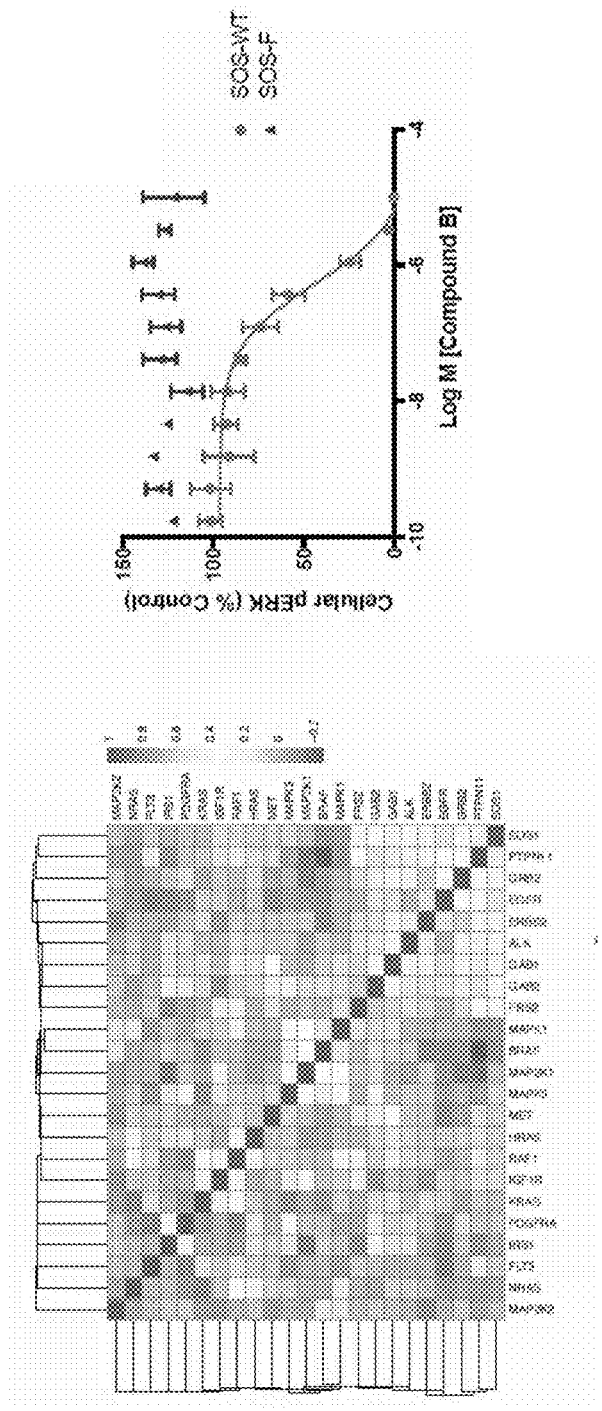
FIG. 14 shows that the effects of SHP2 inhibition on RAS activation proceed through SOS1.
FIG. 14A shows correlation analysis of the cellular effects of genetic knockdown of signaling molecules in the RTK/RAS pathway in Project DRIVE. Knockdown of PTPN11 (SHP2) is most closely correlated with SOS1 (correlation coefficient 0.51) and GRB2 (correlation coefficient 0.4) suggesting these are all members a core RAS-regulatory module.
FIG. 14B shows the effect of Compound B (Compound B) on cellular p-ERK in HEK293 expressing SOS-WT (wild type) or SOS-F, a SOS-1 mutant that targets SOS protein constitutively to the plasma membrane.

First, we mined data from the recently published Project DRIVE (McDonald, 2017), in which thousands of genes were systematically depleted across hundreds of cell lines to study genetic-dependencies of molecularly-defined cancer cell lines. One way to identify functional modules from high-throughput genetic knockdown experiments is to examine the phenotypic correlation of all possible gene pairs across the full dataset, as knockdown of members of a common functional module tends to yield similar patterns of response over many independent experiments. Taking a hypothesis-driven approach, we pulled data for 23 genes involved in RTK or RAS Pathway signaling and calculated a correlation matrix (FIG. 14A). Two functional modules were readily apparent the MAPK signal relay downstream of activated RAS and the RTK/convergent node module upstream of activated RAS. Of particular note, the most closely correlated knockdowns to PTPN11 (SHP2) are the GEF protein SOS1 (cc=0.51) and the adaptor protein GRB2, which links RTKs to SOS1-mediated GTP-loading of RAS (cc=0.40). In fact, SOS1 and GRB2 are the most closely related gene knockdowns to PTPN11 across all 7,837 genes in the Project DRIVE dataset (data not shown). This analysis implies that SHP2 is an essential member of a core RAS-regulatory module containing SOS1 and GRB2. We therefore hypothesized that Compound B downregulates RAS-GTP by disrupting the SHP2/SOS1/GRB2 module that is required for GTP-loading of RAS.

To test this hypothesis, we first asked whether a dominant, constitutively active mutant form of SOS1 could render cells insensitive to Compound B-mediated suppression of pERK signaling. Indeed, in HEK293 cells, inducible expression of SOS-F, a SOS1 mutant with its C-terminus fused to the HRAS farnesylation motif that targets the protein constitutively to the plasma membrane (Aronheim, 1994), rendered pERK signaling insensitive to EGF stimulation and SHP2 inhibition (FIG. 14B, FIG. 14C). These data show that the suppressive effects of SHP2 inhibition can be bypassed by constitutive SOS1 activation and that SOS1 therefore functions downstream of (or parallel to) PTPN11/SHP2. One possible explanation for these findings is that SHP2 inhibition may interfere with SOS1 plasma membrane localization and activation.

Summary

We have discovered a novel allosteric SHP2 inhibitor, Compound B, and used it and other SHP2 inhibitors to search for molecular markers of SHP2-dependence in tumors bearing mutations in the RAS Pathway. The identification of $KRAS^{G12C}$ $NF1^{LOF}$, and $BRAF^{Class\ III}$ mutations that confer sensitivity to SHP2 inhibition in tumor cells establishes SHP2 inhibition as a novel and promising therapeutic strategy against tumors bearing these oncogenic drivers, for which current treatments are largely ineffective in the clinic.

In NSCLC, these semi-autonomous driver mutations are observed frequently: $KRAS^{G12C}$, $NF1^{LOF}$ and $BRAF^{Class\ III}$ mutations collectively represent about 3% of all cases in the US annually. Importantly, patients whose cancers carry these mutations are dramatically underserved, as no targeted therapies have been approved for these molecular subtypes. The data presented here raise the exciting possibility that a SHP2 inhibitor may make these mutations clinically actionable and improve the outlook for patients.

Our data show that SHP2 is not just a convergent signaling node downstream of multiple RTKs, but instead is an essential regulator of oncogenic RAS activation. Importantly, many tumors remain sensitive to SHP2 inhibition even when the oncogenic 'driver' mutation is apparently downstream of SHP2 in the canonical pathway. The association of SHP2 with SOS1 and GRB2 provide a mechanistic context for SHP2's precise role in the regulation of RAS-GTP levels, and presents clear hypotheses around the impact of allosteric inhibitors on this functional module.

The preserved dependence of $KRAS^{G12C}$, $NF1^{LOF}$, and $BRAF^{Class\ III}$ mutations on SHP2-mediated upstream signals suggests that certain mutant forms of RAS pathway oncogenic drivers amplify, rather than bypass, the homeostatic mechanisms regulating RAS-GTP and pathway output. This contrasts with a common assumption that RAS oncogenes are locked in the "on" GTP-bound state constitutively to drive signaling and cancer, and is consistent with a framework in which certain oncogenic mutations are semi-autonomous, rather than fully-autonomous, drivers of cancer. More broadly, our study highlights the power of developing selective and potent pharmacologic probes to uncover occult features of oncogenic RAS signaling and unanticipated therapeutic opportunities.

Example 6

Effect of SHP2 Allosteric Inhibitor (Compound B) on In Vitro Tumor Cell Growth Alone and in Combination with MEK Inhibitor Trametinib Objective: To evaluate the efficacy of the SHP2 allosteric inhibitor Compound B alone and in combination with trametinib, in vitro, in tumor cells from human non-small cell lung cancer cell lines CALU-1 and NCI-H358.

Methods:

Cells were grown in 3D culture as spheroids. Briefly, 2500 cells/well were seeded in round bottom ultra-low attachment 96-well plates (Corning) in growth media supplemented with 10% fetal bovine serum and 1% penicillin/streptomycin, and allowed to form spheroids for 72 hours at 37° C. in 5% $CO_2$. Spheroid formation was confirmed visually, and spheroids were treated in duplicate with serial 3-fold dilutions of Compound B in complete growth media (final DMSO concentration=0.1%). Following drug exposure for five days, cell viability in spheroids was determined using the CellTiter-Glo assay kit (Promega)

Results:

As shown in FIGS. 16A and 16C, dose-dependent inhibition of CALU-1 NSCLC and H358 NSCLC tumor cell growth was achieved by treatment with each of the SHP2 and MEK inhibitors. Moreover, SHP2 inhibition in combination with MEK inhibition led to synergistic tumor growth inhibition in each of the cells tested (CALU-1 NSCLC tumor cells and H358 NSCLC tumor cells). For example, FIGS. 16B and 16D show a Loewe Model of Additivity fit of the data from FIGS. 16A and 16C, respectively, wherein the numbers in the positive range (mapped in blue) are indicative of synergy.

Example 7

Effect of SHP2 Allosteric Inhibitor (Compound B) on In Vivo Tumor Cell Growth Alone and in Combination with MEK Inhibitor Trametinib Objective: To evaluate the efficacy of the SHP2 allosteric inhibitor Compound B alone and in combination with trametinib, following oral administration, in the human non-small cell lung cancer NCI-H358 xenograft model in nude mice.

Methods:

The effects of a SHP2 inhibitor on tumor cell growth in vivo were evaluated in the NSCLC H358 xenograft model using female athymic nude mice (6-8 weeks old). Mice were implanted with H358 tumor cells in 50% Matrigel ($1\times10^7$ cells/animal) subcutaneously in the flank. Once tumors reached an average size of 200 mm³ mice were randomized to treatment groups and administration of test article or vehicle (50 mM acetate buffer, pH 4.6 containing 10% captisol, unless otherwise indicated) initiated. Trametinib was formulated in a solution of 0.5% Methylcellulose+0.5% Tween 80. Body weight and tumor volume (using calipers) was measured every other day until study endpoints. Compounds were administered by oral gavage according to the schedule set forth in Table 5:

TABLE 5

Repeat dosing evaluation schedule

| Compound/Group | Dose | End of Study PK, n = 3/time point | End of Study PD, pERK, n = 3/time point |
|---|---|---|---|
| Vehicle Control | 10 ml/kg | Single | Single time |
| Trametinib | 1 mg/kg | 0.5, 1, 2, 4, 8, 24 h | 2, 8, 24 h |
| Compound B | 10 mg/kg | 0.5, 1, 2, 4, 8, 24 h | 2, 8, 24 h |
| Compound B | 30 mg/kg | 0.5, 1, 2, 4, 8, 24 h | 2, 8, 24 h |
| Compound B + trametinib | 10 + 1 mg/kg | 0.5, 1, 2, 4, 8, 24 h | 2, 8, 24 h |
| Compound B + trametinib | 30 + 1 mg/kg | 0.5, 1, 2, 4, 8, 24 h | 2, 8, 24 h |

The study endpoints are also shown in Table 5. Mean tumor volume data are reported for all animals that remained on study.

Figure 17:
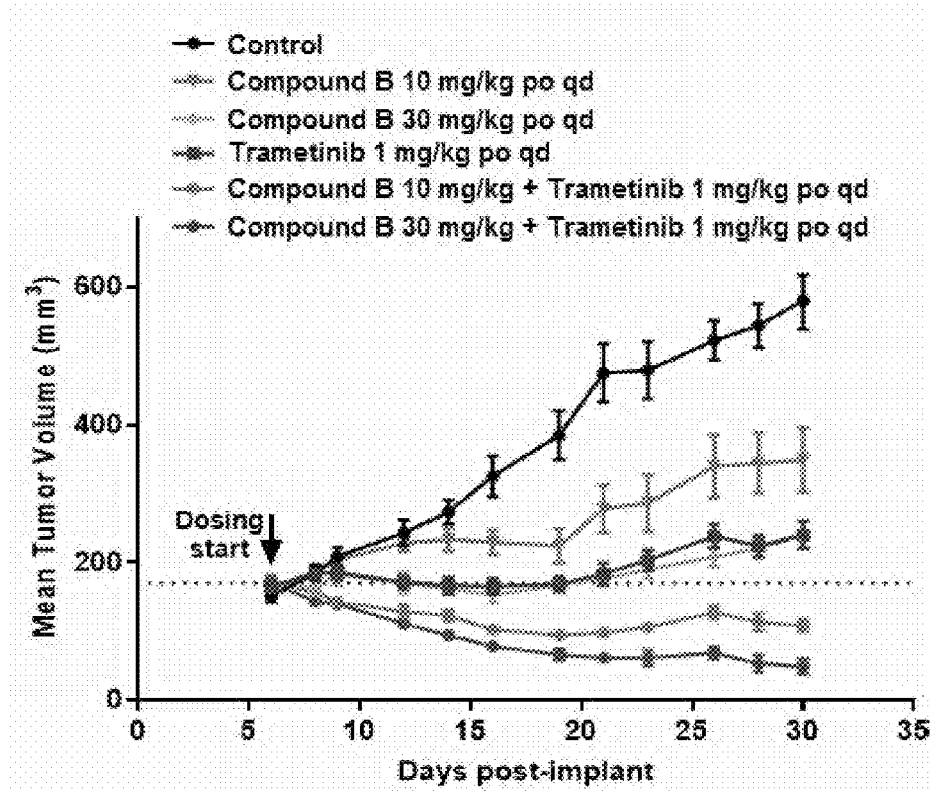
FIG. 17 shows the in vivo efficacy for tumor growth inhibition of repeated daily dosing of Compound B (Compound B) at 10 and 30 mg/kg PO (tumor growth inhibition, TGI=54, 79% respectively) alone, and in combination with trametinib at 1 mg/kg (TGI=79%) in the NCI-H358 model of human non-small cell lung cancer.

Results:

FIG. 17 shows the efficacy of repeated daily dosing of Compound B at 10 and 30 mg/kg PO (tumor growth inhibition, TGI=54, 79% respectively), and trametinib at 1 mg/kg (TGI=79%) in the NCI-H358 model of human non-small cell lung cancer. Compound B at both doses and trametinib as a single agent caused significant tumor growth inhibition as compared to the vehicle control. Note that the efficacy observed at 10 and 30 mg/kg treatment with Compound B reproduced previous data reported in Example 1 in the NCI-H358 xenograft model (FIG. 7).

The combination of trametinib at 1 mg/kg and Compound B at 10 mg/kg resulted in a mean tumor regression of 36%, and the same dose of trametinib in combination with 30 mg/kg Compound B resulted in a mean tumor regression of 71%, p=0.001, *p<0.0001, respectively, assessed by an ordinary one way ANOVA of tumor volumes along with multiple comparisons via a post-hoc Tukey's test in Graphpad Prism software. Three out of ten animals who received Compound B at 30 mg/kg and trametinib at 1 mg/kg achieved a complete regression of tumor which persisted at day 30.

Figure 18:
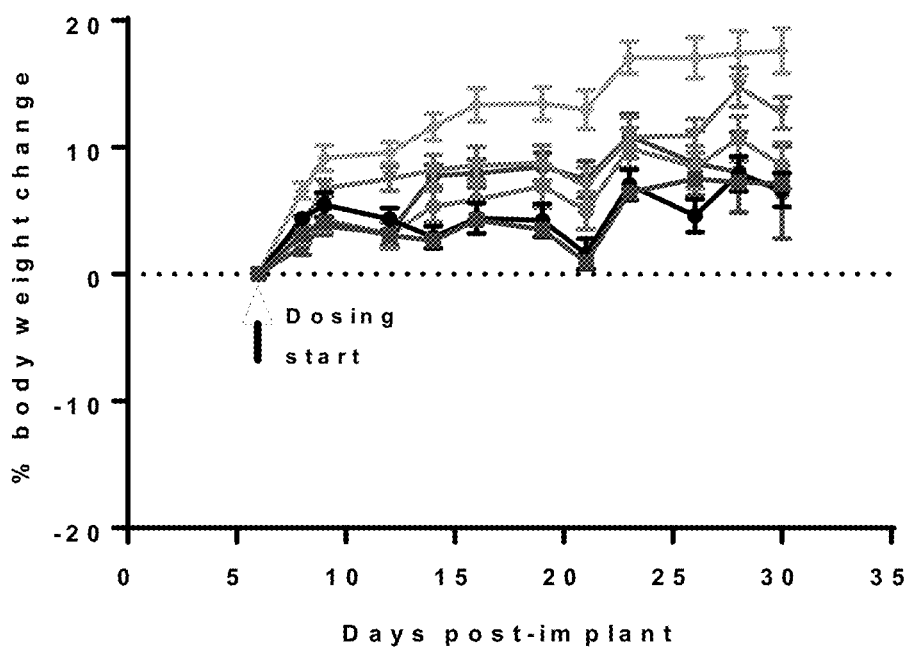
FIG. 18 shows the effect of Compound B (Compound B) alone and in combination with trametinib on body weight in NCI-H358 tumor bearing nude mice. Note that one animal in the Compound B (Compound B) 30 mg/kg+trametinib group (dark green) lost >20% body weight on day 30 and was removed from the study.

FIG. 18: All regimens were well tolerated for the duration of the study as evaluated by body weight, with the exception of one animal in the 30 mg/kg Compound B combination with 1 mg/kg trametinib, that lost >20% body weight on the last day of dosing and was euthanized for humane reasons.

Conclusion:

Compound B exhibits statistically significant, biologically significant and dose-dependent efficacy in the NCI-H358 non-small cell lung cancer xenograft model following oral administration at 10 mg/kg daily and 30 mg/kg daily. Trametinib also exhibited efficacy in this model at 1 mg/kg, a dose level previously predicted to be clinically relevant. Importantly, both doses of Compound B in combination with this dose of trametinib were tolerated and caused significant tumor regressions, some of which were complete regression.

Example 8

Effect of SHP2 Allosteric Inhibitor (Compound C) on In Vivo Tumor Cell Growth Alone and in Combination with MEK Inhibitor Trametinib Objective: To evaluate the efficacy of the SHP2 allosteric inhibitor Compound C alone and in combination with Trametinib (MEK Inhibitor), Cobimetinib (MEK Inhibitor), Ulixertinib (ERK Inhibitor), and Abemaciclib (CDK4/6 Inhibitor) following oral administration, in a human non-small cell lung cancer NCI-H358 xenograft model (Trametinib, Cobimetinib, Ulixertinib) or in a human pancreatic carcinoma MIA-Pa-Ca-2 xenograft model (Abemaciclib) in nude mice.

Methods:

The effects on tumor cell growth in vivo of another SHP2 inhibitor (Compound C) as a monotherapy or as a combination therapy with various Ras pathway inhibitors were evaluated in the NSCLC H358 KRas$^{G12C}$ and MIA-Pa-Ca-2 xenograft models as described above in Example 1, except that the test article and vehicle formulation was (2% HPMC E-50, 0.5% Tween 80 in 50 mM Sodium Citrate Buffer, pH 4.0)+/− the inhibitor compound(s). As before, body weight and tumor volume (using calipers) was measured biweekly until study endpoint. Test compounds or vehicle control were administered by oral gavage daily. The study endpoint was defined as a mean tumor volume of 2000 mm$^3$ in the control group or 22 days post-dosing, whichever came first. Mean tumor volume data are reported for all animals that remained on study.

Results:

FIG. 21 shows the efficacy of repeated daily dosing of Compound C ("Cmp C") at 10 mg/kg PO with or without co-administration of a Ras pathway inhibitor in the H358 KRas$^{G12C}$ model of human non-small cell lung cancer. FIGS. 21A and 21B show Compound C and Trametinib studies; FIGS. 21C and 21D show Compound C and Cobimetinib studies; and FIGS. 21E and 21F show Compound C and Ulixertinib studies. Each of Compound C (FIGS. 21A, 21C, and 21E), Trametinib (FIG. 21A), Cobimetinib (FIG. 21C) and Ulixertinib (FIG. 21E) caused significant tumor growth inhibition as a single agent as compared to the vehicle control. Note that the efficacy observed at 10 mg/kg treatment with Compound C reproduced previous NCI-H358 xenograft model data reported in Example 1 with Compound A and Compound B (FIG. 7) and data reported in Example 7 with Compound B (FIG. 17).

The combination of Trametinib at 1 mg/kg and Compound C at 10 mg/kg resulted in a significant increase in tumor regression (***p<0.0005), assessed by an ordinary one way ANOVA of tumor volumes along with multiple comparisons via a post-hoc Tukey's test in Graphpad Prism software (FIG. 21A).

Similarly, each of the combinations of Cobimetinib at 2.5 mg/kg with Compound C at 10 mg/kg (FIG. 21C) and of Ulixertinib at 100 mg/kg with Compound C at 10 mg/kg (FIG. 21E) resulted in a significant increase in tumor regression (***p<0.0005), assessed by an ordinary one way ANOVA of tumor volumes along with multiple comparisons via a post-hoc Tukey's test in Graphpad Prism software.

Figure 22:
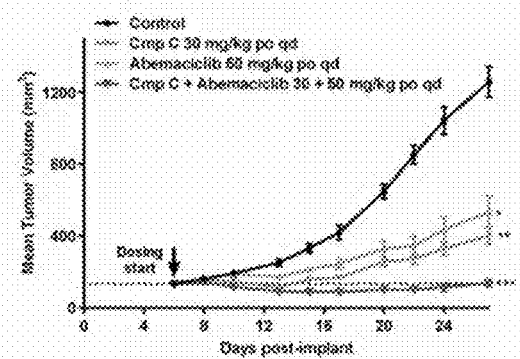
FIG. 22 shows the efficacy of repeated daily dosing of SHP2 inhibitor Compound C ("Cmp C") at 30 mg/kg PO with or without co-administration of Abemaciclib (CDK inhibitor) at 50 mg/kg in the human pancreatic carcinoma MIA-Pa-Ca-2 xenograft model.
Figure 22:
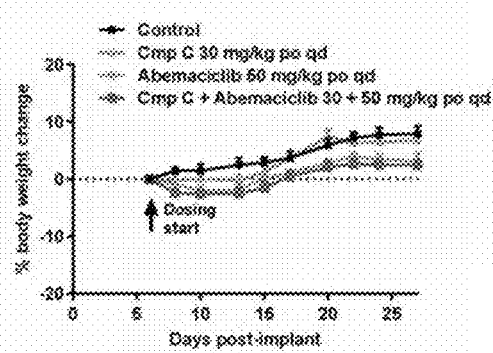

FIG. 22 shows the efficacy of repeated daily dosing of Compound C at 30 mg/kg PO with or without co-administration of Abemaciclib at 50 mg/kg in the human pancreatic carcinoma MIA-Pa-Ca-2 xenograft model. Each of Compound C and Abemaciclib caused significant tumor growth inhibition as a single agent as compared to the vehicle control (FIG. 22A). Moreover, the combination of Abemaciclib at 50 mg/kg and Compound C at 30 mg/kg resulted in a significant increase in tumor regression (***p<0.0005), assessed by an ordinary one way ANOVA of tumor volumes along with multiple comparisons via a post-hoc Tukey's test in Graphpad Prism software (FIG. 22A).

All regimens were well tolerated for the duration of the study as evaluated by body weight (FIGS. 21B, 21D, 21F, and 22B).

Conclusion:

Like Compounds A and B, Compound C exhibits statistically significant, biologically significant, and dose-dependent efficacy in the NCI-H358 non-small cell lung cancer and in the MIA-Pa-Ca-2 xenograft models following oral administration at 10 mg/kg daily and 30 mg/kg daily. Trametinib also exhibited efficacy in this model at 1 mg/kg, a dose level previously predicted to be clinically relevant, as did Cobimetinib, Ulixertinib, and Abemaciclib at clinically relevant doses of 2.5, 100, and 50 mg/kg, respectively.

Importantly, in all cases, doses of the Compound C SHP2 inhibitor in combination with the dose of the other Ras pathway inhibitors were tolerated and caused significant tumor regressions, some of which were complete regression.

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of treating a subject having a disease or disorder comprising a cell containing a mutation encoding the KRAS$^{G12C}$ variant, comprising providing to the subject an inhibitor of SHP2, wherein the inhibitor of SHP2 is a compound of Formula I-V2:

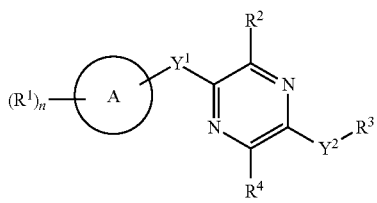

I-V2 or a pharmaceutically acceptable salt and/or stereoisomer thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$Y^1$ is —S—, a direct bond, —NH—, —S(O)$_2$—, —S(O)$_2$—NH—, —C(=CH$_2$)—, —CH—, or —S(O)—;

$Y^2$ is —NR$^a$—, wherein the bond on the left side of $Y^2$, as drawn, is bound to the pyrazine ring and the bond on the right side of the $Y^2$ moiety, as drawn, is bound to $R^3$;

$R^3$ is combined with $R^a$ to form a 3- to 12-membered polycyclic heterocycle or a 5- to 12-membered spiroheterocycle, wherein each heterocycle or spiroheterocycle is optionally substituted with one or more —C$_1$-C$_6$alkyl, halogen, —OH, —OR$^b$, —NHR$^b$, heteroaryl, heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —CF$_3$, —CHF$_2$, —CH$_2$F, or =O;

each R¹ is independently —H, -D, —C₁-C₆alkyl, —C₂-C₆alkenyl, —C₄-C₈cycloalkenyl, —C₂-C₆alkynyl, —C₃-C₈cycloalkyl, —OH, —OR⁶, halogen, —NO₂—, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, —CO₂R⁵, —C(O)NR⁵R⁶, —NR⁵C(O)R⁶, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO₂, oxo, =O, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R² is —NH₂, —OR^b, —CN, —C₁-C₆alkyl, —C₂-C₆alkenyl, —C₄-C₈cycloalkenyl, —C₂-C₆alkynyl, halogen, —C(O)OR^b, —C₃-C₈cycloalkyl, aryl, heterocyclyl containing 1-5 heteroatoms selected from N, S, P, and O, or heteroaryl containing 1-5 heteroatoms selected from N, S, P, and O; wherein each alkyl, alkenyl, cycloalkenyl, alkynyl, cycloalkyl, heterocyclyl, aryl, or heteroaryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl; and wherein the heterocyclyl or heteroaryl is not attached via a nitrogen atom;

each R^b is independently —H, -D, —OH, —C₁-C₆alkyl, —C₃-C₈cycloalkyl, —C₂-C₆alkenyl, —(CH₂)ₙ-aryl, heterocyclyl containing 1-5 heteroatoms selected from N, S, P, and O, or heteroaryl containing 1-5 heteroatoms selected from N, S, P, and O; wherein each alkyl, cycloalkyl, alkenyl, heterocyclyl, heteroaryl, or —(CH₂)ₙ-aryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)NR⁵R⁶, —NR⁵C(O)R⁶, heterocyclyl, aryl, heteroaryl, —(CH₂)ₙOH, —C₁-C₆alkyl, —CF₃, —CHF, or —CH₂F;

R⁴ is —H, -D, —C₁-C₆alkyl, —C₁-C₆haloalkyl, —C₁-C₆hydroxyalkyl, —CF₂OH, —CHFOH, —NH—NHR⁵, —NH—OR⁵, —O—NR⁵R⁶, —NHR⁵, —OR⁵, —NHC(O)R⁵, —NHC(O)NHR⁵, —NHS(O)₂R⁵, —NHS(O)₂NHR⁵, —S(O)₂OH, —C(O)OR⁵, —NH(CH₂)ₙOH, —C(O)NH(CH₂)ₙOH, —C(O)NH(CH₂)ₙR^b, —C(O)R^b, —OH, —CN, —C(O)NR⁵R⁶, —S(O)₂NR⁵R⁶, C₃-C₈cycloalkyl, aryl, heterocyclyl containing 1-5 heteroatoms selected from N, S, P, and O, or heteroaryl containing 1-5 heteroatoms selected from N, S, P, and O, wherein each alkyl, cycloalkyl, or heterocyclyl is optionally substituted with one or more —OH, —NH₂, —OR^b, halogen, or oxo; wherein each aryl or heteroaryl is optionally substituted with one or more —OH, —NH₂—, or halogen;

each R⁵ and R⁶ is independently —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocyclyl, —OR⁷, —SR⁷, halogen, —NR⁷R⁸, —NO₂, —CF₃, or —CN;

each R⁷ and R⁸ is independently —H, -D, —C₁-C₆alkyl, —C₂-C₆alkenyl, —C₄-C₈cycloalkenyl, —C₂-C₆alkynyl, —C₃-C₈cycloalkyl, —OR^b, or a monocyclic or polycyclic 3-to 12-membered heterocyclyl, wherein each alkyl, alkenyl, cycloalkenyl, alkynyl, cycloalkyl, or heterocyclyl is optionally substituted with one or more —OH, —SH, —NH₂, —NO, or —CN; and each n is independently 0, 1, 2, 3, 4, 5, 6, 7, 8, 9, or 10.

2. A method of treating a subject having a disease or disorder associated with a RAS pathway mutation in a cell of the subject that renders the cell at least partially dependent on signaling flux through SHP2, comprising providing to the subject an inhibitor of SHP2, wherein the inhibitor of SHP2 is a compound of Formula I-V2:

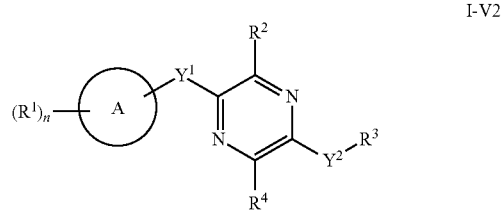

I-V2 or a pharmaceutically acceptable salt and/or stereoisomer thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic, Y¹ is —S—, a direct bond, —NH—, —S(O)₂—, —S(O)₂—NH—, —C(=CH₂)—, —CH—, or —S(O)—;

Y² is —NR^a—, wherein the bond on the left side of Y², as drawn, is bound to the pyrazine ring and the bond on the right side of the Y² moiety, as drawn, is bound to R³;

R³ is combined with R¹ to form a 3- to 12-membered polycyclic heterocyclyl or a 5- to 12-membered spiroheterocyclyl, wherein each heterocyclyl or spiroheterocyclyl is optionally substituted with one or more —C₁-C₆alkyl, halogen, —OH, —OR^b, —NH₂, —NHR^b, heteroaryl, heterocyclyl, —(CH₂)ₙNH₂, —(CH₂)ₙOH, —COOR^b, —CONHR^b, —CONH(CH₂)ₙCOOR^b, —NHCOOR^b, —CF₃, —CHF₂, —CH₂F, or =O;

each R¹ is independently —H, -D, —C₁-C₆alkyl, —C₂-C₆alkenyl, —C₄-C₈cycloalkenyl, —C₂-C₆alkynyl, —C₃-C₈cycloalkyl, —OH, —OR⁶, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, —CO₂R⁵, —C(O)NR⁵R⁶, —NR⁵C(O)R⁶, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO₂, oxo, =O, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R² is —NH, —OR^b, —CN, —C₁-C₆alkyl, —C₂-C₆alkenyl, —C₄-C₈cycloalkenyl, —C₂-C₆alkynyl, halogen, —C(O)OR^b, —C₃-C₈cycloalkyl, aryl, heterocyclyl containing 1-5 heteroatoms selected from N, S, P, and O, or heteroaryl containing 1-5 heteroatoms selected from N, S, P, and O; wherein each alkyl, alkenyl, cycloalkenyl, alkynyl, cycloalkyl, heterocyclyl, aryl, or heteroaryl is optionally substituted with one or more —OH, halogen, —NO, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

each $R^b$ is independently —H, -D, —OH, —$C_1$-$C_6$alkyl, —$C_3$-$C_8$cycloalkyl, —$C_2$-$C_6$alkenyl, —$(CH_2)_n$-aryl, heterocyclyl containing 1-5 heteroatoms selected from N, S, P, and O, or heteroaryl containing 1-5 heteroatoms selected from N, S, P, and O; wherein each alkyl, cycloalkyl, alkenyl, heterocyclyl, heteroaryl, or —$(CH_2)_n$-aryl is optionally substituted with one or more —OH, halogen, —$NO_2$—, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$, —$NR^5C(O)R^6$, heterocyclyl, aryl, heteroaryl, —$(CH_2)_nOH$, —$C_1$-$C_6$alkyl, —$CF_3$, —$CHF_2$, or —$CH_2F$;

$R^4$ is —H, -D, —$C_1$-$C_6$alkyl, —$C_1$-$C_6$haloalkyl, —$C_1$-$C_6$hydroxyalkyl, —$CF_2OH$, —CHFOH, —NH—$NHR^5$, —NH—$OR^5$, —O—$NR^5R^6$, —$NHR^5$, —$OR^5$, —$NHC(O)R^5$, —$NHC(O)NHR^5$, —$NHS(O)_2R^5$, —$NHS(O)_2NHR^5$, —$S(O)_2OH$, —$C(O)OR^5$, —NH$(CH_2)_nOH$, —$C(O)NH(CH_2)_nOH$, —$C(O)NH(CH_2)_nR^b$, —$C(O)R^b$, —$NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from N, S, P, and O, or heteroaryl containing 1-5 heteroatoms selected from N, S, P, and O, wherein each alkyl, cycloalkyl, or heterocyclyl is optionally substituted with one or more —OH, —$OR^b$, halogen, or oxo; wherein each aryl or heteroaryl is optionally substituted with one or more —OH, —$NH_2$, or halogen;

each $R^5$ and $R^6$ is independently —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocyclyl, —$OR^7$, —$SR^7$, halogen, —$NR^7R^8$, —$NO_2$, —$CF_3$, or —CN;

each $R^7$ and $R^8$ is independently —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$OR^b$, or a monocyclic or polycyclic 3-to 12-membered heterocyclyl, wherein each alkyl, alkenyl, cycloalkenyl, alkynyl, cycloalkyl, or heterocyclyl is optionally substituted with one or more —OH, —SH, —$NO_2$, or —CN; and each n is independently 0, 1, 2, 3, 4, 5, 6, 7, 8, 9, or 10.

3. The method of claim 2, wherein the RAS pathway mutation is selected from a KRAS mutation, an NRAS mutation, a SOS mutation, a BRAF Class III mutation, a Class I MEK1 mutation, a Class II MEK1 mutation, and an NF1 mutation.

4. A method for treating a subject having a tumor comprising:
(a) determining whether a biological sample obtained from the subject is classified as a KRAS mutant; and
(b) administering to the subject an inhibitor of SHP2 if the biological sample is classified as a $KRAS^{G12C}$ mutant, a $KRAS^{G12D}$ mutant, a $KRAS^{G12S}$ mutant, or a $KRAS^{G12V}$ mutant, wherein the inhibitor of SHP2 is a compound of Formula I-V2:

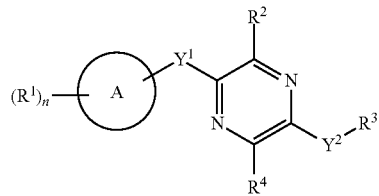

I-V2 or a pharmaceutically acceptable salt and/or stereoisomer thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$Y^1$ is —S—, a direct bond, —NH—, —$S(O)_2$—, —$S(O)_2$—NH—, —$C(=CH_2)$—, —CH—, or —$S(O)$—;

$Y^2$ is —$NR^a$—, wherein the bond on the left side of $Y^2$, as drawn, is bound to the pyrazine ring and the bond on the right side of the $Y^2$ moiety, as drawn, is bound to $R^3$;

$R^3$ is combined with $R^a$ to form a 3- to 12-membered polycyclic heterocyclyl or a 5- to 12-membered spiroheterocyclyl, wherein each heterocyclyl or spiroheterocyclyl is optionally substituted with one or more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O;

each $R^1$ is independently —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO, oxo, =O, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is —$NH_2$, —$OR^b$, —CN, —$C_1$-$C_6$alkyl, —$C_2$-$C_6$alkenyl, —$C_4$-$C_8$cycloalkenyl, —$C_2$-$C_6$alkynyl, halogen, —$C(O)OR^b$, —$C_3$-$C_8$cycloalkyl, aryl, heterocyclyl containing 1-5 heteroatoms selected from N, S, P, and O, or heteroaryl containing 1-5 heteroatoms selected from N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

each $R^b$ is independently —H, -D, —OH, —$C_1$-$C_6$alkyl, —$C_3$-$C_8$cycloalkyl, —$C_2$-$C_6$alkenyl, —$(CH_2)_n$-aryl, heterocyclyl containing 1-5 heteroatoms selected from N, S, P, and O, or heteroaryl containing 1-5 heteroatoms selected from N, S, P, and O; wherein each alkyl, cycloalkyl, alkenyl, heterocyclyl, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocyclyl, aryl, heteroaryl, —(CH$_2$)$_n$OH, —C$_1$-C$_6$alkyl, —CHF$_2$, or —CH$_2$F;

R$^4$ is —H, -D, —C$_1$-C$_6$alkyl, —C$_1$-C$_6$haloalkyl, —C$_1$-C$_6$hydroxyalkyl, —CF$_2$OH, —CHFOH, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —CN, —C(O)NR$^5$R$^6$, —S(O)$_2$NR$^5$R$^6$, C$_3$-C$_8$cycloalkyl, aryl, heterocyclyl containing 1-5 heteroatoms selected from N, S, P, and O, or heteroaryl containing 1-5 heteroatoms selected from N, S, P, and O, wherein each alkyl, cycloalkyl, or heterocyclyl is optionally substituted with one or more —OH, —NH$_2$, —OR$^b$, halogen, or oxo; wherein each aryl or heteroaryl is optionally substituted with one or more —OH, —NH$_2$, or halogen;

each R$^5$ and R$^6$ is independently —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocyclyl, —OR$^7$, —SR$^7$, halogen, —NR$^7$R$^8$, —CF, or —CN;

each R$^7$ and R$^8$ is independently —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3- to 12-membered heterocyclyl, wherein each alkyl, alkenyl, cycloalkenyl, alkynyl, cycloalkyl, or heterocyclyl is optionally substituted with one or more —OH, —SH, —NO, or —CN; and each n is independently 0, 1, 2, 3, 4, 5, 6, 7, 8, 9, or 10.

5. A method for treating a subject having a tumor comprising:
(a) determining whether a biological sample obtained from the subject is classified as an NF1$^{LOF}$ mutant; and
(b) administering to the subject an inhibitor of SHP2 if the biological sample is classified as an NF1$^{LoF}$ mutant,
wherein the inhibitor of SHP2 is a compound of Formula I-V2:

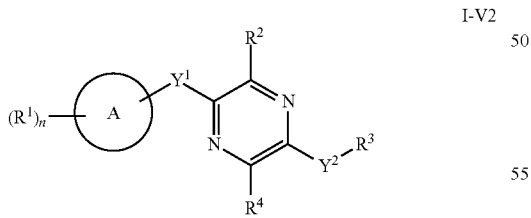

I-V2 or a pharmaceutically acceptable salt and/or stereoisomer thereof, wherein:
A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;
Y$^1$ is —S—, a direct bond, —NH—, —S(O)$_2$—, —S(O)$_2$—NH—, —C(=CH$_2$)—, —CH—, or —S(O)—;

Y$^2$ is —NR$^a$—, wherein the bond on the left side of Y$^2$, as drawn, is bound to the pyrazine ring and the bond on the right side of the Y$^2$ moiety, as drawn, is bound to R$^3$;

R$^3$ is combined with R$^1$ to form a 3- to 12-membered polycyclic heterocyclyl or a 5- to 12-membered spiroheterocyclyl, wherein each heterocyclyl or spiroheterocyclyl is optionally substituted with one or more —C$_1$-C$_6$alkyl, halogen, —OH, —OR$^b$, —NH$_2$, —NHR$^b$, heteroaryl, heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —CF$_3$, —CHF$_2$, —CH$_2$F, or =O;

each R$^1$ is independently —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO, oxo, =O, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^2$ is —NH$_2$, —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from N, S, P, and O, or heteroaryl containing 1-5 heteroatoms selected from N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

each R$^b$ is independently —H, -D, —OH, —C$_1$-C$_6$alkyl, —C$_3$-C$_8$cycloalkyl, —C$_2$-C$_6$alkenyl, —(CH$_2$)$_n$-aryl, heterocyclyl containing 1-5 heteroatoms selected from N, S, P, and O, or heteroaryl containing 1-5 heteroatoms selected from N, S, P, and O; wherein each alkyl, cycloalkyl, alkenyl, heterocyclyl, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocyclyl, aryl, heteroaryl, —(CH$_2$)$_n$OH, —C$_1$-C$_6$alkyl, —CF$_3$, —CHF$_2$, or —CH$_2$F;

R$^4$ is —H, -D, —C$_1$-C$_6$alkyl, —C$_1$-C$_6$haloalkyl, —C$_1$-C$_6$hydroxyalkyl, —CF$_2$OH, —CHFOH, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —CN, —C(O)NR$^5$R$^6$, —S(O)$_2$NR$^5$R$^6$, C$_3$-C$_8$cycloalkyl, aryl, heterocyclyl containing 1-5 heteroatoms selected from N, S, P, and O, or heteroaryl containing 1-5 heteroatoms selected from N, S, P, and O, wherein each alkyl, cycloalkyl, or heterocyclyl is optionally substituted with one or more —OH, —NH$_2$, —OR$^b$, halogen, or oxo; wherein each aryl or heteroaryl is optionally substituted with one or more —OH, —NH$_2$, or halogen;

each R$^5$ and R$^6$ is independently —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocyclyl, —OR', —SR', halogen, —NR$^7$R$^8$, —NO$_2$, —CF$_3$, or —CN;

each R$^7$ and R$^8$ is independently —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3-to 12-membered heterocyclyl, wherein each alkyl, alkenyl, cycloalkenyl, alkynyl, cycloalkyl, or heterocyclyl is optionally substituted with one or more —OH, —SH, —NH$_2$, —NO$_2$, or —CN; and each n is independently 0, 1, 2, 3, 4, 5, 6, 7, 8, 9, or 10.

6. A method for treating a subject having a tumor comprising:
(a) determining whether a biological sample obtained from the subject is classified as a Class 3 BRAF mutant; and
(b) administering to the subject an inhibitor of SHP2 if the biological sample is classified as a Class 3 BRAF mutant, wherein the inhibitor of SHP2 is a compound of Formula I-V2:

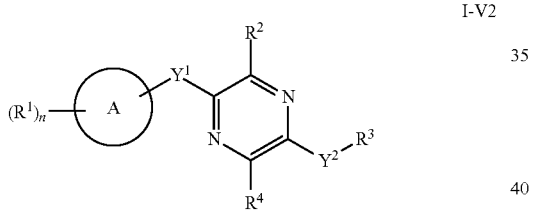

I-V2 or a pharmaceutically acceptable salt and/or stereoisomer thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

Y$^1$ is —S—, a direct bond, —NH—, —S(O)$_2$—, —S(O)$_2$—NH—, —C(=CH$_2$)—, —CH—, or —S(O)—;

Y$^2$ is —NR$^a$—, wherein the bond on the left side of Y$^2$, as drawn, is bound to the pyrazine ring and the bond on the right side of the Y$^2$ moiety, as drawn, is bound to R$^3$;

R$^3$ is combined with R$^a$ to form a 3- to 12-membered polycyclic heterocyclyl or a 5- to 12-membered spiroheterocyclyl, wherein each heterocyclyl or spiroheterocyclyl is optionally substituted with one or more —C$_1$-C$_6$alkyl, halogen, —OH, —OR$^b$, —NHR$^b$, heteroaryl, heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —CF$_3$, —CHF$_2$, —CH$_2$F, or =O;

each R$^1$ is independently —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO$_2$, oxo, =O, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^2$ is —NH$_2$, —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from N, S, P, and O, or heteroaryl containing 1-5 heteroatoms selected from N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

each R$^b$ is independently —H, -D, —OH, —C$_1$-C$_6$alkyl, —C$_3$-C$_8$cycloalkyl, —C$_2$-C$_6$alkenyl, —(CH$_2$)$_n$-aryl, heterocyclyl containing 1-5 heteroatoms selected from N, S, P, and O, or heteroaryl containing 1-5 heteroatoms selected from N, S, P, and O; wherein each alkyl, cycloalkyl, alkenyl, heterocyclyl, heteroaryl, or —(CH$_2$)$_n$-aryl is optionally substituted with one or more —OH, halogen, —NO, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocyclyl, aryl, heteroaryl, —(CH$_2$)$_n$OH, —C$_1$-C$_6$alkyl, —CF$_3$, —CHF$_2$, or —CH$_2$F, R$^4$ is —H, -D, —C$_1$-C$_6$alkyl, —C$_1$-C$_6$haloalkyl, —C$_1$-C$_6$hydroxyalkyl, —CF$_2$OH, —CHFOH, —NHNHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —CN, —C(O)NR$^5$R$^6$, —S(O)$_2$NR$^5$R$^6$, C$_3$-C$_8$cycloalkyl, aryl, heterocyclyl containing 1-5 heteroatoms selected from N, S, P, and O, or heteroaryl containing 1-5 heteroatoms selected from N, S, P, and O, wherein each alkyl, cycloalkyl, or heterocyclyl is optionally substituted with one or more —OH, —NH$_2$, —OR$^b$, halogen, or oxo; wherein each aryl or heteroaryl is optionally substituted with one or more —OH, —NH$_2$, or halogen;

each R$^5$ and R$^6$ is independently —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocyclyl, —OR$^7$, —SR$^7$, halogen, —NR$^7$R$^8$, —NO$_2$, —CF$_3$, or —CN;

each R$^7$ and R$^8$ is independently —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3- to 12-membered heterocyclyl, wherein each alkyl, alkenyl, cycloalkenyl, alkynyl, cycloalkyl, or heterocyclyl is optionally substituted with one or more —OH, —SH, —NH$_2$, —NO$_2$, or —CN, and each n is independently 0, 1, 2, 3, 4, 5, 6, 7, 8, 9, or 10.

7. A method for treating or preventing drug resistance in a subject receiving administration of a RAS pathway inhibitor, comprising administering to the subject an inhibitor of SHP2, wherein the inhibitor of SHP2 is a compound of Formula I-V2:

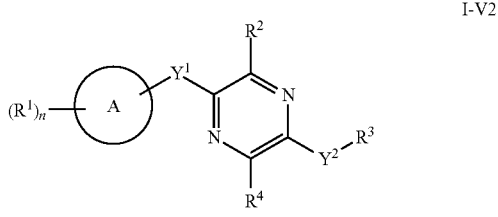

I-V2 or a pharmaceutically acceptable salt and/or stereoisomer thereof, wherein:
A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;
Y$^1$ is —S—, a direct bond, —NH—, —S(O)$_2$—, —S(O)$_2$—NH—, —C(═CH$_2$)—, —CH—, or —S(O)—;
Y$^2$ is —NR$^a$—, wherein the bond on the left side of Y$^2$, as drawn, is bound to the pyrazine ring and the bond on the right side of the Y$^2$ moiety, as drawn, is bound to R$^3$;
R$^3$ is combined with R$^1$ to form a 3- to 12-membered polycyclic heterocyclyl or a 5- to 12-membered spiroheterocyclyl, wherein each heterocyclyl or spiroheterocyclyl is optionally substituted with one or more —C$_1$-C$_6$alkyl, halogen, —OH, —OR$^b$, —NH$_2$, —NHR$^b$, heteroaryl, heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —CF$_3$, —CHF$_2$, —CH$_2$F, or ═O;
each R$^1$ is independently —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO$_2$, oxo, ═O, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;
R$^2$ is —NH$_2$, —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from N, S, P, and O, or heteroaryl containing 1-5 heteroatoms selected from N, S, P, and O; wherein each alkyl, alkenyl, cycloalkenyl, alkynyl, cycloalkyl, heterocyclyl, aryl, or heteroaryl is optionally substituted with one or more —OH, halogen, —NO, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;
each R$^b$ is independently —H, -D, —OH, —C$_1$-C$_6$alkyl, —C$_3$-C$_8$cycloalkyl, —C$_2$-C$_6$alkenyl, —(CH$_2$)$_n$-aryl, heterocyclyl containing 1-5 heteroatoms selected from N, S, P, and O, or heteroaryl containing 1-5 heteroatoms selected from N, S, P, and O; wherein each alkyl, cycloalkyl, alkenyl, heterocyclyl, heteroaryl, or —(CH$_2$)$_n$-aryl is optionally substituted with one or more —OH, halogen, —NO, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocyclyl, aryl, heteroaryl, —(CH$_2$)$_n$OH, —C$_1$-C$_6$alkyl, —CF$_3$, —CHF$_2$, or —CH$_2$F;
R$^4$ is —H, -D, —C$_1$-C$_6$alkyl, —C$_1$-C$_6$haloalkyl, —C$_1$-C$_6$hydroxyalkyl, —CF$_2$OH, —CHFOH, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —CN, —C(O)NR$^5$R$^6$, —S(O)$_2$NR$^5$R$^6$, C$_3$-C$_8$cycloalkyl, aryl, heterocyclyl containing 1-5 heteroatoms selected from N, S, P, and O, or heteroaryl containing 1-5 heteroatoms selected from N, S, P, and O, wherein each alkyl, cycloalkyl, or heterocyclyl is optionally substituted with one or more —OH, —NH$_2$, —OR$^b$, halogen, or oxo; wherein each aryl or heteroaryl is optionally substituted with one or more —OH, —NH$_2$, or halogen;
each R$^5$ and R$^6$ is independently —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocyclyl, —OR$^7$, —SR$^7$, halogen, —NR$^7$R$^8$, —NO$_2$, —CF$_3$, or —CN;
each R$^7$ and R$^8$ is independently —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3-to 12-membered heterocyclyl, wherein each alkyl, alkenyl, cycloalkenyl, alkynyl, cycloalkyl, or heterocyclyl is optionally substituted with one or more —OH, —SH, —NH$_2$, —NO$_2$, or —CN; and each n is independently 0, 1, 2, 3, 4, 5, 6, 7, 8, 9, or 10.

8. The method of any one of the preceding claim 1, 2, 3, 4, 5, 6, or 7, wherein the inhibitor of SHP2 is selected from:
(i) Compound A having the structure:

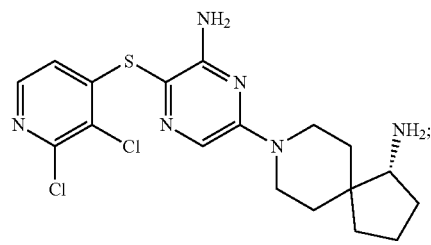 [SMILES: Nc1nc(N2CCC3(CCC[C@H]3N)CC2)cnc1Sc1ccnc(Cl)c1Cl]

(ii) Compound B having the structure:

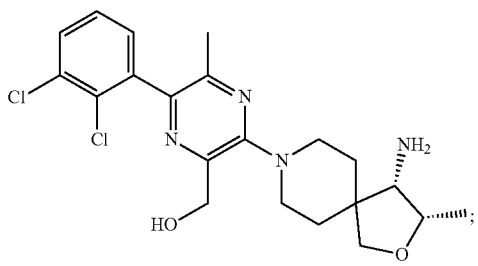 [SMILES: Cc1nc(N2CCC3(CC2)CO[C@@H](C)[C@H]3N)c(CO)nc1-c1cccc(Cl)c1Cl]

and (iii) the compound of the following structure:

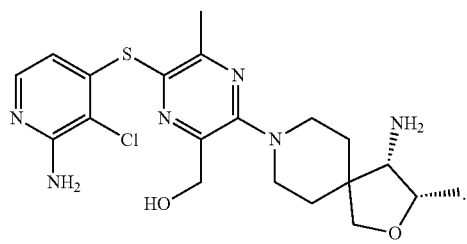 [SMILES: Cc1nc(N2CCC3(CC2)CO[C@@H](C)[C@H]3N)c(CO)nc1Sc1ccnc(N)c1Cl]

9. The method of claim 1, wherein the inhibitor of SHP2 is:

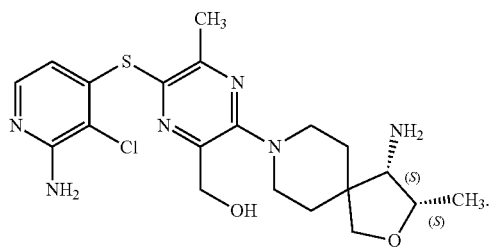

10. The method of claim 2, wherein the inhibitor of SHP2 is:

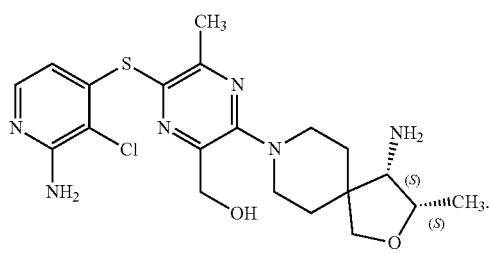

11. The method of claim 4, wherein the inhibitor of SHP2 is:

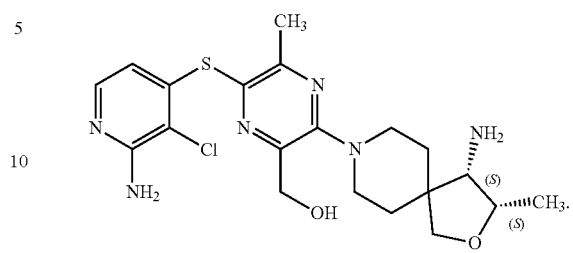

12. The method of claim 5, wherein the inhibitor of SHP2 is:

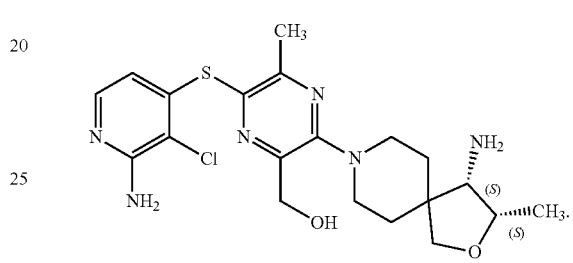

13. The method of claim 6, wherein the inhibitor of SHP2 is:

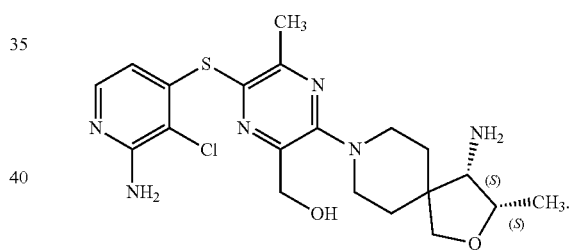

14. The method of claim 7, wherein the inhibitor of SHP2 is:

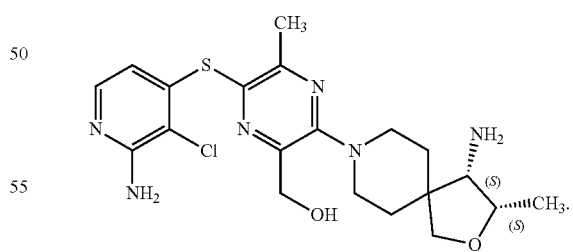

15. The method of claim 1, wherein the inhibitor of SHP2 is selected from a compound of Formula I-V2 wherein $Y^1$ is —S— or a direct bond, or a pharmaceutically acceptable salt and/or stereoisomer thereof.

16. The method of claim 2, wherein the inhibitor of SHP2 is selected from a compound of Formula I-V2 wherein $Y^1$ is —S— or a direct bond, or a pharmaceutically acceptable salt and/or stereoisomer thereof.

17. The method of claim 4, wherein the inhibitor of SHP2 is selected from a compound of Formula I-V2 wherein $Y^1$ is —S— or a direct bond, or a pharmaceutically acceptable salt and/or stereoisomer thereof.

18. The method of claim 5, wherein the inhibitor of SHP2 is selected from a compound of Formula I-V2 wherein $Y^1$ is —S— or a direct bond, or a pharmaceutically acceptable salt and/or stereoisomer thereof.

19. The method of claim 6, wherein the inhibitor of SHP2 is selected from a compound of Formula I-V2 wherein $Y^1$ is —S— or a direct bond, or a pharmaceutically acceptable salt and/or stereoisomer thereof.

20. The method of claim 7, wherein the inhibitor of SHP2 is selected from a compound of Formula I-V2 wherein $Y^1$ is —S— or a direct bond, or a pharmaceutically acceptable salt and/or stereoisomer thereof.

21. The method of claim 3, wherein the RAS pathway mutation is a KRAS mutation.

\* \* \* \* \*

UNITED STATES PATENT AND TRADEMARK OFFICE
CERTIFICATE OF CORRECTION

| | |
|---|---|
| PATENT NO. | : 11,596,633 B2 |
| APPLICATION NO. | : 16/810525 |
| DATED | : March 7, 2023 |
| INVENTOR(S) | : Robert J. Nichols et al. |

It is certified that error appears in the above-identified patent and that said Letters Patent is hereby corrected as shown below:

In the Claims

<u>In Claim 1</u>

Column 176, Line 64, "halogen, –OH, –OR$^b$, –NHR$^b$, heteroaryl," should read -- halogen, –OH, –OR$^b$, –NH$_2$, –NHR$^b$, heteroaryl, --

Column 177, Line 3, "–C$_3$-C$_8$cycloalkyl, –OH, –OR$^6$, halogen, –NO$_2$–," should read -- –C$_3$-C$_8$cycloalkyl, –OH, –OR$^6$, halogen, –NO$_2$, --

Column 177, Line 44, "–(CH$_2$)$_n$OH, –C$_1$-C$_6$alkyl, –CF$_3$, –CHF, or" should read -- –(CH$_2$)$_n$OH, –C$_1$-C$_6$alkyl, –CF$_3$, –CHF$_2$, or --

Column 177, Line 52, "–C(O)R$^b$, –OH, –CN, –C(O)NR$^5$R$^6$," should read -- –C(O)R$^b$, –NH$_2$, –OH, –CN, –C(O)NR$^5$R$^6$, --

Column 178, Line 5, "with one or more –OH, –SH, –NH$_2$, –NO, or" should read -- with one or more –OH, –SH, –NH$_2$, –NO$_2$, or --

<u>In Claim 2</u>

Column 178, Line 37, "R$^3$ is combined with R$^1$ to form a 3- to 12-membered" should read -- R$^3$ is combined with R$^a$ to form a 3- to 12-membered --

Column 178, Line 61, "R$^2$ is –NH, –OR$^b$, –CN, –C$_1$-C$_6$alkyl," should read -- R$^2$ is –NH$_2$, –OR$^b$, –CN, –C$_1$-C$_6$alkyl, --

Column 179, Line 2, "one or more –OH, halogen, –NO, oxo, –CN, –R$^5$," should read -- one or more –OH, halogen, NO$_2$, oxo, –CN, –R$^5$, --

Signed and Sealed this
Thirteenth Day of June, 2023

Katherine Kelly Vidal
*Director of the United States Patent and Trademark Office*

CERTIFICATE OF CORRECTION (continued)
U.S. Pat. No. 11,596,633 B2

Column 179, Line 36, "with one or more –OH, –OR$^b$, halogen, or oxo;" should read -- with one or more –OH, –NH$_2$, –OR$^b$, halogen, or oxo; --

Column 179, Line 51, "with one or more –OH, –SH, –NO$_2$, or –CN; and" should read -- with one or more –OH, –SH, –NH$_2$, –NO$_2$, or –CN; and --

In Claim 4

Column 180, Line 43, "with one or more –OH, halogen, –NO, oxo, =O," should read -- with one or more –OH, halogen, –NO$_2$, oxo, =O, --

Column 181, Line 7, "–(CH$_2$)$_n$OH, –C$_1$C$_6$alkyl, –CHF$_2$, or –CH$_2$F;" should read -- –(CH$_2$)$_n$OH, –C$_1$C$_6$alkyl, –CF$_3$, –CHF$_2$, or –CH$_2$F; --

Column 181, Line 29, "halogen, –NR$^7$R$^8$, –CF, or –CN;" should read -- halogen, –NR$^7$R$^8$, –NO$_2$, –CF$_3$, or –CN; --

Column 181, Line 37, "with one or more –OH, –SH, –NO, or –CN; and" should read -- with one or more –OH, –SH, –NH$_2$, –NO$_2$ or –CN; --

In Claim 5

Column 182, Line 5, "R$^3$ is combined with R$^1$ to form a 3- to 12-membered" should read -- R$^3$ is combined with R$^a$ to form a 3- to 12-membered --

Column 182, Line 24, "with one or more –OH, halogen, –NO, oxo, =O," should read -- with one or more –OH, halogen, –NO$_2$, oxo, =O, --

Column 183, Line 10, "cyclic 3- to 12-membered heterocyclyl, –OR', –SR'," should read -- cyclic 3- to 12-membered heterocyclyl, –OR$^7$, –SR$^7$, --

In Claim 6

Column 183, Line 60, "halogen, –OH, –OR$^b$, –NHR$^b$, heteroaryl," should read -- halogen, –OH, –OR$^b$, –NH$_2$, –NHR$^b$, heteroaryl, --

Column 184, Line 35, "more –OH, halogen, –NO, oxo, –CN, –R$^5$, –OR$^5$," should read -- more –OH, halogen, –NO$_2$, oxo, –CN, –R$^5$, –OR$^5$, --

In Claim 7

Column 185, Line 35, "R$^3$ is combined with R$^1$ to form a 3- to 12-membered" should read -- R$^3$ is combined with R$^a$ to form a 3- to 12-membered --

Column 186, Line 1, "one or more –OH, halogen, –NO, oxo, –CN, –R$^5$," should read -- one or more –OH, halogen, –NO$_2$, oxo, –CN, –R$^5$ --

Column 186, Line 14, "more –OH, halogen, –NO, oxo, –CN, –$R^5$, –$OR^5$," should read -- more –OH, halogen, –$NO_2$, oxo, –CN, –$R^5$, –$OR^5$, --